(12) United States Patent
Balyasnikova et al.

(10) Patent No.: US 11,827,712 B2
(45) Date of Patent: *Nov. 28, 2023

(54) IL13Rα2 BINDING AGENTS AND USE THEREOF

(71) Applicant: The University of Chicago, Chicago, IL (US)

(72) Inventors: Irina V. Balyasnikova, Chicago, IL (US); Maciej S. Lesniak, Chicago, IL (US)

(73) Assignee: The University of Chicago, Chicago, IL (US)

(*) Notice: Subject to any disclaimer, the term of this patent is extended or adjusted under 35 U.S.C. 154(b) by 372 days.

This patent is subject to a terminal disclaimer.

(21) Appl. No.: 16/949,900

(22) Filed: Nov. 19, 2020

(65) Prior Publication Data

US 2021/0221895 A1 Jul. 22, 2021

Related U.S. Application Data

(63) Continuation of application No. 16/385,853, filed on Apr. 16, 2019, now Pat. No. 10,851,169, which is a continuation of application No. 15/545,945, filed as application No. PCT/US2016/014984 on Jan. 26, 2016, now Pat. No. 10,308,719.

(60) Provisional application No. 62/107,984, filed on Jan. 26, 2015.

(51) Int. Cl.
*C07K 16/28* (2006.01)
*A61P 35/00* (2006.01)
*C07K 14/725* (2006.01)
*C07K 14/705* (2006.01)
*C07K 16/30* (2006.01)
*C12N 7/00* (2006.01)
*G01N 33/574* (2006.01)
*A61K 39/00* (2006.01)

(52) U.S. Cl.
CPC .......... *C07K 16/2866* (2013.01); *A61P 35/00* (2018.01); *C07K 14/7051* (2013.01); *C07K 14/70521* (2013.01); *C07K 16/3053* (2013.01); *C12N 7/00* (2013.01); *G01N 33/57407* (2013.01); *A61K 2039/505* (2013.01); *C07K 2317/30* (2013.01); *C07K 2317/56* (2013.01); *C07K 2317/622* (2013.01); *C07K 2317/76* (2013.01); *C07K 2317/92* (2013.01); *C07K 2319/00* (2013.01); *C07K 2319/02* (2013.01); *C07K 2319/03* (2013.01); *C07K 2319/21* (2013.01); *C07K 2319/41* (2013.01); *C12N 2710/10343* (2013.01); *G01N 2333/71* (2013.01)

(58) Field of Classification Search
CPC ....... A61P 35/00; C12N 7/00; C07K 16/3053; G01N 33/57407
See application file for complete search history.

(56) References Cited

U.S. PATENT DOCUMENTS

| | | |
|---|---|---|
| 3,773,919 A | 11/1973 | Boswell et al. |
| 4,342,776 A | 8/1982 | Cragoe, Jr. et al. |
| 4,399,276 A | 8/1983 | Miyasaka et al. |
| 4,450,150 A | 5/1984 | Sidman |
| 4,472,509 A | 9/1984 | Gansow et al. |
| 4,473,692 A | 9/1984 | Miyasaka et al. |
| 4,513,138 A | 4/1985 | Miyasaka et al. |
| 4,526,988 A | 7/1985 | Hertel |
| 4,545,880 A | 10/1985 | Miyasaka et al. |
| 4,604,463 A | 8/1986 | Miyasaka et al. |
| 4,808,614 A | 2/1989 | Hertel |
| 4,946,778 A | 8/1990 | Ladner et al. |
| 4,965,392 A | 10/1990 | Fritzberg et al. |
| 5,004,758 A | 4/1991 | Boehm et al. |
| 5,021,236 A | 6/1991 | Gries et al. |
| 5,037,630 A | 8/1991 | Fritzberg et al. |
| 5,223,608 A | 6/1993 | Chou et al. |
| 5,225,539 A | 7/1993 | Winter |

(Continued)

FOREIGN PATENT DOCUMENTS

| | | |
|---|---|---|
| DE | 3218121 | 11/1983 |
| EP | 0074770 | 3/1983 |

(Continued)

OTHER PUBLICATIONS

Adjei, et al. "Pulmonary Delivery of Peptide Drugs: Effect of Particle Size on Bioavailability of Leuprolide Acetate in Healthy Male Volunteers," *Pharmaceutical Research*, 7(6): 565-569 (1990).

(Continued)

*Primary Examiner* — Elly-Gerald Stoica
(74) *Attorney, Agent, or Firm* — Norton Rose Fulbright US LLP

(57) ABSTRACT

Provided are specific binding molecules, or fragments thereof, that bind to an epitope of IL13Rα2, a receptor polypeptide preferentially found on the surface of cancer cells rather than healthy cells. Exemplary specific binding molecules are bispecific binding molecules that comprise a fragment of an IL13Rα2 binding molecule and a peptide providing a second function providing a signaling function of the signaling domain of a T cell signaling protein, a peptide modulator of T cell activation, or an enzymatic component of a labeling system. Also provided are polynucleotides encoding such a specific binding molecule (e.g., bispecific binding molecule), vectors, host cells, pharmaceutical compositions and methods of preventing, treating or ameliorating a symptom associated with a cancer disease such as a solid tumor disease (e.g., glioblastoma multiforme).

19 Claims, 42 Drawing Sheets

Specification includes a Sequence Listing.

(56) References Cited

U.S. PATENT DOCUMENTS

| | | | |
|---|---|---|---|
| 5,403,484 | A | 4/1995 | Ladner et al. |
| 5,530,101 | A | 6/1996 | Queen et al. |
| 5,545,806 | A | 8/1996 | Lonberg et al. |
| 5,569,825 | A | 10/1996 | Lonberg et al. |
| 5,571,698 | A | 11/1996 | Ladner et al. |
| 5,585,089 | A | 12/1996 | Queen et al. |
| 5,620,985 | A | 4/1997 | Jacquesy et al. |
| 5,639,641 | A | 6/1997 | Pedersen et al. |
| 5,693,761 | A | 12/1997 | Queen et al. |
| 5,693,762 | A | 12/1997 | Queen et al. |
| 5,702,892 | A | 12/1997 | Mulliaan-Kehoe |
| 5,714,352 | A | 2/1998 | Jakobovits |
| 5,780,279 | A | 7/1998 | Matthews et al. |
| 5,821,047 | A | 10/1998 | Garrard et al. |
| 5,824,520 | A | 10/1998 | Mulligan-Kehoe |
| 5,837,500 | A | 11/1998 | Ladner et al. |
| 5,855,885 | A | 1/1999 | Smith et al. |
| 5,858,657 | A | 1/1999 | Winter et al. |
| 5,871,907 | A | 2/1999 | Winter et al. |
| 5,969,108 | A | 10/1999 | McCafferty et al. |
| 6,057,098 | A | 5/2000 | Buechler et al. |
| 6,225,447 | B1 | 5/2001 | Winter et al. |
| 6,265,150 | B1 | 7/2001 | Terstappen et al. |
| 6,630,124 | B1 | 10/2003 | Gozes et al. |
| 6,699,843 | B2 | 3/2004 | Pietras et al. |
| 7,355,008 | B2 | 4/2008 | Stavenhagen et al. |
| 7,381,408 | B2 | 6/2008 | Mezo et al. |
| 8,234,784 | B2 | 8/2012 | Younger |
| 10,308,719 | B2 | 6/2019 | Balyasnikova et al. |
| 2002/0197266 | A1 | 12/2002 | Debinski |
| 2003/0118592 | A1 | 6/2003 | Ledbetter et al. |
| 2004/0043401 | A1 | 3/2004 | Sadelain et al. |
| 2005/0282233 | A1 | 12/2005 | Eriksson et al. |
| 2006/0099652 | A1 | 5/2006 | Gately et al. |
| 2012/0009181 | A1 | 1/2012 | Ab et al. |
| 2012/0128679 | A1 | 5/2012 | Okamoto et al. |
| 2013/0280220 | A1 | 10/2013 | Ahmed et al. |
| 2014/0271582 | A1 | 9/2014 | Forman et al. |
| 2014/0271635 | A1 | 9/2014 | Brogdon et al. |
| 2014/0274909 | A1 | 9/2014 | Orentas et al. |
| 2014/0286973 | A1 | 9/2014 | Powell, Jr. |
| 2014/0286987 | A1 | 9/2014 | Spencer et al. |
| 2014/0301993 | A1 | 10/2014 | Powell, Jr. et al. |
| 2014/0322183 | A1 | 10/2014 | Milone et al. |
| 2014/0322212 | A1 | 10/2014 | Brogdon et al. |
| 2014/0322275 | A1 | 10/2014 | Brogdon et al. |
| 2014/0369977 | A1 | 12/2014 | Zhang et al. |

FOREIGN PATENT DOCUMENTS

| | | |
|---|---|---|
| EP | 52322 | 4/1983 |
| EP | 88046 | 2/1984 |
| EP | 0088642 | 3/1984 |
| EP | 36676 | 7/1984 |
| EP | 0133988 | 3/1985 |
| EP | 0056692 | 8/1985 |
| EP | 58481 | 10/1986 |
| EP | 0074256 | 11/1986 |
| EP | 0239400 | 9/1987 |
| EP | 184365 | 1/1988 |
| EP | 0137145 | 4/1988 |
| EP | 143949 | 10/1988 |
| EP | 0321122 | 12/1990 |
| EP | 418099 | 1/1992 |
| EP | 2814846 | 11/2015 |
| GB | 2188638 | 5/1990 |
| WO | WO 1999/040942 | 8/1999 |
| WO | WO 2000/032218 | 6/2000 |
| WO | WO 2002/060950 | 2/2003 |
| WO | WO 2004/033036 | 9/2004 |
| WO | WO 2005/087812 | 9/2005 |
| WO | WO 2007/141411 | 12/2007 |
| WO | WO 2007/133747 | 3/2008 |
| WO | WO 2008/130158 | 10/2008 |
| WO | WO 2010/025177 | 3/2010 |
| WO | WO 2014/190273 | 1/2014 |
| WO | WO 2014/055657 | 4/2014 |
| WO | WO 2014/152361 | 9/2014 |
| WO | WO 2014/153270 | 9/2014 |
| WO | WO 2014/179759 | 11/2014 |
| WO | WO 2014/180306 | 11/2014 |
| WO | WO 2014/184143 | 11/2014 |
| WO | WO 2014/186469 | 11/2014 |
| WO | WO 2014/208760 | 12/2014 |

OTHER PUBLICATIONS

Ahmed et al., "HER2-specific T cells target primary Glioblastoma stem cells and induce regression of autologous experimental tumors," *Clin Cancer Res* 16:474-485 (2010).
Akaiwa et al., "Localization of Human Interleukin 13 Receptor in Non-Haematopoietic Cells," *Cytokine* 13:75-84 (2001).
Allen et al "Interleukin-13 displaying retargeted oncolytic measles virus strains have significant activity against gliomas with improved specificity," *Mol Ther* 16:1556-1564 (2008).
Aman et al, "cDNA Cloning and Characterization of the Human Interleukin 13 Receptor α Chain," *J. Biol. Chem.* 271:29265-29270 (1996).
Amann et al., "Therapeutic Window of MuS110, a Single-Chain Antibody Construct Bispecific for Murine EpCAM and Murine CD3," *Cancer Res* 68:143-51 (2008).
Arima et al., "Characterization of the Interaction between Interleukin-13 and Interleukin-13 Receptors," *J. Biol. Chem.* 280:24915-24922 (2005).
Armour et al., "Recombinant human IgG molecules lacking Fcγ receptor I binding and monocyte triggering activities," *Eur. J. Immunol.* 29:2613-2624 (1999).
Asaoka et al,, "Dependence of efficient adenoviral gene delivery in malignant glioma cells on the expression levels of the Coxsackievirus and adenovirus receptor," *J Neurosurg* 92:1002-1008 (2000).
ASHP Handbook on Injectable Drugs, Toissel, 4th ed,, pp. 622-630 (1986).
Auffnger et al., "The role of glioma stem cells in chemotherapy resistance and glioblastoma multiforme recurrence," *Expert Review of Neurotherapeutics*, 1-12 (2015).
Ausubel et al., Current Protocols in Molecular Biology, Greene Publishing Associates and John Wiley & Sons, New York, N.Y. (1994).
Balyasnikova et al., "Characterization and immunotherapeutic implications for a novel antibody targeting interleukin (IL)-13 receptor α2," *The Journal of biological chemistry* 287:30215-30227 (2012).
Balyasnikova et al., "Cloning and characterization of a single-chain fragment of monoclonal antibody to ACE suitable for lung endothelial targeting," *Microvascular Research* 80:355-364 (2010).
Banker and Chalmers, eds,, Pharmaceutics and Pharmacy Practice, J. B. Lippincott Company, Philadelphia, PA, pp. 238-250 (1982).
Barderas et al,, "High Expression of IL-13 Receptor α2 in Colorectal Cancer Is Associated with Invasion, Liver Metastasis, and Poor Prognosis," *Cancer Research* 72:2780-2790 (2012).
Bartolazzi et al., "Glycosylation of CD44 Is Implicated in CD4-mediated Cell Adhesion to Hyaluronan," *J. Cell Biol.* 132:1199-1208 (1996).
Bartoloméet al., "IL 13 Receptor α2 Signaling Requires a Scaffold Protein, FAM120A, to Activate the FAK and PI3K Pathways in Colon Cancers Metastasis," 75:2434-2444 (2015).
Beard et al., "Gene Expression Profiling using Nanostring Digital RNA Counting to Identify Potential Target Antigens for Melanoma Immunotherapy," *Clin Cancer Res* 19:4941-4950 (2013).
Beatty et al,, "Mesothelin-specific chimeric antigen receptor mRNA-engineered T cells induce anti-tumor activity in solid malignancies," *Cancer immunology research* 2:112-120 (2014).
Bergelson et al., "Isolation of a common receptor for Coxsackie B viruses and adenoviruses 2 and 5," *Science* 275:1320-1323 (1997).
Brien et al., "Protection by Immunoglobulin Dual-Affinity Retargeting Antibodies against Dengue Virus," *J Virol* 87:7747-7753 (2013).

(56) References Cited

OTHER PUBLICATIONS

Brischwein et al,, "MT110: a novel bispecific single-chain antibody construct with high efficacy in eradicating established tumors," *Mol Immunol* 43:1129-1143 (2006).
Brown et al., "Adaptive Transfer of Autologous IL 13-zetakine+ Engineered T Cell Clones for the Treatment of Recurrent Glioblastoma: Lessons from the Clinic," Molecular Therapy 19:S136-S137 (2011).
Brown et al,, "Bioactivity and Safety of IL13Rα2-Redirected Chimeric Antigen Receptor CD8+ T Cells in Patients with Recurrent Glioblastoma," *Clinical Cancer Research* 21 (18):4062-4072 (2015).
Brown et al,, "Glioma IL13Rα2 Is Associated with Mesencymal Signature Gene Expression and Poor Patient Prognosis," *PLoS One* 8:e77769 (2013).
Brown et al,, "Stem-like tumor-initiating cells isolated from IL13Rα2 expressing gliomas are targeted and killed by IL 13-zetakine-redirected T Cells," *Clinical cancer research: an official journal of the American Association for Cancer Research* 18:2199-2209 (2012).
Burmeister et al,, "Crystal structure of the complex of rat neonatal Fc receptor with Fc," *Nature* 372:379-383 (1994).
Cartron et al,, "From the bench to the bedside: ways to improve rituximab efficacy," *Blood* 104:2635-2642 (2004).
Chakravarti et al., "Quantitatively Determined Survivin Expression Llevels are of Prognostic Value in Human Gliomas," *Journal of Clinical Oncology: Official Journal of the American Society of Clinical Oncology* 20:1063-1068 (2002).
Choi et al,, "Systemic administration of a bispecific antibody targeting EGFRvIII successfully treats intracerebral glioma," *Proceedings of the National Academy of Sciences of the United States of America* 110:270-275 (2013).
Chow et al., "T Cells Redirected to EphA2 for the Immunotherapy of Glioblastoma," *Mol Ther* 21 :629-637 (2013).
Cioffi et al "EpCAM/CD3-Bispecific T-cell Engaging Antibody MT100 Eliminates Primary Human Pancreatic Cancer Stern Cells," *Clin Cancer Res* 18:465-474 (2012).
Cole et al., the EBV-Hybridoma technique and its application to human lung cancer, *Monoclonal Antibodies and Cancer Therapy*. 77-96 (1985).
Cote et al,, "Generation of human monoclonal antibodies reactive with cellular antigens," *Proc Natl Acad Sci* 80:2026-2030 (1983).
Curiel, "Strategies to Adapt Adenoviral Vectors for Targeted Delivery," *Annals of the New York Academy of Sciences* 886:158-171 (1999).
De Haij et al., "In vivo Cytotoxicity of Type I CD20 Antibodies Critically Depends on Fc Receptor ITAM Signaling," Cancer Res. 70:3209-3217 (2010).
De Oliveira et al., "Modification of Hematopoietic Stem/Progenitor Cells with CD19-Specific Chimeric Antigen Receptors as a Novel Approach for Cancer Immunotherapy," *Human Gene Therapy* 24:824-839 (2013).
Debinski et al. "Novel anti-brain tumor cytotoxins specific for cancer cells," *Nat. Biotechnol.* 16:449-453 (1998).
Debinski et al., "Expression of a restrictive receptor for interleukin 13 is associated with glial transformation," *J. Neurooncol*. 48:103-111 (2000).
Debinski et al., "Human glioma cells overexpress receptors for interleukin 13 and are extremely sensitive to a novel chimeric protein composed of interleukin 13 and pseudomonas exotoxin," *Clinical cancer research: an official journal of the American Association for Cancer Research* 1 :1253-1258 (1995).
Donaldson et al,, "The Murine IL-13 Receptor α2: Molecular Cloning, Characterization, and Comparison with Murine IL-13 Receptor α1," *J. Immunol.* 161:2317-2324 (1998).
Dotti et al., "Design and Development of Therapies using Chimeric Antigen Receptor-Expressing T Cells" *Immunol Rev* 257: 107-126 (2014).
Epstein et al., "Biological activity of liposome-encapsulated murine interferon y is mediated by a cell membrane receptor," *Proc. Natl. Acad. Sci. USA*, 82:3688-3692 (1985).
European Search Report from Application No. 16743989.2 dated Jun. 11, 2018.

Extended European Search Report from Application No. 16743990.0 dated Jun. 20, 2018.
Fernandes et al,, "Glyosylation-induced Conformational Modification Positively Regulates Receptor-Receptor Association," *J. Biol. Chem*. 276:5375-5383 (2001).
Fichtner-Feigl et al,, "IL-13 signaling through the IL-13α2 receptor is involved in induction of TFGβ1 production and fibrosis," *Nat. Med*. 12, 99-106 (2006).
Fournier et al., "Bispecific Antibodies and Trispecific Immunocytokines for Targeting the Immune System Against Cancer," *BioDrugs* 27:35-53 (2013).
Friend et al,, "Phase I Study of an Engineered Aglycosylated Humanized CD3 Antibody in Renal Transplant Rejection," Transplantation 68:1632-1637 (1999).
Fujisawa et al., "A Novel Role of Interleukin-13 Receptor α2 in Pancreatic Cancer Invsion and Metastasis," *Cancer Res*. 69:8678-8685 (2009).
Fujisawa et al., "IL-13 regulates cancer invasion and metastasis through IL-13Rα2 via ERK/AP-1 pathway in mouse model of human ovarian cancer," *Int. J. Cancer* 131 :344-356 (2012).
Fuxe et al,, "Expression of the coxsackie and adenovirus receptor in human astrocytic tumors and xenografts," *International Journal of Cancer* 103:723-729 (2003).
Gan et al., "The EGFRvIII variant in glioblastoma multiforme," *Journal of Clinical Neuroscience*, 16:748-754 (2009).
Gauchat et al., "A novel 4-kb interleukin-13 receptor α mRNA expressed in human B, T, and endothelial cells encoding an alternate type-II interleukin-4/interleukin-13 receptor," *Eur. J. Immunol*. 27:971-978 (1997).
Gold et al,, "Aptamers As Therapeutic and Diagnostic Agents," *J. Biotechnol*. 74:5-13 (2000).
Gottschalk et al., "Generating CTL against the subdominant Epstein-Barr virus LMP1 antigen for the adaptive Immunotherapy of EBV-associated malignancies," *Blood* 101 :1905-1912 (2003).
Guest et al., "The Role of Extracellular Spacer Regions in the Optimal Design of Chimeric Immune Receptors: Evaluation of Four Different scFvs and Antigens," *J Immunother* 28: 203-211 (2005).
Hansen et al,, "Characterization of Second-Generation Monoclonal Antibodies Against Carcinoembryonic Antigen," *Cancer* 71 :3478-3485 (1993).
Harlow and Lane (eds.), Antibodies: a Laboratory Manual, CSH Press (1988).
Haskard et al., "The Production of Human Monoclonal Autoantibodies from Patients with Rheumatoid Arthritis by the EBV-Hybridoma Technique," *J. Immunol. Methods*, 74(2):361-67 (1984).
Haso et al., "Anti-CD22-chimeric antigen receptors targeting B-cell precursor acute lymphoblastic leukemia," *Blood* 121: 1165-117 4 (2013).
Hedley et al., "An adenovirus vector with a chimeric fiber incorporating stabilized single chain antibody achieves targeted gene delivery," *Gene Ther* 13:88-94 (2006).
Henry et al,, "Participation of the N-Terminal Region of Cε3 in the Binding of Human IgE to Its Hiqh-Affinity Receptor FcεRI," *Biochemistry* 36:15568-15578 (1997).
Hoyos et al., "Engineering CD19-specific T lymphocytes with interleukin-15 and a suicide gene to enhance their anti-lymphoma/leukemia effects and safety," *Leukemia* 24:1160-1170 (2010).
Hsi et al., "Silencing IL-13Rα2 Promotes Glioblastoma Cell Death via Endogenous Signaling," *Mol Cancer Ther* 10:1149-1160 (2011).
Hsu et al., "Complement activation mediates cetuximab inhibition of non-small cell lung cancer tumor growth invo," *Mol. Cancer* 9:139 (2010).
Hudecek et al., "Receptor affinity and extracellular domain modifications affect tumor recognition by ROR1-specific chimeric antigen receptor T cells," *Clin Cancer Res* 19:3153-3164 (2013).
Husain et al., "Interleukin-13 fusion cytotoxin as a potent targeted agent for AIDS-Kaposi's sarcoma xenograft," *Blood* 95:3506-3513 (2000).
Husain et al., Receptor for Interkeukin 13 on AIDS-associated Kaposi's Sarcoma Cells Serves as a New Target for a Potent Pseudomonas Exotoxin-based Chimeric Tonix Protein, *Clin. Cancer Res*. 3:151-156 (1997).

(56) References Cited

OTHER PUBLICATIONS

Huse et al., "Generation of a large combinatorial library of the immunoglobulin repertoire in phage lambda," *Science*. 246:1275-81 (1989).
Hwang et al., "Hepatic uptake and degradation of unilamellar sphingomyelin/cholesterol liposomes: A kinetic study," *Proc. Natl. Acad. Sci. USA*, 77:4030-4034 (1980).
International Preliminary Report on Patentability from Application No.PCT/US2016/014984 dated Aug. 1, 2017.
International Preliminary Report on Patentability from International Application No. PCT/US2016/014985 dated Aug. 1, 2017.
International search report and written opinion from International Application No. PCT/US16/14984 dated Apr. 8, 2016.
International Search Report and Written Opinion from International Application No. PCT/US16/14985 dated Apr. 7, 2016.
Jacobs et al., "Surface Modification for Improved Blood Compatibility," *Artif. Organs* 12:500-501 (1988).
Janeway et al. (eds.), Immunobiology, 5th Ed,, Garland Publishing, New York, NY (2001).
Janeway et al., Immunobiology, 2nd Edition, Garland Publishing, New York, (1996).
Jarboe et al" Expression of interleukin-13 receptor α2 in glioblastoma multiforme: implications for targeted therapies," *Cancer Res* 67: 7983-7986 (2007).
Jensen et al., "Designing Chimeric Antigen Receptors to Effectively and Safely Target Tumors," *Curr Opin Immunol* 33:9-15 (2015).
Johnson et al., "Rationaldevelopment and characterization of humanized anti-EGFR variant III chimeric antigen receptor T cells for glioblastoma," *Sci Transl Med* 7:275ra22 (2015).
Johnson et al., "Effector cell recruitment with novel Fv-based dual-affinity re-targeting protein leads to potent tumor cytolysis and in vivo B-cell depletion," *J. Mol. Biol.* 399:436-449 (2010).
Jones et al,, "Replacing the complementarity-determining regions in a human antibody with those from a mouse," *Nature* 321 :522-525 (1986).
Joshi et al., "Identification and Characterization of Interleukin-13 Receptor in Human Medulloblastoma and Targeting These Receptors with Interleukin-13-Pseudomonas Exotoxin Fusion Protein," *Croat. Med. J.* 44:455-462 (2003).
Joshi et al., "Identification of interleukin-13 receptor α2 chain overexpression in situ in high-grade diffusely infiltrative pediatric brainstem glioma," *Neuro Oncol* 10:265-274 (2008).
Joshi et al., "Interleukin-13 receptor a chain: a novel tumor-associated transmembrane protein in primary explants of human malignant gliomas," *Cancer Res* 60:1168-1172 (2000).
Kabat et al., Sequences of Proteins of Immunological Interest, U.S. Department of Health and Human Services (1983).
Kahlon et al., "Specific Recognition and Killing of Glioblastoma Multiforme by Interleukin 13-Zetakine Redirected Cytolytic T Cells," *Cancer Res* 64:9160-9166 (2004).
Kaliberov et al., "Adenoviral targeting using genetically incorporated camelid single variable domains," *Laboratory Investigation* 94:893-905 (2014).
Kane et al., "Sui generis: gene therapy and delivery systems for the treatment of glioblastoma," Neuro-oncology 17(S2):ii24-ii36 (2015).
Karpovsky et al., "Production of Target-Specific Effector Cells Using Hetero-Cross-Linked Aggregates Containing Anti-Target Cell and Anti-Fcγ Receptor Antibodies," *J. Exp. Med.* 160:1686-701 (1984).
Kawakam et al., "Interleukin-13 Receptor α2 Chain in Human Head and Neck Cancer Serves as a Unique Diagnostic Marker," *Clin. Cancer Res.* 9:6381-6388 (2003).
Kawakami et al. "Intratumor Administration of Interleukin 13 Receptor-targeted Cytotoxin Induces Apoptotic Cell Death in Human Malignant Glioma Tumor Xenografts," *Mol. Cancer Ther*. 1 :999-1007 (2002).
Kawakami et al., "Characterization of a Novel Human Tumor Antigen Interleukin-13 Receptor α2 Chain," *Cancer Res*. 66:4434-4442 (2006).

Kawakami, et al., "Analysis of interleukin-13 receptor alpha2 expression in human pediatric brain tumors," *Cancer* 101 :1036-1042 (2004).
Kawashima et al., "Pulmonary delivery of insulin with nebulized DL-lactide/glycolide copolymer (PLGA) nanospheres to prolong hypoglycemic effect," *J Controlled Release* 62:279-287 (1999).
Kim et al., "A Genetically Modified Adenoviral Vector with a Phage Display Derived Peptide Incorporated into Fiber Fibritin Chimera Prolongs Survival in Experimental Glioma," *Human Gene Therapy* 26(9):635-646 (2015).
Kim et al., "A novel single-chain antibody redirects adenovirus to IL13Rα2-expressing brain tumors," *Scientific Reports* 5(1):1-12 (2015).
Kim et al., "High Cleavage Efficiency of a 2A Peptide Derived from Porcine Teschovirus-1 in Human Cell Lines, Zebrafish and Mice," *PLoS One* 6(4):1-8 (2011).
Kim et al., "Nonthrombogenic Bioactive Surfaces," Ann. N.Y. Acad. Sci. 516:116-30 (1987).
Kioi et al., "Targeting IL-13Rα2-positive cancer with a novel recombinant immunotoxin composed of a single-chain antibody and mutated Pseudomonas exotoxin,". *Mol Cancer Ther* 7, 1579-1587 (2008).
Kioi et al., "Teach evolution, learn science: we're ahead of Turkey, but behind Iran," *FASEB J.* 20:2378-2380 (2006).
Kipriyanov et al,, "Rapid detection of recombinant antibody fragments directed against cell-surface antigens by flow cytometry," *Journal of Immunological Methods* 196:51-62 (1996).
Köhler et al,, "Continuous cultures of fused cells secreting antibody of predefined specificity," *Nature* 256:495-497 (1975).
Kong et al., "Suppression of human glioma xenografts with second-generation IL13R-specific chimeric antigen receptor-modified T cells," *Clinical Cancer Research* 18:5949-5960 (2012).
Kortt et al,, "Dimeric and trimeric antibodies: high avidity scFvs for cancer targeting," *Biomol Eng*. 18:95-108 (2001).
Kozbor et al., "The production of monoclonal antibodies from human lymphocytes," Immunol Today 4:72-79 (1983).
Krapp et al,, "Structural Analysis of Human IgG-Fc Glycoforms Reveals a Correlation Between Glycosylation and Structural Integrity," *J. Mol. Biol*. 325:979-989 (2003).
Krasnykh et al,, "Genetic Targeting of an Adenovirus Vector Via Replacement of the Fiber Protein with the Phage T4 Fibritin," *Journal of Virology* 75:4176-4183 (2001).
Krebs et al., "T cells redirected to interleukin-13Rα2 with interleukin-13 mutein-chimeric antigen receptors have anti-glioma activity but also recognize interleukin-13Rα1 ," *Cytotherapy* 16:1121-1131 (2014).
Krenciute et al,, "Characterization and Functional Analysis of scFv-based Chimeric Antigen Receptors to Redirect T Cells to IL13Rα2-positive Glioma,"*Molecular Therapy: The Journal of the American Society of Gene Therapy*, 24(2):354-363 (2016).
Kuan et al. "Increased Binding Affinity Enhances Targeting of Glioma Xenografts by EGFRVIII-Specific scFv," *Int. J. Cancer* 88:962-969 (2000).
Kunkele et al., "Functional Tuning of CARs Reveals Signaling Threshold above Which CDS+ CTI Antitumor Potency Is Attenuated due to Cell Fas-FasL-Dependent AICD," *Cancer Immunol Res* 3: 368-379 (2015).
Kunwar et al,, "Direct Intracerebral Delivery of Cintredekin Besudotox (IL13-PE38QQR) in Recurrent Malignant Glioma: A Report by the Cintredekin Besudotox Intraparenchymal Study Group," *J. Clin. Oncol.* 25:837-844 (2007).
Kunwar et al,, "Phase III randomized trial of CED of IL13-PE38QQR vs Gliadel wafers for recurrent Glioblastoma," *Neuro-Oncology* 12:871-881 (2010).
Langer et al., "Biocompatibility of polymeric delivery systems for macromolecules," *J. Biomed. Mater. Res.* 15:267-277 (1981).
Langer, "Controlled release of macromolecules," Chem. Tech. 12:98-105 (1982).
Leon et al,, "Sequencing, Annotation, and Characterization of the Influenza Ferret Infectome," *Journal of Virology* 87(4):1957-1966 (2013).

(56) References Cited

OTHER PUBLICATIONS

Lewis et al. "Structural Requirements for the Interaction of Human IgA with the Human Polymeric Ig Receptor," *J Immunol.* 175:6694-701 (2005).
Liu et al., "Pulmonary Delivery of Free and Liposomal Insulin," *Pharm Res* 10(2):228- 232 (1993).
Livak et al., "Analysis of relative gene expression data using real-time quantitative PCR and the 2($\Delta\Delta C_\tau$) Method," *Methods* 25:402-408 (2001).
Imperiali et al., "Conformational implications of asparagine-linked glycosylation," *Proc. Natl. Acad. Sci. U.S.A.* 92:97-101 (1995).
Iwami et al., "Peptide-pulsed dendritic cell vaccination targeting interleukin-13 receptor alpha2 chain in recurrent malignant glioma patients with HLA-A*24/A*02 allele," *Cytotherapy* 14:733-742 (2012).
McAleese et al., "Recruit-TandAbs; harnessing the immune system to kill cancer cells," *Future Oncol* 8:687-695 (2012).
McKenzie et al., "Interleukin 13, a T-cell-derived bytokine that regulates human monocyte and B-cell function," *Proc. Natl. Acad. Sci. U.S.A.* 90:3735-3739 (1993).
Minn et al,, "Distinct organ-specific metastatic potential of individual breast cancer cells and primary tumors," *J. Clin. Investig.* 115:44-55 (2005).
Moore et al,, "Application of dual affinity retargeting molecules to achieve optimal redirected T-cell killing of B-cell lymphoma," *Blood* 117:4542-4551 (2011 ).
Morrison et al., "Chimeric human antibody molecules: Mouse antigen-binding domains with human constant region domains," *Proc. Natl. Acad. Sci.* 81 :6851-6855 (1984).
Murphy et al., "The human glioma pathogenesis-related protein is structurally related to plant pathogenesis-related proteins and its gene is expressed specifically in brain tumors," *Gene* 159:131-135 (1995).
Neuberger et al,, "Recombinant antibodies possessing novel effector functions," *Nature* 312:604-608 (1984).
Nitta et al,, "Recent Advances in Chemotherapy," Proc. 14th International Congr. Chemotherapy, Kyoto, Tokyo Press, Anticancer Section 1, p. 28-30 (1985).
Ogden et al., "Identification of A2B5+ CD133– Tumor-Initiating Cells in Adult Human Gliomas," *Neurosurgery* 62:505-514 (2008).
Okada et al., ". Induction of CDS+ T-Cell Responses Against Novel Glioma-Associated Antigen Peptides and Clinical Activity by Vaccinations with a-Type 1 Polarized Dendritic Cells and Polyinosinic-Polycytidylic Acid Stabilized by Lysine and Carboxymethylcellulose in Patients with Recurrent Malignant Glioma," *J Clin Oncol* 29:330-336 (2011).
Okada et al., "Expression of glioma-associated antigens in pediatric brain stem and non-brain stem gliomas," *J Neurooneol* 88: 245-250 (2008).
Okada et al., "Immunotherapeutic Approaches for Glioma," *Crit Rev Immunol* 29:1-42 (2009).
Orlandi et al., "Cloning immunoglobulin variable domains for expression by the polymerase chain reaction," *Proc. Natl. Acad. Sci.* 86:3833-3837 (1989).
Owens et al., "The genetic engineering of monoclonal antibodies," *J. Immunol. Meth.*, 168:149-165 (1994).
Park et al,, "Blood compatibility of SPUU-PEO-heparin graft copolymers," *J. Biomed. Mat. Res.* 26:739-45 (1992).
Park et al,, "Synthesis and Characterization of SPUU-PEO-Heparin Graft Copolymers," *J. Poly. Sci, Part A* 29:1725-31 (1991).
Patel et al., "The future of glioblastoma therapy: synergism of standard of care and immunotherapy," *Cancers* 6:1953-1985 (2014).
Pedersen et al., "Comparison of Surface Accessible Residues in Human and Murine Immunoglobulin Fv Domains," *J. Mol. Biol.* ,235:959-973 (1994).
Pini et al., "Phage Display of Antibody Fragments," *Curr. Protein Pept. Sci.* 1 :155-169 (2000).
Portner et al., "T and NK cells of B cell NHL patients exert cytotoxicity against lymphoma cells following binding of bispecific tetravalent antibody CD19 × CD3 or CD19 × CD16," *Cancer Immunol Immunother* 61 :1869-1875 (2012).
Pule et al., "A Chimeric T Cell Antigen Receptor that Augments Cytokine Release and Supports Clonal Expansion of Primary Human T Cells," *Mol Ther* 12:933-941 (2005).
Puri et al., "Targeting of Interleukin-13 Receptor on Human Renal Cell Carcinoma Cells by a Recombinant Chimeric Protein Composed of Interleukin-13 and a Truncated Form of Pseudomonas Exotoxin a (PE38QQR)," *Blood* 87:4333-4339 (1996).
Qian et al,, "Pulmonary delivery of a GLP-1 receptor agonist, BMS-686117," *Int J Pharm* 366: 218-220 (2009).
Qian et al,, "Sustained release subcutaneous delivery of BMS-686117, a GLP-1 receptor peptide agonist, via a zinc adduct," *J Pharm* 374:46-52 (2009).
Qin et al,, "Comparative genomics of the marine bacterial genus *Glaciecola* reveals the high degree of genomic diversity and genomic characteristic for cold adaptation," *Environmental Microbiology* 16(6):1642-1653 (2014).
Rahaman et al., "IL-13R$\alpha$2, a Decoy Receptor for IL-13 Acts as an Inhibitor of IL-4-dependent Signal Transduction in Glioblastoma Cells," *Cancer Res.* 62:1103-1109 (2002).
Reardon et al., "Immunotherapy Advances for Glioblastoma," *Neuro Oncol* 16: 1441- 1458 (2014).
Reiter et al,, "Engineering interchain disulfide bonds into conserved framework regions of Fv fragments: improved biochemical characteristics of recombinant immunotoxins containing disulfide-stabilized Fv," *Protein Engineering*, 7:697-704 (1994).
Remington's Pharmaceutical Sciences, 18th edition, A. R. Gennaro, ed,, Mack Publishing Company (1990).
Reusch et al,, "A novel tetravalent bispecific TandAb (CD30/CD16A) efficiently recruits NK cells for the lysis of CD30+ tumor cells," *MAbs* 6:728 (2014).
Riccione et al., "Generation of CAR T Cells for Adaptive Therapy in the Context of Glioblastoma Standard of Care," Journal of Visualized Experiments, 96:e52397, 10 pages (2015).
Rich et al., "RTVP-1, a novel human gene with sequence similarity to genes of diverse species, is expressed in tumor cell lines of glial but not neuronal origin," *Gene* 180:125-130 (1996).
Riechmann et al., "Reshaping human antibodies for therapy," *Nature* 332:323-327 (1988).
Roder et al., "The EBV-hybridoma technique," *Methods Enzymol.* 121 :140-67 (1986).
Ross et al,, "Anticancer Antibodies," *Am. J. Clin. Pathol.* 119:472-485 (2003).
Rossi et al., "A new class of bispecific antibodies to redirect T cells for cancer immunotherapy," *MAbs* 6:381-91 (2014).
Routledge et al. "The Effect of Aglycosylation on the Immunogenicity of a Humanized Therapeutic CD3 Monoclonal Antibody," *Transplantation* 60:847-853 (1995).
Sadelain et al., "The basic principles of chimeric antigen receptor design," *Cancer Discov* 3 :388-398 (2013).
Sambrook et al. (eds.), Molecular Cloning, a Laboratory Manual, 3rd Edition, Cold Spring Harbor Laboratory Press, New York (2001).
Sambrook et al., Molecular Cloning: a Laboratory Manual, 2nd Edition, Cold Spring Harbor, New York (1989).
Sampson et al,, "Unarmed, tumor-specific monoclonal antibody effectively treats brain tumors," *Proc. Natl. Acad. Sci. U.S.A.* 97:7503-7508 (2000).
Sawhney et al,, "Bioerodible Hydrogels Based on Photopolymerized Poly(ethylene glycol)-co-poly($\alpha$-hydroxy acid) Diacrylate Macromers," *Macromolecules* 26:581-587 (1993).
Sayers et al. "The Importance of Lys-352 of Human Immunoglobulin E in Fc$\epsilon$RII/CD23 Recognition," *J Biol Chem.* 279(34):35320-32325 (2004).
Schlereth et al,, "Eradication of Tumors from a Human Color Cancer Cell Line and from Ovarian Cancer Metastases in Immunodeficient Mice by a Single-Chain Ep-CAM/CD3-Bispecific Antibody Construct," *Cancer Res* 65:2882-2889 (2005).
Schlereth et al,, "Potent inhibition of local and disseminated tumor growth in immunocompetent mouse models by a bispecific antibody construct specific for Murine CD3," *Cancer Immunol Immunother* 55:785-796 (2006).

(56) References Cited

OTHER PUBLICATIONS

Shields et al. "High Resolution Mapping of the Binding Site on Human IgG1 for FcγRI, FcγRII, FcγRIII, and FcRn and Design of IgG1 Variants with Improved Binding to the FcγR," *J. Biol. Chem.* 276:6591-6604 (2001).
Shimamura et al., "Interleukin 13 Mediates Single Transduction through Interleukin 13 Receptor α2 in Pancreatic Ductal Adenocarcinoma: Role of IL-13 Pseudomonas Exotoxin in Pancreatic Cancer Therapy," *Clin. Cancer Res.* 16, 577-586 (2010).
Sidman et al,, "Controlled Release of Macromolecules and Pharmaceuticals from Synthetic Polypeptides Based on Glutamic Acid," *Biopolymers* 22:547-556 (1983).
Sondermann et al., "The 3.2-A crystal structure of the human IgG1 Fc fragment-FcγRIII complex," *Nature* 406:267-273 (2000).
Souriau et al,, "Recombinant antiodies for cancer diagnosis and therapy," *Expert Opin. Biol. Ther.* 3:305-318 (2003).
Springer, "Suicide Gene Therapy: Methods and Reviews" *ChemBioChem* 5:1605 (2004).
Stupp et al., "Radiotherapy plus concomitant and adjuvant temozolomide for glioblastoma," *N Engl J Med* 352:987-996 (2005).
Suryadevara et al., "Immunotherapy for malignant glioma," *Surg Neurol Int* 6: S68-S77 (2015).
Takeda et al,, "Construction of chimaeric processed immunoglobulin genes containing mouse variable and human constant region sequences," *Nature* 314:452-454 (1985).
Takenouchi et al., "Epigenetic Modulation Enhances the Therapeutic Effect of Anti-IL-13Ra2 Antibody in Human Mesothelioma Xenografts," *Clinical Cancer Research* 17(9):2819-2829 (2011).
Thaci et al., "Significance of interleukin-13 receptor alpha 2-targeted glioblastoma therapy," *Neuro-Oncology* 16(10):1304-1312 (2014).
Titus et al,, "Human T Cells Targeted with Anti-T3 Cross-Linked to Antitumor Antibody Prevent Tumor Growth in Nude Mice," *J. Immunol*, 138:4018-22 (1987).
Todorovska et al., "Design and application of diabodies, triabodies and tetrabodies for cancer targeting," *J Immunol Methods*. 248:47-66 (2001).
Toleikis et al,, "Cloning Single-Chain Antibody Fragments (scFv) from Hybridoma Cells," *Methods in Molecular Medicine* 94:447-458 (2004).
Tomko et al., "HCAR and MCAR: the human and mouse cellular receptors for subgroup C adenoviruses and group B coxsackieviruses," *Proceedings of the National Academy of Sciences of the United States of America* 94:3352-3356 (1997).
Uematsu et al,, "Prognostic significance of the immunohistochemical index of survivin in glioma: a comparative study with the MIB-1 index," *Journal of Neuro-Oncology* 72:231-238 (2005).
Ulasov et al., "Combination of adenoviral virotherapy and temozolomide chemotherapy eradicates malignant glioma through autophagic and apoptotic cell death in vivo," *British Journal of Cancer* 100:1154-1164 (2009).
Ulasov et al., "Comparative evaluation of survivin, midkine and CXCR4 promoters for transcriptional targeting of glioma gene therapy," *Cancer Biology & Therapy* 6:679-685 (2007).
Ulasov et al., "Novel Recombinant Adenoviral Vector That Targets the Interleukin-13 Receptor α2 Chain Permits Effective Gene Transfer to Malignant Glioma," *Human Gene Therapy* 18: 118-129 (2007).

Ulasov et al., "Survivin-Driven and Fiber-Modified Oncolytic Adenovirus Exhibits Potent Antitumor Activity in Established Intracranial Glioma," *Human Gene Therapy* 18:589-602 (2007).
Van Gool, "Brain Tumor Immunotherapy: What have We Learned so Far?," *Front Oncol* 5(98):14 pages (2015).
Van Houdt et al,, "The human survivin promoter: a novel transcriptional targeting strategy for treatment of glioma," *J Neurosurg* 104:583-592 (2006).
Van Tellingen et al, "Pharmacology, Bio-analysis and Pharmacokinetics of the Vinca Alkaloids and Semi-synthetic Derivatives (Review)," *Anticancer Research* 12:1699-1716 (1992).
Vera et al., "T lymphocytes redirected against the kappa light chain of human immunoglobulin efficiently kill mature B lymphocyte-derived malignant cells," *Blood* 108:3890-3897 (2006).
Verhoeyen et al,, "Reshaping Human Antibodies: Grafting an Antilysozyme Activity," *Science* 239:1534-1536 (1988).
Veronese et al., "Preparation and Properties of Monomethoxypoly(ethylene glycol)-modified Enzymes for Therapeutic Applications," *Poly(Ethylene Glycol) Chemistry—Biotechnical and Biomedical Applications*, 127-36 ( 1992).
Wani et al, "Plant Antitumor Agents. Synthesis and Biological Activity of Camptothecin Analogues," *J. Med. Chem.* 23:554-560 (1980).
Wani et al,, "Plant Antitumor Agents. Synthesis and Antileukemic Activity of Camptothecin Analogues," *J. Med. Chem.* 29:2358-2363 (1986).
Wani et. al., "Plant Antitumor Agents. Total Synthesis and Antileukemic Activity of Ring A Substituted Camptothecin Analogues. Structure-Activity Correlations," *J. Med. Chem.* 30:1774-1779 (1987).
Ward et al., "The effector functions of immunoglobulines: implications for therapy," *Therapeutic Immunoloqy* 2:77-94 (1995).
Wels et al., "Construction, Bacterial Expression and Characterization of a Bifunctional Single-Chain Antibody-Phosphatase Fusion Protein Targeted to the Human erbB-2 Receptor," *Biotechnology* (NY) 10:1128-1132 (1992).
Wilkinson-Ryan et al., "Incorporation of porcine adenovirus 4 fiber protein enhances infectivity of adenovirus vector on dendritic cells: implications for immune-mediated cancer therapy," *PLoS One* 10, e0125851, 14 pages (2015).
Winter et al,, "Man-made antibodies," *Nature* 349:293-299 (1991 ).
Wu et al., "Remote control of therapeutic T cells through a small molecule-gated chimeric receptor," *Science* 350, 21 pages (2015).
Wykosky et al., "Interleukin-13 Receptor α2, EphA2, and Fos-Related Antigen 1 as Molecular Denominators of High-Grade Astrocytomas and Specific Targets for Combinatorial Therapy," *Clin. Cancer Res.* 14:199-208 (2008).
Xu et al., "Closely related T-memory stem cells correlate with in vivo expansion of CAR.CD19-T cells and are preserved by IL-7 and IL 15," *Blood* 123: 3750-3759 (2014).
Yan et al., "Glioma cancer stem cells secrete Gremlin1 to promote their maintenance within the tumor hierarchy," *Genes & Development* 28:1085-1100 (2014).
Zheng et al,, "Fiber-knob modifications enhance adenoviral tropism and gene transfer in malignant glioma," *The Journal of Gene Medicine* 9:151-160 (2007).
Zitron et al., "Targeting and killing of glioblastoma with activated T cells armed with bispecific antibodies," *BMC Cancer* 13:83, 14 pages (2013).

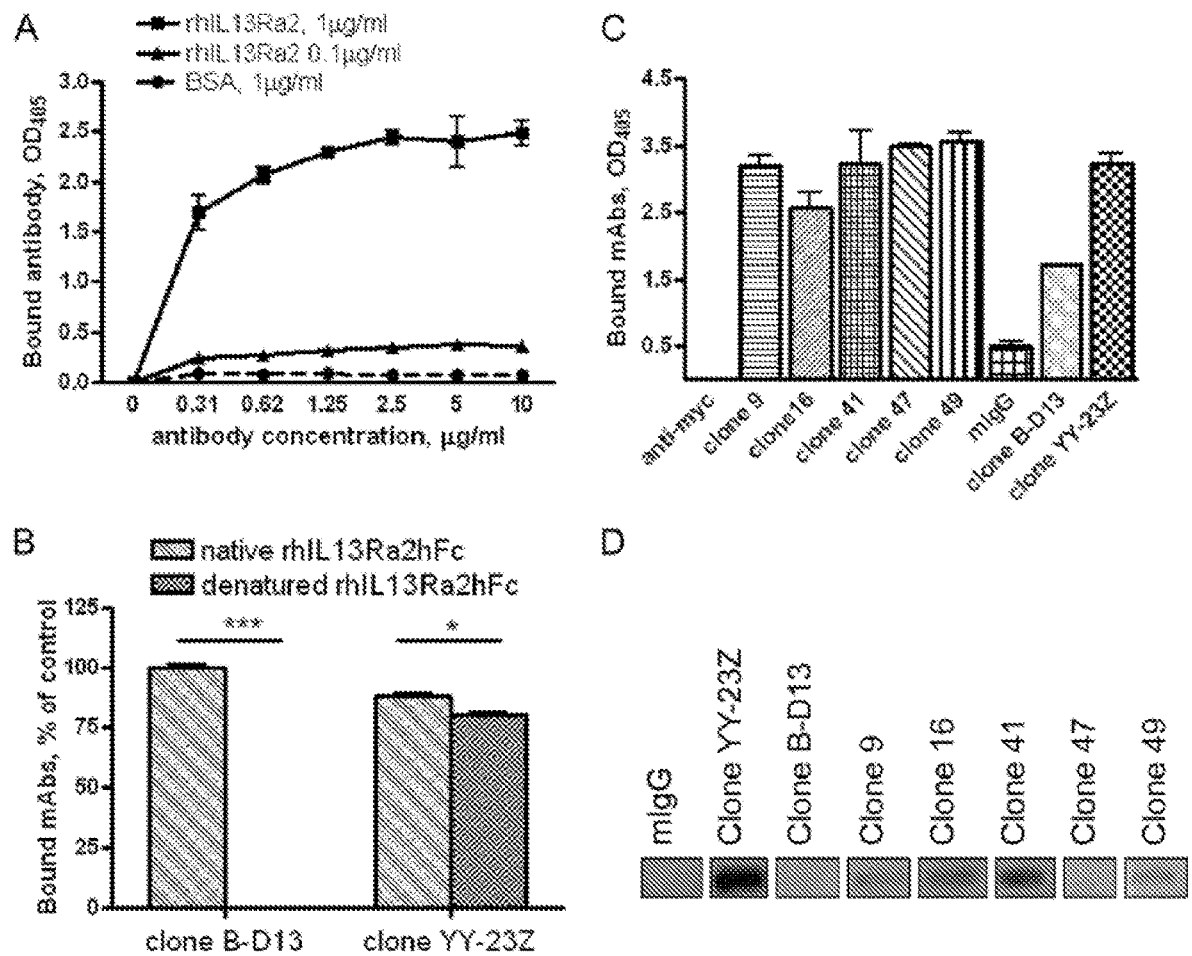
FIG. 1A-D

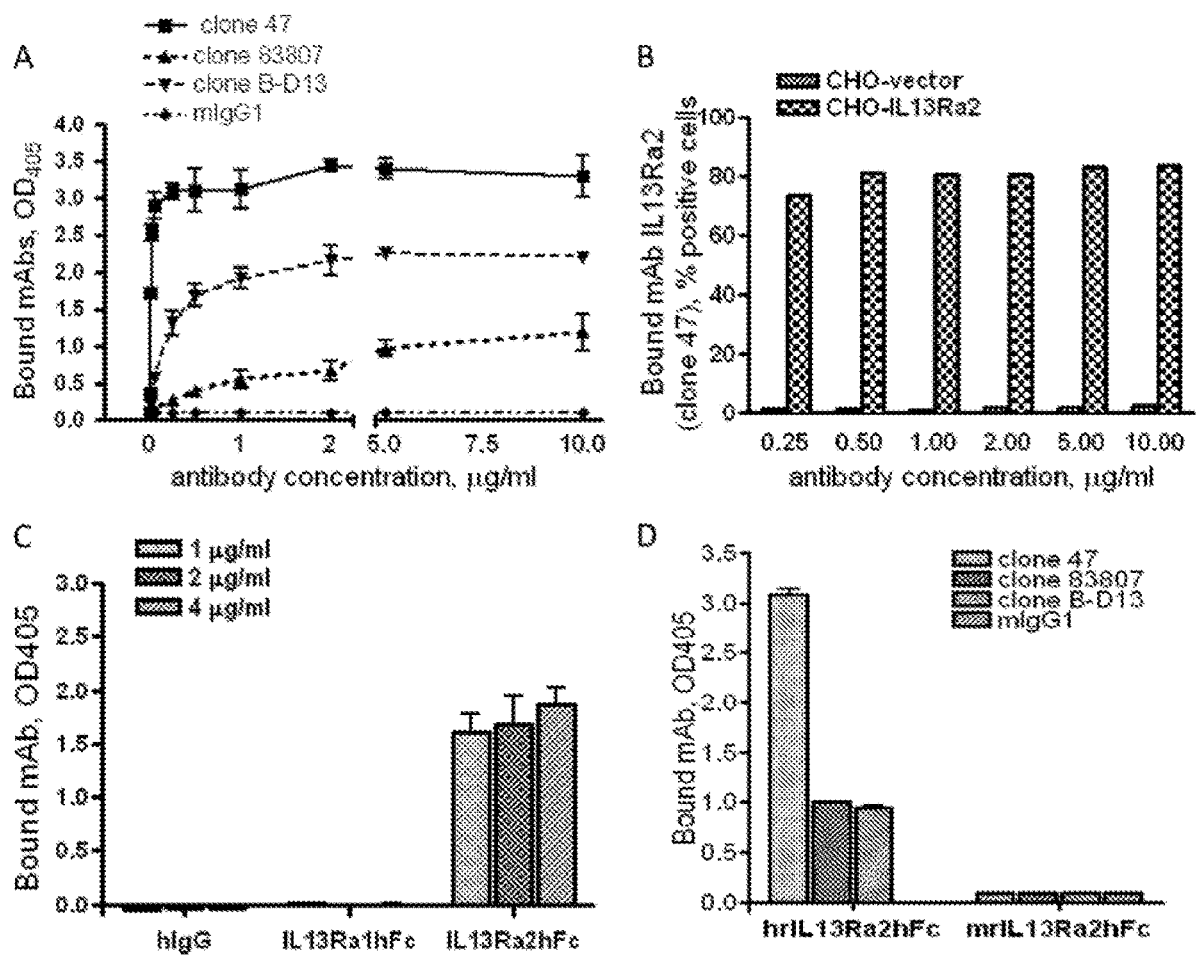
FIG. 2A-D

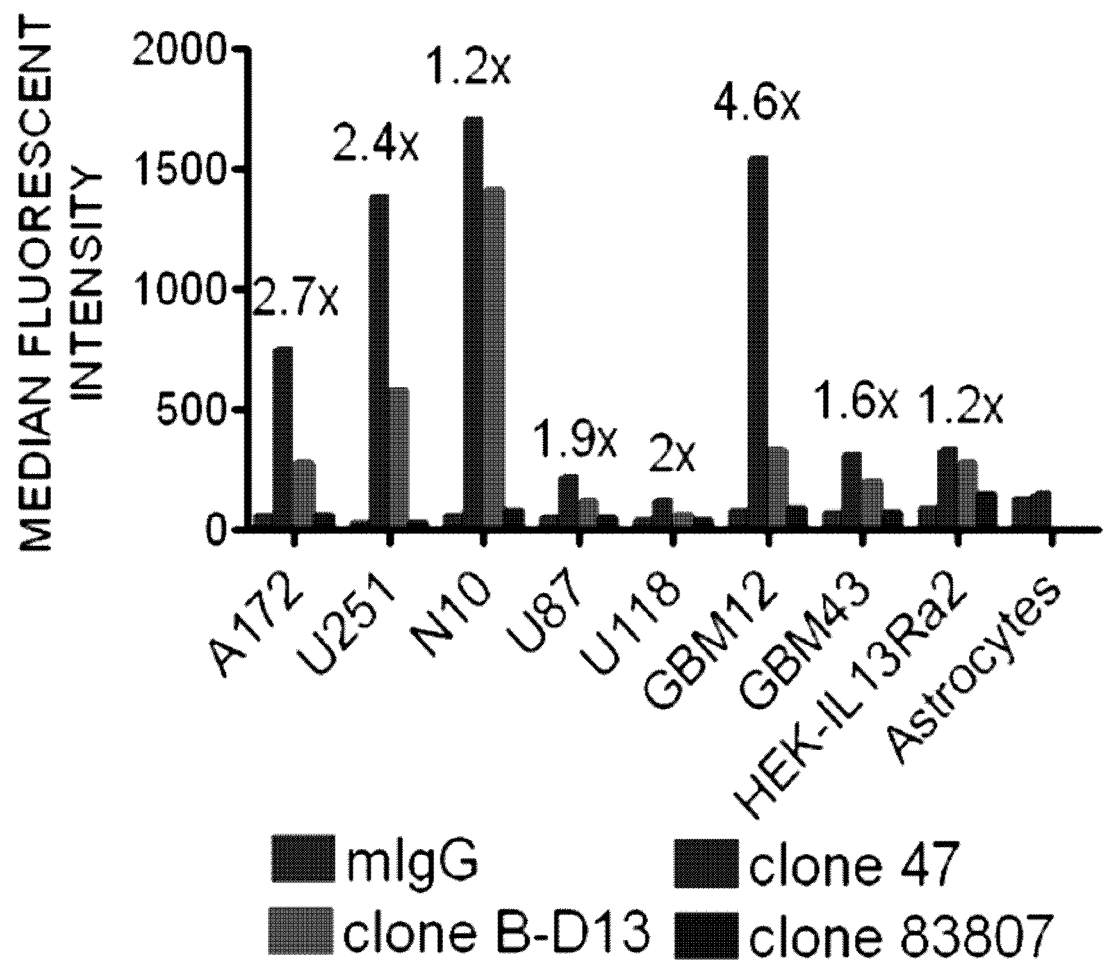
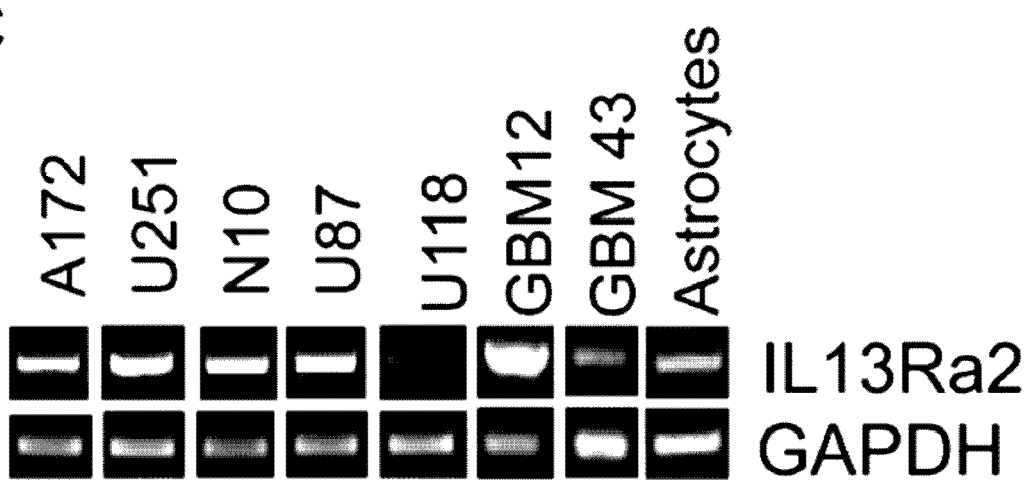
FIG. 3B-C

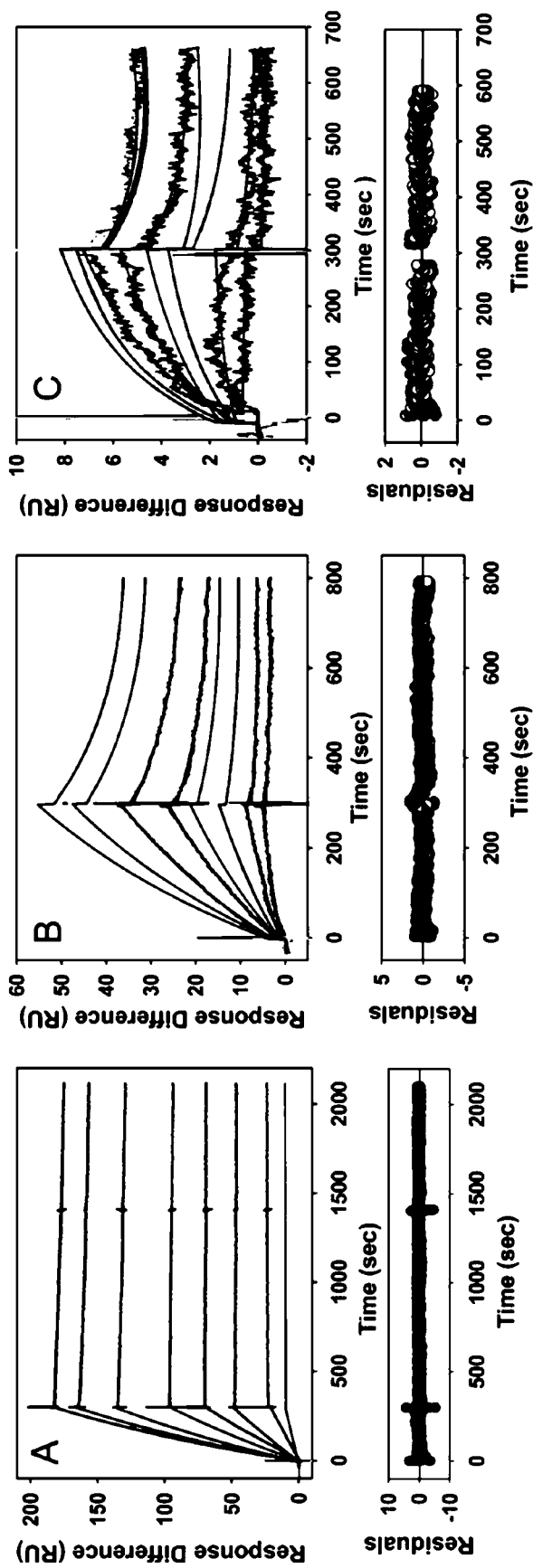
FIG. 4A-C

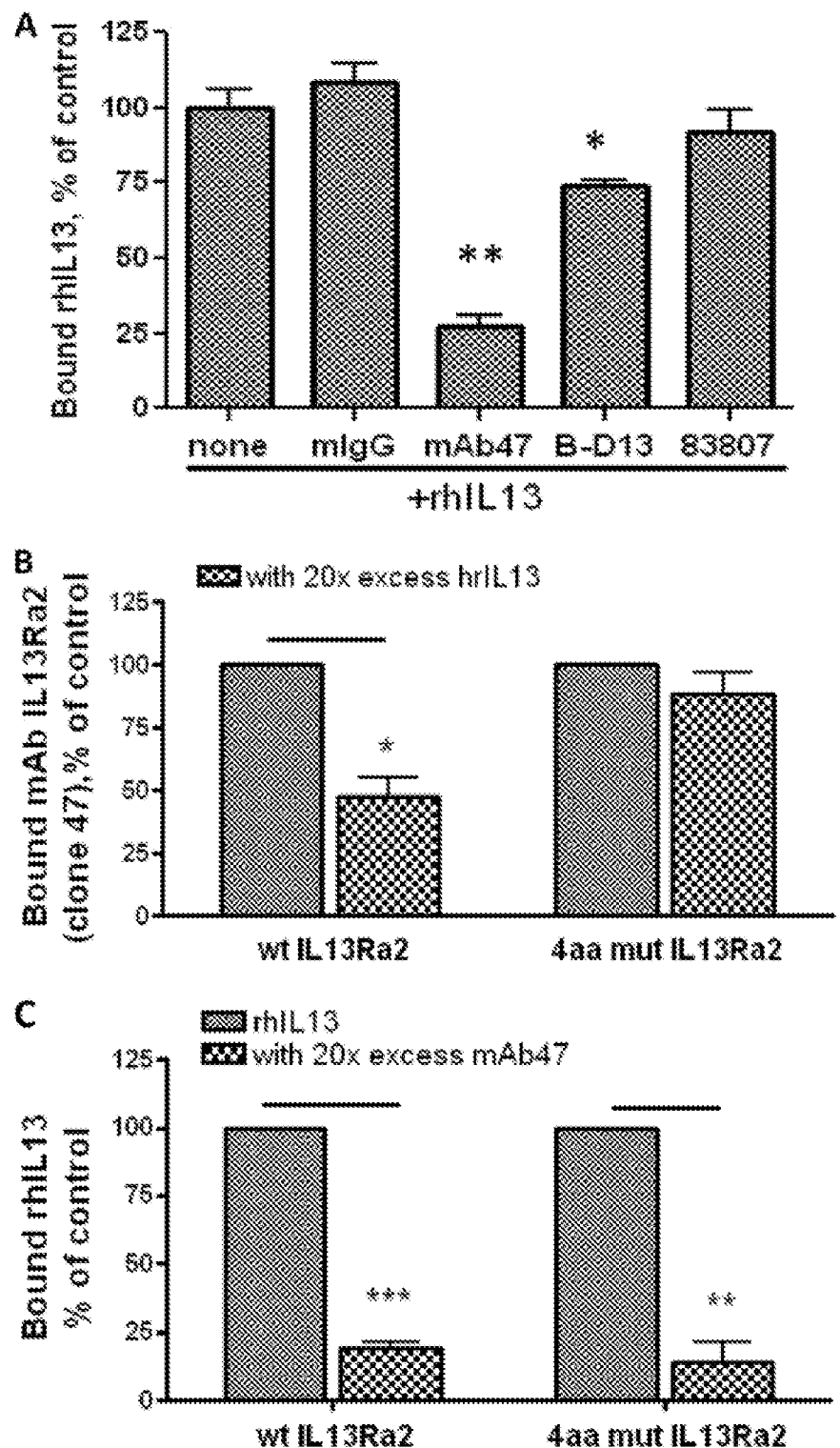
FIG. 5A-C

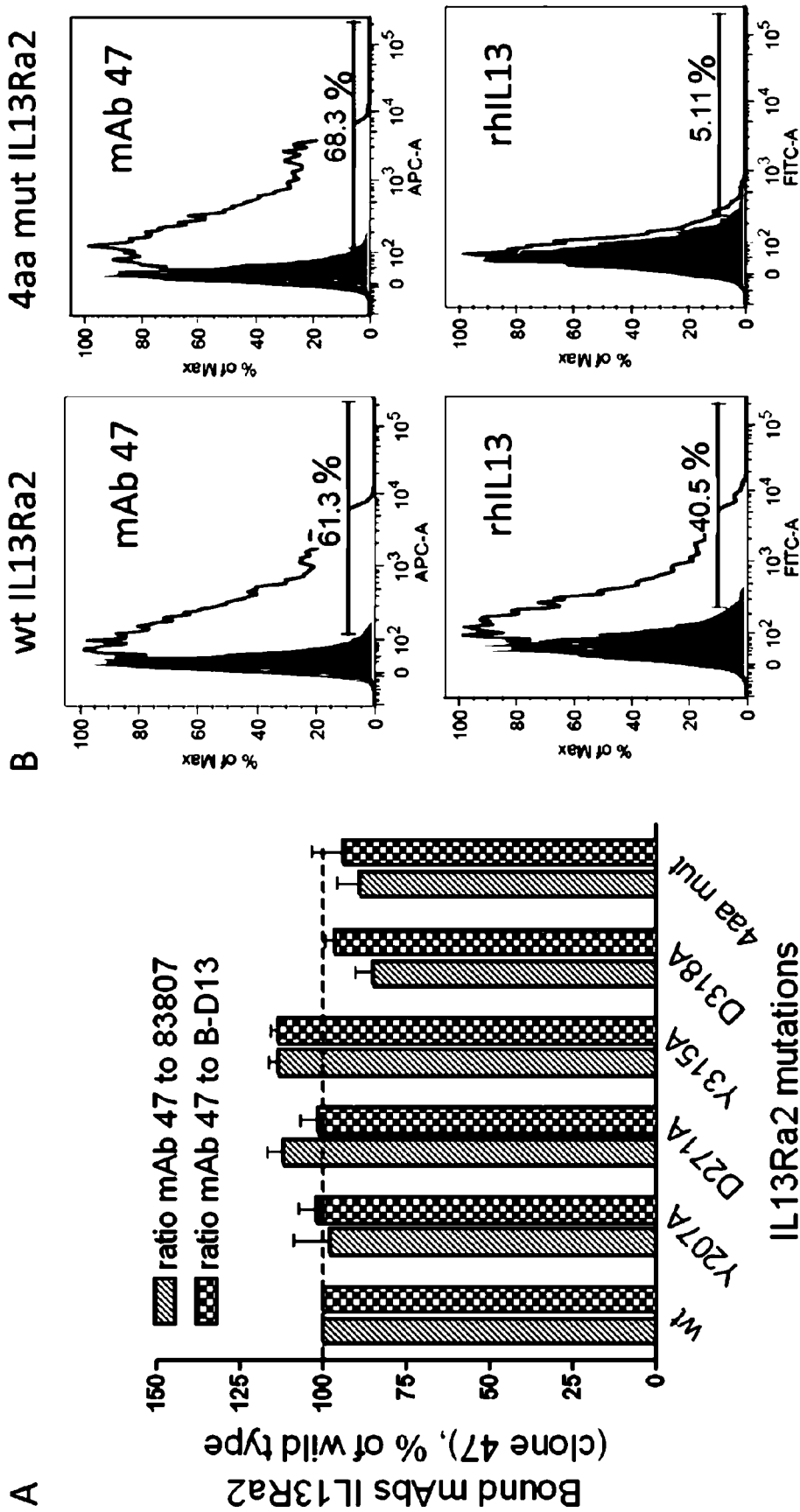
FIG. 6A-B

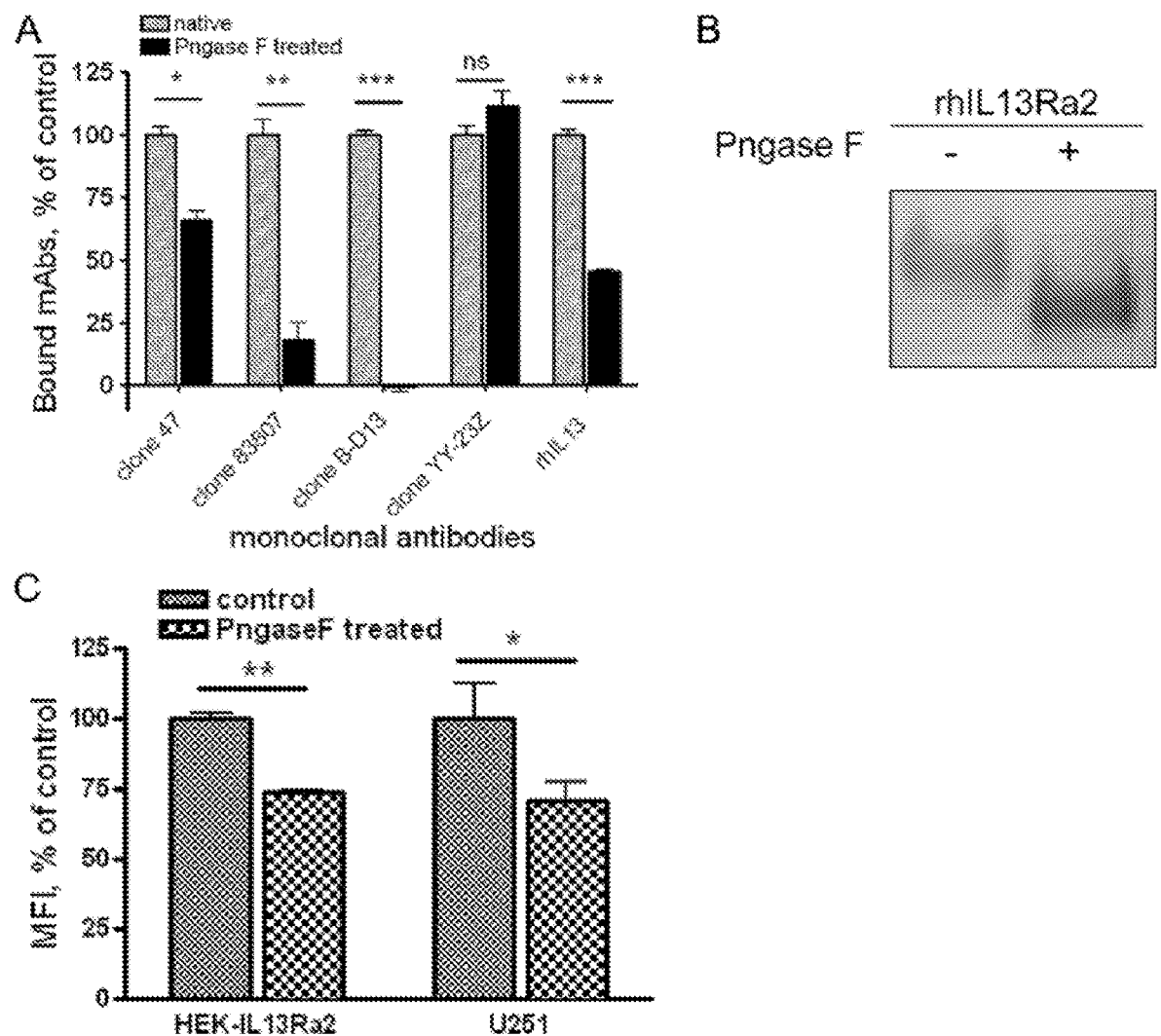
FIG. 7A-C

| | Expression (WB) | Cell surface expression | Cyto | IFNγ | IL2 | Anti-glioma activity in vivo |
|---|---|---|---|---|---|---|
| SH2Δ | n/a | + | - | - | - | - |
| SH3Δ | n/a | + | - | - | - | - |
| SH2 | + | + | + | ++ | + | + |
| LH2 | + | + | + | ++ | - | - |
| SH3 | + | +/- | + | + | - | ND |
| LH3 | + | + | + | + | - | ND |

FIG. 22

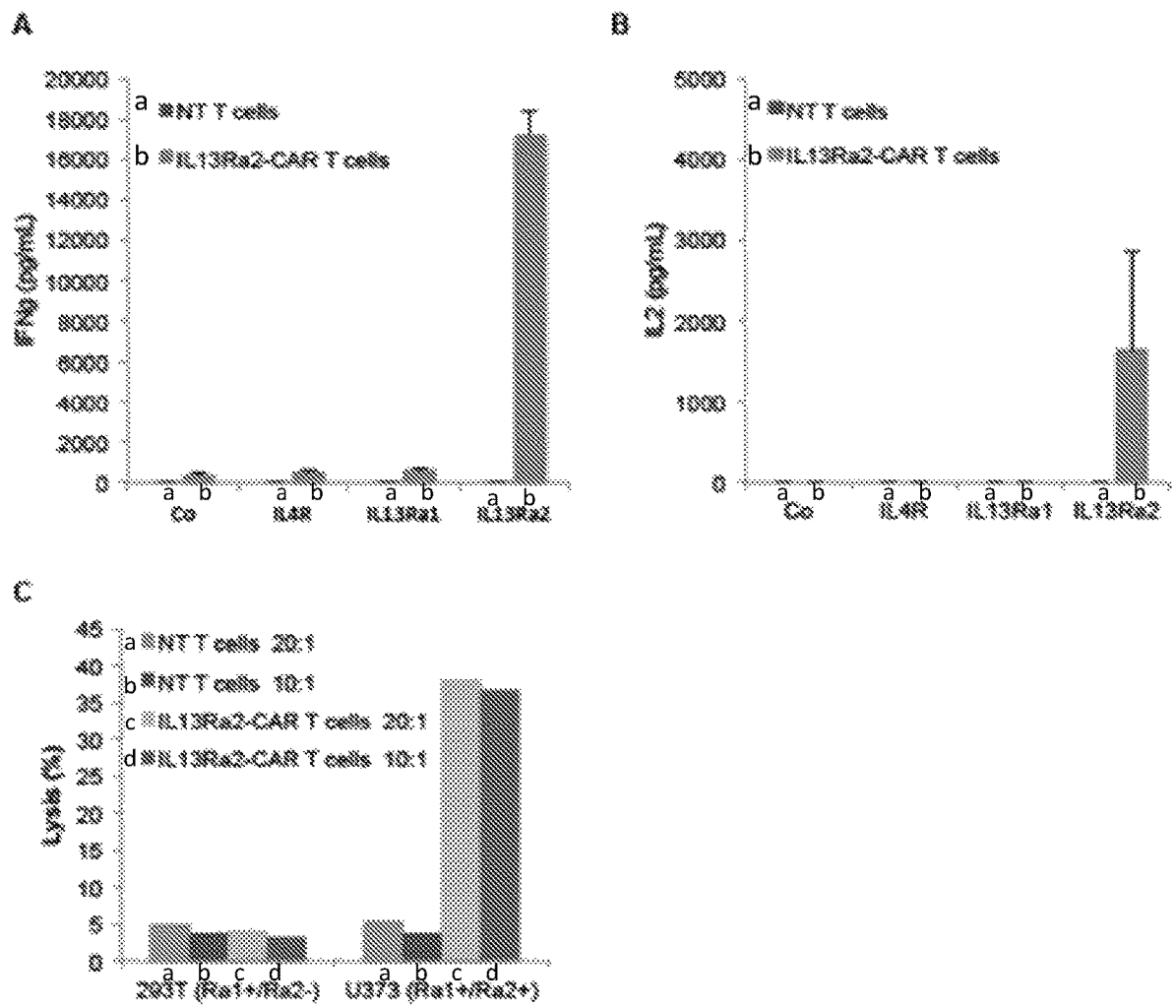
FIG. 30A-C

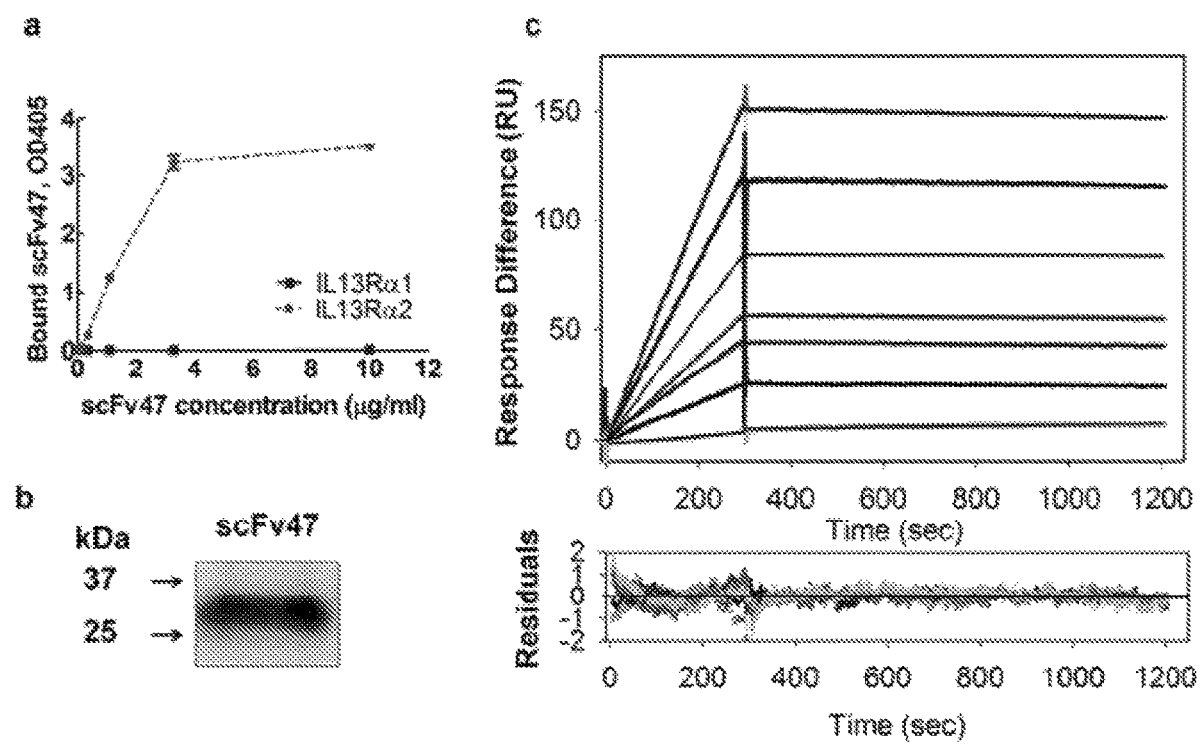
FIG. 31A-C

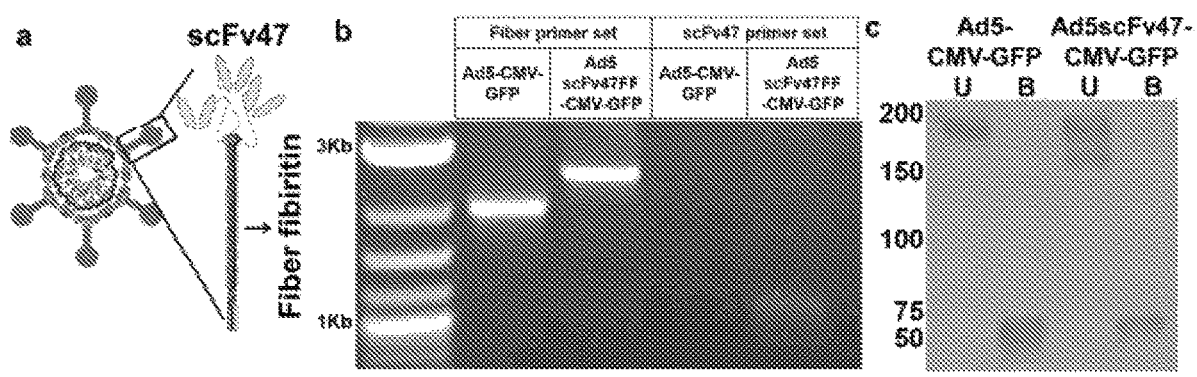
FIG. 32A-C

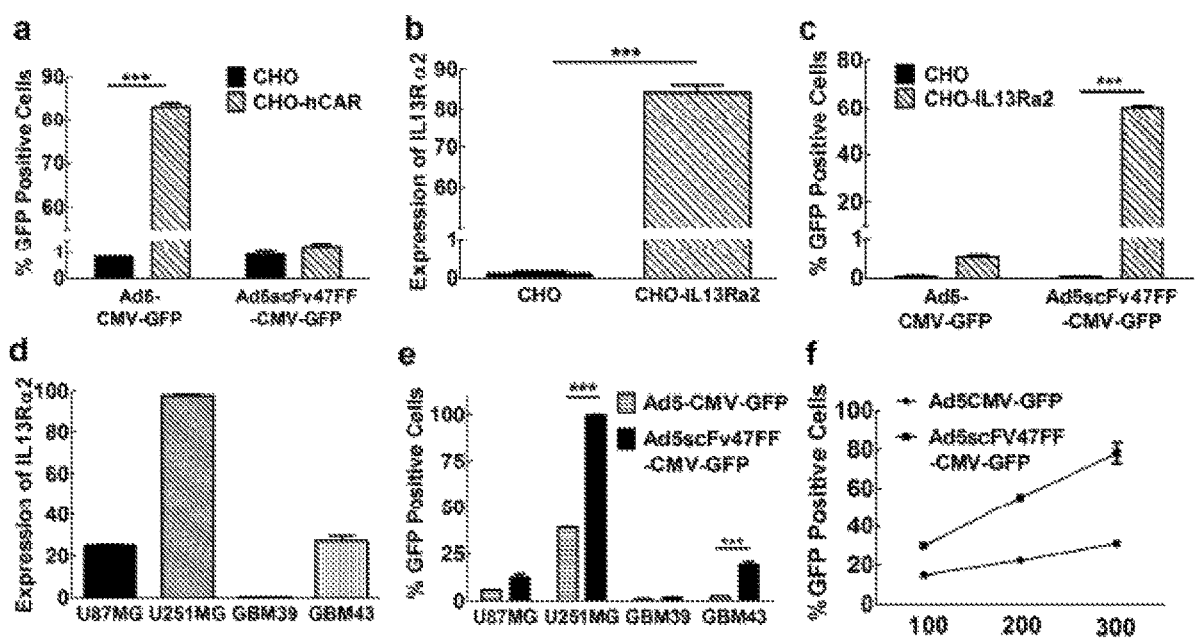
FIG. 33A-F

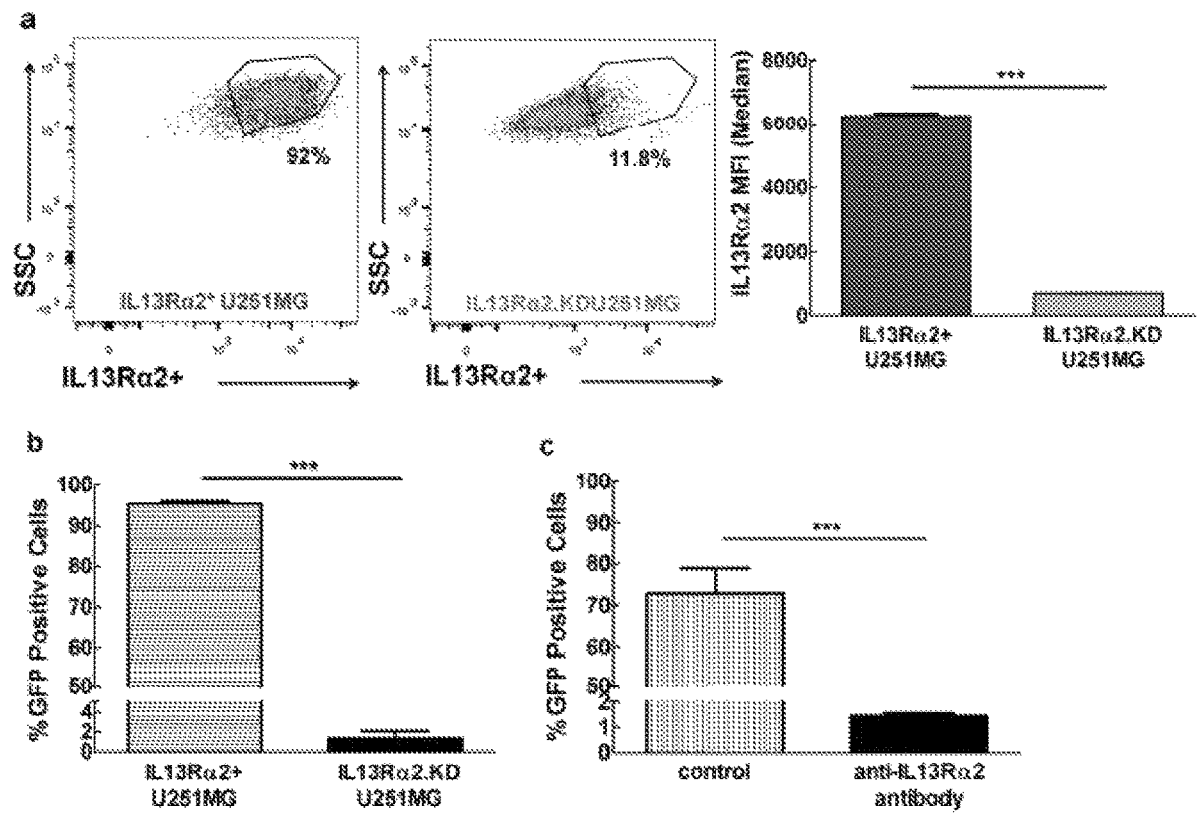
FIG. 34A-C

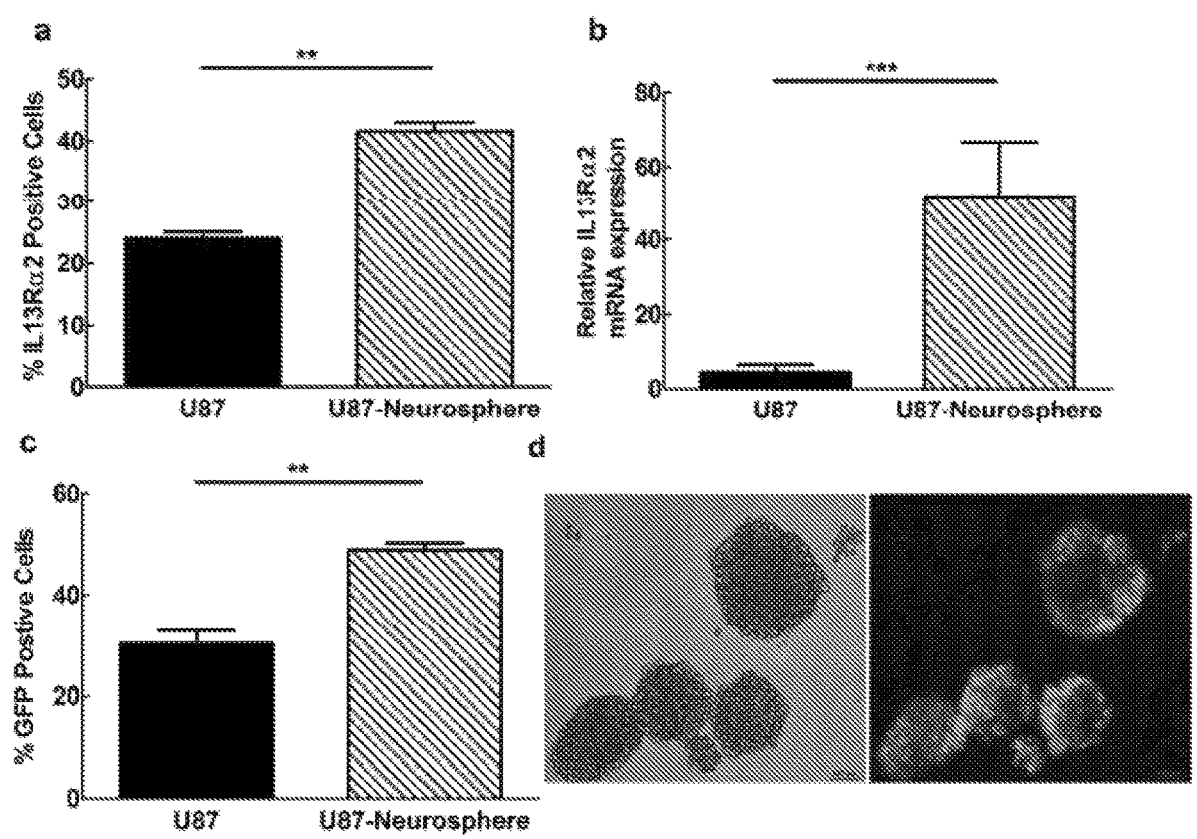
FIG. 35A-D

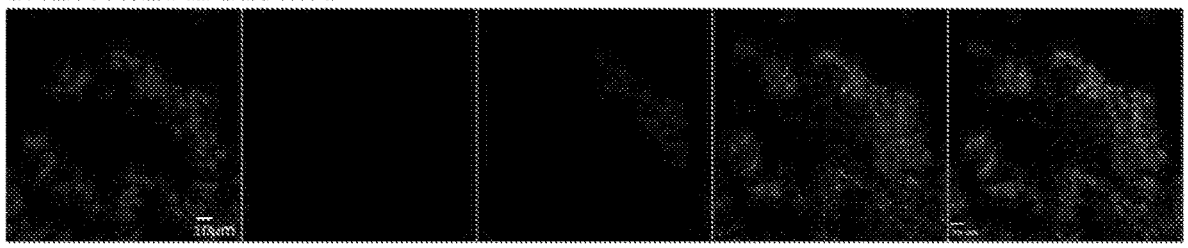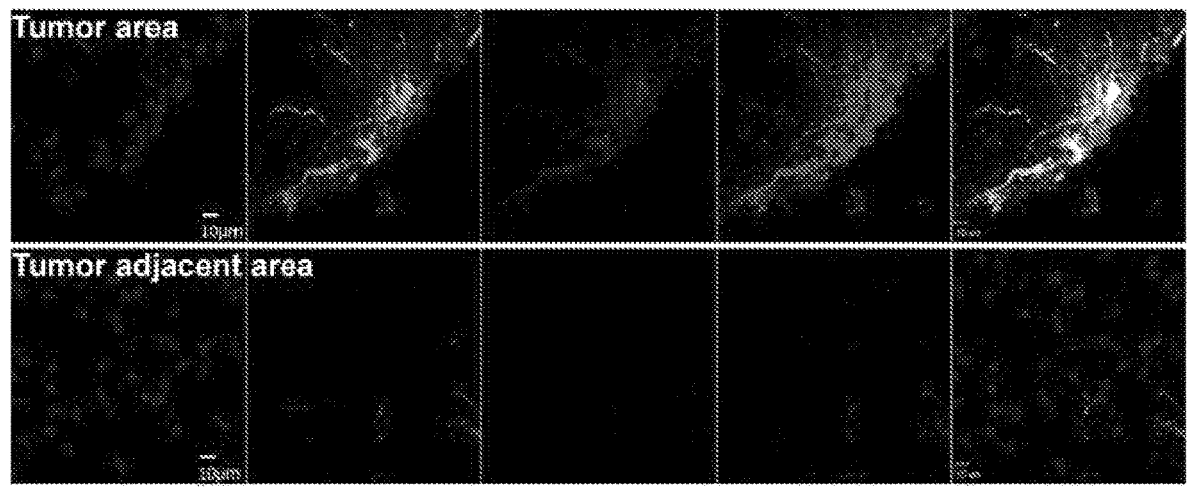
FIG. 36A-B

IL13Rα2 BINDING AGENTS AND USE THEREOF

CROSS-REFERENCE TO RELATED APPLICATIONS

This application is a continuation of U.S. patent application Ser. No. 16/385,853 filed Apr. 16, 2019, which is a continuation of U.S. patent application Ser. No. 15/545,945 filed Jul. 24, 2017, which is a national phase application under 35 U.S.C. § 371 of International Application No. PCT/US2016/014984 filed Jan. 26, 2016, which claims the benefit of priority of U.S. Provisional Patent Application No. 62/107,984, filed Jan. 26, 2015, all of which are hereby incorporated by reference in their entirety.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: ARCDP0695USC2_Sequences.txt; 176,128 bytes, created Oct. 28, 2020.

FIELD OF THE DISCLOSURE

The disclosure relates generally to the fields of cancer biology and to molecular antibody-receptor technology.

BACKGROUND

Cancer is a major threat to human and non-human animal health, leading to reduced quality of life and, in too many cases, death. The burden placed on national, regional and local healthcare organizations to treat and prevent the various forms of cancer is significant in terms of the resources and manpower required. One of the main weapons vertebrates, including humans, have to combat disease is a functioning immune system. A brief consideration of immunotherapies to treat or prevent cancer might lead one to conclude that the effort held out little hope of success because immune systems guard against foreign, or non-self, materials and cancer cells arise from within, i.e., they are self materials. Continued progress in our understanding of cancer and immunology is modifying that view, however.

Mutant antigens are powerful targets for tumor destruction, e.g., in mice, and tumor-infiltrating lymphocytes targeting these mutations cause durable tumor regression in patients. Nevertheless, non-mutant antigens have been presumed by many scientists to be cancer-specific or "relatively cancer-specific" and safe antigens for vaccine approaches. However, adoptively transferred T cells can be orders of magnitude more effective and destructive than vaccinations. As a result, targeting MAGE-A3, HER-2 or CEA with T cells has caused death or serious toxicity in clinical trials now halted (8-11). As was shown in 2002, cancer cells with extremely high or very low expression levels of a target antigen differ only in the induction of immune responses, but not at the effector phase (15).

The high affinity interleukin-13 receptor α2 (IL13Rα2) is selectively expressed at a high frequency by glioblastoma multiforme (GBM) as well as several other tumor types. One approach for targeting this tumor-specific receptor utilizes the cognate ligand, IL-13, conjugated to cytotoxic molecules. This approach, however, lacks specificity because the lower affinity receptor for IL-13, IL13Rα1, is widely expressed by normal tissues.

Most human cancers lack specific antigens that are predictably present and serve as effective targets for eradication by T cells. Every cancer cell type harbors a unique set of mutations causing different tumor-specific antigens. Identifying an effective unique antigen and isolating an appropriate TCR for transduction of autologous T cells for adoptive immunotherapy is still difficult despite the enormous technological progress being made. Adoptive immunotherapy using antibodies or T cells is clinically as well as experimentally the most effective immunotherapy, at least when clinically relevant cancers are considered (22). The remarkable success of adoptive immunotherapy with chimeric antibody receptors (CARs) and bispecific T cell engaging proteins (BiTEs) is, however, largely restricted to those specific for CD19/CD20-eradicating B cell malignancies and normal B cells in patients, i.e., hematopoietic cancers. Thus, there is a need to identify shared, yet tumor-specific, antigens on a wide range of solid tumors, and a concomitant need to develop prophylactics and therapeutics that can diagnose, prevent, treat or ameliorate a symptom of these cancers, along with methods for diagnosing, preventing and treating various cancers.

SUMMARY

The disclosure provides (i) the sequences of heavy (SEQ ID NO:7) and light (SEQ ID NO:8) chain variable regions of a monoclonal antibody specifically targeting human tumor-associated antigen, IL13Rα2, and (ii) data demonstrating the functionality of the protein encoded by the heavy and light chain cDNAs in the format of an scFv antibody or fusion to other functional moieties. The heavy and light chain can be arranged in different formats, such as single-chain antibody, diabodies, bi- and tri-specific antibodies, fusions with therapeutic proteins and other moieties, human or humanized whole antibodies as well as human or humanized Fab fragments and other functional derivatives. The single-chain antibody or other arrangements of the protein encoded by the heavy and light chains, e.g., a bispecific binding molecule, may be expressed and conjugated to therapeutic carriers (e.g., viruses, cells, nanomaterials) for specific delivery of therapeutic to IL13Rα2-overexpressing tumors or for imaging tumor burden.

Proteins expressed by tumor cells but not by normal cells are attractive molecules for the selective delivery of cytotoxic molecules. Accordingly, interleukin-13 receptor α2 (IL13Rα2), the high affinity receptor for interleukin-13 (IL-13), is a promising candidate. IL13Rα2 is expressed at a high frequency in the aggressive and incurable form of primary brain tumor known as glioblastoma multiforme (GBM) (1-3), as well as by other solid tumors (4). In contrast, normal tissues express little to no IL13Rα2, with the exception of the testes (6). Notably, IL13Rα1, a different receptor with low affinity for IL-13, is expressed ubiquitously by many tissues (7-9), making it a poor candidate for selective targeting of tumor-specific immunotherapeutic applications.

Several studies have investigated the therapeutic properties of an IL-13 fusion protein conjugated to a recombinant cytotoxin derived from *Pseudomonas* exotoxin A (IL-13PE) that induces apoptosis in IL13Rα2-expressing glioma cells in vitro, in preclinical animal models, and in patients tested in clinical trials (17-22). Such agents, however, lack a high specificity of interaction with IL13Rα2 because they alternatively bind to the ubiquitously expressed IL13Rα1. Therefore, developing highly selective antibody fragments that can be combined with effectors (e.g., T-cells, toxins) for specificity to IL13Rα2-expressing cells is expected to yield therapeutically beneficial results.

The disclosure captures the tumor specificity of IL13Rα2 by providing protein binding partners specific for IL13Rα2, rather than mimicking IL13 itself, which would result in a molecule exhibiting a capacity to bind to both IL13Rα1 and IL13Rα2. In addition, the disclosure provides a polynucleotide encoding one of these cancer-specific IL13Rα2 binding partners, including polynucleotides comprising codon-optimized coding regions for binding partners specific for an epitope of one of these IL13Rα2 binding partners. Expressly contemplated are fusion proteins or chimeras that comprise an IL13Rα2 binding partner as defined above in operable linkage to a peptide providing a second function, such as a signaling function of the signaling domain of a T cell signaling protein, a peptide modulator of T cell activation or an enzymatic component of a labeling system. Exemplary T cell signaling proteins include 4-1BB (CD137), CD3ζ, and fusion proteins, e.g., CD28-CD3ζ and 4-1BB-CD3ζ. 4-1BB (CD137) and CD28 are co-stimulatory molecules of T cells; CD3ζ is a signal-transduction component of the T-cell antigen receptor. The peptide or protein providing a second function may provide a modulator of T cell activation, such as IL-15, IL-15Rα, of an IL-15/IL-15Rα fusion, or it may encode a label or an enzymatic component of a labeling system useful in monitoring the extent and/or location of binding, in vivo or in vitro. Agent encoding these prophylactically and therapeutically active biomolecules placed in the context of T cells, such as autologous T cells, provide a powerful platform for recruiting adoptively transferred T cells to prevent or treat a variety of cancers in some embodiments of the disclosure. Codon optimization of the coding regions for binding partners specific for epitopes found on cancer cells provides an efficient approach to delivery of the diagnostic, prophylactic, and/or therapeutic proteins disclosed herein.

In one aspect, the disclosure provides an Interleukin 13 Receptor α2 (IL13Rα2) binding partner comprising the antibody heavy chain variable fragment ($V_H$) complementarity determining region 1 (CDR1) of SEQ ID NO:1, the $V_H$ CDR2 of SEQ ID NO: 2, the $V_H$ CDR3 of SEQ ID NO: 3, the light chain ($V_L$) complementarity determining region 1 (CDR1) of SEQ ID NO: 4, the $V_L$ CDR2 of SEQ ID NO: 5, and the $V_L$ CDR3 of SEQ ID NO: 6, wherein the IL13Rα2 binding partner specifically binds to an epitope of IL13Rα2. In some embodiments, the $V_H$ sequence is set forth as SEQ ID NO: 7 and in some of the same and some of different embodiments, the $V_L$ sequence is set forth as SEQ ID NO: 8.

A related aspect of the disclosure provides a bispecific binding molecule comprising a fragment of the IL13Rα2 binding partner described herein that binds to the IL13Rα2 epitope covalently linked to a peptide providing a second function to form a bispecific binding molecule. In some embodiments, the second function of the peptide is selected from the group consisting of a signaling function of the signaling domain of a T cell signaling protein, a peptide modulator of T cell activation, and an enzymatic component of a labeling system. In some embodiments, the fragment is a single-chain variable fragment (scFv), which may be contained within a bi-specific T-cell engager (BiTE) or a chimeric antigen receptor (CAR). Some embodiments are provided wherein the bispecific binding molecule as described herein is conjugated to a therapeutic carrier.

Another aspect of the disclosure is drawn to a pharmaceutical composition comprising the IL13Rα2 binding partner as described herein and a pharmaceutically acceptable carrier, adjuvant or diluent.

A related aspect provides a kit comprising the pharmaceutical composition described herein and a protocol for administration of the composition. Also related is an aspect providing a polynucleotide encoding the IL13Rα2 binding partner as described herein and a vector comprising the polynucleotide as described herein. In exemplary embodiments, the vector is a virus, such as an adenovirus. In particular embodiments, the adenovirus is adenovirus serotype 5. Another aspect of the disclosure is a recombinant polynucleotide comprising the vector disclosed herein and the nucleic acid disclosed herein. In some embodiments, the recombinant polynucleotide is Ad5FFscFv47. Yet another aspect is directed to a host cell comprising the polynucleotide described herein or the vector described herein.

Yet another aspect of the disclosure provides a method of preventing, treating or ameliorating a symptom of a cancer disease comprising administering a therapeutically effective amount of the pharmaceutical composition as described herein. In some embodiments, the cancer is a solid tumor, such as a glioblastoma multiforme (GBM). In some embodiments, the cancer is treated by inhibiting the growth rate of the solid tumor. In some embodiments, the symptom ameliorated is pain.

More particularly, one aspect of the disclosure is drawn to an IL13Rα2 binding agent comprising each of the amino acid sequences of: NYLMN (SEQ ID NO: 1); RIDPYDG-DIDYNQNFKD (SEQ ID NO: 2); GYGTAYGVDY (SEQ ID NO: 3); RASESVDNYGISFMN (SEQ ID NO: 4); AAS-RQGSG (SEQ ID NO: 5); and QQSKEVPWT (SEQ ID NO: 6). In some embodiments, the IL13Rα2 binding agent disclosed herein comprises one or both of the amino acid sequences of SEQ ID NO: 7 and/or SEQ ID NO: 8. In some embodiments, the amino acid sequence of SEQ ID NO: 7 is fused to the amino acid sequence of SEQ ID NO: 8 through a linker. In some embodiments, the linker comprises the amino acid sequence of EEGEFSEAR (SEQ ID NO 10). In some embodiments, the IL13Rα2 binding agent disclosed herein comprises the amino acid sequence of SEQ ID NO: 13. In some embodiments, the IL13Rα2 binding agent disclosed herein further comprises an amino acid sequence of SEQ ID NO: 28, or an amino acid sequence which is at least 90% identical to SEQ ID NO: 28. In some embodiments, the IL13Rα2 binding agent disclosed herein further comprises an amino acid sequence of SEQ ID NO: 30, or an amino acid sequence which is at least 90% identical to SEQ ID NO: 30. In some embodiments, the IL13Rα2 binding agent disclosed herein is an antibody, or an antigen-binding fragment thereof, wherein the antigen-binding fragment thereof comprises at least the amino acid sequences of SEQ ID NOs: 1-6. In some embodiments, the binding agent is an antigen binding fragment that is a single chain variable fragment (scFv). In some embodiments, the IL13Rα2 binding agent disclosed herein further comprises an Ig kappa leader sequence of METDTLLLWVLLLWVPGSTGD (SEQ ID NO: 9). In some embodiments, the IL13Rα2 binding agent disclosed herein further comprises a linker sequence of EEGEFSEAR (SEQ ID NO 10). In some embodiments, the IL13Rα2 binding agent disclosed herein further comprises a Myc tag sequence of GGPEQKLI-SEEDLN (SEQ ID NO: 11). In some embodiments, the IL13Rα2 binding agent disclosed herein further comprises a His tag sequence of TF HHIHHH (SEQ ID NO: 12). In some embodiments, the IL13Rα2 binding agent disclosed herein comprises the amino acid sequence of SEQ ID NO: 14. In some embodiments, the IL13Rα2 binding agent disclosed herein binds to human IL13Rα2 but does not bind to human IL13Rα1. In some embodiments, the IL13Rα2 binding agent disclosed herein has an equilibrium dissociation constant ($K_D$) for human IL13Rα2 which is no greater than about $1.39 \times 10^{-9}$ M.

In a related aspect, the disclosure provides a conjugate comprising an IL13Rα2 binding agent disclosed herein covalently linked to an effector domain. In some embodiments, the conjugate is a fusion protein or a chimeric protein. In some embodiments, the effector domain is a cytotoxin, an apoptosis tag, a T-cell signaling domain, or a label. In some embodiments, the effector domain is a T-cell signaling domain and the conjugate is an IL13Rα2-specific chimeric antigen receptor (CAR). In some embodiments, the apoptosis tag is a TRAIL protein, or a portion thereof, optionally, wherein the apoptosis tag comprises the amino acid sequence of SEQ ID NO: 27. In some embodiments, the conjugate comprises the amino acid sequence of SEQ ID NO: 25. In some embodiments, the label is a radiolabel, a fluorescent label, an enzyme that catalyzes a calorimetric or fluorometric reaction, an enzymatic substrate, a solid matrix, biotin or avidin. In some embodiments, the effector domain is a radiolabel, a fluorescent label, biotin or avidin.

In another aspect, the disclosure provides a nucleic acid encoding the IL13Rα2 binding agent disclosed herein or the conjugate of any such binding agent as disclosed herein. In some embodiments, the nucleic acid disclosed herein comprises the sequence of SEQ ID NO: 15 or SEQ ID NO: 16, or both SEQ ID NOs: 15 and 16.

In another aspect, the disclosure presents a vector comprising a nucleic acid disclosed herein.

Yet another aspect is drawn to a host cell comprising the vector disclosed herein. Another aspect is directed to a pharmaceutical composition comprising a binding agent disclosed herein, a conjugate disclosed herein, a nucleic acid disclosed herein, a vector disclosed herein, or a host cell disclosed herein, and a pharmaceutically acceptable carrier.

Another aspect is a method of treating a cancer in a subject, comprising administering to the subject a binding agent disclosed herein, or a conjugate disclosed herein, in an amount effective to treat the cancer in the subject. In some embodiments, the cancer is colon cancer.

Yet another aspect is a method of identifying an IL13Rα2-positive cancer cell comprising contacting a biological sample with a detectable amount of a binding agent as disclosed herein, or a conjugate as disclosed herein; and measuring the amount of the binding agent or conjugate bound to at least one cell of the biological sample, thereby identifying an IL13Rα2-positive cancer cell. In some embodiments, the biological sample is a cellular mass, tissue or organ within the body of a subject, and in other embodiments the biological sample is an ex vivo cellular mass, tissue(s) and/or organ(s). In some embodiments, the IL13Rα2-positive cancer cell is a glioma cell. In some embodiments, the binding agent comprises scFv47. In some embodiments, the binding agent is a conjugate as disclosed herein, wherein the effector domain is a radiolabel, a fluorescent label, an enzyme that catalyzes a calorimetric or fluorometric reaction, an enzymatic substrate, a solid matrix, biotin or avidin. In some embodiments, the effector domain is a radiolabel, a fluorescent label, biotin or avidin.

Other features and advantages of the disclosure will become apparent from the following detailed description, including the drawing. It should be understood, however, that the detailed description and the specific examples, while indicating preferred embodiments, are provided for illustration only, because various changes and modifications within the spirit and scope of the invention will become apparent to those skilled in the art from the detailed description.

BRIEF DESCRIPTION OF THE DRAWINGS

FIG. 1A-D. Characterization of antigen recognition and screening of hybridoma clones. A, binding of B-D13 mAb to ELISA plates coated with rhIL13Rα2hFc at 0.1 and 1 µg/ml. B, binding of IL13Rα2 mAb to native and denatured (at 95° C. in the presence of 0-mercaptoethanol) rhIL13Rα2hFc in a plate-bound ELISA. A paired t test was used to evaluate the difference between control groups (n=4). *, p<0.1; ***, p<0.001. Error bars represent S.D. These data are representative of two independent experiments. C, screening of selected hybridoma populations against rhIL13Rα2hFc in a plate-bound ELISA. D, screening of selected hybridoma populations against rhIL13Rα2hFC using a Western blot.

FIG. 2A-D. The IL13Rα2 (clone 47) mAb specifically binds to rhIL13Rα2 and IL13Rα2 expressed on the cell surface of CHO cells. A, binding of IL13Rα2 (clone 47, 83807, and B-D13) mAbs to rhIL13Rα2 in a plate-bound ELISA. B, binding of the IL13Rα2 (clone 47) mAb to human IL13Rα2 expressed on the surface of CHO cells. C, cross-reactivity of the IL13Rα2 (clone 47) mAb with hrIL13Rα1. D, cross-reactivity of IL13Rα2 (clones 47, 83807, and B-D13) mAbs with mouse rIL13Rα2. Error bars represent S.D.

FIG. 3A-D. Binding of IL13Rα2 mAb to glioma cells. A, flow charts of IL13Rα2 (clones 47, 83807, and B-D13) mAbs binding to the surface of glioma cells, normal human primary astrocytes, and HEK cells transfected with IL13Rα2. B, data of the median fluorescence intensity of binding between the IL13Rα2 (clones 47, 83807, and B-D13) mAbs to various cell lines analyzed by flow cytometry. Numbers above the bars represent the difference in the binding of clone 47 when compared with clone B-D13 for each cell line. The color key is the same for A and B. C, mRNA expression for IL13Rα2 in glioma cells as well as normal human primary astrocytes. D, panels a-c, flow cytometry demonstrating the specific binding of the IL13Rα2 (clone 47) mAb to GFP-tagged U251 glioma cells from an intracranial xenograft (xeno). The curve with a clear area under the curve in sub-panel b depicts the binding of mAb IL13Rα2 (clone 47) to GFP negative cells; the curve with a clear area under the curve in sub-panel c depicts the binding of mAb IL13Rα2 (clone 47) to GFP positive cells. Curves in sub-panels b and c with gray areas under the curves show the results when exposing control IgG to GFP-negative (sub-panel b) or GFP-positive (sub-panel c) cells. neg, negative. A, area; SSC-A, side scatter area; APC-A, allophycocyanin area.

FIG. 4A-C. The affinity between the IL13Rα2 (clone 47) mAb and rhIL13Rα2. The kinetics of interaction of IL13Rα2 (clone 47) mAb (A) and the commercially available mAb clones 83807 (B) and B-D13 (C) with rhIL13Rα2 as visualized by SPR in a Biacore 3000 are shown. The rhIL13Rα2 was injected at concentrations ranging from 1 to 100 nM (1 nM, 2.5 nM, 5 nM, 7.5 nM, 10 nM, 15 nM, 20 nM, 25 nM concentrations shown, lower to upper curves) at a constant flow rate of 20 µl/minute over immobilized antibodies and over a control dextran surface (these values were subtracted from the signal). The association and dissociation phases were monitored for 300 s by following the change in SPR signal (colored curves) given in RU. Black curves represent the fit of the data to a one-site binding model. For derived kinetic parameters, see Table 1. Lower three panels show residuals from a one-site binding model, indicating an excellent fit.

FIG. 5A-C. The IL13Rα2 (clone 47) mAb competes with rhIL-13 for the binding site of IL13Rα2. A, using a competitive binding plate assay, the IL13Rα2 (clone 47) mAb but not control mIgG or antibody clones 83807, B-D13, and YY-23Z significantly abolished the binding of rhIL-13 to the rhIL13Rα2Fc chimera absorbed to plastic. One-way analysis of variance followed by Dunnett's post hoc test was performed. Data from a single representative experiment are shown. B, recombinant human IL-13 competes with the IL13Rα2 (clone 47) mAb for the binding site of WT IL13Rα2 but not with the 4-amino acid (4aa) mutant IL13Rα2 expressed on the surface of HEK cells. C, the IL13Rα2 (clone 47) mAb competes with rhIL-13 for the binding site of the WT and 4-amino acid mutant form of IL13Rα2. A paired t test was performed. Data represent the summary of three independent experiments shown in B and C. *, $p<0.05$; , $p<0.01$; *, $p<0.001$. Error bars represent S.D.

FIG. 6A-B. The contribution of Tyr207, Asp271, Tyr315, and Asp318 residues of IL13Rα2 to the binding of the IL13Rα2 (clone 47) mAb. A, variants of cDNA encoding individual mutations to Ala or a combinatorial 4-amino acid mutant (4aa mut) of IL13Rα2 was generated. HEK cells were transfected with a control vector or a vector encoding the IL13Rα2 variants. After 48 hours, binding of the IL13Rα2 (clone 47) mAb to the surface of transfected cells was analyzed by flow cytometry. Anti-IL13Rα2 antibody clones 83807 and B-D13 were used as reference antibodies in this assay. Binding of antibodies was determined as the percentage of positive cells. The ratio of bound clones was determined for each IL13Rα2 mutant and compared with that of the wild-type receptor. One-way analysis of variance followed by Dunnett's post hoc test was performed. Data represent a summary of four independent experiments. Error bars represent S.D. B, representative graphs of flow cytometry data demonstrating the binding of clone 47 or rhIL-13 to the WT and 4-amino acid-mutated variant of the IL13Rα2 receptor expressed on the surface of HEK cells. Filled curves: negative control, staining with isotype control IgG+ secondary antibody; Open curves: staining with the anti-IL13Rα2 (clone 47) monoclonal antibody+secondary antibody. A, area; APC-A, allophycocyanin area; FITC-A, fluorescein isothiocyanate area.

FIG. 7A-C. Effect of N-linked glycosylation on the binding of IL13Rα2 to recombinant IL13Rα2. A, binding of IL13Rα2 to control and Pngase F-treated rhIL13Rα2. Plates were coated with hrIL13Rα2 at 1 µg/ml and treated with native buffer or with 1 milliunit/well Pngase F in native buffer for 3 hours at 37° C. An ELISA for binding of the IL13Rα2 (clone 47) mAb in comparison with antibody clones B-D13, 83807, and YY-23Z and rhIL-13 was performed, and the data of one representative experiment from three independent experiments are shown. A paired t test was used to evaluate the difference between control and Pngase F-treated groups (n=4). *, $p<0.5$; , $p<0.01$; *, $p<0.001$. B, a Western blot shows the lower molecular weight of Pngase F-treated rhIL13Rα2 due to removal of N-linked glycosylation adducts from the molecule. C, flow cytometry shows the binding of IL13Rα2 mAbs to IL13Rα2-expressing U251 and HEK293 cells treated with 1 milliunit of Pngase F for 1 hour at 37° C. The data are representative of three independent experiments. A paired t test was used to evaluate the difference between control and Pngase F-treated groups. *, $p<0.5$. MFI, mean fluorescence intensity. Error bars represent S.D.

FIG. 22. Properties of m47 CAR T cell agent. The m47-CAR T cells recognize IL13Rα2$^+$, but not IL13Rα1$^+$ targets. The data show that the short hinge CD28z-CAR (SH2) T cells perform better in terms of effector function than CD28z-CAR (SH3), CD28z-CAR (LH2), CD28z-CAR (LH3), CD28z-CAR (SH2Δ), or CD28z-CAR (SH3Δ).

FIG. 30A-C. Characterization of IL13Rα2-CAR T cells. (A, B) Co-culture assay with recombinant protein demonstrated interferon γ and interleukin 2 production in an IL14Rα2-dependent fashion; (C) Cytolytic activity in standard chromium release assay.

FIG. 31A-C. Binding characteristics of scFv47 to IL13Rα2. (a) Binding of purified soluble scFv47 with rhIL13Rα 2 and rhIL13Rα1 proteins was determined in plate ELISA. (b) Western blot analysis of soluble scFv47. The scFv47 protein runs under reducing conditions as a 30 kDa protein, in agreement with the predicted molecular weight. (c) The kinetics of interactions between the scFv47 and rhIL13Rα 2 were visualized by SPR in a Biacore 3000. The scFv47 was injected at concentrations ranging from 1 to 50 nM (lower to upper curves) at a constant flow rate of 20 µL/min over immobilized rhIL13Rα 2. The association phase was monitored for 30 sec, dissociation phase for 900 sec, followed by the change in SPR signal (colored curves), given in RU. Black curves represent the fit of the data to a one-site binding model. For derived kinetic parameters, see Table 1. Lower panels show residuals from the one-site binding model, indicating an excellent fit.

FIG. 32A-C. Design, Generation, and Confirmation of IL13Rα2 Tropic Virus Structure and Stability. (a) Schematic diagram of anti-IL13Rα 2 scFv-specific chimera fiber of Ad5FFscFv47-CMV-GFP. The fiber knob and shaft domains of Ad5 were replaced with a fiber fibritin trimerization domain, and anti-IL13Rα2 scFv47 was incorporated into the C-terminus of the chimeric fiber. (b) PCR confirmation of fiber modification. (c) Validation of the chimeric fiber structure. Western blot analysis detected the stable fiber trimerization when the chimeric fiber was unboiled (U: incubated at room temperature for 10 min), and detected denatured monomeric structures when the fiber was boiled (B: incubated at 95° C. for 10 min).

FIG. 33A-F. Confirmation of Tropism Modification of Ad5FFscFv47-CMV-GFP. (a) CAR-independent infectivity of Ad5FFscFv47-CMV-GFP virus. CAR-negative CHO and CAR-positive CHO-hCAR cell lines were infected with Ad5CMV-GFP or Ad5FFscFv47-CMV-GFP virus. Cells were analyzed for GFP expression 72 hours post-infection by flow cytometry. (b) The expression of IL13Rα 2 on the surface of CHO-IL13Rα2 cell line detected using mAb IL13Rα2 (clone 47). (c) IL13Rα2-dependent infectivity of Ad5FFscFv47-CMV-GFP demonstrated by efficient transduction of CHO-IL13Rα2 cells and lack of transduction of IL13Rα2-negative CHO cells. (d) The IL13Rα2 expression on the surface of U87MG, U251MG, GBM39, and GBM43 glioma cell lines. Data presented as percent of positive cells. (e) The transduction efficiency of Ad5FFscFv47-CMV-GFP, but not Ad5CMV-GFP virus, strongly correlates with a level of IL13Rα2 expression in U87MG, U251MG, GBM39, and GBM43 glioma cells. Transduced glioma cells were analyzed by flow cytometry for GFP expression 72 hours post-infection. (f) Steady increase in the infectivity of Ad5FFscFv47-CMV-GFP with an increase of MOI. U251MG cells were infected with Ad5FFscFv47-CMV-GFP or Ad5CMV-GFP at MOI. 100, 200, and 300 vp/cell. 72 hours post-infection, a flow cytometric analysis for GFP expression in cells was performed. Each data point is an average of 3 independent replicates in all figures. Data presented as mean±SEM. ***p<0.001.

FIG. 34A-C. IL13Rα2-specific Infectivity of Ad5FFscFv47-CMV-GFP. (a) Flow cytometry analysis of IL13Rα2 expression in U251MG cells following knockdown with control shRNA (IL13Rα 2+U251MG) or IL13Rα2-specific shRNA (IL13Rα 2KDU251MG) presented as percent of positive cells (flow charts) and median fluorescent intensity (MFI). (b) IL13Rα2-dependent infectivity of Ad5FFscFv47-CMV-GFP demonstrated by differential expression of GFP in in IL13Rα2+U251MG and IL13Rα2.KDU251MG cell lines. (c) Competitive binding assay. U251MG cells were pre-treated with anti-IL13Rα 2 mAb as described herein. Control and treated cells were then infected with the Ad5scFv47-CMV-GFP virus. Cells were analyzed for GFP transgene expression 72 hours later by flow cytometry. Each data point is an average of 3 independent replicates. Mean±SEM is plotted. ***p<0.001.

FIG. 35A-D. Infection of neurospheres by Ad5FFscFv47-CMV-GFP. (a) Comparison of IL13Rα2 expression in U87MG cells growing as an adherent culture or as neurospheres. (b) Relative IL13Rα2 mRNA expression in U87MG glioma cells grown as adherent culture or as neurospheres was analyzed by RT-PCR. (c) Ad5FFscFv47-CMV-GFP infectivity of U87MG glioma cells grown as adherent culture versus neurospheres was determined by flow cytometry analysis for GFP-positive cells. (d) Microscopic image of U87MG neurospheres (phase contrast image-left panel) infected with Ad5FFscFv47-CMV-GFP. GFP expression (right panel) is shown in green fluorescence. Scale bar is 100 m. Each data point is an average of 3 independent replicates. Mean±SEM is plotted. *p<0.001, p<0.01.

FIG. 36A-B. IL13Rα2-specific infection in xenograft model of glioma. Mouse brains were sectioned and stained for DAPI (Blue), GFP (viral infection), anti-GFP (Purple), and anti-human nestin (Red, tumor). (a) Immunohistochemistry analysis of IL13Rα 2.KDU251MG cells implanted mice. There were no observable GFP-positive cells in tumor area. (b) Immunohistochemistry analysis of IL13Rα2+ U251MG cell implanted mice. While GFP-positive cells were observed in tumor area, there were no observable virus-infected cells in the tumor adjacent area, indicating the infectivity of Ad5FFscFv47-CMV-GFP is highly specific to the IL13Rα2 expression level. Scale bar is 10 m.

DETAILED DESCRIPTION

Figure 3A:
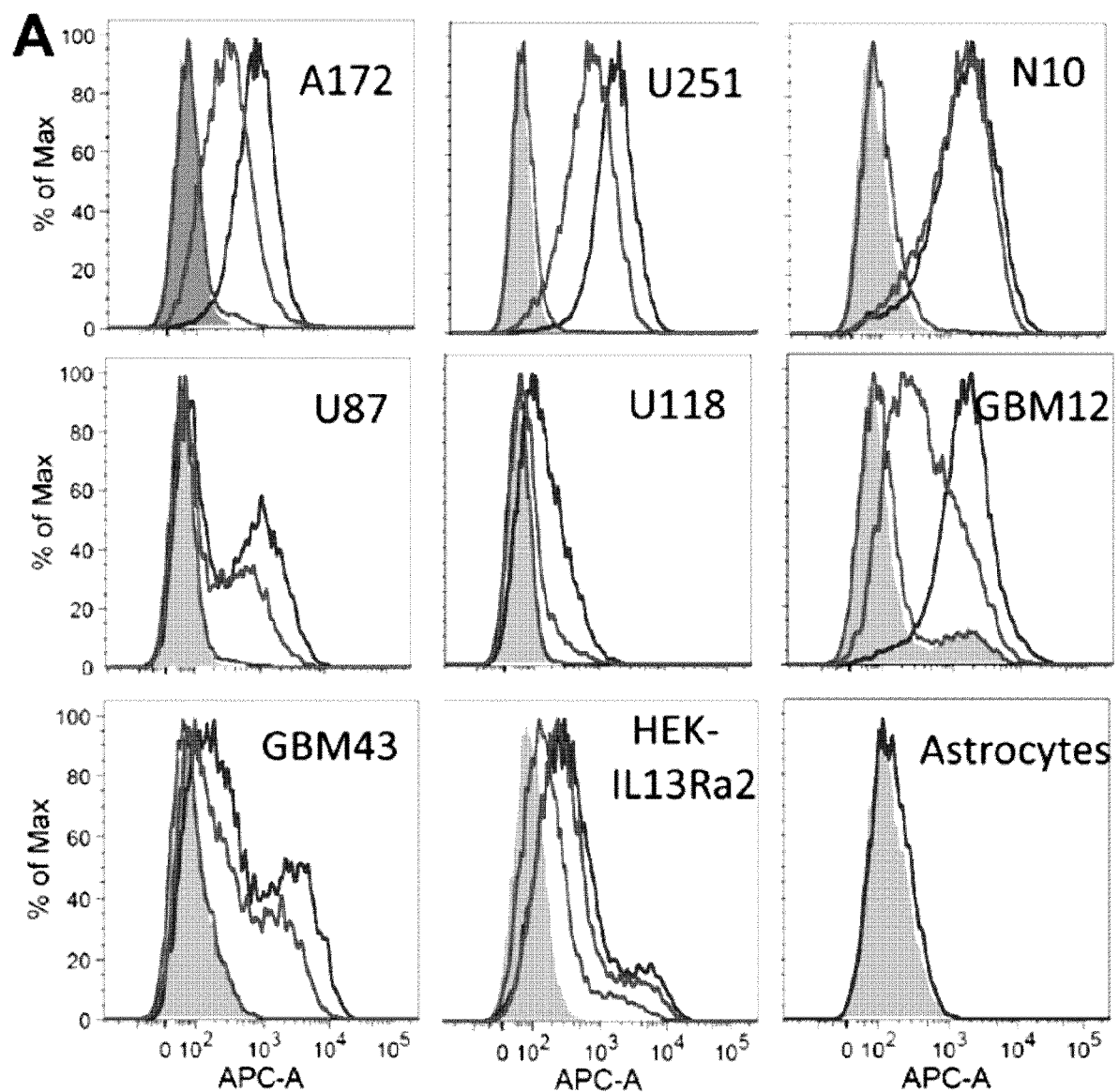

The disclosure provides binding agents, or partners, that specifically recognize interleukin 13 receptorα2 (IL13Rα2) for use in diagnosing, preventing, treating or ameliorating a symptom of any of a wide range of cancers characterized by cells presenting IL13Rα2. More particularly, the disclosure provides (i) the sequences of the six complementarity determining regions of a monoclonal antibody (m47) that specifically targets human tumor-associated antigen, i.e., interleukin 13 receptor α2 (IL13Rα2), and (ii) data demonstrating the functionality of the protein encoded by the heavy and light chain cDNAs in the format of an scFv antibody or conjugate (e.g., fusion) to other functional moieties. The six complementarity determining regions of the m47 monoclonal antibody confer binding specificity for IL13Rα2, consistent with the understanding in the immunological arts. In some embodiments, the scFv comprises the complete heavy and light chain variable regions of antibody m47, or the complete heavy and light chains of antibody m47. In some embodiments, the heavy and light chain fragments comprise, e.g., the m47 CDRs, or the m47 variable regions, and these domains can be arranged in different formats, such as a single-chain variable fragment of an antibody, i.e., a scFv, a diabody, a bi-specific antibody fragment, a tri-specific antibody fragment, a fusion protein with any of a wide variety of therapeutic proteins and/or other moieties, a humanized antibody fragment, a Fab fragment, a Fab' fragment, a F(ab)2' fragment and any other functional format for a bi-functional peptide providing a targeting function and an effector function. Moreover, the single-chain antibody or other arrangements of the protein encoded by the heavy and light chains could be expressed and conjugated to therapeutic carriers (e.g., viruses, cells, nanomaterials) for specific delivery of a therapeutic to an IL13Rα2-expressing tumor. The materials according to the disclosure are also useful in imaging tumor burden.

The technology addresses the most serious obstacle to progress in immunotherapy, i.e., the virtual absence of defined, tumor-specific antigens that can be predictably found on at least a larger subgroup of human cancers and that can serve as effective targets for cancer eradication. Finding such antigens would move the field beyond the methods for treating CD19/CD20-expressing B cell malignancies.

The terms used throughout this disclosure are given their ordinary and accustomed meanings in the art, unless a different meaning is made clear from the text when considered in the context of the disclosure as a whole.

The disclosure describes the development and characterization of a monoclonal antibody (mAb) fragment specific to IL13Rα2 for the therapeutic purpose of targeting IL13Rα2-expressing tumors. The high affinity IL13Rα2 is selectively expressed at a high frequency by glioblastoma multiforme (GBM) as well as several other tumor types. One approach for targeting this tumor-specific receptor utilizes the cognate ligand, IL-13, conjugated to cytotoxic molecules. This approach, however, lacks specificity because the lower affinity receptor for IL-13, IL13Rα1, is widely expressed by normal tissues. A monoclonal antibody (mAb) specific to IL13Rα2 was expected to overcome the lack of specificity afflicting methodologies that recognized both IL13 receptors, i.e., IL13Rα1 as well as IL13Rα2. Such a mAb would be therapeutically useful in targeting and treating IL13Rα2-expressing cancers, including tumors.

As disclosed herein, hybridoma cell lines were generated and compared for binding affinities to recombinant human IL13Rα2 (rhIL13Rα2). Clone 47 demonstrated binding to the native conformation of IL13Rα2 and was therefore chosen for further studies. Clone 47 bound specifically and with high affinity (KD=$1.39 \times 10^{-9}$ M) to rhIL13Rα2 but not to rhIL13Rα1 or murine IL13Rα2. Furthermore, clone 47 specifically recognized wild-type IL13Rα2 expressed on the surface of CHO and HEK cells as well as several glioma cell lines. Competitive binding assays revealed that clone 47 also significantly inhibited the interaction between human soluble IL-13 and IL13Rα2 receptor. Moreover, N-linked glycosylation of IL13Rα2 contributes in part to the interaction of the antibody to IL13Rα2. In vivo, the IL13Rα2 mAb improved the survival of nude mice intracranially implanted with a human U251 glioma xenograft.

The disclosure is based, at least in part, on the discovery that IL13Rα2 is found preferentially on cancer cells such as tumor cells. This receptor functions as a cancer-, or tumor-, specific antigen that has been used to elicit the high-affinity monoclonal antibody m47, along with antigen binding fragments of that antibody. The $V_L$ and $V_H$ variable regions of the m47 antibody have been engineered into a single chain (sc) variable fragment (scFv) to generate conjugates, such as chimeric antigen receptors (i.e., CARs), for introduction into T cells for adoptive transfer. Thus, CAR-transduced T cells are expected to target a tumor-specific IL13Rα2 epitope, leading to eradication of cancer cells presenting the receptor. It is believed that CAR-transduced T cells recognizing IL13Rα2 will destroy large solid tumors. CAR-transduced T cells, however, target cancer cells only directly and antigen-negative cancer cells may escape. It is expected that CAR-transduced T cells also will be effective in eliminating antigen-negative cancer cells via the bystander effect.

The protein conjugates according to the disclosure are specific for IL13Rα2, which is associated with cancers, e.g., tumors. In addition, the disclosure provides a polynucleotide encoding one of these cancer-specific binding partners, including polynucleotides comprising codon-optimized coding regions for binding partners specific for an epitope of IL13Rα2. The polynucleotides of the disclosure encode conjugates, or bi-functional polypeptides, useful in diagnosing, preventing, treating, or ameliorating a symptom of cancer, such as any of a variety of human cancers, including those forming solid tumors. Also contemplated are vectors comprising a polynucleotide as disclosed herein, a host cell comprising such a polynucleotide and/or a vector as described above, and methods of treating, preventing or ameliorating a symptom of, a cancer disease, e.g., a solid tumor, a primary cancer site or a metastasized cancer.

The various forms of conjugates known in the art are contemplated by the disclosure. These conjugates provide exquisitely cancer—as well as protein-specific antibody receptors that can be incorporated into a variety of backbones providing effector function, such as bispecific T cell Engagers (BiTEs) or chimeric antigen receptors (CARs), as noted below. Exemplary conjugates of the disclosure include CARs, fusion proteins, including fusions comprising single-chain variable (antibody) fragment (scFv) multimers or scFv fusions to coding regions encoding products useful in treating cancer, e.g., IL-15, IL15Rα, or IL-15/IL15Rα agent, diabodies, tribodies, tetrabodies, and bispecific bivalent scFvs, including bispecific tandem bivalent scFvs, also known as bispecific T cell engagers, or BiTEs. Any of these conjugate forms, moreover, may exhibit any of various relative structures, as it is known in the art that different domain orders (e.g., $H_2N-V_H$-linker-$V_L$-$CO_2H$ and $H_2N$-$V_L$-linker-$V_H$-$CO_2H$) are compatible with specific binding. Higher order forms of the conjugates described herein are also contemplated, such as peptibodies comprising at least one form of the conjugates disclosed herein. The conjugates of the disclosure specifically bind to a cancer-specific epitope (e.g., an IL13Rα2) and the polynucleotides encoding them may be codon-optimized, e.g., for maximal translation, for expression in the targeted cells (e.g., human or mouse cells). Codon optimization in the context of expressing the conjugates of the disclosure, such as CARs, is important to ensuring that production of the protein is both efficient and robust enough to be useful as a source of therapeutic.

The disclosure also contemplates conjugates in which a targeting moiety (an anti-IL13Rα2 antibody or fragment thereof) is linked to a peptide providing a second function, e.g., an effector function, such as a T cell signaling domain involved in T cell activation, a peptide that affects or modulates an immunological response to cancer cells, or an enzymatic component of a labeling system that results in a CAR encoded by a polynucleotide according to the disclosure, if the coding region for the conjugate is codon-optimized for expression in a target cell. Exemplary conjugates include an anti-IL13Rα2 scFv linked to a hinge, a transmembrane domain, and an effector compound or domain, e.g., CD28, CD3ζ, CD134 (OX40), CD137 (41BB), ICOS, CD40, CD27, or Myd88, thereby yielding a CAR.

The polynucleotide aspect of the disclosure comprises embodiments in which an unexpected variation on codon optimization in slower-growing higher eukaryotes such as vertebrates, e.g., humans, is provided that is focused on translation optimization (maximizing high-fidelity translation rates) rather than the typical codon optimization used in such organisms, which is designed to accommodate mutational bias and thereby minimize mutation. Also disclosed are the methods of diagnosing, preventing, treating or ameliorating a symptom of a cancer. Schematically described, the polynucleotides comprise a codon-optimized coding region for an antigen receptor specifically recognizing an IL13Rα2 epitope linked to any one of the following: a coding region for a T cell signaling domain involved in T cell activation, a gene product that affects or modulates an immunological response to cancer cells such as an IL15/IL15Rα fusion, or a labeling component such as an enzymatic component of a labeling system. The linked coding regions result in polynucleotides encoding conjugates according to the disclosure, such as BiTEs or chimeric antigen receptors (CARs).

In methods of diagnosing, preventing, treating or ameliorating a symptom of a cancer, the compositions of the disclosure are typically administered in the form of a conjugate-transduced cell, such as a T cell, an NK cell, or a lymphocyte other than a T cell, although administration of a vector comprising a polynucleotide of the disclosure or administration of a polynucleotide of the disclosure are also contemplated, depending on the functionalities of the conjugate. As used throughout this disclosure, the term "identifying" and other forms of that term (e.g., identify) are used interchangeably with the term "diagnosing" and other forms of that term (e.g., diagnose). Combining a polynucleotide, vector or host cell of the disclosure with a physiologically suitable buffer, adjuvant or diluent yields a pharmaceutical composition according to the disclosure, and these pharmaceutical compositions are suitable for administration to diagnose, prevent, treat, or ameliorate a symptom of, a cancer.

In the course of experimental work described herein, hybridoma cell lines were generated and compared for binding affinities to recombinant human IL13Rα2 (rhIL13Rα2). Clone 47 demonstrated binding to the native conformation of IL13Rα2 and was therefore characterized further. Clone 47 bound specifically and with high affinity (KD $1.39 \times 10^{-9}$ M) to rhIL13Rα2 but not to rhIL13Rα1 or murine IL13Rα2. Furthermore, clone 47 specifically recognized wild-type IL13Rα2 expressed on the surface of CHO and HEK cells as well as several glioma cell lines. Competitive binding assays revealed that clone 47 also significantly inhibited the interaction between human soluble IL-13 and IL13Rα2 receptor. Moreover, N-linked glycosylation of IL13Rα2 was found to contribute, in part, to the interaction of the antibody with IL13Rα2. In vivo, the IL13Rα2 monoclonal antibody improved the survival of nude mice intracranially implanted with a human U251 glioma xenograft. Collectively, these data establish the efficacy of the immunomodulatory treatment of cancer disclosed herein.

Overexpression of IL13Rα2 in gliobastoma multiforme (GBM) but not in normal brain tissue uniquely positions this receptor as a candidate for targeting tumor cells. GBM is a highly infiltrative tumor, often making complete surgical removal impossible. Moreover, GBM is highly resistant to radiation and chemotherapy (16), warranting further development of novel and targeted therapies for the treatment of patients.

A phage display library approach has been used to select small antibody fragments specific to human IL13Rα2, followed by their evaluation in vitro and in vivo (23). Despite the high specificity of interaction with IL13Rα2, conjugation with toxins has failed to increase cytotoxicity in IL13Rα2-expressing glioma and renal cell carcinoma cell lines when compared with the effects of IL-13PE38. The low affinity of generated antibody fragments is the most reasonable explanation for the lack of success. Antibody fragments derived from phage display libraries are known to be lower in affinity and avidity than antibodies generated by conventional hybridoma technology (24). Modifications of those small antibody fragments are often required to enhance their affinity and avidity to targeted proteins. In recent years, monoclonal antibodies have shown increasing success as targeted anticancer and diagnostic agents (25, 26), and a further search for high affinity reagents with restricted specificity to tumor-associated antigens is needed. The experiments disclosed herein were designed to discover, develop, and characterize a high affinity antibody that specifically recognizes IL13Rα2 expressed on the surface of cancer cells. Consistent with that design, disclosed herein are experiments establishing the generation of an antibody possessing the properties critical for immunotherapeutic targeting of IL13Rα2-expressing tumors in vivo, and potentially suitable for various other applications.

Monoclonal antibodies appear to be valuable research and diagnostic tools as well as therapeutic agents. Monoclonal antibodies specific for tumor-associated antigens have significant advantages over systemic chemotherapies due to the ability to specifically target cancer cells while avoiding interaction with untransformed tissue. Therefore, the search for novel "magic bullets" continues to grow, confirmed by a global market for therapeutic antibodies worth $48 billion as of 2010. Therapeutic antibodies are products of traditional hybridoma technology or screening of libraries for antibody fragments and their subsequent engineering into humanized fragments or full size molecules. Prior to this study, the hybridoma cell line secreting a high affinity antibody to the tumor-specific antigen IL13Rα2 was unavailable to the scientific community. Here, we describe the generation and characterization of a high affinity antibody to the tumor-specific antigen IL13Rα2 and discuss its potential use in different applications.

The specificity of interaction of newly discovered antibodies to human IL13Rα2 was analyzed by ELISA using the rhIL13Rα2hFc fusion protein, recombinant human IL13Rα2 expressed on the surface of CHO and HEK cells, and several glioma cell lines expressing IL13Rα2 at various levels by flow cytometry. The antibody identified herein, and agent using the binding domain thereof, demonstrated a specificity of interaction to human IL13Rα2 and did not cross-react with human IL13Rα1 or mouse IL13Rα2. Moreover, the specificity of binding to IL13Rα2 was confirmed in competitive binding assays using rhIL13Rα2hFc fusion protein by ELISA or by flow cytometry for detection of IL13Rα2 expressed on the surface of HEK cells. In these assays, IL13Rα2 (clone 47) mAb competed with recombinant human IL-13 for its epitope and was able to block about 80% of the binding between IL-13 and IL13Rα2. Conversely, human recombinant IL-13 was able to block about 50% of antibody binding to IL13Rα2. Similarly, a significant decrease in the binding of IL13Rα2 (clone 47) mAb to N10 glioma cells was observed when rhIL13R2hFc chimera and rhIL-13 were used as competitors. The binding of rhIL-13 to N10 cells was also abolished by IL13Rα2 (clone 47) mAb. These data indicate that the two molecules have significant overlap in their recognition sites for IL13Rα2.

IL-13 is a small 10-kDa molecule (31), whereas an antibody is about 15 times greater in molecular mass. The ability of rhIL-13 to compete with an antibody for a binding site suggests that the inhibitory property of the antibody is likely due to the specific interaction with amino acid residues contributing to the binding of IL-13 to the cognate receptor rather than to steric hindrance, which can also prevent the interaction of IL-13 with its receptor. Previously, Tyr207, Asp271, Tyr315, and Asp318 were identified as critical residues of IL13Rα2 necessary for interaction with IL-13 (28). In the assays disclosed herein, the binding of IL-13 to a mutant IL13Rα2 carrying a combination of all 4 amino acid mutations to alanine was significantly abolished when compared with the wild-type receptor. Binding of the IL13Rα2 mAb to either the individual or the 4-amino acid mutant form of IL13Rα2, however, was not significantly affected. These findings indicate that Tyr207, Asp271, Tyr315, and Asp318 residues are not critical for the recognition of IL13Rα2 by the IL13Rα2 mAb. The human IL13Rα2 and murine IL13Rα2 are structurally conserved and share 59% amino acid identity (32). Moreover, Tyr207, Asp271, Tyr315, and Asp318 residues are conserved in human and murine IL13Rα2. Absence of binding of the IL13Rα2 mAb to murine IL13Rα2hFc fusion further supports the expectation that these amino acid residues contribute to the binding of IL-13 to IL13Rα2 and are not critical for the interaction of this antibody with the receptor.

To further characterize the interaction of IL13Rα2 with the antibody and antibody agent disclosed herein, the affinity of the IL13Rα2 mAb was measured and compared with the binding properties of two commercially available antibodies using the surface plasmon resonance method. The affinity of the IL13Rα2 mAb was determined to be equal to $1.39 \times 10^{-9}$ M, greatly exceeding the affinity of comparable commercially available antibodies by up to 75-fold. In agreement with the affinity studies, the IL13Rα2 mAb (clone 47) demonstrated superiority to two commercial antibodies in binding to the IL13Rα2 expressed on the surface of various glioma cells and in ELISA. Although many properties of antibodies, including the affinity and avidity, in vivo stability, rate of clearance and internalization, tumor penetration, and retention, should be considered prior to specific usage, it has been reported that higher affinity antibodies are better for immunotherapeutic tumor-targeting applications (33). The single chain antibody fragment (scFv) MR1-1 against epidermal growth factor receptor variant III demonstrates about 15-fold higher affinity than the parental scFvMR1 and also showed on average a 244% higher tumor uptake than that for the scFvMR1 (34). It is likely that the high affinity properties of the IL13Rα2 mAb and agent thereof that are disclosed herein will be advantageous for applications utilizing antibodies or associated derivatives for targeting tumor cells expressing IL13Rα2.

The N-linked glycosylation of IL13Rα2 has been identified as a necessary requirement for efficient binding to IL-13 (30). Taking into consideration that the IL13Rα2 mAb disclosed herein inhibits about 80% of IL-13 binding to the cognate receptor, IL13Rα2, it is reasonable to expect that the binding of this antibody, or an agent containing its binding domain, with the deglycosylated form of IL13Rα2 could also be affected. The IL13Rα2 molecule has four potential sites of N-linked glycosylation. The binding of the antibody to rhIL13Rα2 or to IL13Rα2 expressed on the surface of HEK or U251 cells treated with Pngase F was decreased by 35 and 30%, respectively, when compared with non-treated control. A partial change in binding activity for the clone 47 when compared with clones 83807 and B-D13 suggests that removal of carbohydrate adducts from IL13Rα2 with Pngase F causes conformational changes of the receptor, indirectly affecting the binding of both IL-13 (30) and the IL13Rα2 mAb to IL13Rα2. This also supports the expectation that the antibody binds directly to the IL13Rα2 amino acid backbone rather than interacting with carbohydrate moieties added post-translationally. Supporting this expectation, several studies have previously demonstrated that the conformational profile and structural rigidity of proteins depends on N-linked glycosylation (22, 35-38).

To investigate the therapeutic properties of the IL13Rα2 mAb and its agent, an in vivo study was performed whereby glioma cells and the IL13Rα2 (clone 47) mAb were intracranially co-injected into brain, or antibody was injected into established tumor-bearing mice. Interestingly, the IL13Rα2 mAb was able to delay tumor progression and improve survival of animals with intracranial U251 glioma xenografts most significantly in the co-injected model, demonstrating a trend in the improvement of median survival in animals with established glioma. Although the underlying mechanism for this antitumor effect remains unclear, the result establishes the therapeutic applicability of this antibody, or its agent (containing the IL13Rα2 binding domain in the form of the six CDR regions, or in the form of the two variable domains of the clone 47 anti-IL13Rα2), alone or in combination with a pharmaceutical carrier, thereby providing therapies for the treatment of IL13Rα2-expressing glial and other lineage tumors. Several antibodies have been shown to mediate a cytotoxic effect in tumors through Fc-mediated activation of complement (39). Antibody-dependent cell-mediated cytotoxicity-induced activation of effector cells can also contribute to the cytotoxic effect of antibodies against targeted cells (40, 41). Anti-IL13Rα2 activity derived from the sera of animals challenged with D5 melanoma cells expressing human IL13Rα2 demonstrates the ability to inhibit cellular growth in vitro (4).

Cancers amenable to the described treatments include cancers in which IL13Rα2 has been found to be expressed, including glioblastoma; medulloblastoma; Kaposi sarcoma; and head and neck, ovarian, pancreatic, kidney, and colorectal cancers (2, 43-47). Although the role of IL13Rα2 in some cancers is not yet defined, recent reports have demonstrated that IL13Rα2 contributes to the invasive phenotype of ovarian, pancreatic, and colorectal cancers (5, 13). Moreover, Minn et al. (42) have suggested a relationship between IL13Rα2 expression and breast cancer metastasis to the lung. Additionally, Fichtner-Feigl et al. (11) demonstrated that the interaction of IL-13 with IL13Rα2 upregulates TGF-β1, mediating fibrosis in a bleomycin-induced model of lung fibrosis. In light of this finding, it is expected that the anti-IL13Rα2 antibody (clone 47) and binding agents thereof, will be able to attenuate TGF-β1-induced pulmonary fibrosis.

As disclosed herein, the described experiments led to the generation of an anti-IL13Rα2 antibody and binding agents thereof, all of which are specific to human IL13Rα2. The antibody and its agent possess a high affinity for IL13Rα2 and compete with IL-13 for the binding site on IL13Rα2. The antibody recognizes antigen expressed on the cell surface of glioma cells as well as other IL13Rα2-expressing cells, establishing the suitability for targeting IL13Rα2-expressing tumor cells in vivo. The anti-IL13Rα2 antibody and binding agents thereof are also expected to be efficacious and cost effective in diagnostic imaging, delivery of antibody radionuclide conjugates, bioassays for the detection of IL13Rα2, and as a carrier for therapeutic agents in various types of IL13Rα2-overexpressing tumors.

In methods of diagnosing, preventing, treating or ameliorating a symptom of a cancer, the compositions of the disclosure are typically administered in the form of conjugate-transduced T cells, although administration of a vector comprising a polynucleotide of the disclosure or administration of a polynucleotide of the disclosure are also contemplated, depending on the functionalities of the conjugate. Combining a polynucleotide, vector or host cell of the disclosure with a physiologically suitable buffer, adjuvant or diluent yields a pharmaceutical composition according to the disclosure, and these pharmaceutical compositions are suitable for administration to diagnose, prevent, treat, or ameliorate a symptom of, a cancer.

A conjugate according to the disclosure, such as a fusion protein composed of an scFv-receptor for an IL13Rα2 epitope fused to IL15/IL15Rα, is also contemplated. It is expected that the fusion protein will eliminate clinical size tumors or only incipient and microdisseminated cancer cells. The disclosure further contemplates the simultaneous targeting of two independent IL13Rα2 epitopes on a human cancer, which may be essential for preventing escape from treatment, such as CAR treatment.

Simultaneous targeting of different epitopes of IL13Rα2 by CARs should reduce the chance of escape of a cancer subpopulation, which provides a strong reason for identifying additional IL13Rα2 antibody products and/or epitopes.

The disclosure provides materials and methods that are adaptable and can serve as the basis for a platform technology with considerable growth potential. The cancer-specific nature of IL13Rα2 is expected to provide targets for cancer diagnostics, prophylactics and therapeutics that offer major advantages over previously and presently used targets.

Consistent with the spirit of the foregoing, the following provides a description of the materials and methods provided herein.

Disclosed herein are IL13Rα2 binding agents comprising each of the amino acid sequences of NYLMN (SEQ ID NO: 1); RIDPYDGDIDYNQNFKD (SEQ ID NO: 2); GYGTAYGVDY (SEQ ID NO: 3); RASESVDNYGISFMN (SEQ ID NO: 4); AASRQGSG (SEQ ID NO: 5); and QQSKEVPWT (SEQ ID NO: 6). In exemplary aspects, the binding agent comprises each of the foregoing six amino acid sequences in addition to further sequences which provide a framework to support a three-dimensional conformation that binds to IL13Rα2. In exemplary aspects, the IL13Rα2 binding agent comprises one or both of the amino acid sequences of SEQ ID NO: 7 and/or SEQ ID NO: 8. In exemplary aspects, the IL13Rα2 binding agent comprises the amino acid sequence of SEQ ID NO: 7. In exemplary aspects, the IL13Rα2 binding agent comprises the amino acid sequence of SEQ ID NO: 8. In exemplary aspects, the IL13Rα2 binding agent comprises both the amino acid sequences of SEQ ID NO: 7 and SEQ ID NO: 8. In exemplary aspects wherein both the amino acid sequences of SEQ ID NO: 7 and SEQ ID NO: 8 are present in the binding agent, the amino acid sequence of SEQ ID NO: 7 is fused to the amino acid sequence of SEQ ID NO: 8 through a linker. Suitable linkers are known in the art. In exemplary aspects, the linker comprises a short amino acid sequence of about 5 to about 25 amino acids, e.g., about 10 to about 20 amino acids. In exemplary aspects, the linker comprises the amino acid sequence of EEGEFSEAR (SEQ ID NO 10). In exemplary aspects, the linker comprises the amino acid sequence of AKTTPPKLEEGEFSEARV (SEQ ID NO: 80). In exemplary aspects, IL13Rα2 binding agent comprises the amino acid sequence of SEQ ID NO: 13.

In exemplary embodiments, the binding agent provided herein further comprises additional amino acid sequences. In exemplary aspects, the binding agent further comprises a constant region of a heavy chain and/or a constant region of a light chain. Sequences for heavy and light chain constant regions are publically available. For example, the National Center of Biotechnology Information (NCBI) nucleotide database provides a sequence of the constant region of the IgG1 kappa light chain. See GenBank Accession No. DQ381549.1, incorporated herein by reference. In exemplary aspects, the binding agent comprises an amino acid sequence of SEQ ID NO: 28. In exemplary aspects, the binding agent comprises a modified amino acid sequence of SEQ ID NO: 28. In exemplary aspects, the binding agent comprises an amino acid sequence which is at least 90%, at least 93%, at least 95%, or at least 98% identical to SEQ ID NO: 28. Also, for example, the NCBI nucleotide database provides a sequence of the constant region of the *Mus musculus* IgG1. See GenBank Accession No. DQ381544.1. In exemplary aspects, the binding agent comprises an amino acid sequence of SEQ ID NO: 29. In exemplary aspects, the binding agent comprises a modified amino acid sequence of SEQ ID NO: 29. In exemplary aspects, the binding agent comprises an amino acid sequence which is at least 90%, at least 93%, at least 95%, or at least 98% identical to SEQ ID NO: 29.

In exemplary aspects, the IL13Rα2 binding agent is an antibody, or an antigen-binding fragment thereof. In exemplary aspects, the antibody comprises each of the amino acid sequences of SEQ ID NOs: 1-6. In exemplary aspects, the antibody comprises the amino acid sequence of SEQ ID NO: 7 and/or SEQ ID NO: 8. In exemplary aspects, the antibody comprises the amino acid sequences of SEQ ID NO: 7 and SEQ ID NO: 8. In exemplary aspects, the antibody comprises the amino acid sequences of SEQ ID NO: 7 and SEQ ID NO: 8 and the amino acid sequence of SEQ ID NO: 7 is fused to the amino acid sequence of SEQ ID NO: 8 through a linker. In exemplary aspects, the linker comprises a short amino acid sequence of about 5 to about 25 amino acids, e.g., about 10 to about 20 amino acids. In exemplary aspects, the linker comprises the amino acid sequence of EEGEFSEAR (SEQ ID NO 10). In exemplary aspects, the linker comprises the amino acid sequence of AKTTPPKLEEGEFSEARV (SEQ ID NO: 80). In exemplary aspects, the antibody comprises the amino acid sequence of SEQ ID NO: 13.

In exemplary aspects, the antibody can be any type of immunoglobulin that is known in the art. For instance, the antibody can be of any isotype, e.g., IgA, IgD, IgE, IgG, or IgM. The antibody can be monoclonal or polyclonal. The antibody can be a naturally-occurring antibody, i.e., an antibody isolated and/or purified from a mammal, e.g., mouse, rabbit, goat, horse, chicken, hamster, human, and the like. In this regard, the antibody may be considered to be a mammalian antibody, e.g., a mouse antibody, rabbit antibody, goat antibody, horse antibody, chicken antibody, hamster antibody, human antibody, and the like. The term "isolated" as used herein means having been removed from its natural environment. The term "purified," as used herein relates to the isolation of a molecule or compound in a form that is substantially free of contaminants normally associated with the molecule or compound in a native or natural environment and means having been increased in purity as a result of being separated from other components of the original composition. It is recognized that "purity" is a relative term, and not to be necessarily construed as absolute purity or absolute enrichment or absolute selection. In some aspects, the purity is at least or about 50%, is at least or about 60%, at least or about 70%, at least or about 80%, or at least or about 90% (e.g., at least or about 91%, at least or about 92%, at least or about 93%, at least or about 94%, at least or about 95%, at least or about 96%, at least or about 97%, at least or about 98%, at least or about 99% or is approximately 100%.

In exemplary aspects, the antibody comprises a constant region of an IgG. In exemplary aspects, the antibody comprises a constant region of an $IgG_1$. In exemplary aspects, the antibody comprises a constant region of an IgG kappa light chain. For instance, the antibody may comprise the amino acid sequence of SEQ ID NO: 28. In exemplary aspects, the antibody comprises an amino acid sequence that is highly similar to SEQ ID NO: 28. For instance, the antibody may comprise an amino acid sequence having at least 85% sequence identity to SEQ ID NO: 28, or an amino acid sequence having at least 90% sequence identity to SEQ ID NO: 28, or an amino acid sequence having at least 93% sequence identity to SEQ ID NO: 28, or an amino acid sequence having at least 95% sequence identity to SEQ ID NO: 28, or an amino acid sequence having at least 98% sequence identity to SEQ ID NO: 28.

In exemplary aspects, the antibody comprises a constant region of a *Mus musculus* $IgG_1$. For instance, the antibody may comprise the amino acid sequence of SEQ ID NO: 30. In exemplary aspects, the antibody comprises an amino acid sequence which is highly similar to SEQ ID NO: 30. For instance, the antibody may comprise an amino acid sequence having at least 85% sequence identity to SEQ ID NO: 30, or an amino acid sequence having at least 90% sequence identity to SEQ ID NO: 30, or an amino acid sequence having at least 93% sequence identity to SEQ ID NO: 30, or an amino acid sequence having at least 95% sequence identity to SEQ ID NO: 30, or an amino acid sequence having at least 98% sequence identity to SEQ ID NO: 30.

The anti-IL13Rα2 antibodies and fragments thereof of the disclosure can have any level of affinity or avidity for IL13Rα2. The dissociation constant ($K_D$) may be any of those exemplary dissociation constants described herein with regard to binding units. Binding constants, including dissociation constants, are determined by methods known in the art, including, for example, methods that utilize the principles of surface plasmon resonance, e.g., methods utilizing a Biacore™ system. In accordance with the foregoing, in some embodiments, the antibody is in monomeric form, while in other embodiments, the antibody is in polymeric form. In certain embodiments in which the antibody comprises two or more distinct antigen binding regions or fragments, the antibody is considered bispecific, trispecific, or multi-specific, or bivalent, trivalent, or multivalent, depending on the number of distinct epitopes that are recognized and bound by the binding agent.

Because the binding agent of the disclosures can compete with IL13 for binding to IL13Rα2, the antibody in exemplary aspects is considered to be a blocking antibody or neutralizing antibody. In some aspects, the $K_D$ of the binding agent is about the same as the $K_D$ of the native ligand, IL13, for IL13Rα2. In some aspects, the $K_D$ of the binding agent is lower (e.g., at least 0.5-fold lower, at least 1-fold lower, at least 2-fold lower, at least 5-fold lower, at least 10-fold lower, at least 25-fold lower, at least 50-fold lower, at least 75-fold lower, at least 100-fold lower) than the $K_D$ of IL13 for IL13Rα2. In exemplary aspects, the $K_D$ is between about 0.0001 nM and about 100 nM. In some embodiments, the $K_D$ is at least or about 0.0001 nM, at least or about 0.001 nM, at least or about 0.01 nM, at least or about 0.1 nM, at least or about 1 nM, or at least or about 10 nM. In some embodiments, the $K_D$ is no more than or about 100 nM, no more than or about 75 nM, no more than or about 50 nM, or no more than or about 25 nM. In exemplary aspects, the antibody has a $K_D$ for human IL13Rα2 that is no greater than about $1.39 \times 10^{-9}$ M.

In exemplary aspects, the binding agent, e.g., antibody, or antigen binding fragment thereof, does not bind to human IL13Rα1.

In exemplary embodiments, the antibody is a genetically engineered antibody, e.g., a single chain antibody, a humanized antibody, a chimeric antibody, a CDR-grafted antibody, an antibody that includes portions of CDR sequences specific for IL13Rα2 (e.g., an antibody that includes CDR sequences of SEQ ID NOs: 1-6), a humaneered or humanized antibody, a bispecific antibody, a trispecific antibody, and the like, as defined in greater detail herein. Genetic engineering techniques also provide the ability to make fully human antibodies in a non-human.

In some aspects, the antibody is a chimeric antibody. The term "chimeric antibody" is used herein to refer to an antibody containing constant domains from one species and the variable domains from a second, or more generally, containing stretches of amino acid sequence from at least two species.

In some aspects, the antibody is a humanized antibody. The term "humanized" when used in relation to antibodies is used to refer to antibodies having at least CDR regions from a nonhuman source that are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence, as would be known in the art.

Use of the terms "chimeric or humanized" herein is not meant to be mutually exclusive; rather, is meant to encompass chimeric antibodies, humanized antibodies, and chimeric antibodies that have been further humanized. Except where context otherwise indicates, statements about (properties of, uses of, testing, and so on) chimeric antibodies apply to humanized antibodies, and statements about humanized antibodies pertain also to chimeric antibodies. Likewise, except where context dictates, such statements also should be understood to be applicable to antibodies and antigen binding fragments of such antibodies.

In some aspects of the disclosure, the binding agent is an antigen binding fragment of an antibody that specifically binds to an IL13Rα2 in accordance with the disclosure. The antigen binding fragment (also referred to herein as "antigen binding portion") may be an antigen binding fragment of any of the antibodies described herein. The antigen binding fragment can be any part of an antibody that has at least one antigen binding site, including, but not limited to, Fab, F(ab')₂, dsFv, sFv, diabodies, triabodies, bis-scFvs, fragments expressed by a Fab expression library, domain antibodies, VhH domains, V-NAR domains, V_H domains, V_L domains, and the like. Antibody fragments of the invention, however, are not limited to these exemplary types of antibody fragments.

In exemplary aspects, the IL13Rα2 binding agent is an antigen binding fragment. In exemplary aspects, the antigen binding fragment comprises each of the amino acid sequences of SEQ ID NOs: 1-6. In exemplary aspects, the antigen binding fragment comprises the amino acid sequence of SEQ ID NO: 7 and/or SEQ ID NO: 8. In exemplary aspects, the antigen binding fragment comprises the amino acid sequences of SEQ ID NO: 7 and SEQ ID NO: 8. In exemplary aspects, the antigen binding fragment comprises the amino acid sequences of SEQ ID NO: 7 and SEQ ID NO: 8 and the amino acid sequence of SEQ ID NO: 7 is fused to the amino acid sequence of SEQ ID NO: 8 through a linker. In exemplary aspects, the linker comprises a short amino acid sequence of about 5 to about 25 amino acids, e.g., about 10 to about 20 amino acids. In exemplary aspects, the linker comprises the amino acid sequence of EEGEFSEAR (SEQ ID NO 10). In exemplary aspects, the linker comprises the amino acid sequence of AKTTPPKLEEGEFSEARV (SEQ ID NO: 80). In exemplary aspects, the antigen binding fragment provided herein comprises the amino acid sequence of SEQ ID NO: 13.

In exemplary aspects, the antigen binding fragment comprises a leader sequence. Optionally, the leader sequence, in some aspects, is located N-terminal to the heavy chain variable region. In exemplary aspects, the antigen binding fragment comprises an Ig kappa leader sequence. Suitable leader sequences are known in the art, and include, for example, an Ig kappa leader sequence of METDTLLLWVLLLWVPGSTGD (SEQ ID NO: 9).

In exemplary aspects, an antigen binding fragment comprises one more tag sequences. Tag sequences may assist in the production and characterization of the manufactured antigen binding fragment. In exemplary aspects, the antigen binding fragment comprises one or more tag sequences C-terminal to the light chain variable region. Suitable tag sequences are known in the art and include, but are not limited to, Myc tags, His tags, and the like. In exemplary aspects, an antigen binding fragment comprises a Myc tag of GGPEQKLISEEDLN (SEQ ID NO: 11). In exemplary aspects, an antigen binding fragment comprises a His tag sequence of HHHHHHH (SEQ ID NO: 12).

In exemplary aspects, the antigen binding fragment of the disclosures comprises, from the N- to the C-terminus, a leader sequence, a heavy chain variable region, a linker sequence, a light chain variable region, a Myc tag (e.g., SEQ ID NO: 11), and a His tag (e.g., SEQ ID NO: 12). In exemplary aspects, the antigen binding fragment of the disclosure comprises the amino acid sequence of SEQ ID NO: 14.

In exemplary aspects, the antigen binding fragment is a domain antibody. A domain antibody comprises a functional binding unit of an antibody, and can correspond to the variable regions of either the heavy ($V_H$) or light ($V_L$) chains of antibodies. A domain antibody can have a molecular weight of approximately 13 kDa, or approximately one-tenth the weight of a full antibody. Domain antibodies may be derived from full antibodies, such as those described herein. The antigen binding fragments in some embodiments are monomeric or polymeric, bispecific or trispecific, and bivalent or trivalent.

Antibody fragments that contain the antigen binding, or idiotope, of the antibody molecule share a common idiotype and are contemplated by the disclosure. Such antibody fragments may be generated by techniques known in the art and include, but are not limited to, the F(ab')₂ fragment which may be produced by pepsin digestion of the antibody molecule; the Fab' fragments which may be generated by reducing the disulfide bridges of the F(ab')₂ fragment, and the two Fab' fragments which may be generated by treating the antibody molecule with papain and a reducing agent.

In exemplary aspects, the binding agent provided herein is a single-chain variable region fragment (scFv) antibody fragment. An scFv may consist of a truncated Fab fragment comprising the variable (V) domain of an antibody heavy chain linked to a V domain of an antibody light chain via a synthetic peptide, and it can be generated using routine recombinant DNA technology techniques (see, e.g., Janeway et al., *Immunobiology*, 2nd Edition, Garland Publishing, New York, (1996)). Similarly, disulfide-stabilized variable region fragments (dsFv) can be prepared by recombinant DNA technology (see, e.g., Reiter et al., Protein Engineering, 7, 697-704 (1994)).

In exemplary aspects, the IL13Rα2 binding agent provided herein is an scFv. In exemplary aspects, the scFv comprises each of the amino acid sequences of SEQ ID NOs: 1-6. In exemplary aspects, the scFv comprises the amino acid sequence of SEQ ID NO: 7 or SEQ ID NO: 8. In exemplary aspects, the scFv comprises the amino acid sequences of SEQ ID NO: 7 and SEQ ID NO: 8. In exemplary aspects, the scFv comprises the amino acid sequences of SEQ ID NO: 7 and SEQ ID NO: 8 and the amino acid sequence of SEQ ID NO: 7 is fused to the amino acid sequence of SEQ ID NO: 8 through a linker. In exemplary aspects, the linker comprises a short amino acid sequence of about 5 to about 25 amino acids, e.g., about 10 to about 20 amino acids. In exemplary aspects, the linker comprises the amino acid sequence of EEGEFSEAR (SEQ ID NO 10). In exemplary aspects, the linker comprises the amino acid sequence of AKTTPPKLEEGEFSEARV (SEQ ID NO: 80). In exemplary aspects, the scFv provided herein comprises the amino acid sequence of SEQ ID NO: 13.

Recombinant antibody fragments, e.g., scFvs of the disclosure, can also be engineered to assemble into stable multimeric oligomers of high binding avidity and specificity to different target antigens. Such diabodies (dimers), triabodies (trimers) or tetrabodies (tetramers) are well known in the art. See e.g., Kortt et al., Biomol Eng. 2001 18:95-108, (2001) and Todorovska et al., *J Immunol Methods*. 248:47-66, (2001).

In exemplary aspects, the binding agent is a bispecific antibody (bscAb). Bispecific antibodies are molecules comprising two single-chain Fv fragments joined via a glycine-serine linker using recombinant methods. The V light-chain ($V_L$) and V heavy-chain ($V_H$) domains of two antibodies of interest in exemplary embodiments are isolated using standard PCR methods. The $V_L$ and $V_H$ cDNAs obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present invention. Exemplary bispecific antibodies are taught in U.S. Patent Application Publication No. 2005-0282233A1 and International Patent Application Publication No. WO 2005/087812, both applications of which are incorporated herein by reference in their entireties.

In exemplary aspects, the binding agent is a bispecific T-cell engaging antibody (BiTE) containing two scFvs produced as a single polypeptide chain. In exemplary aspects, the binding agent is a BiTE comprising two scFVs, wherein at least one comprises each of the amino acid sequences of SEQ ID NOs: 1-6 or comprises SEQ ID NO: 7 and/or SEQ ID NO: 8. Methods of making and using BiTE antibodies are described in the art. See, e.g., Cioffi et al., *Clin Cancer Res* 18: 465, Brischwein et al., *Mol Immunol* 43:1129-43 (2006); Amann M et al., *Cancer Res* 68:143-51 (2008); Schlereth et al., *Cancer Res* 65: 2882-2889 (2005); and Schlereth et al., *Cancer Immunol Immunother* 55:785-796 (2006).

In exemplary aspects, the binding agent is a dual affinity re-targeting antibody (DART). DARTs are produced as separate polypeptides joined by a stabilizing interchain disulphide bond. In exemplary aspects, the binding agent is a DART comprising an scFv comprising each of the amino acid sequences of SEQ ID NOs: 1-6 or comprises SEQ ID NO: 7 and/or SEQ ID NO: 8. Methods of making and using DART antibodies are described in the art. See, e.g., Rossi et al., *MAbs* 6: 381-91 (2014); Fournier and Schirrmacher, *BioDrugs* 27:35-53 (2013); Johnson et al., *J Mol Biol* 399:436-449 (2010); Brien et al., *J Virol* 87: 7747-7753 (2013); and Moore et al., *Blood* 117:4542 (2011).

In exemplary aspects, the binding agent is a tetravalent tandem diabody (TandAbs) in which an antibody fragment is produced as a non covalent homodimer folder in a head-to-tail arrangement. In exemplary aspects, the binding agent is a TandAbs comprising an scFv comprising each of the amino acid sequences of SEQ ID NOs: 1-6 or comprises SEQ ID NO: 7 and/or SEQ ID NO: 8. TandAbs are known in the art. See, e.g., McAleese et al., *Future Oncol* 8: 687-695 (2012); Portner et al., *Cancer Immunol Immunother* 61:1869-1875 (2012); and Reusch et al., *MAbs* 6:728 (2014).

In exemplary aspects, the BiTE, DART, or TandAbs comprises the CDRs of SEQ ID NOs: 1-6. In exemplary aspects, the BiTE, DART, or TandAbs comprises the amino acid sequence of SEQ ID NOs: 7 and 8. In exemplary aspects, the BiTE, DART, or TandAbs comprises SEQ ID NOs: 13.

Suitable methods of making antibodies are known in the art. For instance, standard hybridoma methods are described in, e.g., Harlow and Lane (eds.), Antibodies: A Laboratory Manual, CSH Press (1988), and CA. Janeway et al. (eds.), Immunobiology, 5$^{th}$ Ed., Garland Publishing, New York, NY (2001)).

Monoclonal antibodies for use in the invention may be prepared using any technique that provides for the production of antibody molecules by continuous cell lines in culture. These include, but are not limited to, the hybridoma technique originally described by Koehler and Milstein (Nature 256: 495-497, 1975), the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985).

Briefly, a polyclonal antibody is prepared by immunizing an animal with an immunogen comprising a polypeptide of the present invention and collecting antisera from that immunized animal. A wide range of animal species can be used for the production of antisera. In some aspects, an animal used for production of anti-antisera is a non-human animal including rabbits, mice, rats, hamsters, goat, sheep, pigs or horses. Because of the relatively large blood volume of rabbits, a rabbit, in some exemplary aspects, is a preferred choice for production of polyclonal antibodies. In an exemplary method for generating a polyclonal antisera immunoreactive with the chosen IL13Rα2 epitope, 50 μg of IL13Rα2 antigen is emulsified in Freund's Complete Adjuvant for immunization of rabbits. At intervals of, for example, 21 days, 50 μg of epitope are emulsified in Freund's Incomplete Adjuvant for boosts. Polyclonal antisera may be obtained, after allowing time for antibody generation, simply by bleeding the animal and preparing serum samples from the whole blood.

Briefly, in exemplary embodiments, to generate monoclonal antibodies, a mouse is injected periodically with recombinant IL13Rα2 against which the antibody is to be raised (e.g., 10-20 μg IL13Rα2 emulsified in Freund's Complete Adjuvant). The mouse is given a final pre-fusion boost of a IL13Rα2 polypeptide containing the epitope that allows specific recognition of lymphatic endothelial cells in PBS, and four days later the mouse is sacrificed and its spleen removed. The spleen is placed in 10 ml serum-free RPMI 1640, and a single cell suspension is formed by grinding the spleen between the frosted ends of two glass microscope slides submerged in serum-free RPMI 1640, supplemented with 2 mM L-glutamine, 1 mM sodium pyruvate, 100 units/ml penicillin, and 100 μg/ml streptomycin (RPMI) (Gibco, Canada). The cell suspension is filtered through sterile 70-mesh Nitex cell strainer (Becton Dickinson, Parsippany, N.J.), and is washed twice by centrifuging at 200 g for 5 minutes and resuspending the pellet in 20 ml serum-free RPMI. Splenocytes taken from three naive Balb/c mice are prepared in a similar manner and used as a control. NS-1 myeloma cells, kept in log phase in RPMI with 11% fetal bovine serum (FBS) (Hyclone Laboratories, Inc., Logan, Utah) for three days prior to fusion, are centrifuged at 200 g for 5 minutes, and the pellet is washed twice.

Spleen cells ($1 \times 10^8$) are combined with $2.0 \times 10^7$ NS-1 cells and centrifuged, and the supernatant is aspirated. The cell pellet is dislodged by tapping the tube, and 1 ml of 37° C. PEG 1500 (50% in 75 mM Hepes, pH 8.0) (Boehringer Mannheim) is added with stirring over the course of 1 minute, followed by the addition of 7 ml of serum-free RPMI over 7 minutes. An additional 8 ml RPMI is added and the cells are centrifuged at 200 g for 10 minutes. After discarding the supernatant, the pellet is resuspended in 200 ml RPMI containing 15% FBS, 100 μM sodium hypoxanthine, 0.4 μM aminopterin, 16 μM thymidine (HAT) (Gibco), 25 units/ml IL-6 (Boehringer Mannheim) and $1.5 \times 10^6$ splenocytes/ml and plated into 10 Corning flat-bottom 96-well tissue culture plates (Corning, Corning N.Y.).

On days 2, 4, and 6, after the fusion, 100 μl of medium is removed from the wells of the fusion plates and replaced with fresh medium. On day 8, the fusion is screened by ELISA, testing for the presence of mouse IgG binding to IL13Rα2 as follows. Immulon 4 plates (Dynatech, Cambridge, Mass.) are coated for 2 hours at 37° C. with 100 ng/well of IL13Rα2 diluted in 25 mM Tris, pH 7.5. The coating solution is aspirated and 200 μl/well of blocking solution (0.5% fish skin gelatin (Sigma) diluted in CMF-PBS) is added and incubated for 30 minutes at 37° C. Plates are washed three times with PBS containing 0.05% Tween 20 (PBST) and 50 μl culture supernatant is added. After incubation at 37° C. for 30 minutes, and washing as above, 50 μl of horseradish peroxidase-conjugated goat anti-mouse IgG(Fc) (Jackson ImmunoResearch, West Grove, Pa.) diluted 1:3500 in PBST is added. Plates are incubated as above, washed four times with PBST, and 100 μl substrate, consisting of 1 mg/ml o-phenylene diamine (Sigma) and 0.1 μl/ml 30% $H_2O_2$ in 100 mM citrate, pH 4.5, are added. The color reaction is stopped after 5 minutes with the addition of 50 μl of 15% $H_2SO_4$. The $A_{490}$ absorbance is determined using a plate reader (Dynatech).

Selected fusion wells are cloned twice by dilution into 96-well plates and visual scoring of the number of colonies/well after 5 days. The monoclonal antibodies produced by hybridomas are isotyped using the Isostrip system (Boehringer Mannheim, Indianapolis, Ind.).

When the hybridoma technique is employed, myeloma cell lines may be used. Such cell lines suited for use in hybridoma-producing fusion procedures preferably are non-antibody-producing, have high fusion efficiency, and enzyme deficiencies that render them incapable of growing in certain selective media that support the growth of only the desired fused cells (hybridomas). For example, where the immunized animal is a mouse, one may use P3-X63/Ag8, P3-X63-Ag8.653, NS1/1.Ag 41, Sp210-Ag14, FO, NSO/U, MPC-11, MPC11-X45-GTG 1.7 and S194/15XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions. It should be noted that the hybridomas and cell lines produced by such techniques for producing the monoclonal antibodies are contemplated to be compositions of the disclosure.

Depending on the host species, various adjuvants may be used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Alternatively, other methods, such as EBV-hybridoma methods (Haskard and Archer, J. Immunol. Methods, 74(2), 361-67 (1984), and Roder et al.,₅ Methods Enzymol., 121, 140-67 (1986)), and bacteriophage vector expression systems (see, e.g., Huse et al., Science, 246, 1275-81 (1989)) that are known in the art may be used. Further, methods of producing antibodies in non-human animals are described in, e.g., U.S. Pat. Nos. 5,545,806, 5,569,825, and 5,714,352, and U.S. Patent Application Publication No. 2002/0197266 A1).

Antibodies may also be produced by inducing in vivo production in the lymphocyte population or by screening recombinant immunoglobulin libraries or panels of highly specific binding reagents as disclosed in Orlandi et al. (Proc. Natl. Acad. Sci. 86: 3833-3837; 1989), and Winter and Milstein (Nature 349: 293-299, 1991).

Furthermore, phage display can be used to generate an antibody of the disclosure. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150). Related methods also are described in U.S. Pat. Nos. 5,403,484; 5,571,698; 5,837, 500; and 5,702,892. The techniques described in U.S. Pat. Nos. 5,780,279; 5,821,047; 5,824,520; 5,855,885; 5,858, 657; 5,871,907; 5,969,108; 6,057,098; and 6,225,447, are also contemplated as useful in preparing antibodies according to the disclosure.

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539; 5,585,089; and 5,693,761; European Patent No. 0239400 B1; and United Kingdom Patent No. 2188638. Humanized antibodies can also be generated using the antibody resurfacing technology described in U.S. Pat. No. 5,639,641 and Pedersen et al., J. Mol. Biol., 235:959-973 (1994).

Techniques developed for the production of "chimeric antibodies," the splicing of mouse antibody genes to human antibody genes to obtain a molecule with appropriate antigen specificity and biological activity, can be used (Morrison et al., Proc. Natl. Acad. Sci. 81: 6851-6855, 1984; Neuberger et al., Nature 312: 604-608, 1984; and Takeda et al., Nature 314: 452-454; 1985). Alternatively, techniques described for the production of single-chain antibodies (U.S. Pat. No. 4,946,778) can be adapted to produce IL13Rα2-specific single chain antibodies.

A preferred chimeric or humanized antibody has a human constant region, while the variable region, or at least a CDR, of the antibody is derived from a non-human species. Methods for humanizing non-human antibodies are well known in the art. (see U.S. Pat. Nos. 5,585,089, and 5,693, 762). Generally, a humanized antibody has one or more amino acid residues introduced into a CDR region and/or into its framework region from a source which is non-human. Humanization can be performed, for example, using methods described in Jones et al. (*Nature* 321: 522-525, 1986), Riechmann et al., (*Nature,* 332: 323-327, 1988) and Verhoeyen et al. (*Science* 239:1534-1536, 1988), by substituting at least a portion of a rodent complementarity-determining region (CDR) for the corresponding region of a human antibody. Numerous techniques for preparing engineered antibodies are described, e.g., in Owens and Young, *J. Immunol. Meth.,* 168:149-165 (1994). Further changes can then be introduced into the antibody framework to modulate affinity or immunogenicity.

Consistent with the foregoing description, compositions comprising CDRs may be generated using, at least in part, techniques known in the art to isolate CDRs. Complementarity-determining regions are characterized by six polypeptide loops, three loops for each of the heavy or light chain variable regions. The amino acid position in a CDR is defined by Kabat et al., "Sequences of Proteins of Immunological Interest," U.S. Department of Health and Human Services, (1983), which is incorporated herein by reference. For example, hypervariable regions of human antibodies are roughly defined to be found at residues 28 to 35, from 49-59 and from residues 92-103 of the heavy and light chain variable regions [Janeway et al., supra]. The murine CDRs also are found at approximately these amino acid residues. It is understood in the art that CDR regions may be found within several amino acids of the approximated amino acid positions set forth above. An immunoglobulin variable region also consists of four "framework" regions surrounding the CDRs (FR1-4). The sequences of the framework regions of different light or heavy chains are highly conserved within a species, and are also conserved between human and murine sequences.

Compositions comprising one, two, and/or three CDRs of a heavy chain variable region or a light chain variable region of a monoclonal antibody are generated. For example, using antibody of hybridoma clone 47 comprising the CDRs having the sequences of SEQ ID NOs: 1-6, polypeptide compositions comprising these CDRs are generated. Polypeptide compositions comprising one, two, three, four, five and/or six complementarity-determining regions of an antibody are also contemplated. Using the conserved framework sequences surrounding the CDRs, PCR primers complementary to these consensus framework sequences are generated to amplify the CDR sequence located between the primer regions. Techniques for cloning and expressing nucleotide and polypeptide sequences are well-established in the art [see e.g., Sambrook et al., Molecular Cloning: A Laboratory Manual, 2nd Edition, Cold Spring Harbor, New York (1989)]. The amplified CDR sequences are ligated into an appropriate plasmid. The plasmid comprising one, two, three, four, five and/or six cloned CDRs optionally contains additional polypeptide encoding regions linked to the CDR.

It is contemplated that modified polypeptide compositions comprising one, two, three, four, five, or six CDRs of a heavy or light chain of SEQ ID NOs: 1-6 are generated, wherein a CDR is altered to provide increased specificity or affinity or avidity to the target IL13Rα2. Sites at locations in the CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the target site.

Framework regions (FR) of a murine antibody are humanized by substituting compatible human framework regions chosen from a large database of human antibody variable sequences, including over twelve hundred human $V_H$ sequences and over one thousand $V_L$ sequences. The database of antibody sequences used for comparison is downloaded from Andrew C. R. Martin's KabatMan web page (http://www.rubic.rdg.ac.uk/abs/). The Kabat method for identifying CDRs provides a means for delineating the approximate CDR and framework regions of any human antibody and comparing the sequence of a murine antibody for similarity to determine the CDRs and FRs. Best matched human $V_H$ and $V_L$ sequences are chosen on the basis of high overall framework matching, similar CDR length, and minimal mismatching of canonical and $V_H/V_L$ contact residues. Human framework regions most similar to the murine sequence are inserted between the murine CDRs. Alternatively, the murine framework region may be modified by making amino acid substitutions of all or part of the native framework region that more closely resemble a framework region of a human antibody.

"Conservative" amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E). "Insertions" or "deletions" are preferably in the range of about 1 to 20 amino acids, more preferably 1 to 10 amino acids. The variation may be introduced by systematically making substitutions of amino acids in a polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for expressing polypeptide compositions useful in the invention are described in greater detail below.

Additionally, another useful technique for generating antibodies for use in the methods of the disclosure may be one which uses a rational design-type approach. The goal of rational design is to produce structural analogs of biologically active polypeptides or compounds with which they interact (agonists, antagonists, inhibitors, peptidomimetics, binding partners, and the like). In this case, the active polypeptides comprise the sequences of SEQ ID NOs: 1-6 disclosed herein. By creating such analogs, it is possible to fashion additional antibodies which are more immunoreactive than the native or natural molecule. In one approach, one would generate a three-dimensional structure for the antibodies or an epitope binding fragment thereof. This could be accomplished by x-ray crystallography, computer modeling or by a combination of both approaches. An alternative approach, "alanine scan," involves the random replacement of residues throughout a molecule with alanine, and the resulting effect on function is determined.

It also is possible to solve the crystal structure of the specific antibodies. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype antibody is expected to be an analog of the original antigen. The anti-idiotype antibody is then be used to identify and isolate additional antibodies from banks of chemically- or biologically-produced peptides.

Chemically synthesized bispecific antibodies may be prepared by chemically crosslinking heterologous Fab or F(ab')$_2$ fragments by means of chemicals such as heterobifunctional reagent succinimidyl-3-(2-pyridyldithiol)-propionate (SPDP, Pierce Chemicals, Rockford, Ill.). The Fab and F(ab')$_2$ fragments can be obtained from intact antibody by digesting it with papain or pepsin, respectively (Karpovsky et al., J. Exp. Med. 160:1686-701, 1984; Titus et al., J. Immunol., 138:4018-22, 1987).

Methods of testing antibodies for the ability to bind to the epitope of the IL13Rα2, regardless of how the antibodies are produced, are known in the art and include any antibody-antigen binding assay such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Selection of antibodies from an antibody population for purposes herein also include using blood vessel endothelial cells to "subtract" those antibodies that cross-react with epitopes on such cells other than IL13Rα2 epitopes. The remaining antibody population is enriched in antibodies preferential for IL13Rα2 epitopes.

Aptamers

Recent advances in the field of combinatorial sciences have identified short polymer sequences (e.g., oligonucleic acid or peptide molecules) with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds, and phage display has been utilized to discover new peptide sequences with very favorable binding properties. Based on the success of these molecular evolution techniques, it is certain that molecules can be created which bind to any target molecule. A loop structure is often involved with providing the desired binding attributes as in the case of aptamers, which often utilize hairpin loops created from short regions without complementary base pairing, naturally derived antibodies that utilize combinatorial arrangement of looped hyper-variable regions and new phage-display libraries utilizing cyclic peptides that have shown improved results when compared to linear peptide phage display results. Thus, sufficient evidence has been generated to indicate that high affinity ligands can be created and identified by combinatorial molecular evolution techniques. For the present disclosure, molecular evolution techniques can be used to isolate binding agents specific for the IL13Rα2 disclosed herein. For more on aptamers, see generally, Gold, L., Singer, B., He, Y. Y., Brody. E., "Aptamers As Therapeutic And Diagnostic Agents," J. Biotechnol. 74:5-13 (2000). Relevant techniques for generating aptamers are found in U.S. Pat. No. 6,699,843, which is incorporated herein by reference in its entirety.

In some embodiments, the aptamer is generated by preparing a library of nucleic acids; contacting the library of nucleic acids with a growth factor, wherein nucleic acids having greater binding affinity for the growth factor (relative to other library nucleic acids) are selected and amplified to yield a mixture of nucleic acids enriched for nucleic acids with relatively higher affinity and specificity for binding to the growth factor. The processes may be repeated, and the selected nucleic acids mutated and rescreened, whereby a growth factor aptamer is identified. Nucleic acids may be screened to select for molecules that bind to more than target. Binding more than one target can refer to binding more than one simultaneously or competitively. In some embodiments, a binding agent comprises at least one aptamer, wherein a first binding unit binds a first epitope of an IL13Rα2 and a second binding unit binds a second epitope of the IL13Rα2.

With regard to the binding agents of the compositions of the disclosure, ligand-induced activation of the IL13Rα2 is reduced upon binding of the binding agent to the IL13Rα2. As used herein, the term "reduce" as well as like terms, e.g., "inhibit," do not necessarily imply 100% or a complete reduction or inhibition. Rather, there are varying degrees of reduction or inhibition of which one of ordinary skill in the art recognizes as having a potential benefit or therapeutic effect. Accordingly, in some embodiments, ligand-induced activation of the IL13Rα2 is completely abolished. In some embodiments, ligand-induced activation is substantially reduced, e.g., reduced by about 10% (e.g., by about 20%, by about 30%, by about 40%, by about 50%, by about 60%, by about 70%, by about 80%, by about 90%) or more, as compared to ligand-induced activation of the IL13Rα2 when the binding agent is absent or not bound to the IL13Rα2. Methods of measuring ligand-induced activation of an IL13Rα2 are known in the art, and include, for example, the assays described in the Examples, below.

Conjugates

Conjugates comprising a targeting domain and an effector domain are disclosed herein. In exemplary embodiments, the conjugate comprises any one of the binding agents disclosed herein as the targeting domain to localize the conjugate to a cell expressing IL13Rα2, e.g., a tumor cell expressing the same, and an effector domain. In exemplary aspects, the conjugate is a fusion protein. In exemplary aspects, the conjugate is a chimeric protein. As used herein, the term "chimeric" refers to a molecule composed of parts of different origins. A chimeric molecule, as a whole, is non-naturally occurring, e.g., synthetic or recombinant, although the parts which comprise the chimeric molecule may be naturally occurring.

Exemplary Effector Domains

As used herein, the term "effector domain" refers to a portion of a conjugate that effects a desired biological function. In exemplary aspects, the effector domain identifies or locates IL13Rα2-expressing cells. For example, the effector domain may be a diagnostic agent, e.g., a radiolabel, a fluorescent label, an enzyme (e.g., that catalyzes a calorimetric or fluorometric reaction), a substrate, a solid matrix, or a carrier (e.g., biotin or avidin). The diagnostic agent in some aspects is an imaging agent. Many appropriate imaging agents are known in the art, as are methods of attaching the labeling agents to the peptides of the invention (see, e.g., U.S. Pat. Nos. 4,965,392; 4,472,509; 5,021,236; and 5,037,630; each incorporated herein by reference). The imaging agents are administered to a subject in a pharmaceutically acceptable carrier, and allowed to accumulate at a target site having the lymphatic endothelial cells. This imaging agent then serves as a contrast reagent for X-ray, magnetic resonance, positron emission tomography, single photon emission computed tomography (SPECT), or sonographic or scintigraphic imaging of the target site. Of course, it should be understood that the imaging may be performed in vitro where tissue from the subject is obtained through a biopsy, and the presence of lymphatic endothelial cells is determined with the aid of the imaging agents described herein in combination with histochemical techniques for preparing and fixing tissues. Paramagnetic ions useful in the imaging agents of the invention include for example chromium (III), manganese (II), iron (III), iron (II), cobalt (II), nickel (II) copper (II), neodymium (III), samarium (III), ytterbium(III), gadolinium (III), vanadium (II), terbium (III), dysprosium (III), holmium (III) and erbium (III). Ions useful for X-ray imaging include, but are not limited to, lanthanum (III), gold (III), lead (II) and particularly bismuth (III). Radioisotopes for diagnostic applications include for example, $^{211}$astatine, $^{14}$carbon, $^{51}$chromium, $^{16}$chlorine, $^{57}$cobalt, $^{67}$copper, 52europium, 67gallium, hydrogen, $^{123}$iodine, $^{125}$iodine, $^{111}$indium, $^{59}$iron, $^{32}$phosphorus, $^{186}$rhenium, $^{75}$selenium, $^{35}$sulphur, $^{99}$mtechnicium, $^{90}$yttrium, and $^{89}$zirconium.

The effector domain may be one which alters the physicochemical characteristics of the conjugate, e.g., an effector which confers increased solubility and/or stability and/or half-life, resistance to proteolytic cleavage, modulation of clearance. In exemplary aspects, the effector domain is a polymer, a carbohydrate, or a lipid.

The polymer may be branched or unbranched. The polymer may be of any molecular weight. The polymer in some embodiments has an average molecular weight of between about 2 kDa to about 100 kDa (the term "about" indicating that in preparations of a water-soluble polymer, some molecules will weigh more, some less, than the stated molecular weight). The average molecular weight of the polymer is in some aspects between about 5 kDa and about 50 kDa, between about 12 kDa to about 40 kDa or between about 20 kDa to about 35 kDa. In some embodiments, the polymer is modified to have a single reactive group, such as an active ester for acylation or an aldehyde for alkylation, so that the degree of polymerization may be controlled. The polymer in some embodiments is water soluble so that the protein to which it is attached does not precipitate in an aqueous environment, such as a physiological environment. In some embodiments when, for example, the composition is used for therapeutic use, the polymer is pharmaceutically acceptable. Additionally, in some aspects, the polymer is a mixture of polymers, e.g., a co-polymer, a block co-polymer. In some embodiments, the polymer is selected from the group consisting of: polyamides, polycarbonates, polyalkylenes and derivatives thereof, including polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene. In some aspects, the polymer is a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion. In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). In some embodiments, the polymer is a water-soluble polymer or a hydrophilic polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In some aspects, the water-soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C10) alkoxy- or aryloxy-polyethylene glycol); monomethoxy-polyethylene glycol; dextran (such as low molecular weight dextran of, for example, about 6 kD), cellulose; other carbohydrate-based polymers, poly-(N-vinyl pyrrolidone), polyethylene glycol, propylene glycol homopolymers, a polypropylene oxide/ethylene oxide co-polymer, polyoxyethylated polyols (e.g., glycerol) and polyvinyl alcohol. Also encompassed by the disclosure are bifunctional crosslinking molecules which may be used to prepare covalently attached multimers. A particularly preferred water-soluble polymer for use herein is polyethylene glycol (PEG). As used herein, polyethylene glycol is meant to encompass any of the forms of PEG that can be used to derivatize other proteins, such as mono-(C1-C10) alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophobic nature, thus creating a water shell or hydration sphere when attached to other proteins or polymer surfaces. PEG is nontoxic, non-immunogenic, and approved by the Food and Drug Administration for internal consumption. Proteins or enzymes when conjugated to PEG have demonstrated bioactivity, non-antigenic properties, and decreased clearance rates when administered in animals. F. M. Veronese et al., Preparation and Properties of Monomethoxypoly(ethylene glycol)-modified Enzymes for Therapeutic Applications, in J. M. Harris ed., Poly(Ethylene Glycol) Chemistry—Biotechnical and Biomedical Applications, 127-36, 1992, incorporated herein by reference. Without wishing to be bound by theory, these phenomena may be due to the exclusion properties of PEG in preventing recognition by the immune system. In addition, PEG has been widely used in surface modification procedures to decrease protein adsorption and improve blood compatibility. S. W. Kim et al., Ann. N.Y. Acad. Sci. 516: 116-30 1987; Jacobs et al., Artif. Organs 12: 500-501, 1988; Park et al., J. Poly. Sci, Part A 29:1725-31, 1991, each incorporated herein by reference in its entirety. Hydrophobic polymer surfaces, such as polyurethanes and polystyrene, can be modified by the grafting of PEG (MW 3,400) and employed as nonthrombogenic surfaces. Surface properties (contact angle) can be more consistent with hydrophilic surfaces, due to the hydrating effect of PEG. More importantly, protein (albumin and other plasma proteins) adsorption can be greatly reduced, resulting from the high chain motility, hydration sphere, and protein exclusion properties of PEG. PEG (MW 3,400) was determined as an optimal size in surface immobilization studies, Park et al., J. Biomed. Mat. Res. 26:739-45, 1992, while PEG (MW 5,000) was most beneficial in decreasing protein antigenicity. F. M. Veronese et al., In J. M. Harris, et al., Poly (Ethylene Glycol) Chemistry—Biotechnical and Biomedical Applications, 127-36. Methods for preparing pegylated binding agent polypeptides may comprise the steps of (a) reacting the polypeptide with polyethylene glycol (such as a reactive ester or aldehyde derivative of PEG) under conditions whereby the binding agent polypeptide becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-pegylated product. In some embodiments, the binding agent will have a single PEG moiety at the N-terminus. See U.S. Pat. No. 8,234,784, incorporated by reference herein.

In some embodiments, the effector domain is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (e.g., a starch, amylase, amylopectin, cellulose, chitin, callose, laminarin, xylan, mannan, fucoidan, or galactomannan).

In some embodiments, the effector domain is a lipid. The lipid, in some embodiments, is a fatty acid, eicosanoid, prostaglandin, leukotriene, thromboxane, N-acyl ethanolamine, glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, or a phospholipid.

Lethal Domains

In exemplary aspects, the effector domain is a lethal domain that confers lethality, such that when the conjugate is localized to a cell expressing IL13Rα2, e.g., a tumor cell expressing the same. The effector domain confers upon the conjugate the ability to kill an IL13Rα2-expressing cell once the binding agent has found and bound to its IL13Rα2 target.

In exemplary aspects, the effector domain is a cytotoxin (also referred to herein as a "cytotoxic agent"). The cytotoxic agent is any molecule (chemical or biochemical) which is toxic to a cell. In some embodiments, the cytotoxic agent is a chemotherapeutic agent. Chemotherapeutic agents are known in the art and include, but are not limited to, platinum coordination compounds, topoisomerase inhibitors, antibiotics, antimitotic alkaloids and difluoronucleosides, as described in U.S. Pat. No. 6,630,124. In some embodiments, the chemotherapeutic agent is a platinum coordination compound. The term "platinum coordination compound" refers to any tumor cell growth-inhibiting platinum coordination compound that provides the platinum in the form of an ion. In some embodiments, the platinum coordination compound is cis-diamminediaquoplatinum (II)-ion; chloro(diethylenetriamine)-platinum(II)chloride; dichloro(ethylenediamine)-platinum(II), diammine(1,1-cyclobutanedicarboxylato) platinum(II) (carboplatin); spiroplatin; iproplatin; diammine(2-ethylmalonato)-platinum(II); ethylenediaminemalonatoplatinum(II); aqua(1,2-diaminodyclohexane)-sulfatoplatinum(II); (1,2-diaminocyclohexane)malonatoplatinum(II); (4-caroxyphthalato)(1,2-diaminocyclohexane) platinum(II); (1,2-diaminocyclohexane)-(isocitrato) platinum(II); (1,2-diaminocyclohexane)cis(pyruvato) platinum(II); (1,2-diaminocyclohexane)oxalatoplatinum(II); ormaplatin; or tetraplatin. In some embodiments, cisplatin is the platinum coordination compound employed in the compositions and methods of the present invention. Cisplatin is commercially available under the name PLATINOL™ from Bristol Myers-Squibb Corporation and is available as a powder for constitution with water, sterile saline or other suitable vehicle. Other platinum coordination compounds suitable for use in the present invention are known and are available commercially and/or can be prepared by conventional techniques. Cisplatin, or cis-dichlorodiammineplatinum II, has been used successfully for many years as a chemotherapeutic agent in the treatment of various human solid malignant tumors. More recently, other diamino-platinum complexes have also shown efficacy as chemotherapeutic agents in the treatment of various human, solid, malignant tumors. Such diamino-platinum complexes include, but are not limited to, spiroplatinum and carboplatinum. Although cisplatin and other diamino-platinum complexes have been widely used as chemotherapeutic agents in humans, they have had to be delivered at high dosage levels that can lead to toxicity problems such as kidney damage.

In some embodiments, the chemotherapeutic agent is a topoisomerase inhibitor. Topoisomerases are enzymes that are capable of altering DNA topology in eukaryotic cells. They are critical for cellular functions and cell proliferation. Generally, there are two classes of topoisomerases in eukaryotic cells, type I and type II. Topoisomerase I is a monomeric enzyme of approximately 100,000 molecular weight. The enzyme binds to DNA and introduces a transient single-strand break, unwinds the double helix (or allows it to unwind), and subsequently reseals the break before dissociating from the DNA strand. Various topoisomerase inhibitors have recently shown clinical efficacy in the treatment of humans afflicted with ovarian cancer, esophageal cancer or non-small cell lung carcinoma. In some aspects, the topoisomerase inhibitor is camptothecin or a camptothecin analog. Camptothecin is a water-insoluble, cytotoxic alkaloid produced by Camptotheca accuminata trees indigenous to China and Nothapodytes *foetida* trees indigenous to India. Camptothecin exhibits tumor cell growth-inhibiting activity against a number of tumor cells. Compounds of the camptothecin analog class are typically specific inhibitors of DNA topoisomerase I. By the term "inhibitor of topoisomerase" is meant any tumor cell growth-inhibiting compound that is structurally related to camptothecin. Compounds of the camptothecin analog class include, but are not limited to; topotecan, irinotecan and 9-amino-camptothecin. In additional embodiments, the cytotoxic agent is any tumor cell growth-inhibiting camptothecin analog claimed or described in U.S. Pat. No. 5,004,758; European Patent Application Number 88311366.4 (Publication Number EP 0 321 122); U.S. Pat. No. 4,604,463; European Patent Application Publication Number EP 0 137 145; U.S. Pat. No. 4,473,692; European Patent Application Publication Number EP 0 074 256; U.S. Pat. No. 4,545,880; European Patent Application Publication Number EP 0 074 256; European Patent Application Publication Number EP 0 088 642; Wani et al., J. Med. Chem., 29, 2358-2363 (1986); and Nitta et al., Proc. 14th International Congr. Chemotherapy, Kyoto, 1985, Tokyo Press, Anticancer Section 1, p. 28-30. In particular, the disclosure contemplates a compound called CPT-11. CPT-11 is a camptothecin analog with a 4-(piperidino)-piperidine side chain joined through a carbamate linkage at C-10 of 10-hydroxy-7-ethyl camptothecin. CPT-11 is currently undergoing human clinical trials and is also referred to as irinotecan; Wani et al, J. Med. Chem., 23, 554 (1980); Wani et. al., J. Med. Chem., 30, 1774 (1987); U.S. Pat. No. 4,342,776; European Patent Application Publication Number EP 418 099; U.S. Pat. No. 4,513,138; European Patent Application Publication Number EP 0 074 770; U.S. Pat. No. 4,399,276; European Patent Application Publication Number 0 056 692; the entire disclosure of each of which is hereby incorporated by reference. All of the above-listed compounds of the camptothecin analog class are available commercially and/or can be prepared by conventional techniques including those described in the above-listed references. The topoisomerase inhibitor may be selected from the group consisting of topotecan, irinotecan and 9-aminocamptothecin.

The preparation of numerous compounds of the camptothecin analog class (including pharmaceutically acceptable salts, hydrates and solvates thereof) as well as the preparation of oral and parenteral pharmaceutical compositions comprising such a compound of the camptothecin analog class and an inert, pharmaceutically acceptable carrier or diluent, is extensively described in U.S. Pat. No. 5,004,758; and European Patent Application Number 88311366.4 (Publication Number EP 0 321 122), the teachings of each of which are incorporated herein by reference in its entirety.

In still another embodiment of the invention, the chemotherapeutic agent is an antibiotic compound. Suitable antibiotics include, but are not limited to, doxorubicin, mitomycin, bleomycin, daunorubicin and streptozocin. In some embodiments, the chemotherapeutic agent is an antimitotic alkaloid. In general, antimitotic alkaloids can be extracted from *Catharanthus roseus*, and have been shown to be efficacious as anticancer chemotherapy agents. A great number of semi-synthetic derivatives have been studied both chemically and pharmacologically (see, O. Van Tellingen et al, Anticancer Research, 12, 1699-1716 (1992)). The antimitotic alkaloids of the present invention include, but are not limited to, vinblastine, vincristine, vindesine, Taxol and vinorelbine. The latter two antimitotic alkaloids are commercially available from Eli Lilly and Company, and Pierre Fabre Laboratories, respectively (see, U.S. Pat. No. 5,620,985). In one aspect of the disclosure, the antimitotic alkaloid is vinorelbine.

In another embodiment of the invention, the chemotherapeutic agent is a difluoronucleoside. 2'-deoxy-2',2'-difluoronucleosides are known in the art as having antiviral activity. Such compounds are disclosed and taught in U.S. Pat. Nos. 4,526,988 and 4,808,614. European Patent Application Publication 184,365 discloses that these same difluoronucleosides have oncolytic activity. In certain specific aspects, the 2'-deoxy-2',2'-difluoronucleoside used in the compositions and methods of the disclosure is 2'-deoxy-2',2'-difluorocytidine hydrochloride, also known as gemcitabine hydrochloride. Gemcitabine is commercially available or can be synthesized in a multi-step process as disclosed in U.S. Pat. Nos. 4,526,988, 4,808,614 and 5,223,608, the teachings of each of which are incorporated herein by reference in its entirety.

In exemplary aspects, the effector domain is an apoptosis tag which causes the IL13Rα2-expressing cell to apoptose. In exemplary aspects, the apoptosis tag is a TRAIL protein, or a portion thereof. In exemplary aspects, the apoptosis tag comprises the amino acid sequence of SEQ ID NO: 27. In exemplary aspects, the conjugate comprises the amino acid sequence of SEQ ID NO: 25.

In exemplary embodiments, the effector domain is an Fc domain of IgG or other immunoglobulin. For substituents such as an Fc region of human IgG, the fusion can be fused directly to a binding agent or fused through an intervening sequence. For example, a human IgG hinge, CH2 and CH3 region may be fused at either the N-terminus or C-terminus of a binding agent to attach the Fc region. The resulting Fc-fusion agent enables purification via a Protein A affinity column (Pierce, Rockford, Ill.). Peptide and proteins fused to an Fc region can exhibit a substantially greater half-life in vivo than the unfused counterpart. A fusion to an Fc region allows for dimerization/multimerization of the fusion polypeptide. The Fc region may be a naturally occurring Fc region, or may be modified for superior characteristics, e.g., therapeutic qualities, circulation time, reduced aggregation. As noted above, in some embodiments, the binding agent are conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md., incorporated herein by reference. In related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in the blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for antibody-dependent cell-mediated cytotoxicity (ADCC) and complement-dependent cytotoxicity (CDC). Examples of positions within the Fc region that make a direct contact with FcγR are amino acids 234-239 (lower hinge region), amino acids 265-269

(B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J Immunol. 175:6694-701, 2005). Amino acid residues involved in IgE receptor binding are described in Sayers et al. (J Biol Chem. 279 (34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each of which is incorporated by reference herein in its entirety.

In some embodiments, the binding agent is fused to alkaline phosphatase (AP). Methods for making Fc or AP fusion agents are provided in WO 02/060950.

Chimeric Antigen Receptors (CARs)

In exemplary aspects, the effector domain is a T-cell signaling domain. In exemplary aspects, the conjugate is a chimeric antigen receptor (CAR). Chimeric antigen receptors (CARs) are engineered transmembrane proteins that combine the specificity of an antigen-specific antibody with a T-cell receptor's function. In general, CARs comprise an ectodomain, a transmembrane domain, and an endodomain. The ectodomain of a CAR in exemplary aspects comprises an antigen recognition region, which may be an scFV of an antigen-specific antibody. The ectodomain also in some embodiments comprises a signal peptide which directs the nascent protein into the endoplasmic reticulum. In exemplary aspects, the ectodomain comprises a spacer which links the antigen recognition region to the transmembrane domain. The transmembrane (TM) domain is the portion of the CAR which traverses the cell membrane. In exemplary aspects, the TM domain comprises a hydrophobic alpha helix. In exemplary aspects, the TM domain comprises all or a portion of the TM domain of CD28. In exemplary aspects, the TM domain comprises all or a portion of the TM domain of CD8a. The endodomain of a CAR comprises one or more signaling domains. In exemplary aspects, the endodomain comprises the zeta chain of CD3, which comprises three copies of the Immunoreceptor Tyrosine-based Activation Motif (ITAM). An ITAM generally comprises a Tyr residue separated by two amino acids from a Leu or Ile. In the case of immune cell receptors, e.g., the T cell receptor and the B cell receptor, the ITAMs occur in multiples (at least two) and each ITAM is separated from another by 6-8 amino acids. The endodomain of CARs may also comprises additional signaling domains, e.g., portions of proteins that are important for downstream signal transduction. In exemplary aspects, the endodomain comprises signaling domains from one or more of CD28, 41BB or 4-1BB (CD137), ICOS, CD27, CD40, OX40 (CD134), or Myd88. Sequences encoding signaling domains of such proteins are provided herein as SEQ ID NOs: 39-42, 68-79, 81, and 83. Methods of making CARs, expressing them in cells, e.g., T-cells, and utilizing the CAR-expressing T-cells in therapy, are known in the art. See, e.g., International Patent Application Publication Nos. WO2014/208760, WO2014/190273, WO2014/186469, WO2014/184143, WO2014180306, WO2014/179759, WO2014/153270, U.S. Application Publication Nos. US20140369977, US20140322212, US20140322275, US20140322183, US20140301993, US20140286973, US20140271582, US20140271635, US20140274909, European Application Publication No. 2814846, each of which are incorporated by reference in their entirety.

In exemplary aspects, the conjugate of the disclosure is an IL13Rα2-specific chimeric antigen receptor (CAR) comprising a binding agent described herein, a hinge region, and an endodomain comprising a signaling domain of a CD3 zeta chain and a signaling domain of CD28, CD134, and/or CD137. In exemplary aspects, the CAR comprises (A) each of the amino acid sequence of: NYLMN (SEQ ID NO: 1); RIDPYDGDIDYNQNFKD (SEQ ID NO: 2); GYGTAYGVDY (SEQ ID NO: 3); RASESVDNYGISFMN (SEQ ID NO: 4); AASRQGSG (SEQ ID NO: 5); and QQSKEVPWT (SEQ ID NO: 6), (B) a hinge region; and (C) an endodomain comprising a signaling domain of a CD3 zeta chain and a signaling domain of CD28, CD134, and/or CD137. In exemplary aspects, the CD3 zeta chain signaling domain comprises the amino acid sequence of SEQ ID NO: 41. In exemplary aspects, the CAR further comprises a transmembrane (TM) domain based on the TM domain of CD28. In exemplary aspects, the CAR comprises the amino acid sequence of SEQ ID NO: 47. In exemplary aspects, the CAR further comprises a transmembrane (TM) domain based on the TM domain of CD8a. In exemplary aspects, the CAR comprises the amino acid sequence of SEQ ID NO: 85. In exemplary aspects, the hinge region comprises the amino acid sequence of SEQ ID NO: 35 or SEQ ID NO: 37. In exemplary aspects, the CAR comprises the amino acid sequence of SEQ ID NO: 49 or SEQ ID NO: 51. In exemplary aspects, the endodomain of the CAR of the disclosures comprises the amino acid sequence of SEQ ID NO: 53 or SEQ ID NO: 55. In exemplary aspects, the endodomain of the CAR of the disclosure comprises the amino acid sequence of SEQ ID NO: 87 or SEQ ID NO: 89. In exemplary aspects, the endodomain of the CAR of the disclosure comprises the amino acid sequence of SEQ ID NO: 91, SEQ ID NO: 93 or SEQ ID NO: 95. In exemplary aspects, the endodomain of the CAR of the disclosure comprises the amino acid sequence of SEQ ID NO: 97, SEQ ID NO: 99 or SEQ ID NO: 101.

In exemplary aspects, the endodomain further comprises a signaling domain of one or more of: CD137, CD134, CD27, CD40, ICOS, and Myd88. In exemplary aspects, the endodomain comprises one or more of the amino acid sequences of SEQ ID NOs: 68, 70, 72, 74, 76, and 78, which provide a sequence comprising a CD27 signaling domain, a sequence comprising a CD40 signaling domain, a sequence comprising a CD134 signaling domain, a sequence comprising a CD137 signaling domain, a sequence comprising an ICOS signaling domain, and a sequence comprising a Myd88 signaling domain, respectively.

In exemplary aspects, the CAR comprises (A) each of the amino acid sequence of: NYLMN (SEQ ID NO: 1); RIDPYDGDIDYNQNFKD (SEQ ID NO: 2); GYGTAYGVDY (SEQ ID NO: 3); RASESVDNYGISFMN (SEQ ID NO: 4); AASRQGSG (SEQ ID NO: 5); and QQSKEVPWT (SEQ ID NO: 6), (B) a hinge region; (C) an endodomain comprising a signaling domain of a CD3 zeta chain and a signaling domain of CD28 and at least one other signaling domain. In exemplary aspects, the CAR comprises an endodomain comprising a signaling domain of 41BB (CD137). In exemplary aspects the CAR comprises an endodomain comprising an amino acid sequence of SEQ ID NO: 81. In exemplary aspects, the CD137 signaling is N-terminal to a CD3 zeta chain signaling chain. In exemplary aspects, the endodomain comprises the amino acid sequence of SEQ ID NO: 87. In exemplary aspects, the CAR comprises the amino acid sequence of SEQ ID NO: 91. In exemplary aspects, the CAR comprises the amino acid sequence of SEQ ID NO: 97.

In exemplary aspects, the CAR comprises an endodomain comprising a signaling domain of OX40 (CD134). In exemplary aspects the CAR comprises an endodomain comprising an amino acid sequence of SEQ ID NO: 83. In exemplary aspects, the CD137 signaling is N-terminal to a CD3 zeta chain signaling chain. In exemplary aspects, the endodomain comprises the amino acid sequence of SEQ ID NO: 89. In exemplary aspects, the CAR comprises the amino acid sequence of SEQ ID NO: 95. In exemplary aspects, the CAR comprises the amino acid sequence of SEQ ID NO: 99.

In exemplary aspects, the CAR comprises (A) each of the amino acid sequence of: NYLMN (SEQ ID NO: 1); RIDPYDGDIDYNQNFKD (SEQ ID NO: 2); GYGTAYGVDY (SEQ ID NO: 3); RASESVDNYGISFMN (SEQ ID NO: 4); AASRQGSG (SEQ ID NO: 5); and QQSKEVPWT (SEQ ID NO: 6), (B) a hinge region; (C) a transmembrane domain of CD8a chain, and (D) an endodomain comprising a signaling domain of a CD3 zeta chain, and, optionally, at least one other signaling domain. In exemplary aspects, the transmembrane domain comprises the amino acid sequence of SEQ ID NO: 85. In exemplary aspects, the CAR further comprises a CD137 signaling domain and a CD3 zeta chain signaling domain. In exemplary aspects, the CAR comprises the amino acid sequence of SEQ ID NO: 93. In exemplary aspects, the CAR comprises the amino acid sequence of SEQ ID NO: 101.

As an example, sequences of three additional IL13Rα2-specific CARs are provided. One CAR contains a CD8a TM domain, and a 41BB.zeta signaling domain (SEQ ID NO:93 encoded by SEQ ID NO:94). The other two CARs contain a CD28 TM domain and either a CD28.CD134.zeta (SEQ ID NO:99 encoded by SEQ ID NO:100) or CD28.CD137.zeta (SEQ ID NO:101 encoded by SEQ ID NO:102) signaling domain.

Nucleic Acids, Vectors, Host Cells

Further provided by the disclosures is a nucleic acid comprising a nucleotide sequence encoding any of the binding agents and conjugates (e.g., chimeric proteins, fusion proteins, CARs) described herein. The nucleic acid may comprise any nucleotide sequence which encodes any of the binding agents and conjugates described herein. In exemplary aspects, the nucleic acid comprises a nucleotide sequence encoding each of the CDRs of SEQ ID NOs: 1-6. In exemplary aspects, the nucleic acid of the disclosures comprises a nucleic acid sequence which encodes a SEQ ID NO: 7 and/or SEQ ID NO: 8. In exemplary aspects, the nucleic acid of the disclosures comprises a nucleic acid sequence which encodes SEQ ID NO: 13 or SEQ ID NO: 14. In exemplary aspects, the nucleic acid provided herein comprises the sequence of SEQ ID NO: 15 and/or SEQ ID NO: 16. In exemplary aspects, the nucleic acid comprises a nucleotide sequence of SEQ ID NO: 66 or 67. In exemplary aspects, the nucleic acid comprises a nucleotide sequence which encodes the sequence of SEQ ID NO: 25. In exemplary aspects, the nucleic acid comprises a nucleotide sequence of SEQ ID NO: 26. In exemplary aspects, the nucleic acid comprises a nucleotide sequence which encodes each of SEQ ID NOs: 1-6 and encodes SEQ ID NO: 28 or 30. In exemplary aspects, the nucleic acid comprises a nucleotide sequence which encodes each of SEQ ID NOs: 1-6 and encodes an amino acid sequence which is at least 90% identical to SEQ ID NO: 28 or 30. In exemplary aspects, the nucleic acid comprises a nucleotide sequence which encodes each of SEQ ID NOs: 1-6 and comprises SEQ ID NO: 29 or 31. In exemplary aspects, the nucleic acid comprises a nucleotide sequence which encodes SEQ ID NO: 33. In exemplary aspects, the nucleic acid comprises a nucleotide sequence of SEQ ID NO: 34. In exemplary aspects, the nucleic acid comprises a nucleotide sequence which encodes each of SEQ ID NOs: 1-6 and encodes SEQ ID NO: 35 or 37. In exemplary aspects, the nucleic acid comprises a nucleotide sequence which encodes each of SEQ ID NOs: 1-6 and comprises SEQ ID NO: 36 or 38. In exemplary aspects, the nucleic acid comprises a nucleotide sequence which encodes each of SEQ ID NOs: 1-6 and encodes SEQ ID NO: 39 or 41. In exemplary aspects, the nucleic acid comprises a nucleotide sequence which encodes each of SEQ ID NOs: 1-6 and comprises SEQ ID NO: 40 or 42. In exemplary aspects, the nucleic acid comprises a nucleotide sequence which encodes each of SEQ ID NOs: 1-6 and encodes SEQ ID NO: 47. In exemplary aspects, the nucleic acid comprises a nucleotide sequence which encodes each of SEQ ID NOs: 1-6 and comprises SEQ ID NO: 48. In exemplary aspects, the nucleic acid comprises a nucleotide sequence which encodes each of SEQ ID NOs: 1-6 and encodes SEQ ID NO: 49 or 51. In exemplary aspects, the nucleic acid comprises a nucleotide sequence which encodes each of SEQ ID NOs: 1-6 and comprises SEQ ID NO: 50 or 52. In exemplary aspects, the nucleic acid comprises a nucleotide sequence which encodes SEQ ID NO: 53 or 55. In exemplary aspects, the nucleic acid comprises a nucleotide sequence which encodes each of SEQ ID NOs: 1-6 and comprises SEQ ID NO: 54 or 56. In exemplary aspects, the nucleic acid comprises a nucleotide sequence which encodes each of SEQ ID NOs: 1-6 and encodes one or more of SEQ ID NOs: 68, 70, 72, 74, 76, and 78. In exemplary aspects, the nucleic acid comprises a nucleotide sequence which encodes each of SEQ ID NOs: 1-6 and comprises one or more of SEQ ID NOs: 69, 71, 73, 75, 77, and 79. In exemplary aspects, the nucleic acid comprises a nucleotide sequence which encodes each of SEQ ID NOs: 1-6 and comprises one or more of SEQ ID NOs: 82, 84, 86, 88, 90, 92, 94, 96. In exemplary aspects, the nucleic acid comprises a nucleotide sequence comprising one of SEQ ID NOs: 98, 100, and 102.

By "nucleic acid" as used herein includes "polynucleotide," "oligonucleotide," and "nucleic acid molecule," and generally means a polymer of DNA or RNA, which may be single-stranded or double-stranded, synthesized or obtained (e.g., isolated and/or purified) from natural sources, which may contain natural, non-natural or altered nucleotides, and which may contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In exemplary aspects, the nucleic acids of the disclosures are recombinant. As used herein, the term "recombinant" refers to (i) molecules that are constructed outside living cells by joining natural or synthetic nucleic acid segments to nucleic acid molecules that may replicate in a living cell, or (ii) molecules that result from the replication of those described in (i) above. For purposes herein, the replication may be in vitro replication or in vivo replication.

The nucleic acids in exemplary aspects are constructed based on chemical synthesis and/or enzymatic ligation reactions using procedures known in the art. See, for example, Sambrook et al., supra, and Ausubel et al., supra. For example, a nucleic acid may be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that may be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the disclosures may be purchased from companies, such as Macromolecular Resources (Fort Collins, CO) and Synthegen (Houston, TX).

The nucleic acids of the disclosures in exemplary aspects are incorporated into a recombinant expression vector. In this regard, the disclosures provides recombinant expression vectors comprising any of the nucleic acids of the disclosures. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the disclosures are not naturally-occurring as a whole. However, parts of the vectors may be naturally-occurring. The inventive recombinant expression vectors may comprise any type of nucleotides, including, but not limited to DNA and RNA, which may be single-stranded or double-stranded, synthesized or obtained in part from natural sources, and which may contain natural, non-natural or altered nucleotides. The recombinant expression vectors may comprise naturally-occurring or non-naturally occurring internucleotide linkages, or both types of linkages. In exemplary aspects, the altered nucleotides or non-naturally occurring internucleotide linkages do not hinder the transcription or replication of the vector.

The recombinant expression vector of the disclosures may be any suitable recombinant expression vector, and may be used to transform or transfect any suitable host. Suitable vectors include those designed for propagation and expansion or for expression or both, such as plasmids and viruses. The vector may be selected from the group consisting of the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGTIO, λGTI 1, λZapII (Stratagene), λEMBL4, and λNMI 149, also may be used. Examples of plant expression vectors include pBIO1, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors of the disclosures may be prepared using standard recombinant DNA techniques described in, for example, Sambrook et al., supra, and Ausubel et al., supra. Constructs of expression vectors, which are circular or linear, may be prepared to contain a replication system functional in a prokaryotic or eukaryotic host cell. Replication systems may be derived, e.g., from ColE1, 2μ plasmid, λ, SV40, bovine papilloma virus, and the like.

In exemplary aspects, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector may include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector may comprise a native or normative promoter operably linked to the nucleotide sequence encoding the binding agent or conjugate or to the nucleotide sequence which is complementary to or which hybridizes to the nucleotide sequence encoding the binding agent or conjugate. The selection of promoters, e.g., strong, weak, inducible, tissue-specific and developmental-specific, is within the ordinary skill of the artisan.

Similarly, the combining of a nucleotide sequence with a promoter is also within the skill of the artisan. The promoter may be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors may be designed for either transient expression, for stable expression, or for both. Also, the recombinant expression vectors may be made for constitutive expression or for inducible expression. Further, the recombinant expression vectors may be made to include a suicide gene.

As used herein, the term "suicide gene" refers to a gene that causes the cell expressing the suicide gene to die. The suicide gene may be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews. Springer, Caroline J. (Maycer Research UK Centre for Maycer Therapeutics at the Institute of Maycer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

The disclosures further provides a host cell comprising any of the nucleic acids or vectors described herein. As used herein, the term "host cell" refers to any type of cell that may contain the nucleic acid or vector described herein. In exemplary aspects, the host cell is a eukaryotic cell, e.g., plant, animal, fungi, or algae, or may be a prokaryotic cell, e.g., bacteria or protozoa. In exemplary aspects, the host cells is a cell originating or obtained from a subject, as described herein. In exemplary aspects, the host cell originates from or is obtained from a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bo vines (cows) and S wines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In exemplary aspects, the host cell is a cultured cell or a primary cell, i.e., isolated directly from an organism, e.g., a human. The host cell in exemplary aspects is an adherent cell or a suspended cell, i.e., a cell that grows in suspension. Suitable host cells are known in the art and include, for instance, DH5a *E. coli* cells, Chinese hamster ovarian (CHO) cells, monkey VERO cells, T293 cells, COS cells, HEK293 cells, and the like. For purposes of amplifying or replicating the recombinant expression vector, the host cell is preferably a prokaryotic cell, e.g., a DH5a cell. For purposes of producing a binding agent or a conjugate, the host cell is in some aspects a mammalian cell. In exemplary aspects, the host cell is a human cell. While the host cell may be of any cell type, the host cell may originate from any type of tissue, and may be of any developmental stage. In exemplary aspects, the host cell is a hematopoietic stem cell or progenitor cell. See, e.g., Nakamura De Oliveira et al., *Human Gene Therapy* 24:824-839 (2013). The host cell in exemplary aspects is a peripheral blood lymphocyte (PBL). In exemplary aspects, the host cell is a natural killer cell. In exemplary aspects, the host cell is a T cell.

For purposes herein, the T cell may be any T cell, such as a cultured T cell, e.g., a primary T cell, or a T cell from a cultured T cell line, e.g., Jurkat, SupT1, etc., or a T cell obtained from a mammal. If obtained from a mammal, the T cell may be obtained from numerous sources, including but not limited to blood, bone marrow, lymph node, the thymus, or other tissues or fluids. T cells may also be enriched for or purified. The T cell may be obtained by maturing hematopoietic stem cells, either in vitro or in vivo, into T cells. In exemplary aspects, the T cell is a human T cell. In exemplary aspects, the T cell is a T cell isolated from a human. The T cell may be any type of T cell, including NKT cell, and may be of any developmental stage, including but not limited to, CD4+/CD8+ double positive T cells, CDA+ helper T cells, e.g., Th1 and Th2 cells, CD8+ T cells (e.g., cytotoxic T cells), peripheral blood mononuclear cells (PBMCs), peripheral blood leukocytes (PBLs), tumor infiltrating cells (TILs), memory T cells, naive T cells, and the like. Preferably, the T cell is a CD8+ T cell or a CD4+ T cell.

Also provided by the disclosures is a population of cells comprising at least one host cell described herein. The population of cells may be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells may be a substantially homogeneous population, in which the population comprises mainly of host cells (e.g., consisting essentially of) comprising the recombinant expression vector. The population also may be a clonal population of cells, in which all cells of the population are clones of a single host cell comprising a recombinant expression vector, such that all cells of the population comprise the recombinant expression vector. In exemplary embodiments of the disclosures, the population of cells is a clonal population comprising host cells expressing a nucleic acid or a vector described herein.

Pharmaceutical Compositions and Routes of Administration

In some embodiments of the disclosures, the binding agents, conjugates, nucleic acids, vectors, host cells, or populations of cells, are admixed with a pharmaceutically acceptable carrier. Accordingly, pharmaceutical compositions comprising any of the binding agents, conjugates, nucleic acids, vectors, host cells, or populations of cells described herein and comprising a pharmaceutically acceptable carrier, diluent, or excipient are contemplated.

The pharmaceutically acceptable carrier is any of those conventionally used and is limited only by physico-chemical considerations, such as solubility and lack of reactivity with the active binding agent(s), and by the route of administration. The pharmaceutically acceptable carriers described herein, for example, vehicles, adjuvants, excipients, and diluents, are well-known to those skilled in the art and are readily available to the public. In one aspect the pharmaceutically acceptable carrier is one that is chemically inert to the active ingredient(s) of the pharmaceutical composition, e.g., the first binding agent and the second binding agent, and one which has no detrimental side effects or toxicity under the conditions of use. The carrier in some embodiments does not produce adverse, allergic, or other untoward reactions when administered to an animal or a human. The pharmaceutical composition in some aspects is free of pyrogens, as well as other impurities that could be harmful to humans or animals. Pharmaceutically acceptable carriers include any and all solvents, dispersion media, coatings, antibacterial and antifungal agents, isotonic and absorption delaying agents and the like; the use of which are well known in the art.

Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

Therapeutic formulations of the compositions useful for practicing the methods disclosed herein, such as polypeptides, polynucleotides, or antibodies, may be prepared for storage by mixing the selected composition having the desired degree of purity with optional physiologically pharmaceutically-acceptable carriers, excipients, or stabilizers (Remington's Pharmaceutical Sciences, 18th edition, A. R. Gennaro, ed., Mack Publishing Company (1990)) in the form of a lyophilized cake or an aqueous solution. Pharmaceutical compositions may be produced by admixing with one or more suitable carriers or adjuvants such as water, mineral oil, polyethylene glycol, starch, talcum, lactose, thickeners, stabilizers, suspending agents, and the like. Such compositions may be in the form of solutions, suspensions, tablets, capsules, creams, salves, ointments, or other conventional forms.

The composition to be used for in vivo administration should be sterile. This is readily accomplished by filtration through sterile filtration membranes, prior to or following lyophilization and reconstitution. Therapeutic compositions generally are placed into a container having a sterile access port, for example, an intravenous solution bag or vial having a stopper pierceable by a hypodermic injection needle. The pharmaceutical forms suitable for injectable use include sterile aqueous solutions or dispersions and sterile powders for the extemporaneous preparation of sterile injectable solutions or dispersions. In some cases the form should be sterile and should be fluid to the extent that easy syringability exists. It should be stable under the conditions of manufacture and storage and should be preserved against the contaminating action of microorganisms, such as bacteria and fungi. The composition for parenteral administration ordinarily will be stored in lyophilized form or in solution.

The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the inclusion in the compositions of agents delaying absorption, for example, aluminum monostearate and gelatin.

The choice of carrier will be determined in part by the particular type of binding agents of the pharmaceutical composition, as well as by the particular route used to administer the pharmaceutical composition. Accordingly, there are a variety of suitable formulations of the pharmaceutical composition.

The pharmaceutical composition of the present disclosures can comprise any pharmaceutically acceptable ingredient including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution-enhancing agents, dyes, emollients, emulsifying agents, emulsion stabilizers, fillers, film-forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiologically compatible pH. The buffering agents may include any compounds capable of buffering at the desired pH such as, for example, phosphate buffers (e.g., PBS), triethanolamine, Tris, bicine, TAPS, tricine, HEPES, TES, MOPS, PIPES, cacodylate, MES, and others known in the art.

In some embodiments, the pharmaceutical composition comprising the binding agents described herein is formulated for parenteral administration, subcutaneous administration, intravenous administration, intramuscular administration, intraarterial administration, intrathecal administration, or interperitoneal administration. In other embodiments, the pharmaceutical composition is administered via nasal, spray, oral, aerosol, rectal, or vaginal administration. The compositions may be administered by infusion, bolus injection or by implantation device.

The following discussion on routes of administration is merely provided to illustrate exemplary embodiments and should not be construed as limiting the scope of the disclosed subject matter in any way.

Formulations suitable for oral administration can consist of (a) liquid solutions, such as an effective amount of the composition of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise a composition of the disclosure in a flavor, usually sucrose and acacia or tragacanth, as well as pastilles comprising a composition of the disclosure in an inert base, such as gelatin and glycerin, or sucrose and acacia, emulsions, gels, and the like, optionally also containing such excipients as are known in the art.

The compositions of the disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa. In some embodiments, the composition is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Topical formulations are well-known to those of skill in the art. Such formulations are particularly suitable in the context of the invention for application to the skin.

In some embodiments, the pharmaceutical composition described herein is formulated for parenteral administration. For purposes herein, parenteral administration includes, but is not limited to, intravenous, intraarterial, intramuscular, intracerebral, intracerebroventricular, intracardiac, subcutaneous, intraosseous, intradermal, intrathecal, intraperitoneal, retrobulbar, intrapulmonary, intravesical, and intracavernosal injections or infusions. Administration by surgical implantation at a particular site is contemplated as well.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The composition of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,5,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, a suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

The parenteral formulations in some embodiments contain preservatives or buffers. In order to minimize or eliminate irritation at the site of injection, such compositions optionally contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described and known in the art.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, PA, Banker and Chalmers, eds., pages 238-250 (1982), and *ASHP Handbook on Injectable Drugs*, Toissel, 4th ed., pages 622-630 (1986)).

It will be appreciated by one of skill in the art that, in addition to the above-described pharmaceutical compositions, the composition of the disclosure can be formulated as inclusion complexes, such as cyclodextrin inclusion complexes, or liposomes.

Dose

For purposes herein, the amount or dose of the pharmaceutical composition administered is sufficient to effect, e.g., a therapeutic or prophylactic response, in the subject or animal over a reasonable time frame. For example, the dose of the pharmaceutical composition is sufficient to treat or prevent a disease or medical condition in a period of from about 12 hours, about 18 hours, about 1 to 4 days or longer, e.g., 5 days, 6 days, 1 week, 10 days, 2 weeks, 16 to 20 days, or more, from the time of administration. In certain embodiments, the time period is even longer. The dose is determined by the efficacy of the particular pharmaceutical composition and the condition of the animal (e.g., human), as well as the body weight of the animal (e.g., human) to be treated.

Many assays for determining an administered dose are known in the art. In some embodiments, an assay which comprises comparing the extent to which the binding agents block IL13Rα2-mediated cell growth upon administration of a given dose to a mammal among a set of mammals each of which is given a different dose of binding agents is used to determine a starting dose to be administered to a mammal. The extent to which the binding agents block IL13Rα2 mediated cell growth upon administration of a certain dose can be assayed by methods known in the art.

The dose of the pharmaceutical composition also will be determined by the existence, nature and extent of any adverse side effects that might accompany the administration of a particular pharmaceutical composition. Typically, the attending physician will decide the dosage of the pharmaceutical composition with which to treat each individual patient, taking into consideration a variety of factors, such as age, body weight, general health, diet, sex, binding agents of the pharmaceutical composition to be administered, route of administration, and the severity of the condition being treated.

By way of example and not intending to limit the invention, the dose of the binding agent of the present disclosure can be about 0.0001 to about 1 g/kg body weight of the subject being treated/day, from about 0.0001 to about 0.001 g/kg body weight/day, or about 0.01 mg to about 1 g/kg body weight/day. The pharmaceutical composition in some aspects comprise the binding agent of the present disclosure at a concentration of at least A, wherein A is about 0.001 mg/ml, about 0.01 mg/ml, 0 about 1 mg/ml, about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml or higher. In some embodiments, the pharmaceutical composition comprises the binding agent at a concentration of at most B, wherein B is about 30 mg/ml, about 25 mg/ml, about 24 mg/ml, about 23, mg/ml, about 22 mg/ml, about 21 mg/ml, about 20 mg/ml, about 19 mg/ml, about 18 mg/ml, about 17 mg/ml, about 16 mg/ml, about 15 mg/ml, about 14 mg/ml, about 13 mg/ml, about 12 mg/ml, about 11 mg/ml, about 10 mg/ml, about 9 mg/ml, about 8 mg/ml, about 7 mg/ml, about 6 mg/ml, about 5 mg/ml, about 4 mg/ml, about 3 mg/ml, about 2 mg/ml, about 1 mg/ml, or about 0.1 mg/ml. In some embodiments, the compositions may contain an analog at a concentration range of A to B mg/ml, for example, about 0.001 to about 30.0 mg/ml.

Additional dosing guidance can be gauged from other antibody therapeutics, such as bevacizumab (Avastin™ Genentech); Cetuximab (Exbitux™ Imclone), Panitumumab (Vectibix™ Amgen), and Trastuzumab (Herceptin-Genentech).

Timing of Administration

The disclosed pharmaceutical formulations may be administered according to any regimen including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly. Timing, like dosing can be fine-tuned based on dose-response studies, efficacy, and toxicity data, and initially gauged based on timing used for other antibody therapeutics.

Controlled Release Formulations

The pharmaceutical composition is in certain aspects modified into a depot form, such that the manner in which the active ingredients of the pharmaceutical composition (e.g. the binding agents) is released into the body to which it is administered is controlled with respect to time and location within the body (see, for example, U.S. Pat. No. 4,450,150). Depot forms in various aspects, include, for example, an implantable composition comprising a porous or non-porous material, such as a polymer, wherein the binding agents are encapsulated by or diffused throughout the material and/or degradation of the non-porous material. The depot is then implanted into the desired location within the body and the binding agents are released from the implant at a predetermined rate.

Accordingly, the pharmaceutical composition in certain aspects is modified to have any type of in vivo release profile. In some aspects, the pharmaceutical composition is an immediate release, controlled release, sustained release, extended release, delayed release, or bi-phasic release formulation. Methods of formulating peptides (e.g., peptide binding agents) for controlled release are known in the art. See, for example, Qian et al., J Pharm 374: 46-52 (2009) and International Patent Application Publication Nos. WO 2008/130158, WO2004/033036; WO2000/032218; and WO 1999/040942. Suitable examples of sustained-release preparations include semipermeable polymer matrices in the form of shaped articles, e.g., films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman, et al., Biopolymers, 22: 547-556 (1983)), poly (2-hydroxyethyl-methacrylate) (Langer, et al., J. Biomed. Mater. Res., 15:167-277 (1981) and Langer, Chem. Tech., 12:98-105 (1982)), ethylene vinyl acetate (Langer, et al, supra) or poly-D(−)-3-hydroxybutyric acid (EP 133,988). Sustained-release compositions also may include liposomes, which can be prepared by any of several methods known in the art (e.g., DE 3,218,121; Epstein, et al., Proc. Natl. Acad. Sci. USA, 82:3688-3692 (1985); Hwang, et al., Proc. Natl. Acad. Sci. USA, 77:4030-4034 (1980); EP 52,322; EP 36,676; EP 88,046; EP 143,949).

Combinations

The compositions of the disclosures may be employed alone, or in combination with other agents. In some embodiments, more than one type of binding agent are administered. For example, the administered composition, e.g., pharmaceutical composition, may comprise an antibody as well as an scFv. In some embodiments, the compositions of the disclosure are administered together with another therapeutic agent or diagnostic agent, including any of those described herein. Certain diseases, e.g., cancers, or patients may lend themselves to a treatment of combined agents to achieve an additive or even a synergistic effect compared to the use of any one therapy alone.

Uses

Based in part on the data provided herein, the binding agents, conjugates, host cells, populations of cells, and pharmaceutical compositions are useful for treating a neoplasm, tumor, or a cancer.

For purposes of the present disclosure, the term "treat" and "prevent" as well as words stemming therefrom, as used herein, do not necessarily imply 100% or complete treatment (e.g., cure) or prevention. Rather, there are varying degrees of treatment or prevention of which one of ordinary skill hi the art recognizes as having a potential benefit or therapeutic effect. In this respect, the methods of the present disclosures can provide any amount or any level of treatment or prevention of a cancer in a patient, e.g., a human. Furthermore, the treatment or prevention provided by the method disclosed herein can include treatment or prevention of one or more conditions or symptoms of the disease, e.g., cancer, being treated or prevented. Also, for purposes herein, "prevention" can encompass delaying the onset of the disease, or a symptom or condition thereof.

The materials and methods described herein are especially useful for inhibiting neoplastic cell growth or spread; particularly neoplastic cell growth for which the IL13Rα2 targeted by the binding agents plays a role.

Neoplasms treatable by the binding agents, conjugates, host cells, populations of cells, and pharmaceutical compositions of the disclosures include solid tumors, for example, carcinomas and sarcomas. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue. The invention also provides methods of treatment of cancers of myeloid or lymphoid systems, including leukemias, lymphomas, and other cancers that typically are not present as a tumor mass, but are distributed in the vascular or lymphoreticular systems. Further contemplated are methods for treatment of adult and pediatric oncology, growth of solid tumors/malignancies, myxoid and round cell carcinoma, locally advanced tumors, cancer metastases, including lymphatic metastases. The cancers listed herein are not intended to be limiting. Both age (child and adult), sex (male and female), primary and secondary, pre- and post-metastatic, acute and chronic, benign and malignant, anatomical location cancer embodiments and variations are contemplated targets. Cancers are grouped by embryonic origin (e.g., carcinoma, lymphomas, and sarcomas), by organ or physiological system, and by miscellaneous grouping. Particular cancers may overlap in their classification, and their listing in one group does not exclude them from another.

Carcinomas that may be targeted include adrenocortical, acinar, acinic cell, acinous, adenocystic, adenoid cystic, adenoid squamous cell, cancer adenomatosum, adenosquamous, adnexel, cancer of adrenal cortex, adrenocortical, aldosterone-producing, aldosterone-secreting, alveolar, alveolar cell, ameloblastic, ampullary, anaplastic cancer of thyroid gland, apocrine, basal cell, basal cell, alveolar, comedo basal cell, cystic basal cell, morphea-like basal cell, multicentric basal cell, nodulo-ulcerative basal cell, pigmented basal cell, sclerosing basal cell, superficial basal cell, basaloid, basosquamous cell, bile duct, extrahepatic bile duct, intrahepatic bile duct, bronchioalveolar, bronchiolar, bronchioloalveolar, bronchoalveolar, bronchoalveolar cell, bronchogenic, cerebriform, cholangiocelluarl, chorionic, choroids plexus, clear cell, cloacogenic anal, colloid, comedo, corpus, cancer of corpus uteri, cortisol-producing, cribriform, cylindrical, cylindrical cell, duct, ductal, ductal cancer of the prostate, ductal cancer in situ (DCIS), eccrine, embryonal, cancer en cuirasse, endometrial, cancer of endometrium, endometroid, epidermoid, cancer ex mixed tumor, cancer ex pleomorphic adenoma, exophytic, fibrolamellar, cancer fibrosum, follicular cancer of thyroid gland, gastric, gelatiniform, gelatinous, giant cell, giant cell cancer of thyroid gland, cancer gigantocellulare, glandular, granulose cell, hepatocellular, Hurthle cell, hypernephroid, infantile embryonal, islet cell carcinoma, inflammatory cancer of the breast, cancer in situ, intraductal, intraepidermal, intraepithelial, juvenile embryonal, Kulchitsky-cell, large cell, leptomeningeal, lobular, infiltrating lobular, invasive lobular, lobular cancer in situ (LCIS), lymphoepithelial, cancer medullare, medullary, medullary cancer of thyroid gland, medullary thyroid, melanotic, meningeal, Merkel cell, metatypical cell, micropapillary, cancer molle, mucinous, cancer muciparum, cancer mucocellulare, mucoepidermoid, cancer *mucosum*, mucous, nasopharyngeal, neuroendocrine cancer of the skin, noninfiltrating, non-small cell, non-small cell lung cancer (NSCLC), oat cell, cancer ossificans, osteoid, Paget's disease of the bone or breast, papillary, papillary cancer of thyroid gland, periampullary, preinvasive, prickle cell, primary intrasseous, renal cell, scar, schistosomal bladder, Schneiderian, scirrhous, sebaceous, signet-ring cell, cancer simplex, small cell, small cell lung cancer (SCLC), spindle cell, cancer spongiosum, squamous, squamous cell, terminal duct, anaplastic thyroid, follicular thyroid, medullary thyroid, papillary thyroid, trabecular cancer of the skin, transitional cell, tubular, undifferentiated cancer of thyroid gland, uterine corpus, verrucous, villous, cancer *villosum*, yolk sac, squamous cell particularly of the head and neck, esophageal squamous cell, and oral cancers and carcinomas.

Sarcomas that may be targeted include adipose, alveolar soft part, ameloblastic, avian, botryoid, sarcoma botryoi'des, chicken, chloromatous, chondroblastic, clear cell sarcoma of kidney, embryonal, endometrial stromal, epithelioid, Ewing's, fascial, fibroblastic, fowl, giant cell, granulocytic, hemangioendothelial, Hodgkin's, idiopathic multiple pigmented hemorrhagic, immunoblastic sarcoma of B cells, immunoblastic sarcoma of T cells, Jensen's, Kaposi's, kupffer cell, leukocytic, lymphatic, melanotic, mixed cell, multiple, lymphangio, idiopathic hemorrhagic, multipotential primary sarcoma of bone, osteoblastic, osteogenic, parosteal, polymorphous, pseudo-kaposi, reticulum cell, reticulum cell sarcoma of the brain, rhabdomyosarcoma, rous, soft tissue, spindle cell, synovial, telangiectatic, sarcoma (osteosarcoma)/malignant fibrous histiocytoma of bone, and soft tissue sarcomas.

Lymphomas that may targeted include AIDS-related, non-Hodgkin's, Hodgkin's, T-cell, T-cell leukemia/lymphoma, African, B-cell, B-cell monocytoid, bovine malignant, Burkitt's, centrocytic, lymphoma cu'tis, diffuse, diffuse, large cell, diffuse, mixed small and large cell, diffuse, small cleaved cell, follicular, follicular center cell, follicular, mixed small cleaved and large cell, follicular, predominantly large cell, follicular, predominantly small cleaved cell, giant follicle, giant follicular, granulomatous, histiocytic, large cell, immunoblastic, large cleaved cell, large nocleaved cell, Lennert's, lymphoblastic, lymphocytic, intermediate; lymphocytic, intermediately differentiated, plasmacytoid; poorly differentiated lymphocytic, small lymphocytic, well differentiated lymphocytic, lymphoma of cattle; MALT, mantle cell, mantle zone, marginal zone, Mediterranean lymphoma mixed lymphocytic-histiocytic, nodular, plasmacytoid, pleomorphic, primary central nervous system, primary effusion, small b-cell, small cleaved cell, small concleaved cell, T-cell lymphomas; convoluted T-cell, cutaneous t-cell, small lymphocytic T-cell, undefined lymphoma, u-cell, undifferentiated, aids-related, central nervous system, cutaneous T-cell, effusion (body cavity-based), thymic lymphoma, and cutaneous T cell lymphomas.

Leukemias and other blood cell malignancies that may be targeted include acute lymphoblastic, acute myeloid, lymphocytic, chronic myelogenous, hairy cell, lymphoblastic, myeloid, lymphocytic, myelogenous, leukemia, hairy cell, T-cell, monocytic, myeloblastic, granulocytic, gross, hand mirror-cell, basophilic, hemoblastic, histiocytic, leukopenic, lymphatic, Schilling's, stem cell, myelomonocyic, prolymphocytic, micromyeloblastic, megakaryoblastic, megakaryoctyic, rieder cell, bovine, aleukemic, mast cell, myelocytic, plamsa cell, subleukemic, multiple myeloma, nonlymphocytic, and chronic myelocytic leukemias.

Brain and central nervous system (CNS) cancers and tumors that may be targeted include astrocytomas (including cerebellar and cerebral), gliomas (including malignant gliomas, glioblastomas, brain stem gliomas, visual pathway and hypothalamic gliomas), brain tumors, ependymoma, medulloblastoma, supratentorial primitive neuroectodermal tumors, primary central nervous system lymphoma, extracranial germ cell tumor, myelodysplastic syndromes, oligodendroglioma, myelodysplastic/myeloproliferative diseases, myelogenous leukemia, myeloid leukemia, multiple myeloma, myeloproliferative disorders, neuroblastoma, plasma cell neoplasm/multiple myeloma, central nervous system lymphoma, intrinsic brain tumors, astrocytic brain tumors, and metastatic tumor cell invasion in the central nervous system.

Gastrointestinal cancers that may be targeted include extrahepatic bile duct cancer, colon cancer, colon and rectum cancer, colorectal cancer, gallbladder cancer, gastric (stomach) cancer, gastrointestinal carcinoid tumor, gastrointestinal carcinoid tumors, gastrointestinal stromal tumors, bladder cancers, islet cell carcinoma (endocrine pancreas), pancreatic cancer, islet cell pancreatic cancer, prostate cancer rectal cancer, salivary gland cancer, small intestine cancer, colon cancer, and polyps associated with colorectal neoplasia. A discussion of colorectal cancer is described in Barderas et al., *Cancer Research* 72: 2780-2790 (2012).

Bone cancers that may be targeted include osteosarcoma and malignant fibrous histiocytomas, bone marrow cancers, bone metastases, osteosarcoma/malignant fibrous histiocytoma of bone, and osteomas and osteosarcomas. Breast cancers that may be targeted include small cell carcinoma and ductal carcinoma.

Lung and respiratory cancers that may be targeted include bronchial adenomas/carcinoids, esophagus cancer esophageal cancer, esophageal cancer, hypopharyngeal cancer, laryngeal cancer, hypopharyngeal cancer, lung carcinoid tumor, non-small cell lung cancer, small cell lung cancer, small cell carcinoma of the lungs, mesothelioma, nasal cavity and paranasal sinus cancer, nasopharyngeal cancer, nasopharyngeal cancer, oral cancer, oral cavity and lip cancer, oropharyngeal cancer; paranasal sinus and nasal cavity cancer, and pleuropulmonary blastoma.

Urinary tract and reproductive cancers that may be targeted include cervical cancer, endometrial cancer, ovarian epithelial cancer, extragonadal germ cell tumor, extracranial germ cell tumor, extragonadal germ cell tumor, ovarian germ cell tumor, gestational trophoblastic tumor, spleen, kidney cancer, ovarian cancer, ovarian epithelial cancer, ovarian germ cell tumor, ovarian low malignant potential tumor, penile cancer, renal cell cancer (including carcinomas), renal cell cancer, renal pelvis and ureter (transitional cell cancer), transitional cell cancer of the renal pelvis, and ureter, gestational trophoblastic tumor, testicular cancer, ureter and renal pelvis, transitional cell cancer, urethral cancer, endometrial uterine cancer, uterine sarcoma, vaginal cancer, vulvar cancer, ovarian carcinoma, primary peritoneal epithelial neoplasms, cervical carcinoma, uterine cancer and solid tumors in the ovarian follicle), superficial bladder tumors, invasive transitional cell carcinoma of the bladder, and muscle-invasive bladder cancer.

Skin cancers and melanomas (as well as non-melanomas) that may be targeted include cutaneous t-cell lymphoma, intraocular melanoma, tumor progression of human skin keratinocytes, basal cell carcinoma, and squamous cell cancer. Liver cancers that may be targeted include extrahepatic bile duct cancer, and hepatocellular cancers. Eye cancers that may be targeted include intraocular melanoma, retinoblastoma, and intraocular melanoma Hormonal cancers that may be targeted include: parathyroid cancer, pineal and supratentorial primitive neuroectodermal tumors, pituitary tumor, thymoma and thymic carcinoma, thymoma, thymus cancer, thyroid cancer, cancer of the adrenal cortex, and ACTH-producing tumors.

Miscellaneous other cancers that may be targeted include advanced cancers, AIDS-related, anal cancer adrenal cortical, aplastic anemia, aniline, betel, buyo cheek, cerebriform, chimney-sweeps, clay pipe, colloid, contact, cystic, dendritic, cancer a deux, duct, dye workers, encephaloid, cancer en cuirasse, endometrial, endothelial, epithelial, glandular, cancer in situ, kang, kangri, latent, medullary, melanotic, mule-spinners', non-small cell lung, occult cancer, paraffin, pitch workers', scar, schistosomal bladder, scirrhous, lymph node, small cell lung, soft, soot, spindle cell, swamp, tar, and tubular cancers.

Miscellaneous other cancers that may be targeted also include carcinoid (gastrointestinal and bronchal) Castleman's disease chronic myeloproliferative disorders, clear cell sarcoma of tendon sheaths, Ewing's family of tumors, head and neck cancer, lip and oral cavity cancer, Waldenstrom's macroglobulinemia, metastatic squamous neck cancer with occult primary, multiple endocrine neoplasia syndrome, multiple myeloma/plasma cell neoplasm, Wilms' tumor, mycosis fungoides, pheochromocytoma, sezary syndrome, supratentorial primitive neuroectodermal tumors, unknown primary site, peritoneal effusion, malignant pleural effusion, trophoblastic neo-plasms, and hemangiopericytoma.

In exemplary aspects, the cancer is any one of the foregoing described in which IL13Rα2 is expressed on the cells of the cancer. In exemplary aspects, the cancer is colon cancer. In exemplary aspects, the cancer is Glioblastoma Multiforme. In exemplary aspects, the method of treating cancer in a subject in need thereof comprises administering to the subject any of the binding agents, conjugates, nucleic acids, vectors, host cells, cell populations, or pharmaceutical compositions described herein, in an amount effective to treat the cancer. In exemplary aspects, the method comprises administering a conjugate described herein. In exemplary aspects, the method comprises administering host cells of the disclosures and the host cells are autologous cells in relation to the subject being treated. In exemplary aspects, the method comprises administering host cells of the disclosures and the host cells are cells obtained from the subject being treated. In exemplary aspects, the cells are T-lymphocytes. In alternative aspects, the cells are natural killer cells.

The disclosure will be more fully understood by reference to the following examples, which detail exemplary embodiments of the disclosure. The examples should not, however, be construed as limiting the scope of the disclosure.

Example 1

Materials

Lipofectamine 2000 and the pEF6/Myc-His vector were obtained from Invitrogen. Monoclonal antibodies to IL13Rα2 (clones YY-23Z and B-D13) and the IsoStrip mouse monoclonal antibody isotyping kit were purchased from Santa Cruz Biotechnology (Santa Cruz, CA). The mAb to IL13Rα2 (clone 83807) and recombinant human and mouse IL13Rα2hFc and IL13Rα1hFc chimeras were purchased from R&D Systems (Minneapolis, MN). Biotinylated horse anti-mouse antibodies and the Elite kit were obtained from Vector Laboratories (Burlingame, CA). 3,3'-Diaminobenzidine substrate was purchased from Dako (Carpinteria, CA). Goat anti-mouse antibody conjugated with peroxidase was purchased from Chemicon International (Temicula, CA), and Pngase F was purchased from New England Biolabs (Ipswich, MA). The QuikChange Lightning site-directed mutagenesis kit was purchased from Agilent Technologies, Inc. (Santa Clara, CA), and the RNeasy Plus kit was received from Qiagen (Valencia, CA). The cDNA iScript kit, 7.5% Tris-HCl gel, and ImmunStar WesternC developing reagent and protein marker were purchased from Bio-Rad. The human IL-13 ELISA kit was purchased from eBioscience (San Diego, CA). GBM12 and GBM43 were kindly provided by Dr. David C. James (University of California-San Francisco), and the cDNA encoding human wild-type IL13Rα2 was obtained from Dr. Waldemar Debinski (Wake Forest University). Obtaining the cDNA encoding the human wild-type IL13Rα2 or most other proteins involves the use of well-known techniques and readily available reagents.

Immunization

To obtain monoclonal antibodies with specificity to native IL13Rα2, the human recombinant IL13Rα2hFc fusion was used for immunization of animals and in all screening assays. Two 6-week-old female BALB/c mice were immunized with intraperitoneal injection of 10 μg of rhIL13Rα2hFc protein in complete Freund's adjuvant followed by intraperitoneal injection of 10 μg of rhIL13Rα2hFc protein in incomplete Freund's adjuvant at a 2-week interval for 2 months. Two weeks after the last intraperitoneal injection and 3 days before the fusion, a boost was performed by the combination of intravenous and intraperitoneal injection of 10 μg of antigen without Freund's adjuvant. The fusion of mouse spleen cells with the mouse myeloma cell line X63.Ag8.653 subclone P301 was performed by using a procedure described by Kohler and Milstein (27). Hybridoma supernatants were assayed for the presence of IL13Rα2 antibodies using an enzyme-linked immunosorbent assay (ELISA). Selected populations were cloned, and supernatants were assayed to identify the clones with strongest binding.

Generation of CHO Cell Line Expressing Human IL13Rα2

The cDNA encoding human wild-type IL13Rα2 was amplified with the following primer pair: forward, 5'-GCTTGGTACCGAATGGCTTTCGTTTGCTTGGC-3' (SEQ ID NO: 17) and reverse, 5'-GTTTTTGTTCGAATGTATCACAGAAAAATTCTGG-3' (SEQ ID NO: 18). The purified PCR product was restricted with KpnI and BstBI enzymes, agarose gel-purified, and subsequently cloned into the pEF6/Myc-His vector in a reading frame with Myc and His6 tags. CHO cells were plated at 80% confluence and transfected with a plasmid encoding the IL13Rα2 using Lipofectamine 2000. The following day, 4 μg/ml blasticidin was added for selection of cells that had stably incorporated and expressed the IL13Rα2 transcript. A stable population of cells was further subcloned in 96-well plates at a density of one cell/well. Ten days later, single clones were screened by flow cytometry for cell surface expression of IL13Rα2 using an antibody to IL13Rα2 (clone B-D13). The clone with the highest level of IL13Rα2 expression was selected and expanded for subsequent screening of hybridomas secreting IL13Rα2 antibodies.

ELISA 96-well plates were coated with 50 μl of human or mouse recombinant IL13Rα2hFc or IL13Rα1hFc or human control IgG at a concentration of 1 μg/ml overnight at 4° C. Following washes with TBS-Tween 20 buffer and blocking with 1% nonfat dry milk, 50 μl of purified antibodies, serum, or hybridoma supernatants at various dilutions were applied to the plate and incubated for 1 hour at room temperature. Bound antibodies were detected with goat anti-mouse antibodies conjugated to alkaline phosphatase following the development with alkaline phosphatase substrate. Plates were read at A405 using a UniRead 800 plate reader (BioTek).

Flow Cytometry

CHO or HEK cells expressing IL13Rα2; the glioma cell lines A172, N10, U251, U87, and U118; patient-derived GBM12 and GBM43, and primary human astrocytes were stained with IL13Rα2 (clone 47) monoclonal antibody at 1 μg/ml followed by goat anti-mouse Alexa Fluor 647 (1:500). All staining procedures were performed on ice. Samples were analyzed using the BD FACSCanto flow cytometer and FACSDiVa™ software.

PCR

To determine the expression of IL13Rα2 in various glioma cells and astrocytes, total RNA was generated from the cell pellets using the RNeasy Plus kit. 200 ng of total RNA was then converted into cDNA using the cDNA iScript kit. The cDNA was further amplified by PCR for IL13Rα2 and GAPDH for 30 cycles using IL13Rα2 and GAPDH primers and visualized on a 1% agarose gel.

Surface Plasmon Resonance

The affinity and rates of interaction between IL13Rα2 (clone 47) monoclonal antibody, commercially available IL13Rα2 monoclonal antibodies (clones 83807 and B-D13), and target (rhIL13Rα2) were measured with a Biacore 3000 biosensor through surface plasmon resonance (SPR). The monoclonal antibodies were immobilized (covalently) to the dextran matrix of the sensor chip (CM5) using the amino coupling kit. The carboxyl groups on the sensor surfaces were activated with an injection of a solution containing 0.2M N-ethyl-N'-(3-diethylamino-propyl)-carbodiimide and 0.05M N-hydroxysuccinimide. The immobilization procedure was completed by the injection of 1 Methanolamine hydrochloride to block the remaining ester groups. All steps of the immobilization process were carried out at a flow rate of 10 μl/minute. The control surface was prepared similarly with the exception that running buffer was injected rather than monoclonal antibodies. Binding reactions were performed at 25° C. in HBS-P buffer (20 mM HEPES, pH 7.4, 150 mM NaCl, and 0.005% (v/v) surfactant P20) using a flow rate of 20 μl/minute. Target (rhIL13Rα2) was added at various concentrations in the flow during the binding phase. The amount of protein bound to the sensor chip was monitored by the change in refractive index (represented by response units (RU)). The instrument was programmed to perform a series of binding measurements with increasing concentrations of target over the same surface. Triplicate injections of each concentration of target were performed. Sensorgrams (plots of changes in RU on the surface as a function of time) were analyzed using BIAevaluation v4.1. Affinity constants were estimated by curve fitting using a 1:1 binding model.

Data Preparation and Kinetic Analysis

The estimation of kinetic parameters was performed by repetitive injections of a range of target concentrations over the immobilized mAbs. Data were prepared by the method of "double referencing." This method utilizes parallel injections of each target sample over a control dextran surface as well as running buffer injections over both the immobilized mAbs and control dextran surfaces. Subtraction of these sensorgrams yielded the control; this was subtracted from the experimental sensorgram. Each data set (consisting of sensorgrams of increasing target concentrations over the same level of immobilized mAbs) was analyzed using various kinetic models. The BIAevaluation v 4.1 software was then used for data analysis. Affinity constants were estimated by curve fitting using a 1:1 binding model. Sensorgram association and dissociation curves were fit locally or globally. The rate of complex formation during the sample injection is described by an equation of the following type: $dR/dt = k_a C (R_{max} - R) - k_d R$ (for a 1:1 interaction) where R is the SPR signal in RU, C is the concentration of analyte, $R_{max}$ is the maximum analyte binding capacity in RU, and dR/dt is the rate of change of SPR signal. The early binding phase (300 s) was used to determine the association constant ($k_a$) between mAb and target. The dissociation phase ($k_d$) was measured using the rate of decline in RU on introduction of free buffer at the end of target injections. Data were simultaneously fit by the software program (global fitting algorithm), and the dissociation constant ($K_D$) of the complexes was determined as the ratio $k_a/k_d$. For quantitative analysis, three independent replicates were performed for each sample. Data are expressed as mean S.E.

Competitive Binding Assay

For the competitive binding plate assay, a 96-well plate was coated with 50 µl of affinity-purified hrIL13Rα2hFc at 1 µg/ml in carbonate buffer, pH 9.6 and stored overnight at 4° C. After washing with PBS containing 0.05% Tween 20, mAbs to IL13Rα2 (10 µg/ml) or control mIgG were added for 30 minutes at room temperature. After washing, 50 µl of purified rhIL-13 in PBS and 0.1% BSA at 10 ng/ml were added for a 1-hour incubation at room temperature and assayed for bound rhIL-13 using detection reagents from a human IL-13 ELISA kit. Separately, HEK cells expressing wild-type IL13Rα2 or 4-amino-acid mutants (see Example 10) in the IL13Rα2 sequence were pretreated with either rhIL-13 or mAb IL13Rα2 (clone 47) at 2 µg/ml for 30 minutes on ice followed by a 1-hour incubation with IL13Rα2 (clone 47) mAb or rhIL-13 at 100 ng/ml, respectively. Binding of rhIL-13 to IL13Rα2 alone or in the presence of competitor was detected with human IL-13 mAb-FITC. Binding of IL13Rα2 (clone 47) mAb to rhIL13Rα2 alone or in the presence of competitor was detected with anti-mouse antibody conjugated to Alexa Fluor 649 and analyzed by flow cytometry.

Mutagenesis of IL13Rα

Previously, $Tyr^{207}$, $Asp^{271}$, $Tyr^{315}$, and $Asp^{318}$ of the human IL13Rα2 were identified as residues crucial for interaction with human IL-13 (28). To determine whether those residues were important for binding of IL13Rα2 (clone 47) mAb to IL13Rα2, the $Tyr^{207}$, $Asp^{271}$, $Tyr^{315}$, and $Asp^{318}$ residues were mutated to Ala separately or at the same time (4-amino-acid mutant) using the QuikChange Lightning site-directed mutagenesis kit according to the manufacturer's recommendations. Sequencing of selected clones was performed using conventional techniques, which confirmed the presence of the selected mutation. HEK cells were transfected with wild-type or mutated variants of IL13Rα2 cDNA in the pEF6 Myc-His vector using Lipofectamine Plus transfection reagent. 48 hours after transfection, the cells were collected and analyzed for binding to IL13Rα2 (clone 47) mAb via flow cytometry.

Western Blot

The rhIL13Rα2 was applied to a 7.5% Tris-HCl gel (Bio-Rad) at 200 ng/lane and resolved under reducing conditions. After the transfer of proteins to a PVDF membrane (Bio-Rad) and blocking with 2% nonfat dry milk, the membrane was stained with anti-IL13Rα2 mAb (clones YY-23Z and B-D13) at 2 µg/ml or with supernatant collected from hybridoma clones (diluted 10 times), followed by goat antimouse antibody conjugated to peroxidase. ImmunStar WesternC was used to develop reactions. Images were captured using a Bio-Rad ChemiDoc imaging system.

Immunohistochemistry

The GBM tissues were collected in accordance with a protocol approved by the Institutional Review Board at the University of Chicago. Flash-frozen brain-tumor tissues were cut to a thickness of 10 µm. Tissue sections were fixed with −20° C. methanol and stained for human IL13Rα2 using mouse IL13Rα2 (clone 47) mAb at a concentration of 3 µg/ml or isotype control mIgG1. The bound antibodies were detected with biotinylated horse anti-mouse antibodies (1:100). The antigen-antibody binding was detected by the Elite kit with 3,3'-diaminobenzidine substrate. Slides were analyzed using the CRI Panoramic Scan Whole Slide Scanner and Panoramic Viewer software.

Animal Study

All animals were maintained and cared for in accordance with the Institutional Animal Care and Use Committee protocol and according to National Institutes of Health guidelines. The animals used in the experiments were 6- to 7-week-old male athymic nu/nu mice. Mice were anesthetized with an intraperitoneal injection of ketamine hydrochloride/xylazine (25 mg/ml/2.5 mg/ml) mixture. To establish intracranial tumors, a midline cranial incision was made, and a right-sided burr hole was placed 2 mm lateral to the sagittal suture and about 2 mm superior to λ. Animals were positioned in a stereotactic frame, and a Hamilton needle was inserted through the burr hole and advanced 3 mm. Intracranial penetration was followed by (i) injection of $2.5 \times 10^4$ U251 glioma cells in 2.5 µl of sterile PBS in combination with 200 ng of mIgG or IL13Rα2 (clone 47) mAb or (ii) 3 days postintracranial injection of glioma cells with PBS or 10 µg of IL13Rα2 (clone 47 or B-D13) mAb as described previously (29, incorporated herein by reference). All mice were monitored for survival. Three animals from each group were sacrificed at day 17, and brains were harvested and frozen for sectioning, hematoxylin and eosin (H&E) staining, and microscopic analysis.

Statistics

The differences between groups were evaluated by Student's t test or one-way analysis of variance with post hoc comparison Tukey's test or Dunnett's test. For the in vivo survival data, a Kaplan-Meier survival analysis was used, and statistical analysis was performed using a log rank test. $P<0.05$ was considered statistically significant.

Example 2

Characterization of Antigen and Screening of Hybridoma Clones Secreting Anti-IL13Rα2 Antibodies The primary goal of this study was to generate a high affinity monoclonal antibody suitable for targeting of the IL13Rα2 expressed on the surface of tumor cells. We therefore immunized mice and screened the resulting hybridoma clones for reactivity against the antigen, rhIL13Rα2, in its native conformation. A plate-bound ELISA utilizing a hybridoma clone against rhIL13Rα2, YY-23Z, was established for the detection of rhIL13Rα2. The concentration of rhIL13Rα2 absorbed to the plastic at 1 µg/ml was found to be suitable for the detection of antibody binding (FIG. 1A). Next, the rhIL13Rα2hFc was characterized for its "nativity" by utilizing a pair of commercially available antibodies recognizing only the native (found on the cell surface) and denatured (using Western blotting under reducing conditions) forms of IL13Rα2 and for its binding properties to rhIL13Rα2 in ELISA with antibody clones B-D13 and YY-23Z, respectively. Both clones B-D13 and YY-23Z were able to recognize the rhIL13Rα2hFc in a plate-bound ELISA (FIG. 1). Denaturation of antigen at 95° C. for 5 minutes in the presence of β-mercaptoethanol completely abolished the ability of the antibody clone B-D13 to recognize antigen by ELISA, whereas the YY-23Z clone retained the ability to bind the denatured antigen. Thus, the rhIL13Rα2hFc absorbed to the plastic of ELISA plates containing both native and denatured forms of the protein. Analysis of serum from animals immunized with a fusion of rhIL13Rα2 and hFc revealed the presence of antibodies against both rhIL13Rα2 and human Fc fragment. To select antibodies specific for the IL13Rα2 portion of the fusion, human IgG was included as an additional negative control for the screening of hybridoma populations. Of the 39 screened primary populations, only 15 populations were specific to IL13Rα2, and four were reactive with human IgG. Finally, five clones strongly reacting with native IL13Rα2 were further expanded and recloned. The two clones recognizing only denatured antigen were selected from the separate immunization set with rhIL13Rα2hFc chimera. Supernatants from selected clones were compared for their ability to bind hrIL13Rα2 in a plate-bound ELISA (FIG. 1C) and by Western blotting (FIG. 1D). FIG. 1C shows that clone 47 strongly binds to the antigen in plate-bound ELISA but not by Western blotting, indicating the ability of clone 47 to recognize a native conformation of the antigen. Therefore, clone 47 was selected for further characterization and for further experiments. Clone 47 was found to be of the IgG1 isotype, possessing a κ chain.

Example 3

Specificity of Binding for the IL13Rα2 (Clone 47) mAb to Recombinant Human IL13Rα2 and IL13Rα2 Expressed at the Cell Surface We investigated the binding properties of the IL13Rα2 (clone 47) mAb to rhIL13Rα2 versus the commercially available clones 83807 and B-D13 in a plate-bound ELISA. FIG. 2A shows strong and specific binding of clone 47 to rhIL13Rα2 when compared with clones 83807 and B-D13. Clone 47 reached the plateau of binding at the low concentration of 0.05 µg/ml. None of the antibodies showed binding to human IgG utilized as an additional negative control in these experiments. To further verify the specificity of interaction for clone 47 with human IL13Rα2, a clonal line of CHO cells expressing the full size wild-type human IL13Rα2 (clone 6) was generated. Binding of the antibody to control CHO cells transfected with an empty vector was compared with that of CHO cells expressing IL13Rα2. Again, the IL13Rα2 (clone 47) mAb demonstrated strong and specific binding to IL13Rα2 expressed on the cell surface but not to control CHO cells, indicating that this antibody specifically recognizes a native conformation of the IL13Rα2 (FIG. 2B). Clone 47 demonstrated the strongest affinity for IL13Rα2 at the lowest tested concentration of 0.25 µg/ml. Notably, other selected hybridoma clones demonstrated similar specificity of interaction with IL13Rα2 expressed on the cell surface of CHO cells but not with control CHO cells. Data obtained in a plate-bound ELISA also revealed that clone 47 does not interact with the low affinity receptor for IL-13, the IL13Rα1 (FIG. 2C), or mouse recombinant IL13Rα2, further validating the specificity of interaction between clone 47 and IL13Rα2 (FIG. 2D). Clones 83807 and B-D13 did not show binding to mouse rIL13Rα2 in agreement with current understanding of the cross-reactivity of these antibodies with mouse IL13Rα2.

Figure 3D:
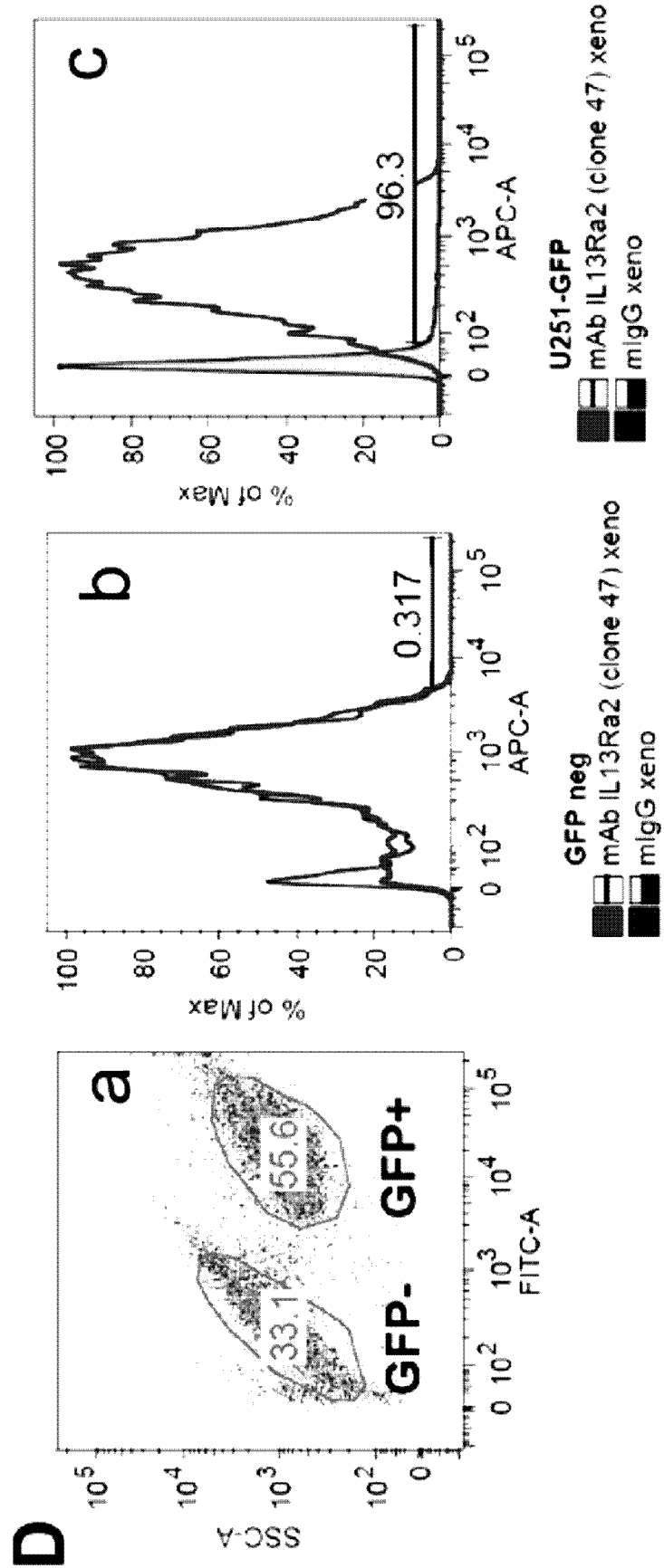
Figure 10:
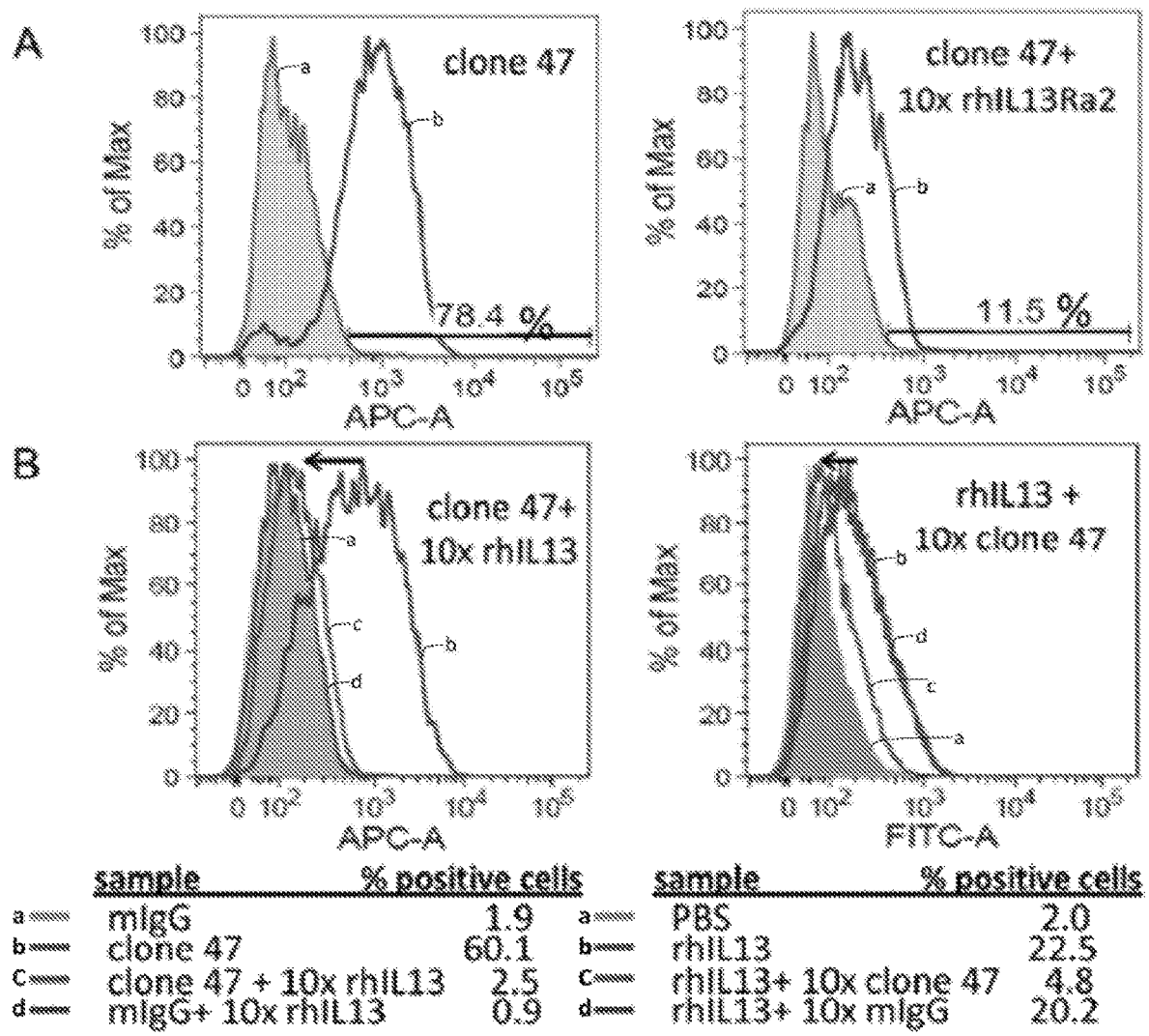
FIG. 10A-B. A competitive binding assay for the IL13Rα2 (clone 47) mAb to the surface of N10 glioma cells. A. The IL13Rα2 (clone 47) mAb was pre-incubated with 10× excess rhIL13Rα2 for 30 minutes on ice. N10 cells were subsequently incubated with isotype control mIgG or IL13Rα2 (clone 47) mAb alone or in the presence of rhIL13Rα2 and bound antibodies were analyzed by flow cytometry. B. N10 glioma cells were pre-incubated either with 10× excess rhIL13 (left panel) or with 10× excess of IL13Rα2 (clone 47) mAb for 30 minutes on ice (right panel). N10 cells were subsequently incubated with isotype control mIgG, IL13Rα2 (clone 47) mAb or rhIL13. Bound antibodies or rhIL13 were detected with secondary antibodies and analyzed by flow cytometry. Data are presented as % of positive cells.

We next characterized the binding capacity of clone 47 with various glioma cell lines, the patient-derived glioma lines GBM12 and GBM43, and normal human astrocytes. Increased expression of the IL13Rα2 gene relative to normal brain tissue is reported in 44-47% of human GBM resected specimens (3) and in up to 82% (14 of 17) primary cell cultures derived from GBM and normal brain explants (2). FIGS. 3, A and B, show the flow charts of the comparative staining of glioma cells, human astrocytes, and HEK cells expressing recombinant human IL13Rα2 on the cell surface with the IL13Rα2 (clones 47, 83807, and B-D13) mAb. FIGS. 3, A and B, reveal (i) various levels of IL13Rα2 expression on the cell surface and (ii) superior binding of the clone 47 versus clones B-D13 (1.2-4.6-fold difference between the cell lines) and 83807 to the surface of analyzed cell lines. Interestingly, we observed a near complete absence of the binding of clone 83807 to glioma cell lines in contrast to HEK cells expressing IL13Rα2. No binding of clone 47 was detected with normal human astrocytes, confirming the specificity of interaction of clone 47 with human glioma cells expressing IL13Rα2. The expression of IL13Rα2 mRNA in these cells generally correlates with the level of IL13Rα2 expression on the cell surface. Moreover, cells expressing low to no mRNA expression for IL13Rα2, including U118 and primary human astrocytes, demonstrated low to no expression for IL13Rα2 on the cell surface (FIG. 3B). In additional experiments, N10 glioma cells were incubated with either the IL13Rα2 (clone 47) mAb at 1 µg/ml or the IL13Rα2 (clone 47) mAb preincubated with a 10-fold excess of rhIL13Rα2 (FIG. 10) and analyzed by flow cytometry. A significant ablation of interaction between the IL13Rα2 (clone 47) mAb in the presence of a 10-fold excess of rhIL13Rα2 was found when compared with clone 47 alone. Similarly, preincubation of N10 cells with either a 10-fold excess of rhIL-13 or IL13Rα2 (clone 47) mAb almost completely blocked the interaction between the antibody or rhIL-13 and N10 cells (supplemental FIG. 1), indicating a specificity of recognition between IL13Rα2 expressed on the surface of glioma cells and clone 47 (FIG. 10).

To verify that the IL13Rα2 (clone 47) mAb possessed the ability to bind IL13Rα2 on the surface of glioma cells in situ, intracranial glioma xenografts of U251 cells expressing green fluorescent protein (GFP) were established in nude mice. Three weeks later, animals were sacrificed, and cells were obtained and placed into in vitro culture conditions. After 48 hours, the cells were collected and stained with control mIgG or IL13Rα2 (clone 47) mAb. Cultured GFP-expressing U251 cells served as a positive control. GFP-positive U251 cells represented about 56% of the total cells (FIG. 3C, panel a), and 96% of the cells were reactive with the IL13Rα2 (clone 47) mAb (FIG. 3C, panel c), whereas GFP-negative cells did not interact with the antibody (FIG. 3C, panel b). These data further confirm that the IL13Rα2 (clone 47) mAb specifically recognizes glioma cells expressing IL13Rα2 in mouse xenografts and is not reactive with other cells from the mouse brain.

Example 4

Affinity Studies

Surface plasmon resonance was used to determine the affinity and rate of interaction between the IL13Rα2 (clone 47) mAb and rhIL13Rα2. All measurements were done in comparison with two commercial antibodies against IL13Rα2, clones 83807 and B-D13. FIG. 4 shows the sensorgrams for each antibody. The measurements are summarized in Table 1.

TABLE 1

Kinetics of monoclonal antibodies binding to the human recombinant IL13Rα2

| mAbs to IL13Rα2 | $k_a$ 1/MS | $k_d$ 1/S | $K_D$ M | $R_{max}$ RU |
|---|---|---|---|---|
| Clone 47 | 9.06e4±322 | 1.26e−4±1.07e−6 | $1.39 \times 10^{-9}$ | 390 |
| Clone 83807 | 2.23e4±620 | 2.31e−3±1.03e−5 | $104 \times 10^{-9}$ | 250 |
| Clone B-D13 | 1.08e5±5.71e3 | 4.99e−3±1.45e−4 | $46.1 \times 10^{-9}$ | 8-16 |

The estimation of kinetic parameters was performed as described in Example 1. The dissociation constant (KD) of the complexes was determined as the ratio $k_a/k_d$. For quantitative analysis, three independent replicates were performed for each sample. Data are expressed as mean S.E. These data demonstrate that the affinity of IL13Rα2 (clone 47) mAb to recombinant IL13Rα2 exceeds the affinity of commercially available mAb clones 83807 and B-D13 by 75-fold and 33-fold, respectively.

FIG. 4A shows that clone 47 demonstrates a prolonged and stable association with rhIL13Rα2 measured over a 30-minute time frame, whereas clones 83807 (FIG. 4B) and B-D13 (FIG. 4C) dissociate relatively quickly. The affinity of binding for the IL13Rα2 (clone 47) mAb to rhIL13Rα2 was calculated at $1.39 \times 10^{-9}$ M. This value exceeded the affinity of the commercially available antibody clones 83807 and B-D13 to rhIL13Rα2 by 75-fold and 33-fold, respectively. Clone 47 demonstrated the highest binding affinity ($R_{max}$) to rhIL13Rα2 at 390 RU when compared with 250 and 8-16 RU for clones 83807 and B-D13, respectively. These data indicate that the IL13Rα2 (clone 47) mAb possesses properties superior to clones 83807 and B-D13 as well as demonstrates a higher affinity toward rhIL13Rα2.

Example 5

A Monoclonal Antibody Competes with rhIL-13 for Binding to IL13Rα2

To determine whether the IL13Rα2 (clone 47) mAb possesses inhibitory properties, competitive binding assays utilizing a rhIL13Rα2hFc chimera and HEK cells transiently expressing the human IL13Rα2 were performed. The competitive binding assay was set up in a plate-bound ELISA format. The rhIL13Rα2hFc absorbed to the plate served as the target antigen. To determine whether the IL13Rα2 mAb specifically inhibits the binding of IL-13 to rhIL13Rα2, plates were preincubated with a 100-fold excess of mIgG, the IL13Rα2 (clone 47) mAb, or other IL13Rα2 mAb clones, including 83807, YY-23Z, and B-D13, followed by incubation with rhIL13. FIG. 5A shows that the IL13Rα2 (clone 47) mAb significantly abolished the binding of rhIL-13 to rhIL13Rα2, whereas the IL13Rα2 mAb clones B-D13 and 83807 exhibited significantly less competition for binding of human IL-13.

To further verify the inhibitory properties of the IL13Rα2 (clone 47) mAb, HEK 293T cells were transfected with an agent encoding wild-type or a 4-amino-acid mutant form of IL13Rα2 cDNA in which Tyr207, Asp271, Tyr315, and Asp318 residues were substituted with Ala. Previously, these residues of the human IL13Rα2 were identified as amino acids required for the interaction with the cognate ligand, IL-13. The presence of all four mutations in one molecule has been shown to result in near complete loss of the binding of IL-13 to the mutated form of IL13Rα2 (28). After 48 hours, the cells were pretreated with a 20-fold excess of rhIL-13 or the IL13Rα2 (clone 47) mAb, followed by incubation of the IL13Rα2 (clone 47) mAb or rhIL-13, respectively. FIG. 5B shows about 50% binding inhibition of IL13Rα2 (clone 47) mAb by a 20-fold excess of rhIL-13 to wild-type (WT) IL13Rα2 but not to the 4-amino-acid mutant form of IL13Rα2. A 20-fold excess of antibody abolished the binding of rhIL-13 to IL13Rα2 when expressed on the cell surface by 80%, which is similar to the result observed in plate ELISA. The residual binding of IL-13 to the 4-amino-acid mutant form of IL13Rα2 was further decreased by an excess of the IL13Rα2 (clone 47) mAb (FIG. 5C). Collectively, these data indicate that the IL13Rα2 (clone 47) mAb specifically competes with rhIL-13 for the binding site on IL13Rα2. Also, these data indicate that the IL13Rα2 (clone 47) mAb and IL-13 have a significant overlap in their recognition site of the IL13Rα2 molecule.

Example 6

Role of the Tyr[207], Asp[271], Tyr[315], and Asp[318] Residues for IL13Rα2 (Clone 47) mAb Binding Taking into consideration that IL-13 and the IL13Rα2 (clone 47) monoclonal antibody can significantly compete with one other for binding of IL13Rα2, we determined whether the residues Tyr207, Asp271, Tyr315, and Asp318 contributing to the interaction of IL-13 with IL13Rα2 (28) were also important for binding of the IL13Rα2 (clone 47) mAb to IL13Rα2. The plasmids encoding cDNA for IL13Rα2 carrying individual mutations of Tyr207, Asp271, Tyr315, or Asp318 residues to Ala or a combination of all four mutations in one molecule were generated and transiently expressed in HEK cells. Binding of the IL13Rα2 (clone 47) mAb to wild-type and mutant forms of IL13Rα2 was analyzed by flow cytometry. The IL13Rα2 mAbs 83807 and B-D13 were used as reference antibodies to exclude a possible influence of variations in the level of expression of wild-type or mutated variants of IL13Rα2 on the surface of HEK cells (FIG. 6A). Data were calculated as a ratio of IL13Rα2 (clone 47) binding to IL13Rα2 when compared with both antibody clones 83807 and B-D13. FIG. 6A demonstrates that the binding of IL13Rα2 (clone 47) mAb was not significantly affected by either the individual mutations or the 4-amino-acid mutant form of IL13Rα2 when compared with wild-type receptor. In contrast, binding of IL-13 to the 4-amino-acid mutant form of IL13Rα2 was nearly abolished (FIG. 6B). These data indicate that the Tyr207, Asp271, Tyr315, and Asp318 residues are not crucial for the interaction of IL13Rα2 (clone 47) mAb with IL13Rα2 but are necessary for binding to IL-13.

Example 7

N-Linked Glycosylation Affects the Affinity of the IL13Rα2 mAb for IL13Rα2

N-Linked glycosylation has previously been demonstrated to be important for efficient binding of IL-13 to the cognate receptor, IL13Rα2 (30). Taking into consideration the significant overlap in epitope recognition between the IL13Rα2 (clone 47) mAb and IL-13, we expected N-linked glycosylation of IL13Rα2 to contribute to binding of the IL13Rα2 (clone 47) mAb. To confirm this expectation, rhIL13Rα2hFc was treated with Pngase F to remove N-linked glycosylation from the protein. The binding of the IL13Rα2 (clone 47) mAb to control and deglycosylated target protein was investigated. Treatment of rhIL13Rα2 with Pngase F was performed under native conditions (in the absence of SDS) to avoid denaturation of the rhIL13Rα2 affecting the binding of antibodies. Additional mAbs to IL13Rα2 (clones 83807, B-D13, and YY23Z) and rhIL-13 were included in the assay to demonstrate the specificity of binding. In a plate-bound ELISA, binding of the IL13Rα2 (clone 47) mAb to Pngase F-treated IL13Rα2 was decreased by 35% when compared with untreated protein (n=4; p<0.001). The binding of the IL13Rα2 (clone 83807) was reduced by 80% when compared with untreated protein and completely absent for the IL13Rα2 mAbs B-D13 and YY-23Z, respectively (n=4; p<0.001) (FIG. 7A). Binding of rhIL-13 with Pngase F-treated rhIL13Rα2 was also significantly diminished. To verify that Pngase F treatment resulted in deglycosylation of the protein, control and Pngase F-treated rhIL13Rα2hFc protein was resolved by Western blot. FIG. 7B shows that Pngase F-treated protein has a lower molecular weight, confirming the removal of N-linked glycans from the IL13Rα2 molecule. Binding of the IL13Rα2 (clone 47) mAb to Pngase F-treated U251 glioma and HEK 293 cells expressing wild-type IL13Rα2 was also decreased by about 30% (n=3; p<0.05) when compared with control untreated cells (FIG. 7C).

Example 8

Immunohistochemistry

Figure 8:
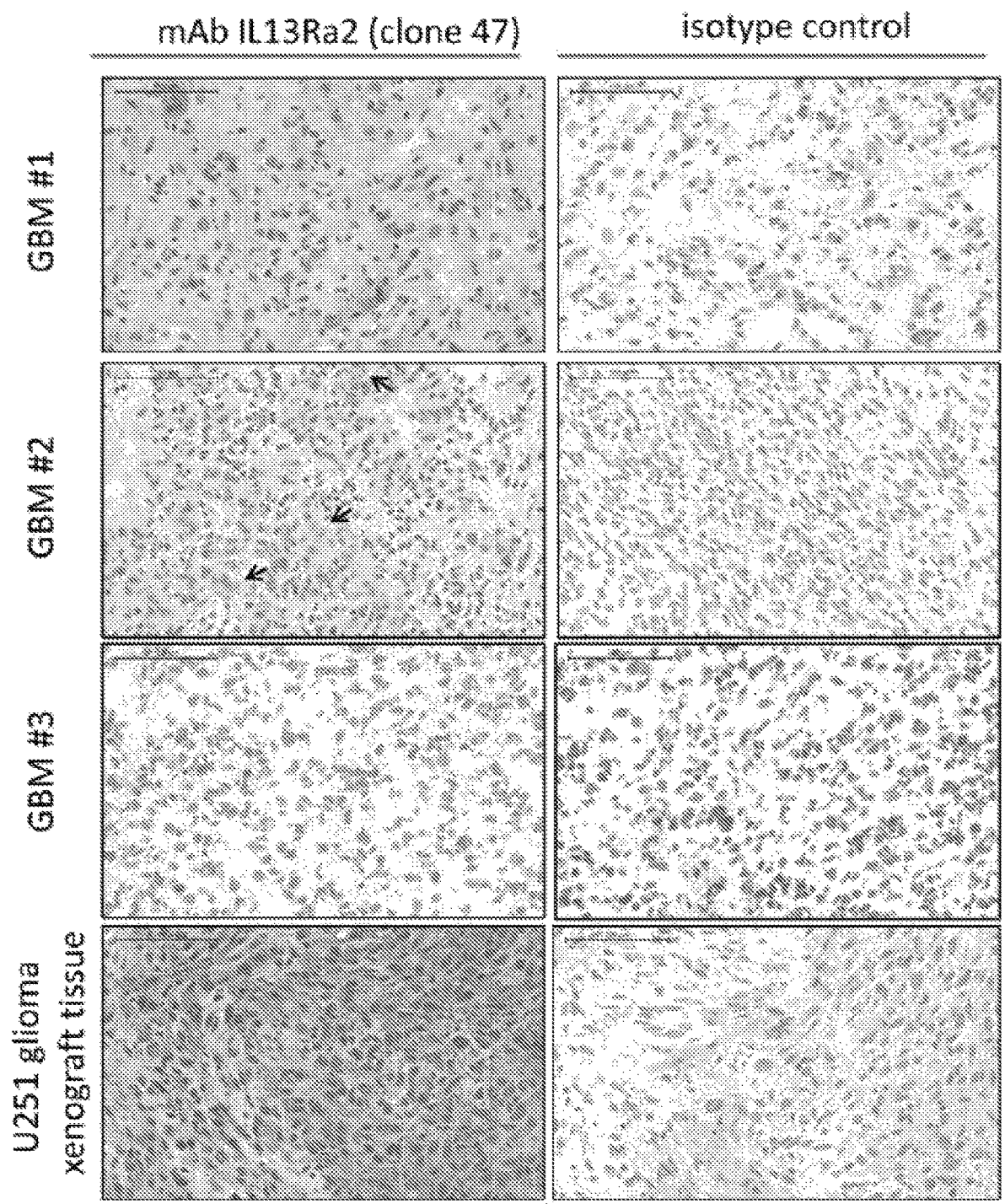
FIG. 8. The IL13Rα2 (clone 47) mAb recognizes IL13Rα2 in GBM tissues and in a human glioma xenograft. Immunohistochemistry on frozen tissue sections from three human GBM samples and a U251 xenograft was performed with the IL13Rα2 (clone 47) mAb or mIgG at a concentration of 3 µg/ml. Staining of GBM tissues demonstrates positive staining of the majority of cells in sample 1, positive reactivity in only a fraction of the cells in sample 2, and negative staining in sample 3. Staining in all three samples was performed in the same experiment. Positive staining was also detected in U251 xenograft tissue. Arrows point to individual positive cells. Scale bars=100 µm.

The ability of the IL13Rα2 (clone 47) mAb to detect IL13Rα2 was evaluated in fresh frozen tissues. Flash-frozen human GBM samples or the U251 glioma flank xenograft was stained with either isotype control mIgG1 or the IL13Rα2 (clone 47) mAb. FIG. 8 shows positive (brown) staining in the two human GBM samples, albeit with different frequency of positive cells in the sample as well as a U251 glioma cell-based glioma xenograft. Positive staining was detected in two of the three GBM samples analyzed, which is consistent with the expectation that fewer than 50% of primary GBM express IL13Rα2 (3). These data are also consistent with the ability of this antibody to recognize the native form of IL13Rα2 expressed on the cell surface and in ELISA applications, as well as the compromised ability of this mAb to detect denatured antigen by Western blotting.

Example 9

Figure 9:
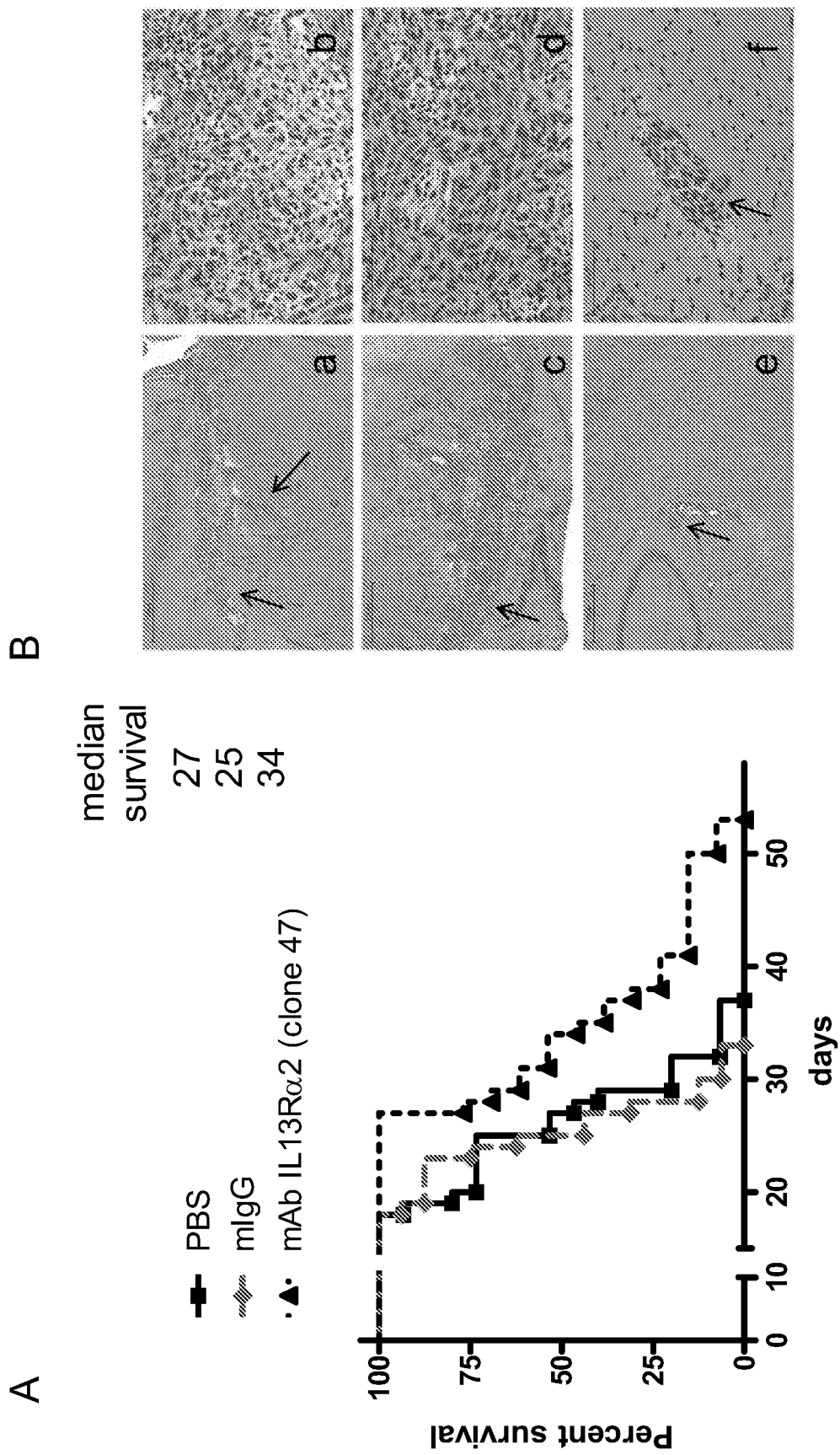
FIG. 9A-B. The IL13Rα2 (clone 47) mAb improves the survival of mice in an orthotopic human glioma xenograft model. A, the survival of animals injected with U251 glioma cells ($2.5\times10^4$) alone or in combination with either control IgG or the IL13Rα2 (clone 47) mAb. B, a representative photomicrograph of 10-µm-thick tissue sections stained with H&E from mice injected with U251 cells alone (panels a and b) or in combination with mIgG (panels c and d) or mAbIL13Rα2 (clone 47) (panels e and f). Arrows point to the tumor and invading cells. Scale bars (panels a, c, and e)=100 µm. Scale bars (panels b, d, and f)=100 µm.
Figure 11:
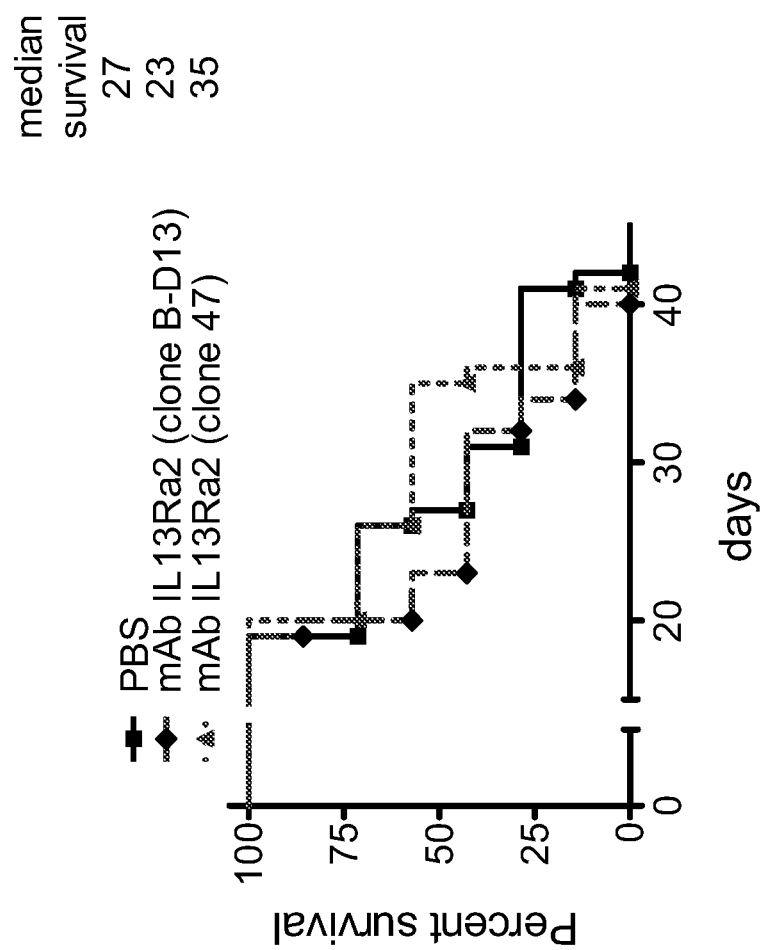
FIG. 11. The effects of IL13Rα2 (clone 47) mAb on the survival of mice with an established human U251 glioma. Mice were intracranially-injected with $2.5\times10^4$ U251 glioma cells and treated three days later with a single injection of PBS (n=7) or 10 µg IL13Rα2 (clone 47 or B-D13) mAb (n=7). The analysis of the animal's survival was performed using the Log-rank test. Median survival was determined to be 27 days in the PBS group, versus 23 and 35 days in the groups treated with B-D13 and 47 IL13Rα2 mAb, respectively ($p>0.05$).

The IL13Rα2 Monoclonal Antibody Prolongs the Survival of Animals with an Intracranial Glioma Xenograft The potential therapeutic properties of the IL13Rα2 (clone 47) mAb were also determined in an orthotopic mouse model of human glioma. U251 glioma cells were intracranially injected into the brain of nude mice alone, in the presence of control mIgG, or with the IL13Rα2 (clone 47) mAb. FIG. 9A shows that animals in the control PBS (n=15) and mIgG (n=16) groups demonstrated a similar median survival of 27 and 25 days, respectively. In contrast, the survival of animals co-injected with the IL13Rα2 (clone 47) mAb (n=13) was significantly increased to a median of 34 days (p=0.0001; mIgG versus the IL13Rα2 mAb group). Analysis of H&E staining of the glioma xenografts from brains collected on day 17 revealed a similar pattern of glioma cell distribution in the brain of control groups. In contrast, the tumor mass in the group of animals co-injected with IL13Rα2 mAb was significantly decreased in size (FIG. 9B). Independently, U251 cells were inoculated in the brains of mice and 3 days later injected through the same burr hole with either PBS or the IL13Rα2 (clone 47 or B-D13) mAb as described previously (29). Interestingly, the mice injected with clone 47 demonstrated improvement in median survival when compared with PBS and clone B-D13 groups (35 days versus 27 and 23 days, respectively; n=7; p>0.05) (FIG. 11), similar to what was found in the co-injection experiment (FIG. 9A). Nevertheless, all animals ultimately succumbed to the disease. These data indicate that the IL13Rα2 (clone 47) mAb shows promise in promoting tumor rejection of IL13Rα2-expressing U251 glioma cells in the mouse brain. This finding leads to the expectation that antibody agent incorporating the IL13Rα2-binding domain of the IL13Rα2 (clone 47) mAb will be efficacious in treating a variety of human and non-human cancers characterized by the presentation of IL13Rα2, such as IL13Rα2-expressing glioma cells and other malignant cell types.

References—for Examples 1-9 and for Citations Throughout the Application Unless Specifically Identified Otherwise 1. Debinski, W., Obiri, N. I., Powers, S. K., Pastan, I., and Puri, R. K. (1995) Clin. Cancer Res. 1, 1253-1258.
2. Joshi, B. H., Plautz, G. E., and Puri, R. K. (2000) Cancer Res. 60, 1168-1172.
3. Jarboe, J. S., Johnson, K. R., Choi, Y., Lonser, R. R., and Park, J. K. (2007) Cancer Res. 67, 7983-7986.
4. Kawakami, K., Terabe, M., Kawakami, M., Berzofsky, J. A., and Puri, R. K. (2006) Cancer Res. 66, 4434-4442.
5. Fujisawa, T., Joshi, B., Nakajima, A., and Puri, R. K. (2009) Cancer Res. 69, 8678-8685.
6. Debinski, W., Slagle, B., Gibo, D. M., Powers, S. K., and Gillespie, G. Y. (2000) J. Neurooncol. 48, 103-111.
7. Aman, M. J., Tayebi, N., Obiri, N. I., Puri, R. K., Modi, W. S., and Leonard, W. J. (1996) J. Biol. Chem. 271, 29265-29270.
8. Gauchat, J. F., Schlagenhauf, E., Feng, N. P., Moser, R., Yamage, M., Jeannin, P., Alouani, S., Elson, G., Notarangelo, L. D., Wells, T., Eugster, H. P., and Bonnefoy, J. Y. (1997) Eur. J. Immunol. 27, 971-978.
9. Akaiwa, M., Yu, B., Umeshita-Suyama, R., Terada, N., Suto, H., Koga, T., Arima, K., Matsushita, S., Saito, H., Ogawa, H., Furue, M., Hamasaki, N., Ohshima, K., and Izuhara, K. (2001) Cytokine 13, 75-84.
10. Rahaman, S. O., Sharma, P., Harbor, P. C., Aman, M. J., Vogelbaum, M. A., and Haque, S. J. (2002) Cancer Res. 62, 1103-1109.
11. Fichtner-Feigl, S., Strober, W., Kawakami, K., Puri, R. K., and Kitani, A. (2006) Nat. Med. 12, 99-106.
12. Shimamura, T., Fujisawa, T., Husain, S. R., Joshi, B., and Puri, R. K. (2010) Clin. Cancer Res. 16, 577-586.
13. Fujisawa, T., Joshi, B. H., and Puri, R. K. (2012) Int. J. Cancer 131, 344-356.
14. Murphy, E. V., Zhang, Y., Zhu, W., and Biggs, J. (1995) Gene 159, 131-135.
15. Rich, T., Chen, P., Furman, F., Huynh, N., and Israel, M. A. (1996) Gene 180, 125-130.
16. Stupp, R., Mason, W. P., van den Bent, M. J., Weller, M., Fisher, B., Taphoorn, M. J., Belanger, K., Brandes, A. A., Marosi, C., Bogdahn, U., Curschmann, J., Janzer, R. C., Ludwin, S. K., Gorlia, T., Allgeier, A., Lacombe, D., Cairncross, J. G., Eisenhauer, E., and Mirimanoff, R. O. (2005) N. Engl. J. Med. 352, 987-996.
17. Kunwar, S., Prados, M. D., Chang, S. M., Berger, M. S., Lang, F. F., Piepmeier, J. M., Sampson, J. H., Ram, Z., Gutin, P. H., Gibbons, R. D., Aldape, K. D., Croteau, D. J., Sherman, J. W., and Puri, R. K. (2007) J. Clin. Oncol. 25, 837-844.
18. Wykosky, J., Gibo, D. M., Stanton, C., and Debinski, W. (2008) Clin. Cancer Res. 14, 199-208.

19. Debinski, W., Gibo, D. M., Obiri, N. I., Kealiher, A., and Puri, R. K. (1998) Nat. Biotechnol. 16, 449-453.
20. Kawakami, M., Kawakami, K., and Puri, R. K. (2002) Mol. Cancer Ther. 1, 999-1007.
21. Husain, S. R., and Puri, R. K. (2000) Blood 95, 3506-3513.
22. Bartolazzi, A., Nocks, A., Aruffo, A., Spring, F., and Stamenkovic, I. (1996) J. Cell Biol. 132, 1199-1208.
23. Kioi, M., Seetharam, S., and Puri, R. K. (2008) Mol. Cancer Ther. 7, 1579-1587.
24. Pini, A., and Bracci, L. (2000) Curr. Protein Pept. Sci. 1, 155-169.
25. Ross, J. S., Gray, K., Gray, G. S., Worland, P. J., and Rolfe, M. (2003) Am. J. Clin. Pathol. 119, 472-485.
26. Souriau, C., and Hudson, P. J. (2003) Expert Opin. Biol. Ther. 3, 305-318.
27. Kohler, G., and Milstein, C. (1975) Nature 256, 495-497.
28. Arima, K., Sato, K., Tanaka, G., Kanaji, S., Terada, T., Honjo, E., Kuroki, R., Matsuo, Y., and Izuhara, K. (2005) J. Biol. Chem. 280, 24915-24922.
29. Sampson, J. H., Crotty, L. E., Lee, S., Archer, G. E., Ashley, D. M., Wikstrand, C. J., Hale, L. P., Small, C., Dranoff, G., Friedman, A. H., Friedman, H. S., and Bigner, D. D. (2000) Proc. Natl. Acad. Sci. U.S.A. 97, 7503-7508.
30. Kioi, M., Seetharam, S., and Puri, R. K. (2006) FASEB J. 20, 2378-2380.
31. McKenzie, A. N., Culpepper, J. A., de Waal Malefyt, R., Briere, F., Punnonen, J., Aversa, G., Sato, A., Dang, W., Cocks, B. G., and Menon, S. (1993) Proc. Natl. Acad. Sci. U.S.A. 90, 3735-3739.
32. Donaldson, D. D., Whitters, M. J., Fitz, L. J., Neben, T. Y., Finnerty, H., Henderson, S. L., O'Hara, R. M., Jr., Beier, D. R., Turner, K. J., Wood, C. R., and Collins, M. (1998) J. Immunol. 161, 2317-2324.
33. Hansen, H. J., Goldenberg, D. M., Newman, E. S., Grebenau, R., and Sharkey, R. M. (1993) Cancer 71, 3478-3485.
34. Kuan, C. T., Wikstrand, C. J., Archer, G., Beers, R., Pastan, I., Zalutsky, M. R., and Bigner, D. D. (2000) Int. J. Cancer 88, 962-969.
35. Imperiali, B., and Rickert, K. W. (1995) Proc. Natl. Acad. Sci. U.S.A. 92, 97-101.
36. Sondermann, P., Huber, R., Oosthuizen, V., and Jacob, U. (2000) Nature 406, 267-273.
37. Krapp, S., Mimura, Y., Jefferis, R., Huber, R., and Sondermann, P. (2003) J. Mol. Biol. 325, 979-989.
38. Fernandes, H., Cohen, S., and Bishayee, S. (2001) J. Biol. Chem. 276, 5375-5383.
39. Hsu, Y. F., Ajona, D., Corrales, L., Lopez-Picazo, J. M., Gurpide, A., Montuenga, L. M., and Pio, R. (2010) Mol. Cancer 9, 139.
40. Cartron, G., Watier, H., Golay, J., and Solal-Celigny, P. (2004) Blood 104, 2635-2642.
41. de Haij, S., Jansen, J. H., Boross, P., Beurskens, F. J., Bakema, J. E., Bos, D. L., Martens, A., Verbeek, J. S., Parren, P. W., van de Winkel, J. G., and Leusen, J. H. (2010) Cancer Res. 70, 3209-3217.
42. Minn, A. J., Kang, Y., Serganova, I., Gupta, G. P., Giri, D. D., Doubrovin, M., Ponomarev, V., Gerald, W. L., Blasberg, R., and Massague, J. (2005) J. Clin. Investig. 115, 44-55.
43. Kawakami, M., Kawakami, K., Kasperbauer, J. L., Hinkley, L. L., Tsukuda, M., Strome, S. E., and Puri, R. K. (2003) Clin. Cancer Res. 9, 6381-6388.
44. Husain, S. R., Obiri, N. I., Gill, P., Zheng, T., Pastan, I., Debinski, W., and Puri, R. K. (1997) Clin. Cancer Res. 3, 151-156.
45. Puri, R. K., Leland, P., Obiri, N. I., Husain, S. R., Kreitman, R. J., Haas, G. P., Pastan, I., and Debinski, W. (1996) Blood 87, 4333-4339.
46. Joshi, B. H., Leland, P., and Puri, R. K. (2003) Croat. Med. J. 44, 455-462.
47. Barderas R, Bartolome R A, Fernandez-Acenero M J, Torres S, Casal J I. Cancer Res. 2012 Jun. 1; 72(11):2780-90.

Example 10

A Single-Chain Antibody for Selective Targeting of IL13Rα2-Expressing Brain Tumors IL13Rα2 is overexpressed in a majority of high-grade astrocytomas and other malignancies, and has been validated as a target for therapeutic applications in various preclinical models. However, current IL13-based therapeutic agents lack specificity due to interaction with the IL13Rα1 receptor, which is widely expressed by normal or healthy cells. The generation of a targeting agent that strictly binds to IL13Rα2 would significantly expand the therapeutic potential for the treatment of IL13Rα2-expressing cancers. Recently, a monoclonal antibody 47 (mAb47) has been developed and extensively characterized. The mAb47 exclusively binds to a native form of human IL13Rα2. Using mAb47, a single-chain antibody (scFv) fragment was engineered from mAb47 expressed by the parental hybridoma cell line. The single-chain antibody (scFv) fragment was tested for its targeting properties as a soluble agent, and an adenovirus (Ad) with a modified fiber incorporating scFv47 as a targeting motif was agented.

The phage-display approach was utilized for selection of a functional combination of variable heavy ($V_H$) and light ($V_L$) chains from established hybridoma cells producing mAb47. Purified phages displaying scFv47 were tested for their interaction with IL13Rα2hFc recombinant protein, i.e., a fusion of IL13Rα2 and the Fc region of an antibody. A competitive ELISA was utilized to verify that the parental mAb47 and the scFv47 fragment bind to the same epitope. The soluble form of scFv47 expressed in E. coli and CHO cells was analyzed by SDS-PAGE, and tested for stability and targeting properties. To generate IL13Rα2-specific Ad, the fiber of a replication-deficient Ad5 encoding green fluorescent protein was replaced with a chimeric fiber gene composed of a T4 fibritin trimerization domain linked at its C-terminal to scFV47 (AdFFscFv47-CMV-GFP). To generate viral particles, an agent encoding the adenoviral genome was rescued in HEK293F28 cells, propagated, and purified. IL13Rα2+ and IL13Rα2-U251 cell lines were established via stable transfection with either control or IL13Rα2-specific shRNAs (U251-IL13Rα2.KO), respectively. The AdFFscFv47-CMV-GFP virus was tested for targeting properties in these U251 cell lines and in IL13Rα2-expressing U87 cells.

The biopanning-selected pool of phages, as well several individual clones, demonstrated specific binding to IL13Rα2hFc protein, but not to hIgG in plate ELISA. Binding of scFv47-displayed phages to IL13Rα2 was completely abolished by mAb47, but not by control IgG or other tested IL13Rα2 mAbs, thus confirming the same IL13Rα2 epitope was recognized by scFv47 as was recognized by the parental mAb47. Similarly to phage-displayed scFv47, the soluble scFv47 showed specific binding to IL123Rα2, but not to IL13Rα1. Interaction of Ad5FFscFv47-CMV-GFP was also specific to IL13Rα2-expressing U251 cells, as judged by flow cytometry for GFP expression in U251-IL13Rα2+ versus U251-IL13Rα2.KO cells. Furthermore, GFP expression in cells infected with Ad5FFscFv47-CMV-GFP strongly correlated with the level of surface expression of IL13Rα2. The specificity of viral infection was further validated in a U251 glioma model.

The data validate scFv47 as a highly selective IL13Rα2 targeting agent that provides a soluble, single-chain biologic useful in diagnosing and treating IL13Rα2-expressing cancers, such as gliomas, colon cancers (see Example 12) and others.

Example 11

Generation of an IL13Rα2-CAR

Figure 18A:
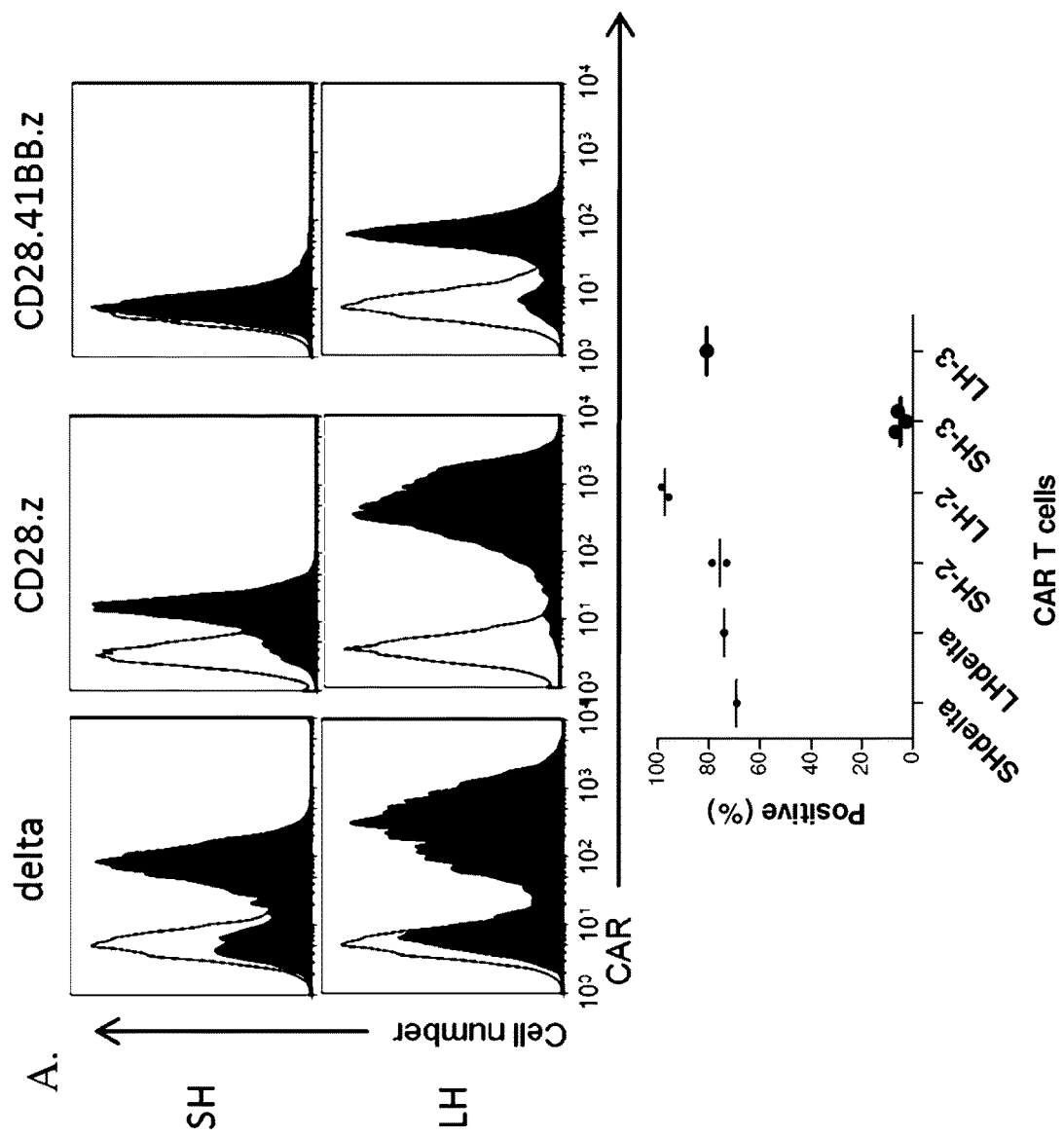
FIG. 18A-B. IL13Rα2-scFv CARs are expressed on the surface of T cells. IL13Rα2-CAR T cells were generated by retroviral transduction and CAR expression was determined by FACS analysis. Short hinge CARs were detected with an antibody specific for murine scFV. Long hinge CARs were detected with an antibody specific for the long hinge. Isotype: open curve; Specific Antibody: filled curve.
Figure 18B:
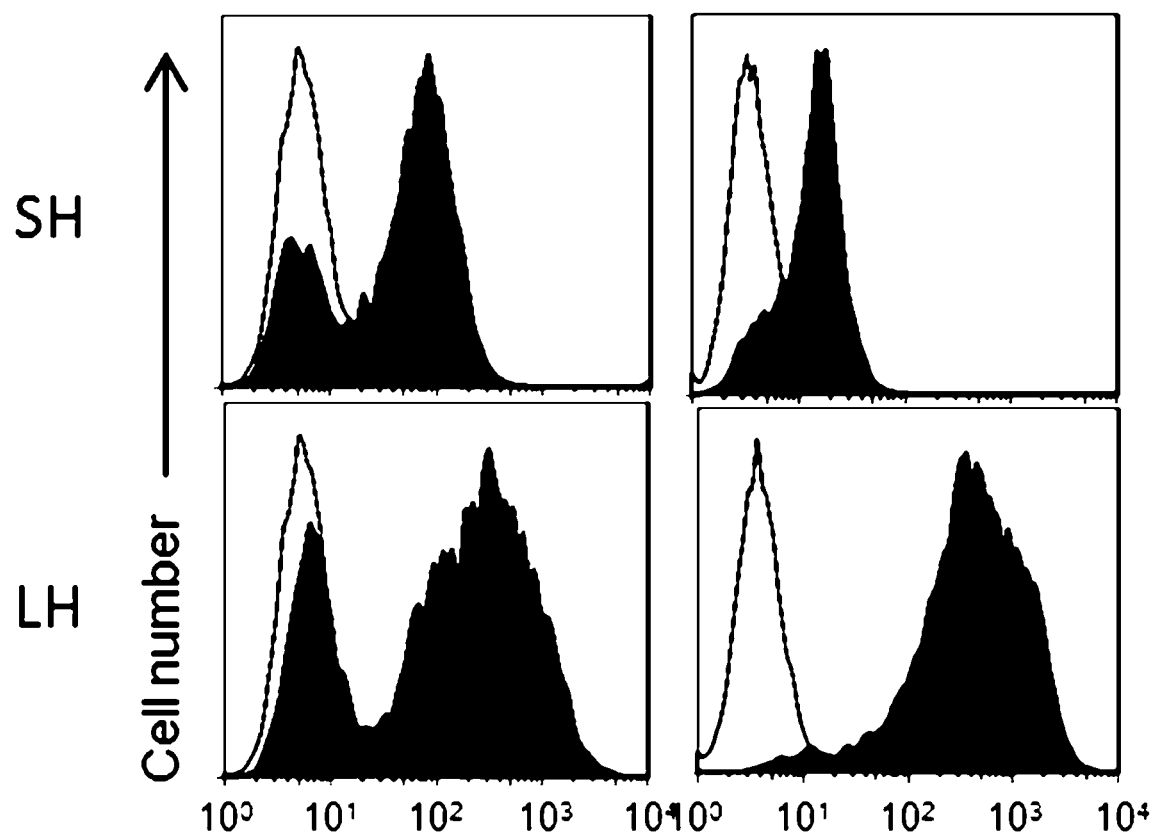
Figure 19:
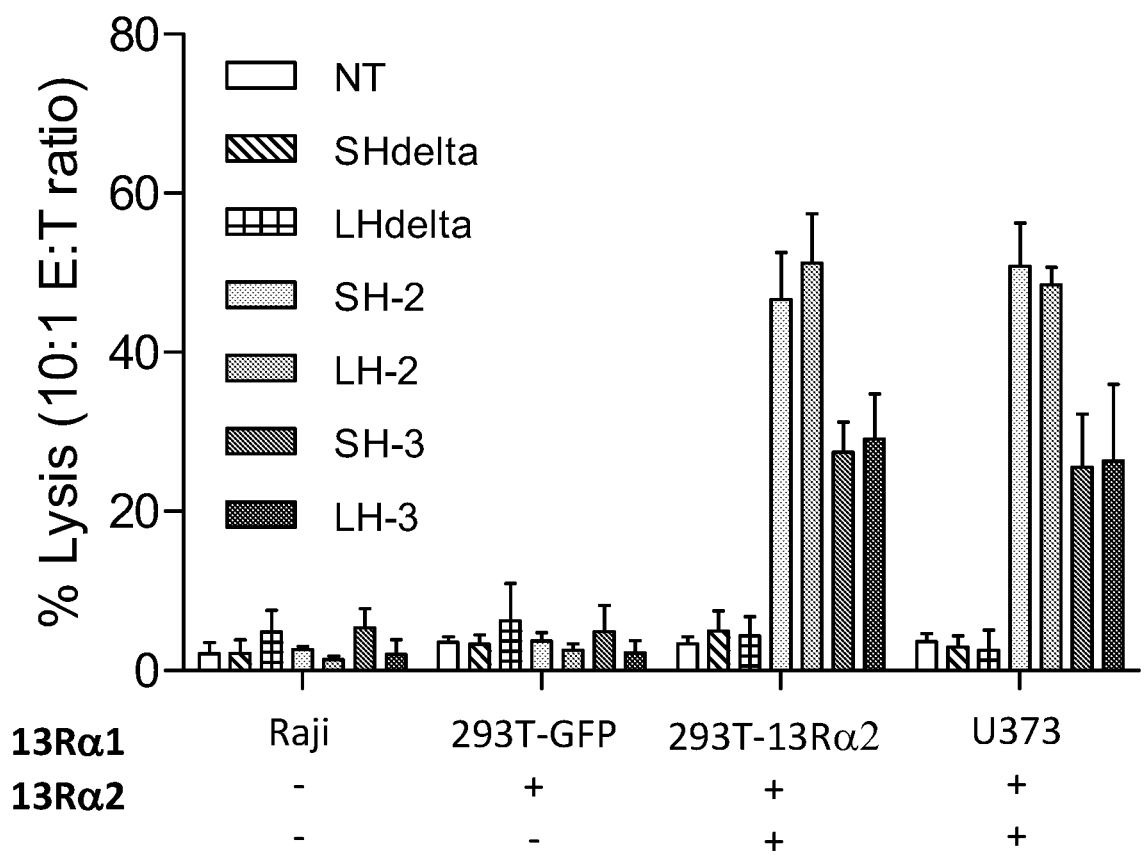
FIG. 19. Functional characterization of IL13Rα2-CAR T cells—Cytotoxicity. Standard $^{51}$Chromium cytotoxicity assays were performed with Raji (IL13Rα1−/IL13Rα2−), 293T (IL13Rα1+/IL13Rα2−), 293T genetically modified to express IL13Rα2 cells (293T-IL13Rα2; IL13Rα1+/IL13Rα2+), or U373 (IL13Rα1+/IL13Rα2+) cells as targets. As effectors nontransduced (NT) T cells, IL13Rα2-CAR.SH.CD28.ζ T cells, IL13Rα2-CAR.LH.CD28.ζ T cells, IL13Rα2-CAR.SH.Δ T cells, or IL13Rα2-CAR.LH.Δ T cells were used. Only IL13Rα2-CAR.SH.CD28.ζ T cells and IL13Rα2-CAR.LH.CD28.ζ T cells killed with IL13Rα2+ target cells (U373 and 293T-IL13Rα2; n=4). T cells expressing nonfunctional CARs (IL13Rα2-CAR.SH.Δ and IL13Rα2-CAR.LH.Δ) had not cytolytic activity, demonstrating that the killing activity depends on the expression of a functional IL13Rα2-CAR. NT T cells killed none of the targets, further confirming specificity.
Figure 20:
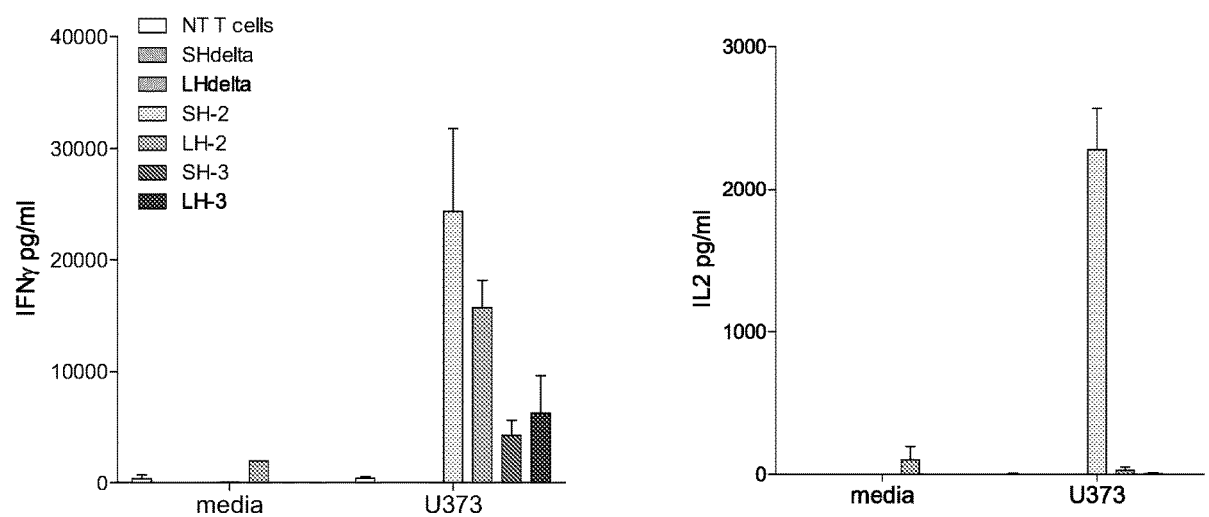
FIG. 20. Functional characterization of IL13Rα2-CAR T cells—IFNγ and IL2 Cytokine secretions. A. NT T cells, IL13Rα2-CAR.SH.CD28.ζ T cells, IL13Rα2-CAR.LH.CD28.ζ T cells, IL13Rα2-CAR.SH.Δ T cells, or IL13Rα2-CAR.LH.Δ T cells were co-cultured with U373 cells for 24 to 48 hours (n=4). Only IL13Rα2-CAR.SH.CD28.ζ T cells and IL13Rα2-CAR.LH.CD28.ζ T cells secreted IFNγ demonstrating target cell recognition in contrast to IL13Rα2-CAR.SH.Δ T cells, IL13Rα2-CAR.LH.Δ T cells or NT T cells. B. NT T cells, IL13Rα2-CAR.SH.CD28.ζ T cells, IL13Rα2-CAR.LH.CD28.ζ T cells, IL13Rα2-CAR.SH.Δ T cells, or IL13Rα2-CAR.LH.Δ T cells were co-cultured with U373 cells for 24 to 48 hours (n=4). Only IL13Rα2-CAR.SH.CD28.ζ T cells secreted IL2, demonstrating that IL13Rα2-CAR.SH.CD28.ζ induces superior T cell activation in comparison to IL13Rα2-CAR.LH.CD28.ζ. IL13Rα2-CAR.SH.Δ T cells, IL13Rα2-CAR.LH.Δ T cells or NT T cells also did not induce IL2 production.

To generate an IL13Rα2-specific T cell, an IL13Rα2-specific chimeric antigen receptor (CAR) was initially agented. A codon-optimized minigene was synthesized that contained the immunoglobulin heavy-chain leader peptide and the heavy and light chains of the IL13Rα2-specific single-chain variable fragment (scFv) separated by a linker (the scFv was derived from hybridoma 47, Balyasnikova et al. J Biol. Chem. 2012; 287(36):30215-30277). The minigene was subcloned into an SFG retroviral vector containing the human IgG1-CH2CH3 domain, a CD28 transmembrane domain, and costimulatory domains derived from CD28 and the CD3ζ-chain. CD3/CD28-activated human T cells were transduced with RD114-pseudotyped retroviral particles and subsequently expanded using IL2. Functional analysis revealed that T cells expressing IL13Rα2-specific CARs (IL13Rα2-CAR T cells) recognized recombinant IL13Rα2 protein as judged by cytokine production (IFNγ and IL2; FIGS. 19 and 20), and killed IL13Rα2-positive cells in a cytotoxicity assay (FIG. 18). Non-transduced (NT) T cells did not produce cytokines and had no cytolytic activity.

Example 12

Redirecting T Cells to IL13Rα2-Positive Pediatric Glioma

IL13Rα2 is aberrantly expressed in Glioblastoma Multiforme and is, therefore, a promising target for CAR T-cell immunotherapy. The antigen recognition domain of CARs normally consists of a single-chain variable fragment (scFv), but current IL13Rα2-specific CARs use IL13 muteins as an antigen recognition domain. IL13 mutein-based CARs, however, have been shown to also recognize IL13Rα1, raising significant safety concerns. To overcome this obstacle, a high affinity IL13Rα2-specific scFv has been agented. This scFv is used in developing a scFv-based IL13Rα2-specific CAR (IL13Rα2-CAR), which, when expressed in T cells, will provide IL13Rα2-CAR T cells having cytotoxic effector function.

Antigen-specific T cells were incorporated into an effective immunotherapy for diffuse intrinsic pontine glioma (DIPG) and glioblastoma (GBM), which are the most aggressive, uniformly fatal, primary human brain tumors in children. IL13Rα2 is expressed at a high frequency in both DIPG and GBM, but not in normal brain, making it a promising target for T-cell immunotherapy, including scFv-based therapy, scFv-CAR T-cell-based therapy, and scFv fusions to other frameworks providing effector function, such as BiTEs and scFv-CAR-NKs. IL13-binding CARs have been generated using mutated forms of IL13 as CAR binding domains, but these CARs also recognize IL13Rα1, raising significant toxicity concerns.

Figure 21:
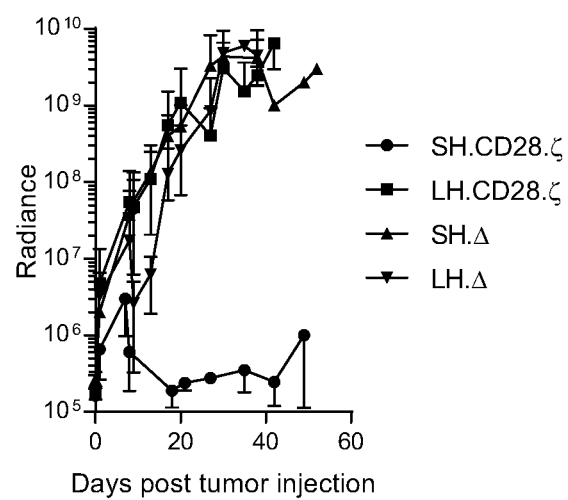
FIG. 21. IL13Rα2-SH CARs have anti-glioma activity in vivo. Severe combined immunodeficient (SCID) mice were injected with 1×10$^5$ firefly luciferase expressing U373 cells intracranially. On day 7 mice were treated either with 1×10$^6$ IL13Rα2-CAR.SH.CD28.ζ T cells, IL13Rα2-CAR.LH.CD28.ζ T cells, IL13Rα2-CAR.SH.Δ T cells, or IL13Rα2-CAR.LH.Δ T cells (5 mice per group). Tumor growth was monitored by bioluminescence imaging. Only IL13Rα2-CAR.SH.CD28.ζ T cells had significant anti-glioma effects with 4/5 mice having a complete response.
Figure 23:
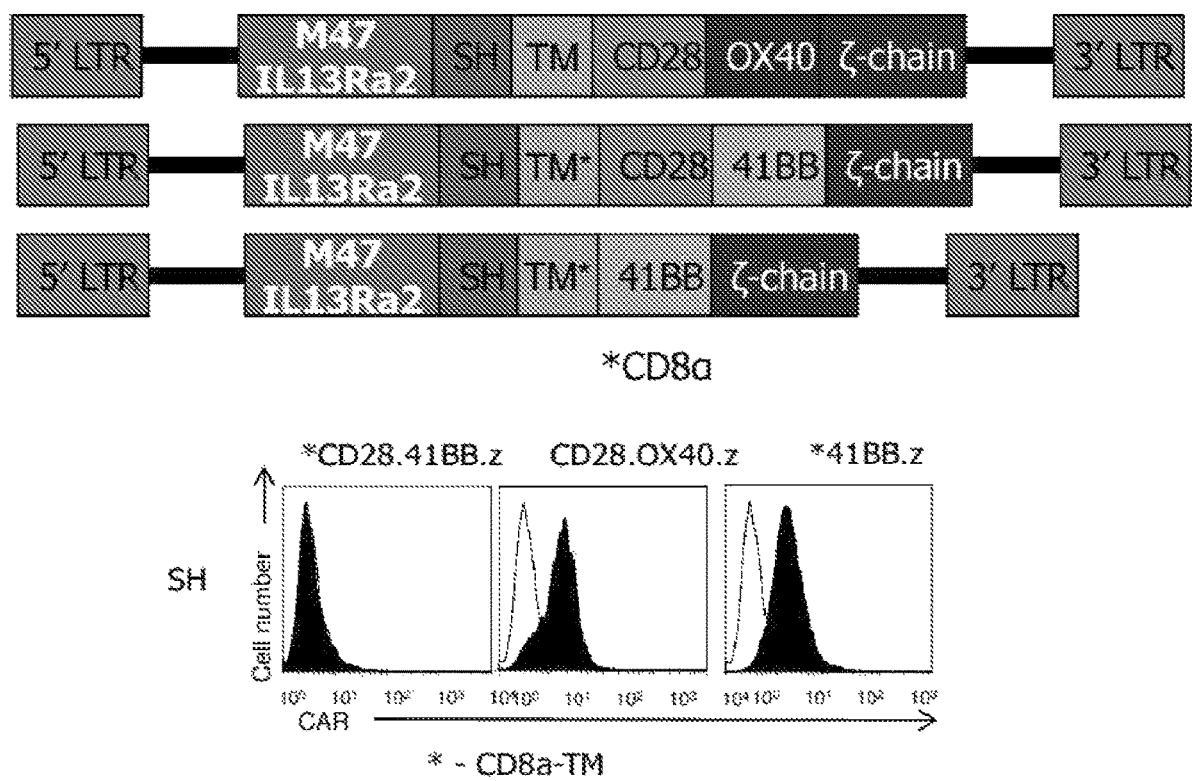
FIG. 23. Functional comparison of m47 CAR T cell agents. Open curve: secondary antibody; Filled curve: IL13Rα2Fc+secondary antibody.
Figure 24:
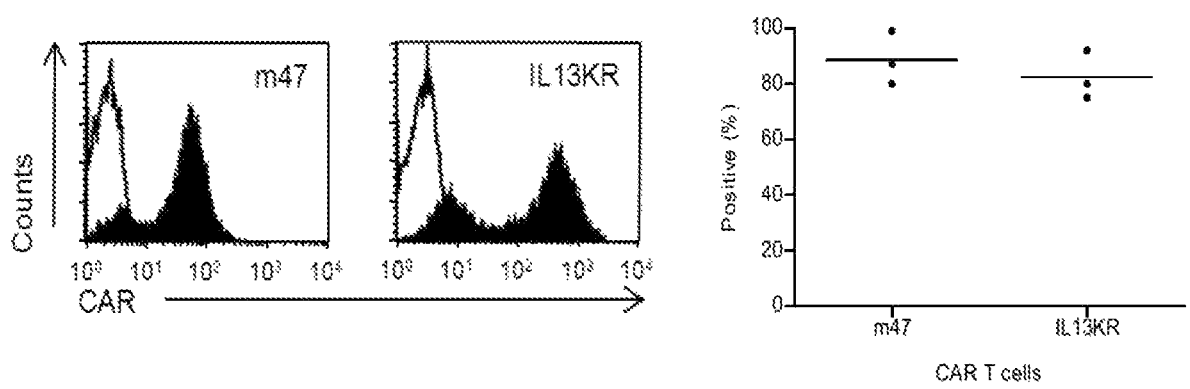
FIG. 24. The m47 CAR T cell agent is highly expressed after transduction. Open curve: secondary antibody; Filled curve: IL13Rα2Fc+secondary antibody.
Figure 25:
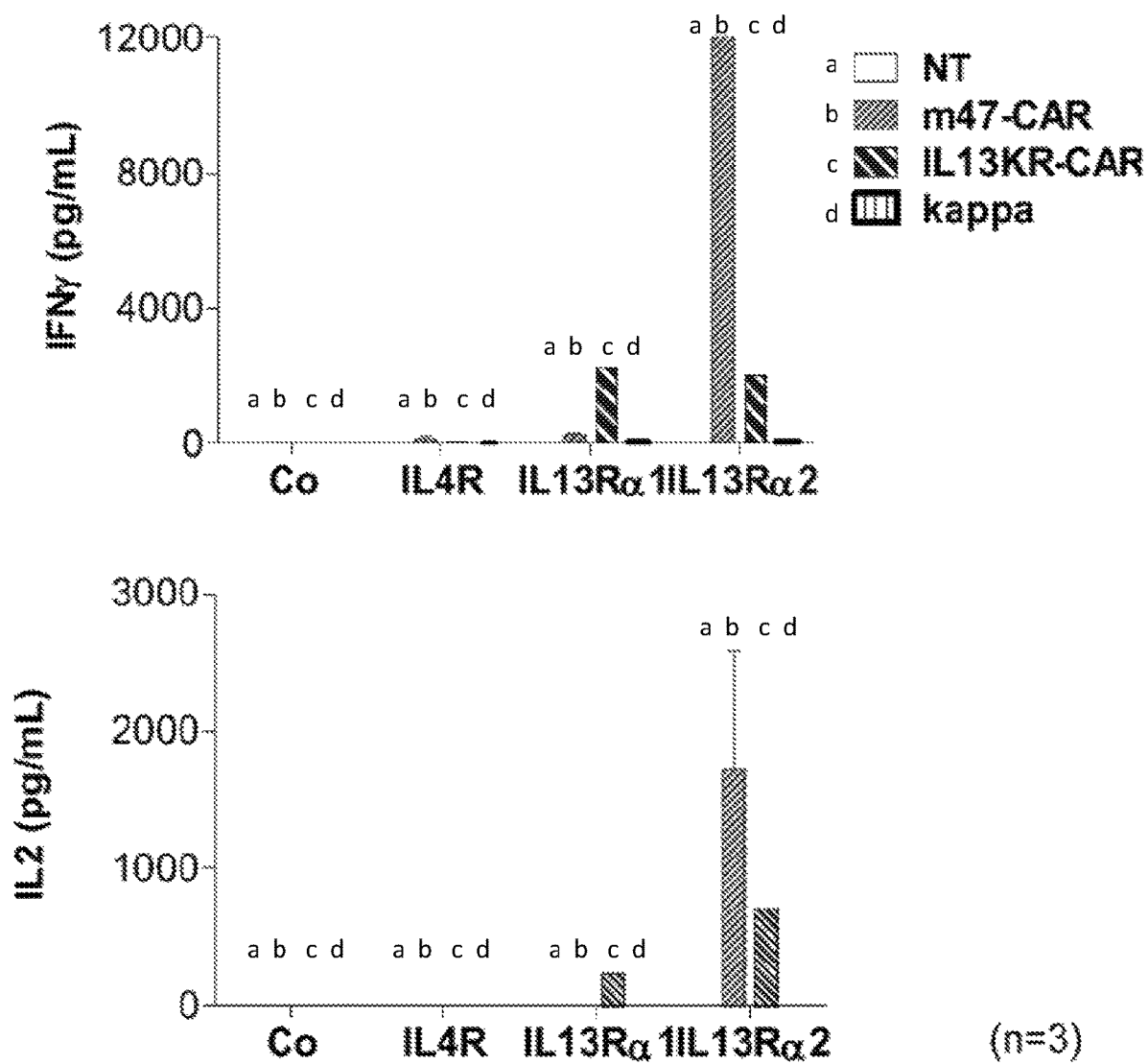
FIG. 25. The m47 CAR T cell produce interferon γ and interleukin 2, but only after IL13Rα2 stimulation.
Figure 26:
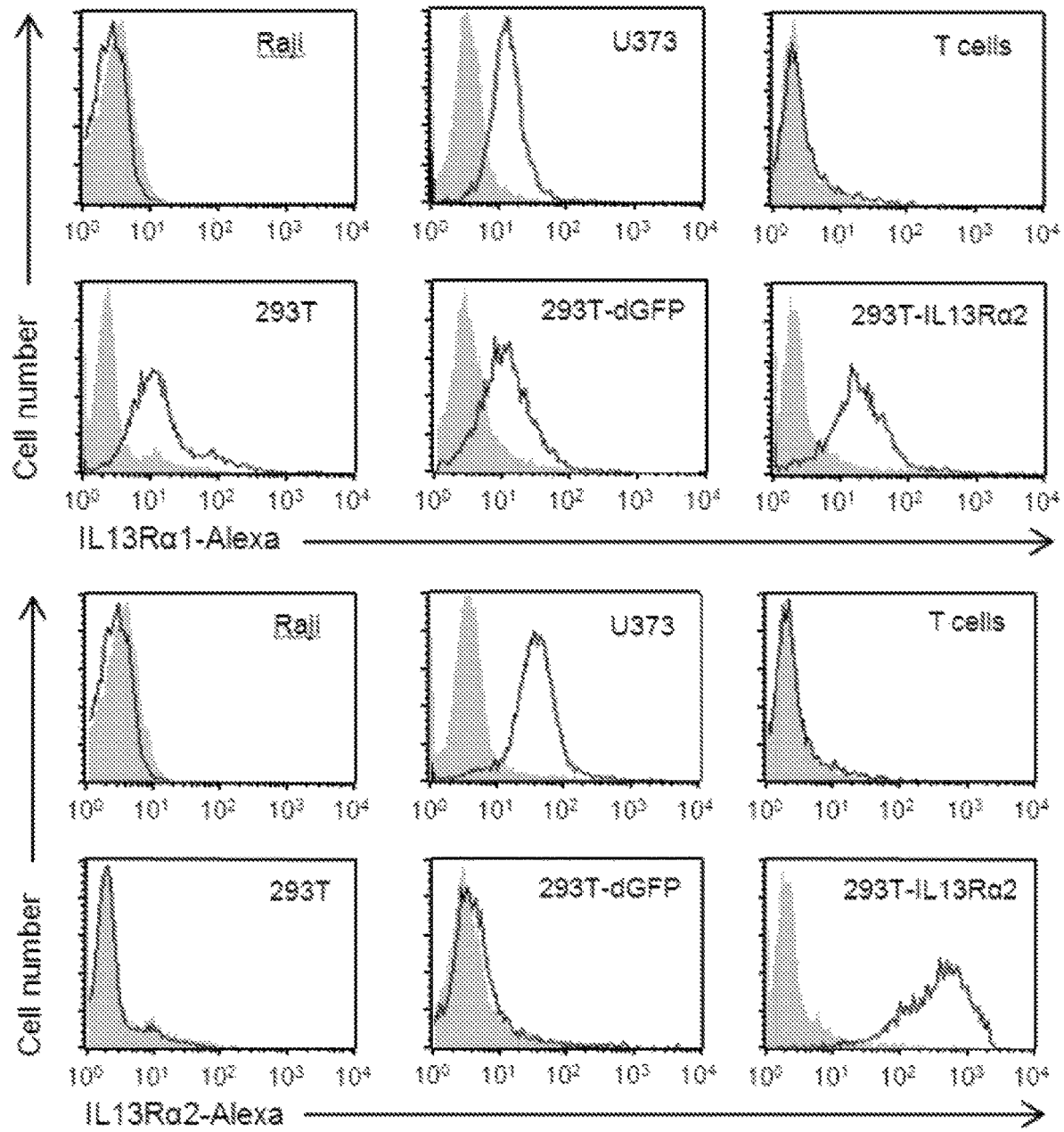
FIG. 26. IL13Rα2- and IL13Rα1-positive cell lines are made by genetic modification of HEK 293T cells. Filled curve: isotype antibody control; Open curve: specific antibody.
Figure 27:
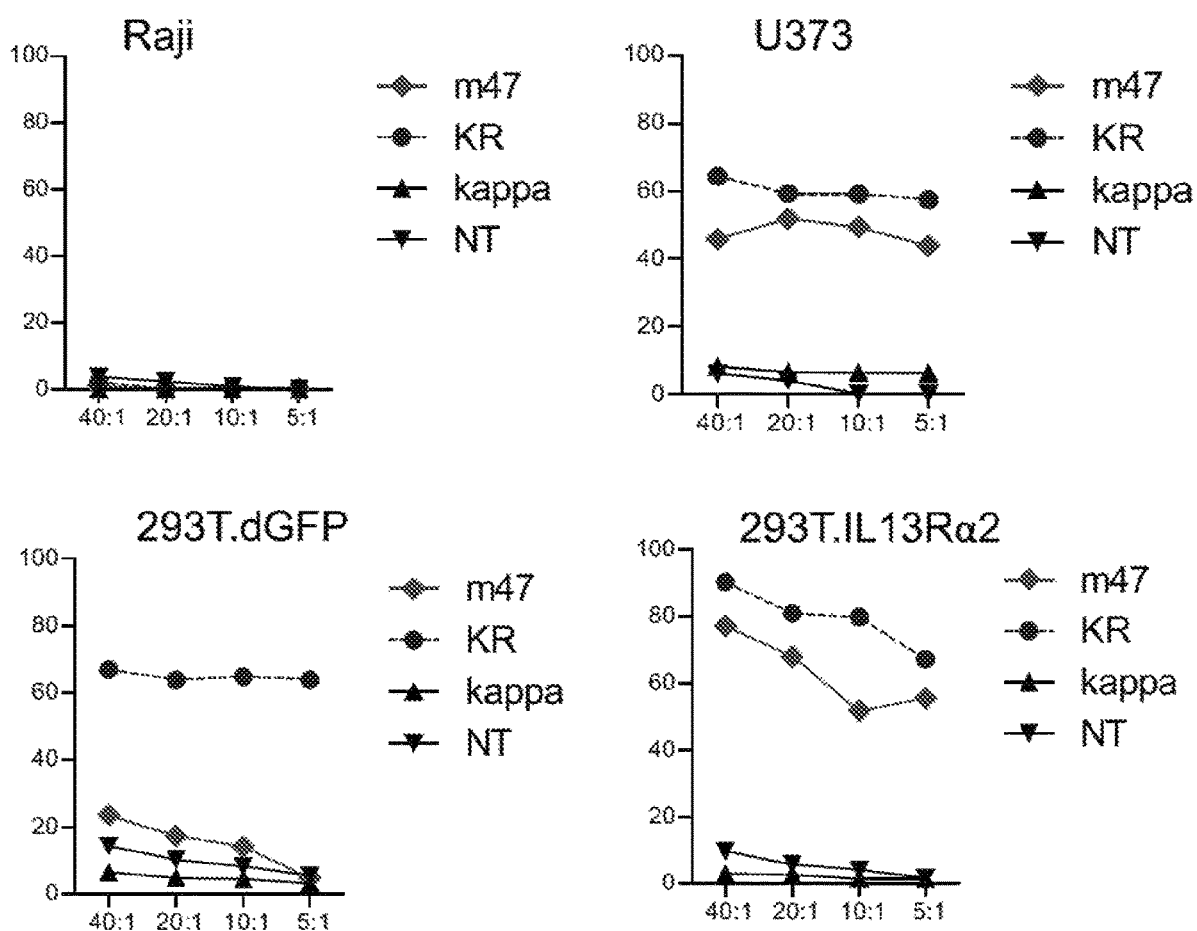
FIG. 27. The m47 CAR T cells kill only IL13Rα2$^+$ cell lines. The in vitro experiments provide data establishing that m47 CAR T cells present a recombinant CAR protein on the cell surface that does not recognize IL4R, IL13Rα1 or any receptor other than its specific recognition of IL13Rα2. The specificity of the recognition extends to a specificity for only those cell lines expressing IL13Rα2.
Figure 28:
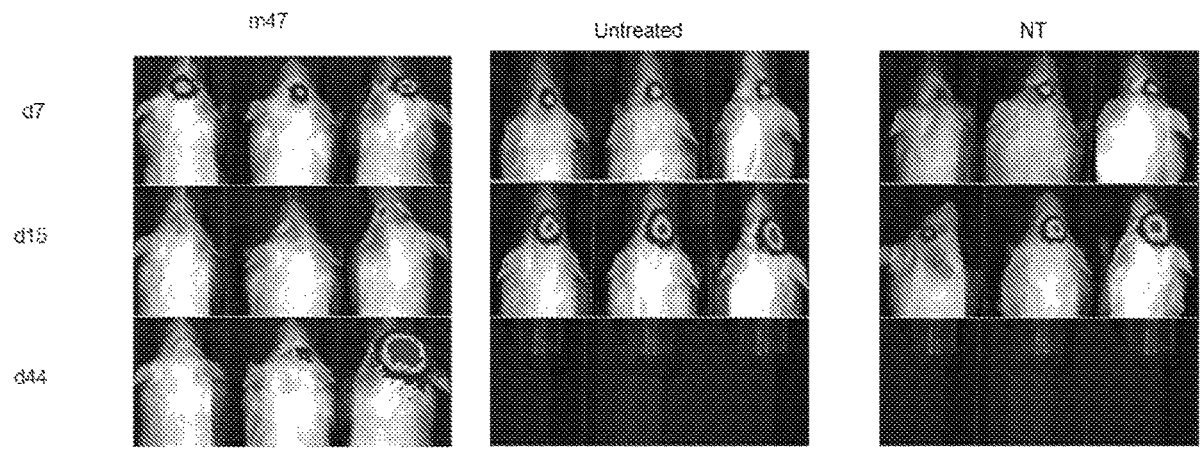
FIG. 28. In vivo data comparing effect of m47 CAR T cell agent, untreated and NT-treated glioblastoma multiforme xenografts in nude mice. The U373 glioblastoma multiforme xenograft mouse model was used. At day 0, 1×10$^5$ GFP-ffluc U373 cells were administered per mouse. On day 7, 2×10$^6$ m47 CAR T cells or NT cells were administered. Untreated samples did not receive treatment on day 7. No exogenous interleukin 2 was administered and results of the survival analysis were recorded by serial bioluminescence imaging. n=3.
Figure 29:
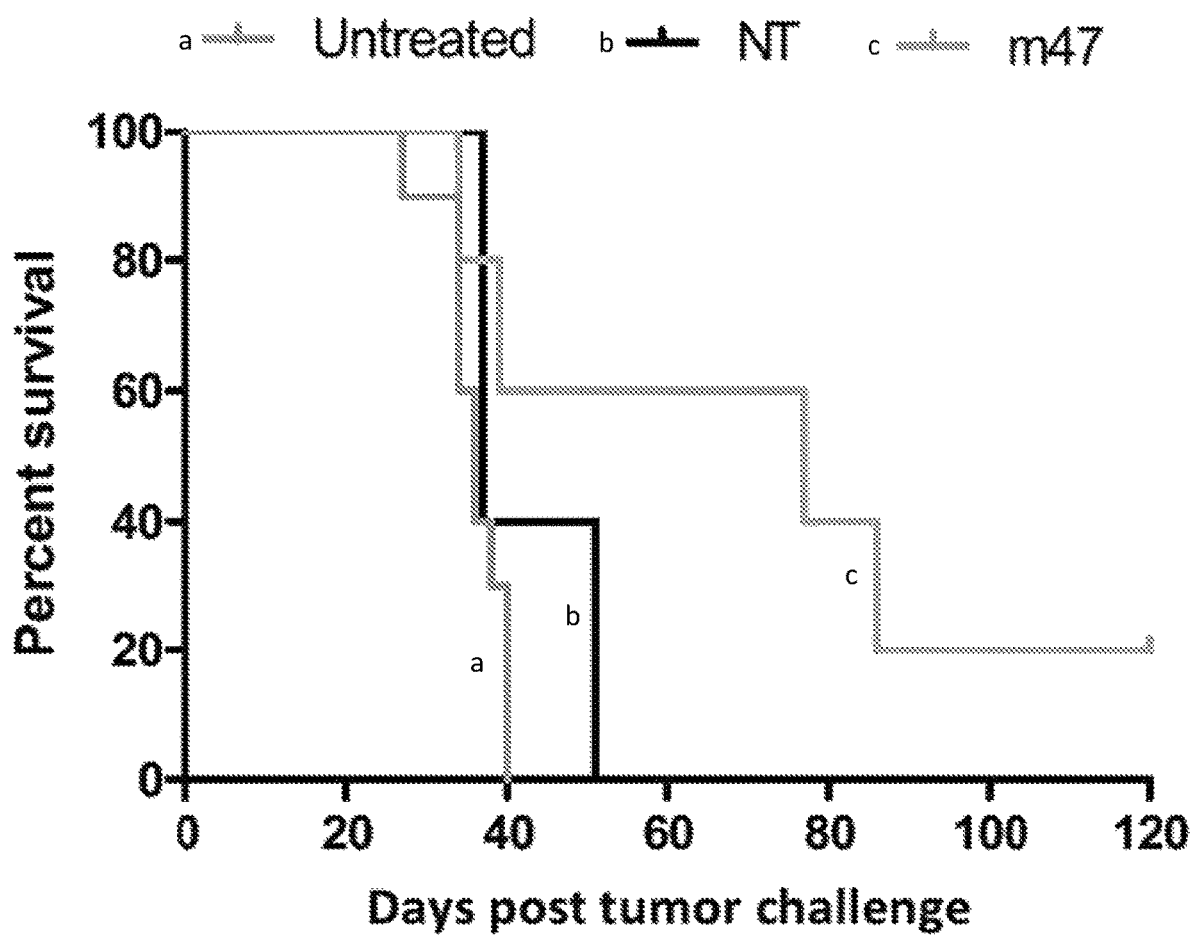
FIG. 29. The m47 CAR T cell agent prolonged the survival of nude mice with glioblastoma multiforme.

To overcome this limitation, a high-affinity IL13Rα2-specific scFv that does not recognize IL13Rα1 was generated. A panel of IL13Rα2-CARs were agented that contain the IL13Rα2-specific scFv as an ectodomain, a short hinge (SH) or a long hinge (LH), a CD28 transmembrane domain, and endodomains that contain signaling domains derived from CD3ζ and co-stimulatory molecules (e.g., CD28.ζ, CD137.ζ, CD28.CD137.ζ, CD28.CD134.ζ). IL13Rα2-CAR T cells were generated by retroviral transduction, and effector function was determined in vitro, using co-culture and cytotoxicity assays, and in vivo, using the U373 brain xenograft model (FIG. 21).

Expression of all CARs in T cells was similar, as judged by Western blot analyses. CAR cell-surface expression varied, however, depending on the hinge and endodomain of the agent. In cytotoxicity assays, the various IL13Rα2-CAR T cells only killed target cells that expressed IL13Rα2 and not IL13Rα1, confirming specificity (FIG. 18). While all IL13Rα2-CAR T cells secreted significant levels of IFNγ in co-culture assays with the IL13Rα2 glioma cell line U373 (FIG. 19), only short-hinge CAR T cells secreted significant amounts of IL2 (FIG. 20). T cells expressing IL13Rα2-CARs with a deleted endodomain (IL13Rα2Δ-CAR) secreted no cytokines, confirming that cytokine production depends on the presence of a functional IL13Rα2-CAR. In vivo, injection of IL13Rα2.SH.CD28.ζ-CAR T cells into U373-bearing mice resulted in regression of glioma xenografts, as judged by bioluminescence imaging (FIG. 21). IL13Rα2.LH.CD28.ζ- or IL13Rα2.Δ-CAR T cells had no antitumor effects. The data establish that a CAR that only recognizes IL13Rα2 and not IL13Rα1 was generated, and that CAR preferentially targets tumor cells expressing IL13Rα2. Comparison of several IL13Rα2-CARs revealed that a CAR with a SH and a CD28.ζ endodomain resulted in significant T cell activation, as judged by IL2 production and in vivo anti-glioma activity. The results show that adoptive immunotherapy of primary human brain tumors, e.g., high-grade gliomas, in children is both feasible and promising.

Example 13

Targeting Cellular Markers In Vitro and In Vivo

In the study disclosed in this Example, scFv47, the scFv targeting IL13Rα2, was shown to possess exclusive specificity of binding to IL13Rα2. Also, scFv47 was shown to recognize the same epitope as the parental monoclonal antibody with a high affinity. Furthermore, as a proof of principle to show its therapeutic applicability, an IL13Rα2-targeted adenoviral vector was constructed by incorporating scFv47 into the fiber knob domain of a fiber-fibritin modified adenovirus[21-23]. The fiber modification successfully redirected the viral tropism specifically to IL13Rα2-expressing glioma cells in vitro and in vivo. The data validate that scFv47 represents a valuable reagent for development of personalized therapeutics that are tailored specifically to a patient's tumor phenotype.

Materials and Methods

Cell Lines and Reagents.

Purified anti-c-myc antibody (clone 9E10) was obtained from the Frank W. Fitch Monoclonal Antibody Facility of the University of Chicago. Anti-M13-HRP antibody was obtained from Amersham Pharmacia Biotech (Uppsala, Sweden). Goat anti-mouse alkaline phosphatase conjugate was purchased from Sigma-Aldrich St. Louis, MO. Human embryonic kidney (HEK) 293, HEK 293-F28 stably expressing Ad5 wild type fibers, Chinese hamster ovary (CHO) cells, CHO-hCAR cells stably expressing human CAR, CHO-IL13Rα 219, U87MG and U251MG glioma cell lines were used. To generate IL13Rα2+U251MG and IL13Rα2.KDU251MG, U251 cells were transduced with lentiviral particles encoding control or IL13Rα2 shRNA (Sigma-Aldrich, St. Louis, MO). Transduced cells were selected with puromycin at 2 µg/ml and analyzed by flow cytometry for IL13Rα2 expression using an anti-IL13Rα2 monoclonal antibody (clone 47)[19]. Cells lines were cultured in DMEM media (Mediatech, Inc., Herndon, VA) supplemented with 10% heat inactivated FBS (Hyclone; Logan, UT) and penicillin-streptomycin (Mediatech, Inc., Herndon, VA). For formation of neurospheres, glioma cells were grown in neurobasal media (Life technologies, Eugene, OR) supplemented with EGF and bFGF at concentrations of 20 ng/ml as well as N10 and B27 supplements (Sigma-Aldrich, St. Louis, MO) for 7 days, as described previously[43]. The patient-derived GBM43 and GBM39 glioma cells were obtained from Dr. Charles D. James from Northwestern University Feinberg School of Medicine. Cells were propagated via serial passaging in the flank of nude mice.

Cloning the scFv Fragment of mAb IL13Rα2 (Clone 47)

The heavy and light chains of monoclonal antibody (clone 47) against human IL13Rα2[19] were cloned using a set of gene-specific primers (Table 2) for immunoglobulin heavy and light chain sequences that were published previously[24,25]. The heavy and light chain cDNA were re-amplified to introduce NcoI and HindIII and MluI and NotI restriction sites, respectively, for subsequent subcloning into phagemid vector pSEX 81, as previously described[44]. XL1 blue cells were transformed by electroporation with a library of scFv encoded by phagemid vector and phages were generated as previously described[25]. Selection of immune reactive phages was performed in three rounds using recombinant human IL13Rα2hFc fusion protein (rhIL13Rα2hFc) (R&D Systems) coated on 96-well plates. Human IgG served as a negative control. DNA of bacterial clones infected with positively selected phages was screened by PCR for the presence of proper size PCR products which consisted of full-size scFv and plasmid sequences upstream and downstream of the scFv insert. Eight PCR products of approximately 1000 bp were purified for subsequent sequence analysis. The obtained scFv against human IL13Rα2 was designated as scFv47. In order to generate soluble protein, the cDNA encoding for scFv47 was re-cloned in a bacterial expression cassette, as described previously[24,44]. XL-1 blue cells were utilized to generate soluble protein according to an established protocol[24].

TABLE 2

| Primer | SEQ ID NO | Heavy Chain | SEQ ID NO | Light Kappa Chain |
|---|---|---|---|---|
| Forward 1 | 117 | 5'-GATGTGAAGCTTCAGGAGTC-3' | 118 | 5'-GATGTTTTGATGACCCAAACT-3' |
| Forward 2 | 119 | 5'-CAGGTGCAGCTGAAGGAGTC-3' | 120 | 5'-GATATTGTGATGACGCAGGCT-3' |
| Forward 3 | 121 | 5'-CAGGTGCAGCTGAAGCAGTC-3' | 122 | 5'-GATATTGTGATAACCCAG-3' |
| Forward 4 | 123 | 5'-CAGGTTACTCTGAAAGAGTC-3' | 124 | 5'-GACATTGTGCTGACCCAATCT-3' |
| Forward 5 | 125 | 5'-GAGGTCCAGCTGCAACAATCT-3' | 126 | 5'-GACATTGTGATGACCCAGTCT-3' |
| Forward 6 | 127 | 5'-GAGGTCCAGCTGCAGCAGTC-3' | 128 | 5'-GATATTGTGCTAACTCAGTCT-3' |
| Forward 7 | 129 | 5'-CAGGTCCAACTGCAGCAGCCT-3' | 130 | 5'-GATATCCAGATGACACAGACT-3' |
| Forward 8 | 131 | 5'-GAGGTGAAGCTGGTGGAGTC-3' | 132 | 5'-GACATCCAGCTGACTCAGTCT-3' |
| Forward 9 | 133 | 5'-GAGGTGAAGCTGGTGGAATC-3' | 134 | 5'-CAAATTGTTCTCACCCAGTCT-3' |
| Forward 10 | 135 | 5'-GATGTGAACTTGGAAGTGTC-3' | 136 | 5'-GACATTCTGATGACCCAGTCT-3' |
| Forward 11 | 137 | 5'-GAGGTGCAGCTGGAGGAGTC-3' | | n/a |
| Reverse | 138 | 5'-GGCCAGTGGATAGTCAGATGGGGGTGTCGTTTTGGC-3' | 139 | 5'-GGATACAGTTGGTGCAGCATC-3' |

ELISA

Supernatant containing phages from all rounds of biopanning were analyzed for their binding specificity to rhIL13Rα2 protein using plate ELISA. Wells coated with human IgG were used as negative controls. Specifically, wells were blocked for 30 min with 2% non-fat dry milk and supernatants containing phages were applied at different dilutions to the wells. After a 30-min incubation with shaking and another 1.5 h without shaking, unbound phages were washed with PBS/0.05% Tween 20 and anti-M13 antibodies conjugated with peroxidase (Amersham Pharmacia Biotech, Uppsala, Sweden) (diluted 1/2000 in the 2% non-fat dry milk) were added. After intensive washing with PBS/0.05% Tween 20, the plates were developed with 1-step slow 3,3' 5,5'-Tetramethyl-benzidine (TMB) substrate for ELISA and read at $OD_{450}$ after the reaction was stopped with 3 N hydrochloric acid.

For analysis of soluble scFv47 for binding with rhIL13Rα2, a clone of XL-1 blue E. coli transformed with an expression vector encoding scFv47 gene-tagged with c-myc and a 6-His sequence was grown overnight in LB medium supplemented with 100 mM glucose and 100 g/ml ampicillin (LBGA), as previously described[24]. Overnight culture was diluted 1/100 and grown in 50 ml of LBGA media with shaking (250 rpm at 37° C.) until density $OD_{600}$=0.8. After incubation, the bacterial culture was centrifuged at 1500 g for 10 min. The pellet was resuspended in 50 ml LBGA media containing 0.4 M sucrose and 0.1 mM IPTG and grown for 20 h at room temperature (RT). The purified soluble scFv47 was obtained from the culture supernatant using Co resin per manufacturer's recommendation (Thermo Scientific, Rockford, IL). Purified scFv47 was tested in plate ELISA and affinity studies as described herein. 96-well plates coated with rhIL13Rα1 or rhIL13Rα2 protein at 1 µg/ml were blocked with 2% non-fat dry milk and scFv47 at various concentrations was applied for 2 h at room temperature (RT). After washing, anti-c-myc monoclonal antibodies (clone 9E10) at 1 µg/ml were added for a 1-hour incubation, washed of unbound antibodies and subsequently developed with anti-mouse antibodies conjugated to alkaline phosphatase (Sigma Aldrich, St. Louis, MO). The reaction was then read in a spectrophotometer at $OD_{405}$.

Competitive Assay

Easy wash 96-well plates (Thermo Scientific, Rockford, IL) were coated with 100 µl of IL13Rα2hFc fusion protein at a concentration of 1 µg/ml and stored overnight at 4° C. After washing with PBS/0.05% Tween 20, wells were blocked with 2% non-fat dry milk and incubated with either PBS or mouse IgG1 as negative controls or a panel of anti-IL13Rα2 mAbs recognizing non-overlapping epitopes with the parental anti-IL13Rα2 mAb (clone 47)[19] at a concentration of 2 µg/ml for 1 h. After washing away unbound antibodies, the supernatant containing phages after the third round of biopanning was applied to all wells for 2 h at RT. Bound phages were detected as described herein.

Surface Plasmon Resonance and Kinetic Analysis

The affinity and rate of interaction between the scFv47 and target (rhIL13Rα2) were measured with a Biacore 3000 biosensor through surface plasmon resonance (SPR), as described[19]. The estimation of kinetic parameters was performed by repetitive injections of a range of target concentrations over the immobilized rhIL13Rα2. Each data set, consisting of sensograms of increasing scFv47 concentrations over the same level of immobilized rhIL13Rα 2, was analyzed using various kinetic models. The BIAevaluation v 4.1 software was used for data analysis. Affinity constants were estimated by curve fitting using a 1:1 binding model. Sensogram association and dissociation curves were fit locally or globally. The rate of complex formation during the sample injection is described by an equation of the following type: $dR/dt = k_a C (R_{max} - R) - k_d R$ (for a 1:1 interaction) (R=SPR signal in RU; C=concentration of analyte; Rmax=maximum analyte binding capacity in RU; dR/dt=rate of change of SPR signal). The early binding phase (300 sec) was used to determine the association constant (ka) between mAb and target. The dissociation phase (kd) was measured using the rate of decline in RU on introduction of free buffer at the end of target injections. Data were simultaneously fit by the software program (global fitting algorithm) and the dissociation constant (KD) of the complexes was determined as the ratio ka/kd. For quantitative analysis, 3 independent replicates were performed for each sample. Data are expressed as mean±SEM.

Adenoviral Genetic Modifications and Virus Production

In order to generate a fiber shuttle vector, the pKan 566 adenoviral genome (kind gift of Dr. Curiel, Washington University in Saint Louis), which contains the gene of fiber fibritin, was used. The cDNA of scFv47, was inserted at the C-terminal end of fiber fibritin by using a standard molecular technique, resulting in pKan-scFv47FF[21,27,45]. With this fiber shuttle vector, recombinant HAd5 backbones containing an enhanced green fluorescence protein (eGFP) under the control of the CMV promoter in the E1 deleted region (replication incompetent Ad5scFv47FF-CMV-GFP) were generated. The recombinant virus were rescued in HEK293-F28 cells and then propagated in HEK293 cells. Viruses were purified by two rounds of CsCl gradient ultracentrifugation[27].

Flow Cytometry

In order to analyze the expression of IL13Rα2 on the cell surface, U87MG and U251MG glioma cell lines were stained with anti-IL13Rα2 (clone 47) mAb at 2 µg/mL, followed by goat anti-mouse Alexa Fluor 647 (1:500). All staining procedures were performed on ice. Transduction of glioma cells with either control or Ad5FFscFv47 virus was assayed based on GFP expression. Samples were analyzed using the BD FACS Canto flow cytometer and FACS DiVa™ software.

PCR Analysis

Viral DNA contained in Ad5-CMV-GFP and Ad5FFscFv47-CMV-GFP viral particles (109) was used as the template for PCR amplification using a HAdV5-specific primer set: forward: 5'-CAGCTCCATCTCCTAACTGT-3' (SEQ ID NO:140) and reverse: 5'-TTCTTGGGCAATGTATGAAA-3' (SEQ ID NO:141) and scFv47-specific primer set: forward: 5'-CAGGTC-CAACTGCAGCA-3' (SEQ ID NO:142) and reverse: 5'-TTTGATTTCCAGCTTGGT-3' (SEQ ID NO:143).

Western Blot

The supernatant of XL1-blue E. coli cells containing the scFv47 or purified adenoviral particles were diluted in Laemmli buffer, incubated either at room temperature (unboiled samples) or at 95° C. (boiled samples) for 10 mins and loaded onto a 7.5% SDS-polyacrylamide gel (Bio-Rad, Hercules, CA). After electrophoretic separation, samples were transferred onto a PVDF membrane and detected with an anti-myc mAb (9E10) at 1 µg/ml for detection of soluble scFv47 or an anti-fiber tail mAb4D2 (1:3,000) (Thermo Scientific, Rockford, IL) followed by HRP-tagged anti-mouse IgG secondary antibody (1:5,000) (Santa Cruz, CA, USA).

Quantitative Real-Time Real Time-PCR (qRT-PCR) Analysis

The expression of IL13Rα2 in U87MG cells growing as an adherent culture or as neurospheres was characterized by qRT-PCR. RNA was isolated from glioma cells using an RNeasy plus kit (Qiagen, Boston, MA) and was reverse-transcribed using an iScript cDNA conversion kit (Biorad, CA, USA). qRT-PCRs were carried out using a SYBR green qPCR kit (Biorad, CA, USA) with the following primers: GAPDH forward primer: 5'-GGTCGGAGTCAACGGAT-TTGG-3' (SEQ ID NO:144); GAPDH reverse primer: 5'-CATGGGTGGAATCATATTGGAAC-3' (SEQ ID NO:145); IL13Rα2 forward primer: 5'-TTGGGACCTAT-TCCAGCAAGGTGT-3' (SEQ ID NO:146); IL13Rα2 reverse primer: 5'-CACTCCACTCACTCCAAATCCCGT-3' (SEQ ID NO:147). For relative quantification of IL13Rα2 expression, all IL13Rα2 values were normalized to the glyceraldehyde 3 phosphate dehydrogenase (GAPDH) expression values. Data analysis was performed using the 2-ΔΔCT method[46].

Viral Infectivity Analysis

Cells ($3 \times 10^5$) were plated in 24-well plates and incubated overnight. For monoclonal anti-IL13Rα2 antibody-mediated inhibition assays, 2 μg of anti-IL13Rα2 mAb (clone 47) was added to the cells and they were allowed to incubate for 1 h at 4° C. Each virus sample was diluted to a multiplicity of infection of 300 viral particles (vp)/cell in 500 μl of infection media containing 2% FBS in DMEM. The cells were infected with Ad5FFscFv47-CMV-GFP for 2 h at 37° C. Virus containing media was then replaced with fresh media containing 2% FBS and cells were kept at 37° C. in atmospheric humidification containing 5% $CO_2$ for 3 days, then flow cytometry analysis was performed as described herein.

Animal Experiments

Male athymic/nude mice were obtained from the Charles River Laboratory (Wilmington, MA) and were cared for in accordance with a study-specific animal protocol approved by the University of Chicago Institutional Animal Care and Use Committee. For tumor cell implantation, mice were anesthetized with a ketamine/xylazine mixture (115/17 mg/kg). A burr hole was made to allow for a stereotactic injection that was performed with a 10 μl Hamilton syringe (Hamilton, Reno, NV). The needle was mounted to a mouse-specific stereotactic apparatus (Harvard Apparatus, Holliston, MA) and was then inserted through the burr hole to an anatomical position of 3 mm in depth. Specifically, mice were implanted with intracranial glioma xenograft of IL13Rα2+U251MG or with IL13Rα2.KDU251MG cells ($5.0 \times 10^5$ cells). Ten days post-tumor implantation, mice were injected in the same coordinates as tumor cells with 109 viral particles (vp) of Ad5FFscFv47-CMV-GFP in 5 μl of PBS and sacrificed 3 days later.

Confocal Microscopy

Flash-frozen brain tumor tissues were cut to a thickness of 10 m. Tissue sections were fixed and stained for human nestin to visualize U251 glioma cells using mouse mAb (R&D systems, Minneapolis, MN). To analyze transduction of glioma cells with Ad5FFscFv47-CMV-GFP, transgene GFP expression was revealed using biotinylated anti-GFP antibody (Life technologies, Eugene, OR) and streptavidin-Alexa Fluor647 (Jackson ImmunoResearch, West Grove, PA). Cell nuclei were visualized using DAPI nuclear stain. Confocal microscopic images were captured with a 3i Marianas Yokogawa-type spinning disk confocal microscope with an Evolve EM-CCD camera (Photometrics, Tucson, AZ) running SlideBook v5.5 software (Intelligent Imaging Innovations, Denver, CO).

Statistical Analysis

All statistical analyses were performed using Graphpad Prism 4 (GraphPad Software Inc., San Diego CA). Sample size for each group was >3 and numerical data were reported as Mean±SEM. Student's t test was used for comparisons between two groups, and ANOVA with Tukey's post hoc test was used for comparisons between more than two groups. All reported p values were two-sided and were considered to be statistically significant at $*p<0.05$, $p<0.01$, $*p<0.001$.

Cloning and Characterization scFv Fragment of mAb47.

Monoclonal anti-IL13Rα 2 (clone 47) antibody possesses unique properties, such as strong binding with the native epitope of IL13Rα2, high affinity of interaction with IL13Rα2, and the ability to compete with IL13 for its recognition site on IL13Rα2[19]. Reported in this Example is the engineering of scFv47 from the hybridoma cell line secreting the parental antibody (clone 47). The analysis of mRNA from this hybridoma cell line revealed the presence of multiple transcripts corresponding to the heavy and light chains of the anti-IL13Rα2 monoclonal antibody (FIG. 12a)[24,25]. In order to obtain a functional combination of heavy chain and light chain variable regions assembled in the scFv47, a phage-display approach[24,25] was used. For that reason, the library of phages for the heavy and light chain variants in a scFv format was generated and screened against recombinant human IL13Rα2 (rhIL13Rα2) as described below.

Figure 12:
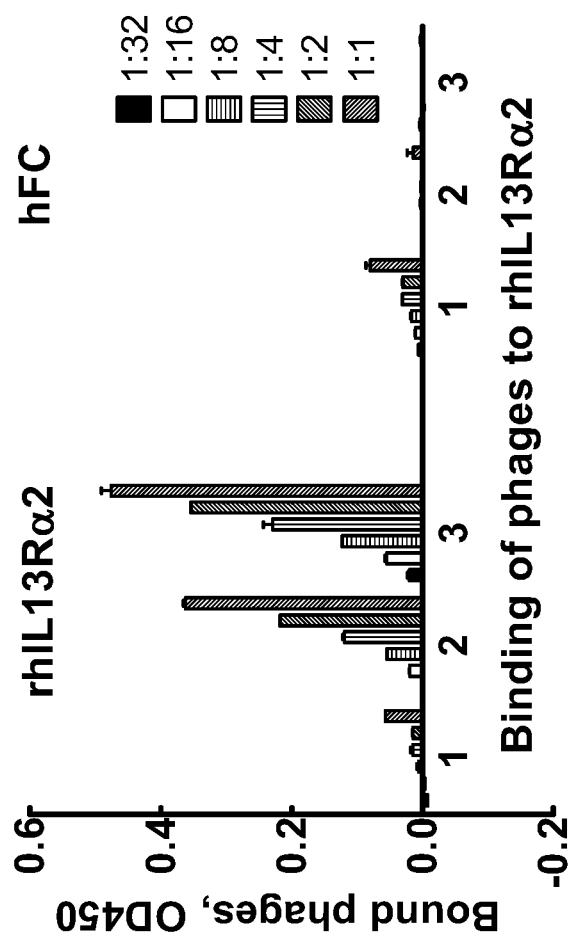
FIG. 12. (a) Screening of parental hybridoma IL13Rα 2 cells mRNA for $V_H$ and $V_L$ using set $V_{H^-}$ and $V_L$-specific primers (Table 2). (b) Binding of IL13Rα2 clone 47 phages with IL13Rα2hFc in plate ELISA. These data demonstrate that phages presenting scFv IL13Rα2 (clone 47) are positively selected against IL13Rα2Fc chimeric protein after 3 rounds of biopanning. Left panel: binding of scFv IL13Rα2 (clone 47) to IL13Rα2Fc after the indicated rounds of biopanning; right panel: binding of scFv IL13Rα2 (clone 47) to control hFC, i.e., the constant region of a control IgG antibody not fused to IL13Rα2. For both panels, the order of bars for each round, moving from left-to-right, reflects dilutions of 1:32, 1:16, 1:8, 1:4, 1:2, and non-diluted (i.e., 1:1).
Figure 13:
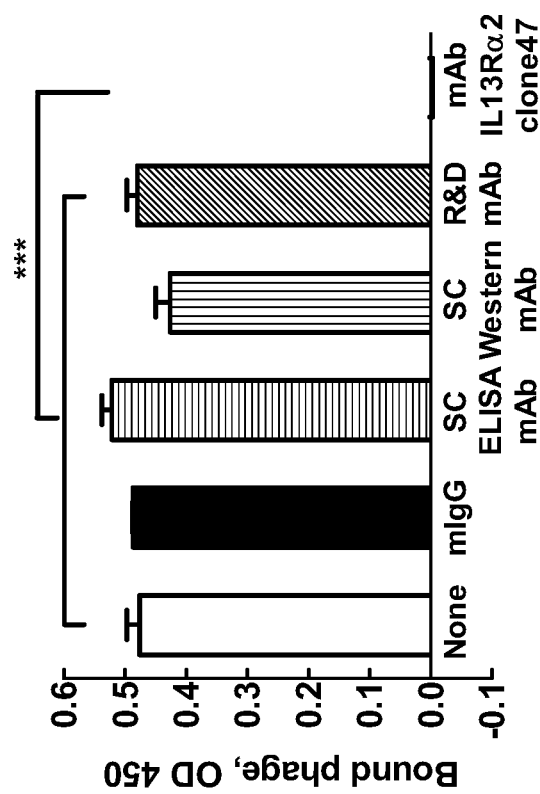
FIG. 13. Specificity of binding scFv IL13Rα2 clone 47 with IL13Rα2hFc-competitive assay. These data show that binding of the scFvIL13Rα2 (clone 47) presented on the phage surface to recombinant IL13Rα2 is completely abolished by parental monoclonal antibody (clone 47), but not other antibodies against IL13Rα2. It indicates that scFvIL13Rα2 (clone 47) and parental monoclonal antibody (clone 47) share the epitope (i.e., recognition site) on the IL13Rα2 molecule.
Figure 14:
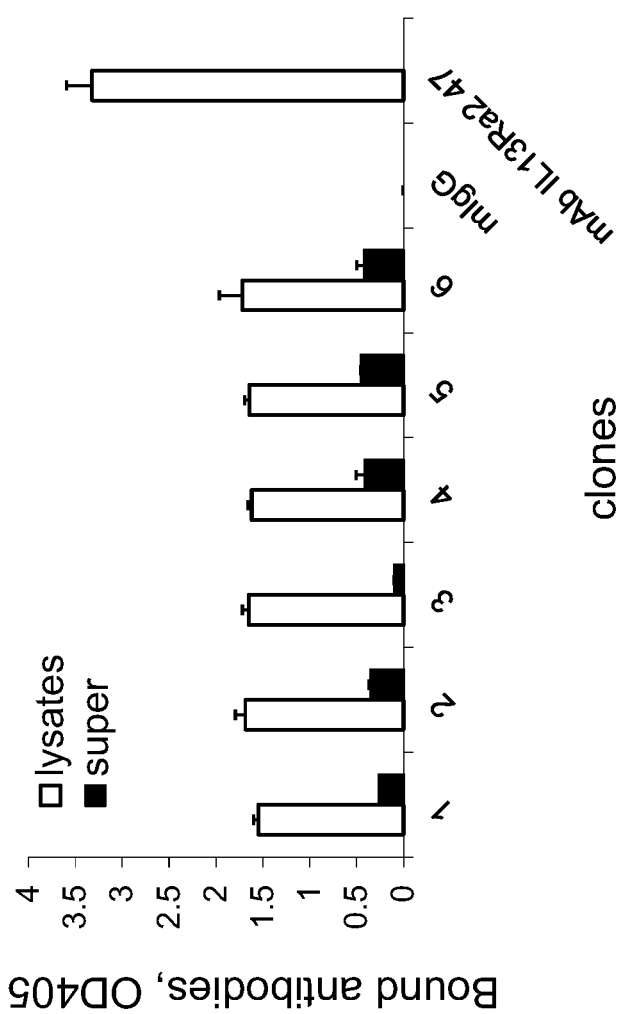
FIG. 14. Binding of soluble scFv IL13Rα2 (clone 47) with IL13Rα2hFc chimera. These data show that soluble scFvIL13Rα2 (clone 47) generated in a prokaryotic expression system (*E. coli*) binds specifically to IL13Rα2Fc recombinant protein. Parental antibody, mAb IL13Rα2 (clone 47), and control mouse IgG served as positive and negative controls, respectively.
Figure 15:
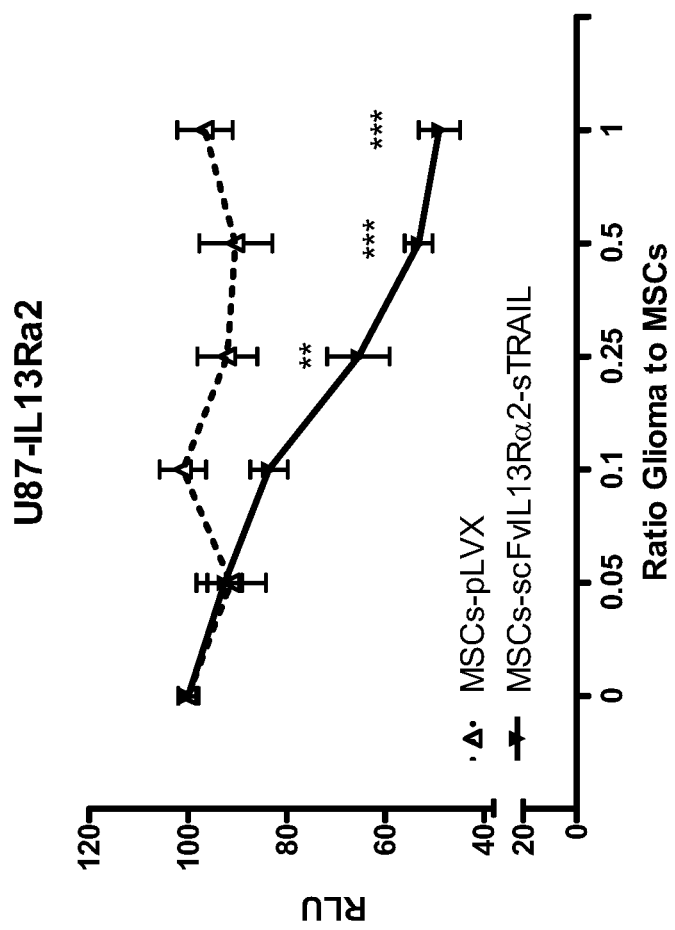
FIG. 15. The effect of mesenchymal stem cells secreting scFvIL13Rα2-sTRAIL fusion protein on the U87-IL13Rα2 glioma cell line. These data show that mesenchymal stem cells modified to secrete a genetic fusion of scFvIL13Rα2 (clone 47) with TRAIL protein exhibit a therapeutic effect in the IL13Rα2-expressing U87 glioma cell line. The results establish the efficacy of conjugating the scFV to a TRAIL cytokine. The amount of cancer cell killing is equivalent to the use of TRAIL alone without the scFV, but it is expected that the scFV-TRAIL would be less harmful to non-cancer tissues, given the specificity conferred by the scFv targeting IL13Rα2.
Figure 16:
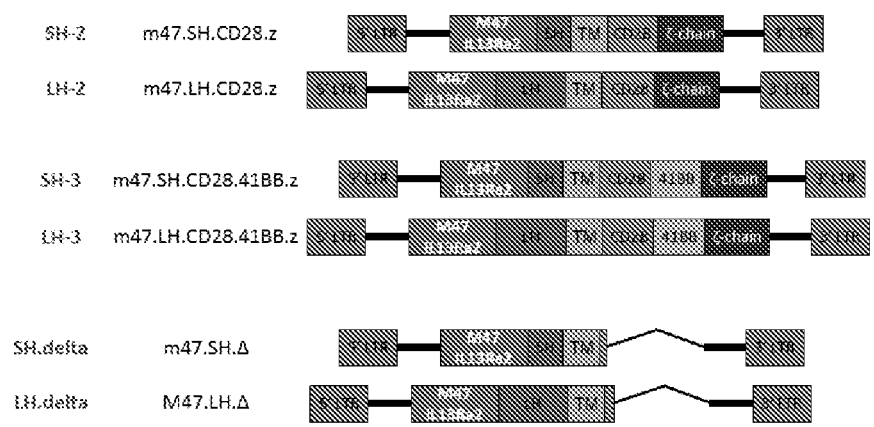
FIG. 16. Schematic maps of retroviral vector encoding IL13Rα2-specific scFv CARs. The CAR consists of the immunoglobulin heavy-chain leader peptide, the IL13Rα2-specific scFv clone 47 (M47), a short hinge (SH) or long hinge (LH), a transmembrane domain (TM) derived from CD28, and a CD28. ζ C endodomain. LTR: long terminal repeat (retroviral backbone). Domains are identified as block structures. Maps are not to scale.
Figure 17:
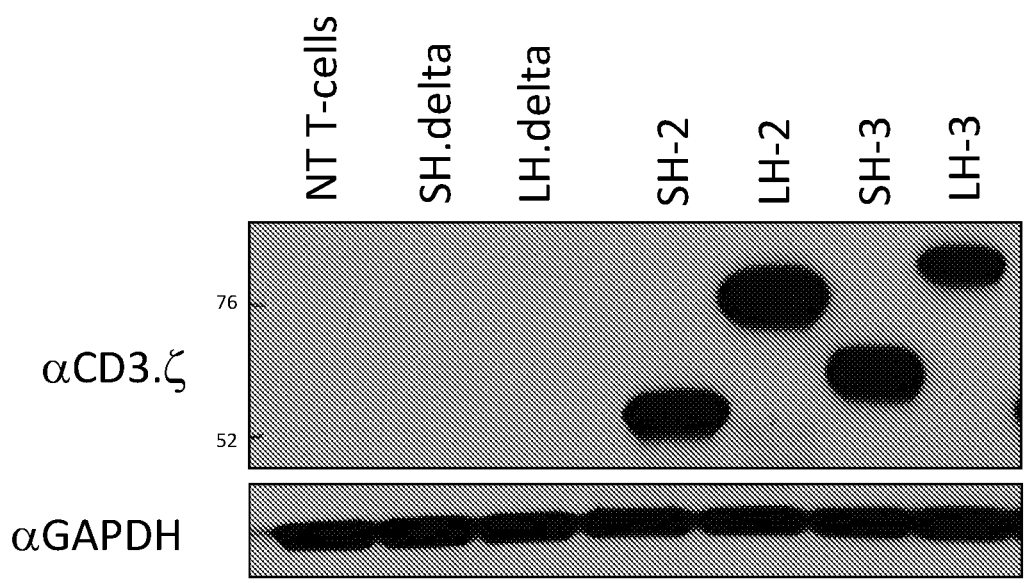
FIG. 17. IL13Rα2-scFv CAR T cell agent: Expression of αCD3.ζ (relative to αGAPDH of CAR agent in T cells. SH: short hinge. LH: long hinge.

After generating scFv47, its binding specificity for rhIL13Rα2 was verified. To this end, supernatant containing phages during all rounds of bio-panning were generated and assayed for binding specificity to rhIL13Rα2 protein by ELISA. FIGS. 12b and 13 show that the specificity of phage interaction with rhIL13Rα2 protein dramatically increased with each subsequent round of biopanning, whereas non-specific binding to the negative control, human IgG, decreased to an undetectable level. After the last round of biopanning, individual phage clones were generated. Sequence analysis of XL1 blue E. coli infected with individual phage clones revealed that all selected phages contained an identical sequence of the scFv47. Thus, these data indicate that scFv47 was successfully generated through three rounds of phage biopanning.

Next, a competitive assay was performed to determine if the newly cloned scFv47 and the parental mAbIL13Rα2 (clone 47) bind to the same epitope on the IL13Rα2 molecule. FIG. 13 shows that mAb IL13Rα2 (clone 47) completely prevented the interaction of scFv47-expressing phages to immobilized rhIL13Rα2 protein. Neither the control mIgG nor three other mAbs against IL13Rα2, which recognize non-overlapping epitopes of the mAb IL13Rα2 (clone 47) on human IL13Rα2[19], interfered with the binding of scFv47 to IL13Rα2. This result demonstrates that scFv47 shares the same recognition site on IL13Rα2 as the parental monoclonal antibody.

The specificity of binding of soluble scFv47 to IL13Rα2 was further validated. For that, soluble scFv47 was generated in XL1 blue E. coli and purified as described herein. An analysis of the binding of soluble scFv47 in plate ELISA demonstrated a lack of interaction with rhIL13Rα1 and specific binding with rhIL13Rα2 (FIG. 31a). FIG. 31b shows that the molecular weight of soluble scFv47 protein is about 30 kDa, which corresponds to its predicted value. Furthermore, the plasmon resonance analysis revealed that soluble scFv47 binds to rhIL13Rα2 with a high affinity (0.9×10$^{-9}$ M) similar to that of the parental antibody[19] (FIG. 31c). In particular, scFv was found to have a $k_a$(1/Ms)= 3.08e3±16, a $k_d$(1/s)=2.63e-6±1.8e-8, a $K_D$(M)=0.9×10$^{-9}$, and an $R_{max}$(RU)=496. The estimation of kinetic parameters for scFv47 binding to the human recombinant IL13Rα2 was performed as described herein. The dissociation constant ($K_D$) of the complexes was determined as the ratio $k_a/k_d$. For quantitative analysis, 3 independent replicates were performed for each sample. Data are expressed as mean±SEM. These data demonstrate that the affinity of scFv47 to rhIL13Rα2 is similar to parental anti-IL13Rα2 mAb (clone 47) (1.39×10$^{-9}$)[19]. Thus, the obtained scFv47 was deemed to be fully functional, as determined by a specific interaction of scFv47-expressing phages and soluble scFv47 to rhIL13Rα2.

Generation of IL13Rα2-Targeted Adenoviral Vector.

Figure 37:
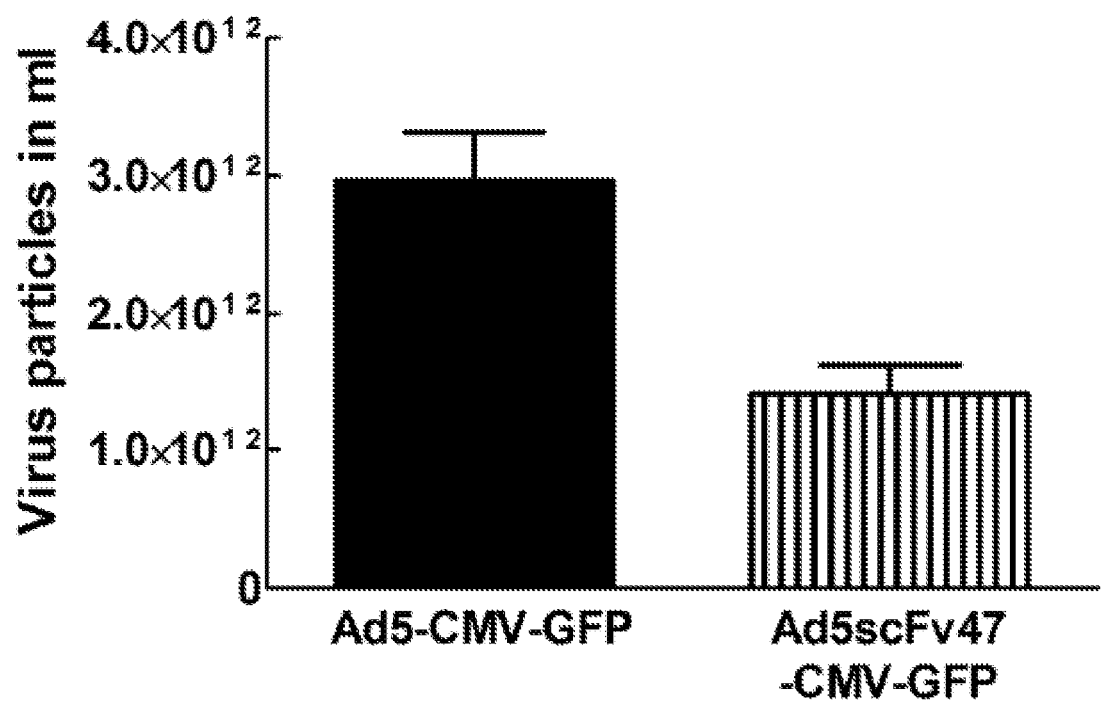
FIG. 37. The efficiency of Ad5FFscFv47-CMV-GFP viral production. Both Ad5-CMV-GFP and Ad5FFscFv47-CMV-GFP were propagated, purified, and titrated as described herein. Each data point is an average of 3 independent replicates. Mean±SEM is plotted.

In order to redirect the viral tropism to IL13Rα2, the viral fiber shaft and knob domains of adenovirus were genetically modified[22,26]. First, the shaft domain was replaced with a fiber-fibritin (FF) trimerization domain to ensure stability of the binding motif structure, and then the scFv47 was incorporated in the C-terminal end of the FF shaft domain (FIG. 32a). The purified Ad5scFv47FF-CMV-GFP virus titer was comparable to that of Ad5-CMV-GFP, indicating that scFv47 incorporation does not affect the yield of virus (FIG. 37). To confirm the genetic modification of the fiber, PCR analysis was performed with purified viral DNAs using either fiber-specific or scFv47-specific primer sets. FIG. 32b demonstrates the successful incorporation of scFv47 in the FF domain of adenovirus (Ad5FFscFv47). Furthermore, western blot analysis of the wild-type and recombinant virus further confirmed (FIG. 32c) that the new chimeric fiber had a composition similar to that of the wild-type fiber, indicating that incorporation of scFv47 does not hinder the fiber's trimerization or cause structural instability of the fiber.

Demonstration of CAR-Independent Infection.

The primary receptor for the human adenovirus serotype 5 (Ad5) is the coxsackie and adenovirus receptor (CAR)[27-29]. It is expected, therefore, that Ad5FFscFv47 virus will infect cells in CAR-independent fashion. To confirm that our modification results in a loss of CAR-binding ability, the viral infectivity of Ad5FFscFv47 encoding for green fluorescent protein under the control of CMV promoter (Ad5FFscFv47-CMV-GFP) and wild-type virus, Ad5-CMV-GFP, was analyzed in the human CAR (hCAR)-negative and hCAR-positive (CHO-hCAR) Chinese hamster ovary cell lines. FIG. 33a demonstrates that wild-type Ad5-CMV-GFP efficiently infected the CHO-hCAR, but not the hCAR-negative CHO cells, whereas Ad5FFscFv47-CMV-GFP showed very little infectivity in either cell line, indicating a loss of CAR-binding ability.

IL13Rα2 Specific Infection of Glioma Cells In Vitro.

In order to demonstrate IL13Rα2-specific infectivity by the Ad5FFscFv47-CMV-GFP virus, the virus was exposed to the CHO and CHO-IL13Rα2 cell lines[19]. As shown in FIG. 33b,c, Ad5FFscFv47-CMV-GFP efficiently infected CHO-IL13Rα2 cells (80% of the IL13Rα2 cells are GFP-positive), but not the control CHO cells, which are IL13Rα2-negative. For further validation of IL-13Rα2-dependent infectivity of Ad5FFscFv47-CMV-GFP, an analysis of viral transduction in U87MG and U251MG cell lines was performed. Ad5FFscFv47-CMV-GFP infectivity was also assessed in patient-derived primary GBM43 and GBM39 glioma cells, which endogenously express IL13Rα2 at different levels (FIG. 33d). The flow cytometry analysis revealed that infectivity of Ad5FFscFv47-CMV-GFP strongly correlated with the level of IL13Rα2 expression in the assayed cell lines. GFP expression was observed in about 20% of U87MG and 90% of U251MG glioma cell lines, as well as in 1% and 20% of GBM39 and GBM43 glioma cells, respectively (FIG. 33e). In contrast, wild-type Ad5-CMV-GFP infection of both glioma cell lines was observed to be at a very low level, in accordance with the well-characterized low level of CAR expression by glioma cells[30,31]. Importantly, the infectivity of Ad5FFscFv47-CMV-GFP in U251MG cells increased proportionally with the viral multiplicity of infection (MOI) used in the assays (FIG. 33f), without causing any observable cytotoxicity.

To further validate IL13Rα2-dependent infectivity of Ad5FFscFv47-CMV-GFP, two cell lines, IL13Rα2+ U251MG and IL13Rα2.KDU251MG, were generated via transduction with lentivirus encoding either control or IL13Rα2-specific shRNA, respectively. IL13Rα2+ U251MG cells retained a very high (above 92% positive cells) expression of IL13Rα2 on their cell surface after lentiviral transduction, whereas IL13Rα2.KDU251MG glioma cells were mostly IL13Rα2 negative (about 12% of IL13Rα2-positive cells) (FIG. 34a). Ad5FFscFv47-CMV-GFP infected over 90% of IL13Rα2+U251MG cells and less than 5% of IL13Rα2.KDU251MG cells (FIG. 34b). Moreover, anti-IL13Rα2 mAb effectively inhibited the infection of U251MG cells by Ad5FFscFv47-CMV-GFP (FIG. 34c) in a competitive assay. Collectively, these data demonstrate that, similarly to the scFv47 protein, the Ad5FFscFv47 is an IL13Rα2-specific viral agent.

Infection of Stem-Like Cancer Glioma Cells by Ad5FFscFv47 Virus.

Figure 38:
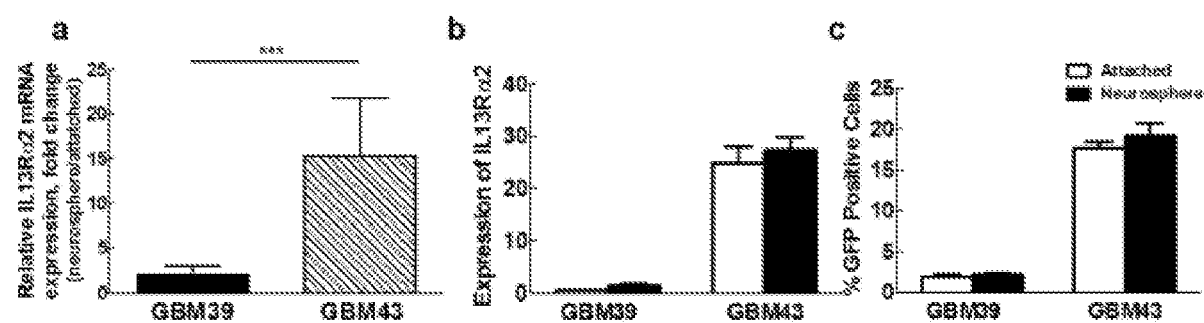
FIG. 38A-C. Infection of primary GBM cells by Ad5FFscFv47-CMV-GFP virus. A. Relative IL13Rα2 mRNA expression in patient-derived primary GBM39 and GBM43 cells grown as adherent or neurosphere cultures was analyzed by qRT-PCR. The level of IL13Rα2 mRNA expression was normalized to GAPDH mRNA expression. B. Comparison of IL13Rα2 expression on the surface of the primary GBM cells grown as an adherent culture or as neurospheres. C. Ad5FFscFv47-CMV-GFP infectivity of the primary GBM cells grown as adherent or neurospheres cultures determined by flow cytometry analysis for GFP-positive cells. Each data point is an average of 3 independent replicates. Mean±SEM is plotted. *** P<0.001.
Figure 39:
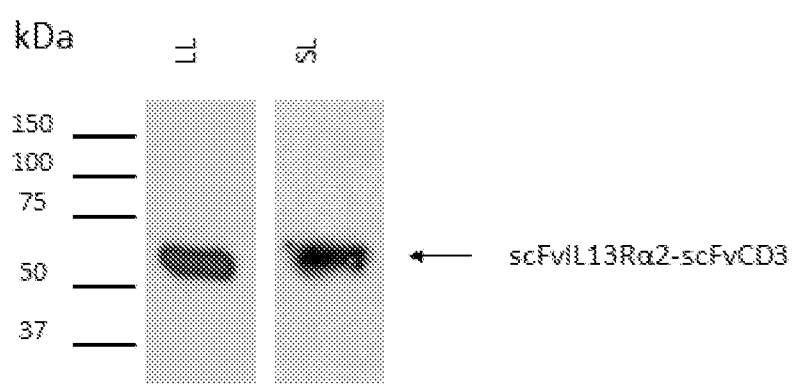
FIG. 39. Expression of soluble bi-specific scFvIL13Rα2-scFvCD3 in *E. coli* expression system. LL-long linker $(Gly_4S)_3$; SL-short linker $Gly_4S$.

As cancer stem cells have emerged as a potential target for glioblastoma treatments, cancer stem cell-like properties were mimicked in vitro by culturing the U87MG cells as neurospheres, as described herein. Analysis of IL13Rα2 expression revealed that U87MG neurospheres had 13 times higher expression of mRNA and 1.7 times higher surface protein expression compared to cells grown in attached (e.g., differentiated) form (FIG. 35a,b). Accordingly, Ad5FFscFv47-CMV-GFP infectivity was about 1.6 times higher in neurospheres than in adherently growing U87MG cells (FIG. 35c,d). To further validate the ability of Ad5FFscFv47-CMV-GFP to transduce neurospheres derived from the of IL13Rα2-expressing glioma cells, patient-derived primary glioma cells GBM39 and GBM43 were analyzed. While a slight increase in IL13Rα2 mRNA expression was observed in both GBM39 and GBM43 cell lines cultured as neurospheres, there was no detectable change in the surface expression of IL13Rα2 or the infectivity with Ad5FFscFv47-CMV-GFP in either cell line (FIG. 38). The Ad5FFscFv47-CMV-GFP infectivity was well-correlated with the level of IL13Rα2 expression on the cell surface in all studied glioma cell lines.

Thus, our data indicate that targeting of IL13Rα2-over-expressing cancer stem cells is highly feasible using scFv47-targeted therapeutic agents such as scFv47-engineered adenovirus.

Demonstration of IL13Rα2-Specific Infection In Vivo.

Collectively, the in vitro assays disclosed herein and described above demonstrate that Ad5FFscFv47-CMV-GFP specifically infects IL13Rα2-expressing glioma cells. Next, the specificity of Ad5FFscFv47-CMV-GFP infectivity was validated in vivo using intracranially implanted IL13Rα2+ U251MG and IL13Rα2.KDU251MG cells in a xenograft murine model of glioma. No infection was detected in the mostly IL13Rα2-negative IL13Rα2.KDU251MG xenograft tissue or in the brain tissue surrounding the tumor, as judged by the lack of GFP transgene expression (FIG. 36a). However, a high level of infection of IL13Rα2-expressing IL13Rα2+U251MG xenografts was observed, and once again there was no detectable GFP signal in the brain tissue adjacent to the tumor (FIG. 36b). Thus, the data confirmed that Ad5FFscFv47-CMV-GFP was capable of specific transduction of IL13Rα2-expressing tumor cells not only in vitro but also in vivo.

Disclosed is an scFv, i.e., scFv47, which was generated from a parental anti-IL13Rα2 monoclonal antibody through a phage-display approach. The scFv47 was shown to specifically recognize native IL13Rα2 with an exclusively high affinity and to recognize the same epitope as the parental anti-IL13Rα2 mAb (clone 47). Furthermore, the scFv47 was demonstrated to be successfully incorporated into an adenoviral vector and the Ad5FFscFv47-CMV-GFP virus also exclusively infected IL13Rα2-expressing glioma cells in vitro and in vivo.

A series of immunotherapeutic agents targeting IL13Rα2 have demonstrated preclinical promise[10,11,32,33] but those agents also recognize the widespread IL13Rα1, indicating that there is an unmet need for specific targeting agents[10,11,34]. In order to improve the specificity of IL13Rα2 targeting, a monoclonal antibody that exclusively recognizes a native epitope on the IL13Rα2 protein was generated. Engineered antibody fragments, however, have an advantage over whole antibodies, because they can be easily genetically manipulated and incorporated into therapeutic agents. With that in mind, the scFv47 single chain variable fragment was engineered as an IL13Rα2-specific targeting moiety for various therapeutic agents.

The data disclosed herein demonstrate that scFv47 has therapeutic applicability by redirecting the tropism of the commonly used anticancer agent, adenovirus, via modification of its fiber. Although the incorporation of scFv into adenoviral fiber is known to be difficult due to the stability of scFv itself and that of fiber trimerization[21,23], the scFv47-modified fiber demonstrated stability comparable to that of the wild-type adenoviral fiber, and Ad5FFscFv47-CMV-GFP was no longer able to recognize the native adenoviral receptor, CAR. Instead, the virus exclusively infected IL13Rα2-expressing cells both in vitro and in vivo. The results disclosed herein validate scFv47 as a highly selective IL13Rα2 targeting agent and confirm that it can be utilized for the redirection of adenoviral tropism to cancer and cancer stem-like glioma cells.

Recently, research has focused on identifying therapeutic agents that can successfully eradicate cancer stem cells, which are resistant to traditional anticancer therapies and thought to be responsible for cancer recurrence following therapeutic treatment[35]. Based on these properties, glioma stem cells are a highly attractive subset of tumor cells for therapeutic targeting. In agreement with previous reports[36,37] expression of IL13Rα2 was maintained in primary patient-derived glioma cells growing as neurospheres, which permitted efficient transduction of these cells by Ad5FFscFv47-CMV-GFP virus. IL13Rα2 expression has recently been associated with an increased malignancy grade and a poorer patient prognosis[17]. Thus, providing a treatment option that specifically targets IL13Rα2-expressing stem cell-like and differentiated glioma cells would be of benefit to the patients with some of the most aggressive and hardest-to-treat cancers.

Previously, it had been shown that nearly 50% of GBM patients have tumors that express IL13Rα2[38], a higher percentage than the other commonly used glioma-specific marker, EGFRvIII[39], which indicates the significance of this molecular target for the majority of GBM patients[38]. Additionally, following glioma cell death, the phenomenon of 'epitope spreading' might enhance the immune response against the tumor and result in further removal of the tumor, including removal of even those cells that do not express the originally targeted antigen[40]. As more glioma-specific agents are developed, personalized treatment cocktails can be administered to achieve heightened specificity and efficacy for a given patient's glioma phenotype.

In conclusion, the scFv47 could serve as a specific targeting agent for IL13Rα2-directed therapeutics, such as T and NK immune cells, fusion proteins, nano carriers, viruses, and other agents. The vast molecular heterogeneity of malignant gliomas may have contributed to the lack of effective targeted therapies. Currently, there are several active and pending clinical trials designed for the personal therapy of patients with glioma. Eventually, with the development of an arsenal of targeted therapies, such as agents that specifically target and destroy IL13Rα2-expressing tumor cells and other tumor-associated antigens such as EGFRvIII, personalized treatment protocols can be implemented in conjunction with traditional disease therapies like surgery and radiation to improve the outcome for patients with GBM.

References for Example 13 Only

1. Stupp, R. et al. Radiotherapy plus concomitant and adjuvant temozolomide for glioblastoma. N Engl J Med 352, 987-996 (2005).
2. Zheng, S. et al. Fiber-knob modifications enhance adenoviral tropism and gene transfer in malignant glioma. The journal of gene medicine 9, 151-160 (2007).
3. Van Houdt, W. J. et al. The human survivin promoter: a novel transcriptional targeting strategy for treatment of glioma. J Neurosurg 104, 583-592 (2006).
4. Ulasov, I. V. et al. Comparative evaluation of survivin, midkine and CXCR4 promoters for transcriptional targeting of glioma gene therapy. Cancer biology & therapy 6, 679-685 (2007).
5. Ulasov, I. V. et al. Survivin-driven and fiber-modified oncolytic adenovirus exhibits potent antitumor activity in established intracranial glioma. Human gene therapy 18, 589-602 (2007).
6. Ulasov, I. V. et al. Combination of adenoviral virotherapy and temozolomide chemotherapy eradicates malignant glioma through autophagic and apoptotic cell death in vivo. British journal of cancer 100, 1154-1164 (2009).
7. Chakravarti, A. et al. Quantitatively determined survivin expression levels are of prognostic value in human gliomas. Journal of clinical oncology: official journal of the American Society of Clinical Oncology 20, 1063-1068 (2002).
8. Uematsu, M. et al. Prognostic significance of the immunohistochemical index of survivin in glioma: a comparative study with the MIB-1 index. Journal of neuro-oncology 72, 231-238 (2005).
9. Choi, B. D. et al. Systemic administration of a bispecific antibody targeting EGFRvIII successfully treats intracerebral glioma. Proceedings of the National Academy of Sciences of the United States of America 110, 270-275 (2013).
10. Kong, S. et al. Suppression of human glioma xenografts with second-generation IL13R-specific chimeric antigen receptor-modified T cells. Clinical cancer research: an official journal of the American Association for Cancer Research 18, 5949-5960 (2012).

11. Krebs, S. et al. T cells redirected to interleukin-13Ralpha2 with interleukin-13 mutein-chimeric antigen receptors have anti-glioma activity but also recognize interleukin-13Ralpha1. Cytotherapy 16, 1121-1131 (2014).
12. Riccione, K. et al. Generation of CAR T Cells for Adoptive Therapy in the Context of Glioblastoma Standard of Care. Journal of visualized experiments: JoVE, doi: 10.3791/52397 (2015).
13. Zitron, I. M. et al. Targeting and killing of glioblastoma with activated T cells armed with bispecific antibodies. BMC cancer 13, 83 (2013).
14. Debinski, W., Obiri, N. I., Powers, S. K., Pastan, I. & Puri, R. K. Human glioma cells overexpress receptors for interleukin 13 and are extremely sensitive to a novel chimeric protein composed of interleukin 13 and pseudomonas exotoxin. Clinical cancer research: an official journal of the American Association for Cancer Research 1, 1253-1258 (1995).
15. Joshi, B. H., Plautz, G. E. & Puri, R. K. Interleukin-13 receptor alpha chain: a novel tumor-associated transmembrane protein in primary explants of human malignant gliomas. Cancer Res 60, 1168-1172 (2000).
16. Jarboe, J. S., Johnson, K. R., Choi, Y., Lonser, R. R. & Park, J. K. Expression of interleukin-13 receptor alpha2 in glioblastoma multiforme: implications for targeted therapies. Cancer Res 67, 7983-7986 (2007).
17. Brown, C. E. et al. Glioma IL13Rα 2 Is Associated with Mesenchymal Signature Gene Expression and Poor Patient Prognosis. PLoS One 8, e77769 (2013).
18. Ulasov, I. V., Tyler, M. A., Han, Y., Glasgow, J. N. & Lesniak, M. S. Novel recombinant adenoviral vector that targets the interleukin-13 receptor alpha2 chain permits effective gene transfer to malignant glioma. Human gene therapy 18, 118-129 (2007).
19. Balyasnikova, I. V. et al. Characterization and immunotherapeutic implications for a novel antibody targeting interleukin (IL)-13 receptor alpha2. The Journal of biological chemistry 287, 30215-30227 (2012).
20. Bartolome, R. A. et al. IL13 Receptor α 2 Signaling Requires a Scaffold Protein, FAM120A, to Activate the FAK and PI3K Pathways in Colon Cancer Metastasis. Cancer Res 75, 2434-2444 (2015).
21. Hedley, S. J. et al. An adenovirus vector with a chimeric fiber incorporating stabilized single chain antibody achieves targeted gene delivery. Gene Ther 13, 88-94 (2006).
22. Krasnykh, V., Belousova, N., Korokhov, N., Mikheeva, G. & Curiel, D. T. Genetic targeting of an adenovirus vector via replacement of the fiber protein with the phage T4 fibritin. Journal of virology 75, 4176-4183 (2001).
23. Kaliberov, S. A. et al. Adenoviral targeting using genetically incorporated camelid single variable domains. Laboratory investigation; a journal of technical methods and pathology 94, 893-905 (2014).
24. Kipriyanov, S. M., Kupriyanova, O. A., Little, M. & Moldenhauer, G. Rapid detection of recombinant antibody fragments directed against cell-surface antigens by flow cytometry. Journal of immunological methods 196, 51-62 (1996).
25. Toleikis, L., Broders, O. & Dubel, S. Cloning single-chain antibody fragments (scFv) from hybridoma cells. Methods in molecular medicine 94, 447-458 (2004).
26. Curiel, D. T. Strategies to adapt adenoviral vectors for targeted delivery. Annals of the New York Academy of Sciences 886, 158-171 (1999).
27. Kim, J. W. et al. A Genetically Modified Adenoviral Vector with a Phage Display Derived Peptide Incorporated into Fiber Fibritin Chimera Prolongs Survival in Experimental Glioma. Human gene therapy (2015).
28. Bergelson, J. M. et al. Isolation of a common receptor for Coxsackie B viruses and adenoviruses 2 and 5. Science (New York, N.Y.) 275, 1320-1323 (1997).
29. Tomko, R. P., Xu, R. & Philipson, L. HCAR and MCAR: the human and mouse cellular receptors for subgroup C adenoviruses and group B coxsackieviruses. Proceedings of the National Academy of Sciences of the United States of America 94, 3352-3356 (1997).
30. Fuxe, J. et al. Expression of the coxsackie and adenovirus receptor in human astrocytic tumors and xenografts. International journal of cancer. Journal international du cancer 103, 723-729 (2003).
31. Asaoka, K., Tada, M., Sawamura, Y., Ikeda, J. & Abe, H. Dependence of efficient adenoviral gene delivery in malignant glioma cells on the expression levels of the Coxsackievirus and adenovirus receptor. J Neurosurg 92, 1002-1008 (2000).
32. Allen, C. et al. Interleukin-13 displaying retargeted oncolytic measles virus strains have significant activity against gliomas with improved specificity. Mol Ther 16, 1556-1564 (2008).
33. Kioi, M., Seetharam, S. & Puri, R. K. Targeting IL-13Ralpha2-positive cancer with a novel recombinant immunotoxin composed of a single-chain antibody and mutated Pseudomonas exotoxin. Mol Cancer Ther 7, 1579-1587 (2008).
34. Kunwar, S. et al. Phase III randomized trial of CED of IL13-PE38QQR vs Gliadel wafers for recurrent glioblastoma. Neuro-oncology 12, 871-881 (2010).
35. Auffinger, B., Spencer, D., Pytel, P., Ahmed, A. U. & Lesniak, M. S. The role of glioma stem cells in chemotherapy resistance and glioblastoma multiforme recurrence. Expert review of neurotherapeutics, 1-12 (2015).
36. Brown, C. E. et al. Stem-like tumor-initiating cells isolated from IL13Ralpha2 expressing gliomas are targeted and killed by IL13-zetakine-redirected T Cells. Clinical cancer research: an official journal of the American Association for Cancer Research 18, 2199-2209 (2012).
37. Ogden, A. T. et al. Identification of A2B5+CD133− tumor-initiating cells in adult human gliomas. Neurosurgery 62, 505-514 (2008).
38. Jarboe, J. S., Johnson, K. R., Choi, Y., Lonser, R. R. & Park, J. K. Expression of Interleukin-13 Receptor a 2 in Glioblastoma Multiforme: Implications for Targeted Therapies. Cancer Research 67, 7983-7986 (2007).
39. Gan, H. K., Kaye, A. H. & Luwor, R. B. The EGFRvIII variant in glioblastoma multiforme. Journal of clinical neuroscience: official journal of the Neurosurgical Society of Australasia 16, 748-754 (2009).
40. Beatty, G. L. et al. Mesothelin-specific chimeric antigen receptor mRNA-engineered T cells induce anti-tumor activity in solid malignancies. Cancer immunology research 2, 112-120 (2014).
41. Kane, J. R. et al. Sui generis: gene therapy and delivery systems for the treatment of glioblastoma. Neuro-oncology 17 Suppl 2, ii24-ii36 (2015).
42. Patel, M. A., Kim, J. E., Ruzevick, J., Li, G. & Lim, M. The future of glioblastoma therapy: synergism of standard of care and immunotherapy. Cancers 6, 1953-1985 (2014).
43. Yan, K. et al. Glioma cancer stem cells secrete Gremlin1 to promote their maintenance within the tumor hierarchy. Genes & development 28, 1085-1100 (2014).
44. Balyasnikova, I. V. et al. Cloning and characterization of a single-chain fragment of monoclonal antibody to ACE suitable for lung endothelial targeting. Microvascular research 80, 355-364 (2010).

45. Wilkinson-Ryan, I. et al. Incorporation of porcine adenovirus 4 fiber protein enhances infectivity of adenovirus vector on dendritic cells: implications for immune-mediated cancer therapy. PLoS One 10, e0125851 (2015).
46. Livak, K. J. & Schmittgen, T. D. Analysis of relative gene expression data using real-time quantitative PCR and the 2(−Delta Delta C(T)) Method. Methods 25, 402-408 (2001).

Each of the references cited herein is hereby incorporated by reference in its entirety or in relevant part, as would be apparent from the context of the citation.

From the disclosure herein it will be appreciated that, although specific embodiments of the disclosure have been described herein for purposes of illustration, various modifications may be made without deviating from the spirit and scope of the disclosure.

The invention claimed is:

1. A humanized IL13Rα2 binding agent comprising:
   (i) each of the amino acid sequences of: complementarity determining region 1 NYLMN (SEQ ID NO: 1); complementarity determining region 2 RIDPYDGDIDYNQNFKD (SEQ ID NO: 2); complementarity determining region 3 GYGTAYGVDY (SEQ ID NO: 3); complementarity determining region 4 RASESVDNYGISFMN (SEQ ID NO: 4); complementarity determining region 5 AASRQGSG (SEQ ID NO: 5); and complementarity determining region 6 QQSKEVPWT (SEQ ID NO: 6); or
   (ii) a humanized version of a variable heavy chain region of SEQ ID NO:7 and a variable light chain region of SEQ ID NO:8.

2. The IL13Rα2 binding agent of claim 1, comprising i) each of the amino acid sequences of: complementarity determining region 1 NYLMN (SEQ ID NO: 1); complementarity determining region 2 RIDPYDGDIDYNQNFKD (SEQ ID NO: 2); complementarity determining region 3 GYGTAYGVDY (SEQ ID NO: 3); complementarity determining region 4 RASESVDNYGISFMN (SEQ ID NO: 4); complementarity determining region 5 AASRQGSG (SEQ ID NO: 5); and complementarity determining region 6 QQSKEVPWT (SEQ ID NO: 6).

3. The IL13Rα2 binding agent of claim 1, comprising a variable heavy chain region fused to a variable light chain region through a linker.

4. The IL13Rα2 binding agent of claim 3, wherein the linker comprises the amino acid sequence of EEGEFSEAR (SEQ ID NO 10).

5. The IL13Rα2 binding agent of claim 1, which is an antibody, an antigen-binding fragment of an antibody, or a single chain variable fragment (scFv).

6. The IL13Rα2 binding agent of claim 1, further comprising an Ig kappa leader sequence of METDTLLLWVLLLWVPGSTGD (SEQ ID NO: 9).

7. The IL13Rα2 binding agent of claim 1, further comprising a Myc tag sequence of GGPEQKLISEEDLN (SEQ ID NO: 11) or a His tag sequence of HHHHHH (SEQ ID NO: 12).

8. A nucleic acid encoding the IL13Rα2 binding agent of claim 1.

9. A vector comprising the nucleic acid of claim 8.

10. The vector of claim 9 wherein the vector is a virus.

11. The vector of claim 10 wherein the virus is adenovirus.

12. The vector of claim 11 wherein the adenovirus is adenovirus serotype 5.

13. A recombinant polynucleotide comprising the vector of claim 9.

14. The recombinant polynucleotide of claim 13 wherein the polynucleotide is Ad5FFscFv47.

15. A host cell comprising the vector of claim 9.

16. A pharmaceutical composition comprising the binding agent of claim 1.

17. A method of treating a cancer in a subject, comprising administering to the subject the binding agent of claim 1.

18. The method of claim 17, wherein the cancer is glioblastoma multiforme or colon cancer.

19. A method of identifying an IL13Rα2-positive cancer cell comprising
   a. contacting a biological sample with a detectable amount of the binding agent of claim 1; and
   b. measuring the amount of the binding agent or conjugate bound to at least one cell of the biological sample, thereby identifying an IL13Rα2-positive cancer cell;
wherein the biological sample comprises a cellular mass, tissue, or organ in vivo or ex vivo.

* * * * *

SEQUENCE LISTING

```
<160> NUMBER OF SEQ ID NOS: 108

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 1

Asn Tyr Leu Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 2

Arg Ile Asp Pro Tyr Asp Gly Asp Ile Asp Tyr Asn Gln Asn Phe Lys
1               5                   10                  15

Asp

<210> SEQ ID NO 3
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 3

Gly Tyr Gly Thr Ala Tyr Gly Val Asp Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 4

Arg Ala Ser Glu Ser Val Asp Asn Tyr Gly Ile Ser Phe Met Asn
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Synthetic Polypeptide
```

```
<400> SEQUENCE: 5

Ala Ala Ser Arg Gln Gly Ser Gly
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 6

Gln Gln Ser Lys Glu Val Pro Trp Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 7

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Ser Asn Tyr
            20                  25                  30

Leu Met Asn Trp Val Lys Gln Arg Pro Glu Gln Asp Leu Asp Trp Ile
        35                  40                  45

Gly Arg Ile Asp Pro Tyr Asp Gly Asp Ile Asp Tyr Asn Gln Asn Phe
    50                  55                  60

Lys Asp Lys Ala Ile Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Ser Val Thr Val Ser Ser
        115

<210> SEQ ID NO 8
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Arg Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95
```

```
Glu Val Pro Trp Thr Phe Gly Gly Gly Thr Lys Leu Glu Ile Lys
            100                 105                 110

<210> SEQ ID NO 9
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 9

Met Glu Thr Asp Thr Leu Leu Leu Trp Val Leu Leu Leu Trp Val Pro
1               5                   10                  15

Gly Ser Thr Gly Asp
            20

<210> SEQ ID NO 10
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 10

Glu Glu Gly Glu Phe Ser Glu Ala Arg
1               5

<210> SEQ ID NO 11
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 11

Gly Gly Pro Glu Gln Lys Leu Ile Ser Glu Glu Asp Leu Asn
1               5                   10

<210> SEQ ID NO 12
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 12

His His His His His His
1               5

<210> SEQ ID NO 13
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 13

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Ser Asn Tyr
            20                  25                  30

Leu Met Asn Trp Val Lys Gln Arg Pro Glu Gln Asp Leu Asp Trp Ile
        35                  40                  45

Gly Arg Ile Asp Pro Tyr Asp Gly Asp Ile Asp Tyr Asn Gln Asn Phe
```

```
                  50                  55                  60
Lys Asp Lys Ala Ile Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly Tyr Gly Thr Ala Tyr Gly Val Asp Tyr Trp Gly Gln Gly
                100                 105                 110

Thr Ser Val Thr Val Ser Ser Ala Lys Thr Thr Pro Pro Lys Leu Glu
                115                 120                 125

Glu Gly Glu Phe Ser Glu Ala Arg Val Asp Ile Val Leu Thr Gln Ser
            130                 135                 140

Pro Ala Ser Leu Ala Val Ser Leu Gly Gln Arg Ala Thr Ile Ser Cys
145                 150                 155                 160

Arg Ala Ser Glu Ser Val Asp Asn Tyr Gly Ile Ser Phe Met Asn Trp
                165                 170                 175

Phe Gln Gln Lys Pro Gly Gln Pro Pro Lys Leu Leu Ile Tyr Ala Ala
                180                 185                 190

Ser Arg Gln Gly Ser Gly Val Pro Ala Arg Phe Ser Gly Ser Gly Ser
            195                 200                 205

Gly Thr Asp Phe Ser Leu Asn Ile His Pro Met Glu Glu Asp Asp Thr
            210                 215                 220

Ala Met Tyr Phe Cys Gln Gln Ser Lys Glu Val Pro Trp Thr Phe Gly
225                 230                 235                 240

Gly Gly Thr Lys Leu Glu Ile Lys
                245

<210> SEQ ID NO 14
<211> LENGTH: 297
<212> TYPE: PRT
<213> ORGANISM: Artificial Sequence
<220> FEATURE:
<223> OTHER INFORMATION: Synthetic Polypeptide

<400> SEQUENCE: 14

Met Glu Thr Asp Thr Leu Leu Leu Trp Val Leu Leu Leu Trp Val Pro
 1               5                  10                  15

Gly Ser Thr Gly Asp Gln Val Gln Leu Gln Gln Pro Gly Ala Glu Leu
                20                  25                  30

Val Arg Pro Gly Ala Ser Val Lys Leu Ser Cys Lys Ala Ser Gly Tyr
            35                  40                  45

Thr Phe Ser Asn Tyr Leu Met Asn Trp Val Lys Gln Arg Pro Glu Gln
        50                  55                  60

Asp Leu Asp Trp Ile Gly Arg Ile Asp Pro Tyr Asp Gly Asp Ile Asp
 65                  70                  75                  80

Tyr Asn Gln Asn Phe Lys Asp Lys Ala Ile Leu Thr Val Asp Lys Ser
                85                  90                  95

Ser Ser Thr Ala Tyr Met Gln Leu Ser Ser Leu Thr Ser Glu Asp Ser
            100                 105                 110

Ala Val Tyr Tyr Cys Ala Arg Gly Tyr Gly Thr Ala Tyr Gly Val Asp
        115                 120                 125

Tyr Trp Gly Gln Gly Thr Ser Val Thr Val Ser Ser Ala Lys Thr Thr
    130                 135                 140

Pro Pro Lys Leu Glu Glu Gly Glu Phe Ser Glu Ala Arg Val Asp Ile
145                 150                 155                 160

Val Leu Thr Gln Ser Pro Ala Ser Leu Ala Val Ser Leu Gly Gln Arg
```

|     |     |     |     |     | 165 |     |     |     |     | 170 |     |     |     |     | 175 |
| --- | --- | --- | --- | --- | --- | --- | --- | --- | --- | --- | --- | --- | --- | --- | --- |
Ala Thr Ile Ser Cys Arg Ala Ser Glu Ser Val Asp Asn Tyr Gly Ile
                    180                 185                 190

Ser Phe Met Asn Trp Phe Gln Gln Lys Pro Gly Gln Pro Pro Lys Leu
            195                 200                 205

Leu Ile Tyr Ala Ala Ser Arg Gln Gly Ser Gly Val Pro Ala Arg Phe
        210                 215                 220

Ser Gly Ser Gly Ser Gly Thr Asp Phe Ser Leu Asn Ile His Pro Met
225                 230                 235                 240

Glu Glu Asp Asp Thr Ala Met Tyr Phe Cys Gln Gln Ser Lys Glu Val
                245                 250                 255

Pro Trp Thr Phe Gly Gly Gly Thr Lys Leu Glu Ile Lys Ala Ala Ala
            260                 265                 270

Arg Gly Gly Pro Glu Gln Lys Leu Ile Ser Glu Glu Asp Leu Asn Ser
        275                 280                 285

Ala Val Asp His His His His His His
        290                 295

<210> SEQ ID NO 15
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 15
caggtccaac tgcagcagcc tggggctgag ctggtgaggc ctggggcttc agtgaagctg      60
tcctgcaagg cttctggcta cacgttctcc aactacttga tgaactgggt taagcagagg     120
cctgagcaag accttgactg gattggaagg attgatcctt acgatggtga cattgactac     180
aatcaaaact tcaaggacaa ggccatattg actgtagaca atcctccag cacagcctac      240 atgcaactca gcagcctgac atctgaggac tctgcggtct attactgtgc aagaggttat     300
ggcacggcct atggtgtgga ctactggggt caaggaacct cagtcaccgt ctcctca       357

<210> SEQ ID NO 16
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 16
gatattgtgc taactcagtc tccagcttct ttggctgtgt ctctaggaca gagggccacc      60
atctcctgca gagccagcga aagtgttgat aattatggca ttagttttat gaactggttc     120
caacagaaac aggacagcc acccaaactc ctcatctatg ctgcatccag gcaaggatcc      180
ggggtccctg ccaggtttag tggcagtggg tctgggacag acttcagcct caacatccat     240
cctatggagg aggatgatac tgcaatgtat ttctgtcagc aaagtaagga ggttccgtgg     300
acgttcggtg gaggcaccaa gctggaaatc aaa                                  333

<210> SEQ ID NO 17
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 17

```
gcttggtacc gaatggcttt cgtttgcttg gc                                    32
```

<210> SEQ ID NO 18
<211> LENGTH: 34
<212> TYPE: PRT
<213> ORGANISM: Artificial Sequence
<220> FEATURE:
<223> OTHER INFORMATION: Synthetic Polynucleotide

<400> SEQUENCE: 18

```
Gly Thr Thr Thr Thr Thr Gly Thr Thr Cys Gly Ala Ala Thr Gly Thr
1               5                   10                  15
Ala Thr Cys Ala Cys Ala Gly Ala Ala Ala Ala Thr Thr Cys Thr
            20                  25                  30
Gly Gly
```

<210> SEQ ID NO 19
<211> LENGTH: 146
<212> TYPE: PRT
<213> ORGANISM: Homo sapiens
<220> FEATURE:
<221> NAME/KEY: SIGNAL
<222> LOCATION: (1)..(34)
<220> FEATURE:
<221> NAME/KEY: mat_peptide
<222> LOCATION: (35)..(132)

<400> SEQUENCE: 19

```
Met His Pro Leu Leu Asn Pro Leu Leu Leu Ala Leu Gly Leu Met Ala
                -30                 -25                 -20
Leu Leu Leu Thr Thr Val Ile Ala Leu Thr Cys Leu Gly Gly Phe Ala
            -15                 -10                 -5
Ser Pro Gly Pro Val Pro Pro Ser Thr Ala Leu Arg Glu Leu Ile Glu
        -1  1               5                   10
Glu Leu Val Asn Ile Thr Gln Asn Gln Lys Ala Pro Leu Cys Asn Gly
15                  20                  25                  30
Ser Met Val Trp Ser Ile Asn Leu Thr Ala Gly Met Tyr Cys Ala Ala
                35                  40                  45
Leu Glu Ser Leu Ile Asn Val Ser Gly Cys Ser Ala Ile Glu Lys Thr
            50                  55                  60
Gln Arg Met Leu Ser Gly Phe Cys Pro His Lys Val Ser Ala Gly Gln
65                  70                  75
Phe Ser Ser Leu His Val Arg Asp Thr Lys Ile Glu Val Ala Gln Phe
            80                  85                  90
Val Lys Asp Leu Leu Leu His Leu Lys Lys Leu Phe Arg Glu Gly Gln
95                  100                 105                 110
Phe Asn
```

<210> SEQ ID NO 20
<211> LENGTH: 1282
<212> TYPE: DNA
<213> ORGANISM: Homo sapiens

<400> SEQUENCE: 20

```
aagccaccca gcctatgcat ccgctcctca atcctctcct gttggcactg ggcctcatgg    60
cgcttttgtt gaccacggtc attgctctca cttgccttgg cggctttgcc tccccaggcc    120
ctgtgcctcc ctctacagcc ctcagggagc tcattgagga gctggtcaac atcacccaga    180
accagaaggc tccgctctgc aatggcagca tggtatggag catcaacctg acagctggca    240
```

-continued

```
tgtactgtgc agccctggaa tccctgatca acgtgtcagg ctgcagtgcc atcgagaaga      300
cccagaggat gctgagcgga ttctgcccgc acaaggtctc agctgggcag ttttccagct      360
tgcatgtccg agacaccaaa atcgaggtgg cccagtttgt aaaggacctg ctcttacatt      420
taaagaaact ttttcgcgag ggacagttca actgaaactt cgaaagcatc attatttgca      480
gagacaggac ctgactattg aagttgcaga ttcattttc tttctgatgt caaaaatgtc      540
ttgggtaggc gggaaggagg gttagggagg ggtaaaattc cttagcttag acctcagcct      600
gtgctgcccg tcttcagcct agccgacctc agccttcccc ttgcccaggg ctcagcctgg      660
tgggcctcct ctgtccaggg ccctgagctc ggtggaccca gggatgacat gtccctacac      720
ccctcccctg ccctagagca cactgtagca ttacagtggg tgccccctt gccagacatg       780 tggtgggaca gggacccact tcacacacag gcaactgagg cagacagcag ctcaggcaca      840
cttcttcttg gtcttattta ttattgtgtg ttatttaaat gagtgtgttt gtcaccgttg      900
gggattgggg aagactgtgg ctgctagcac ttggagccaa gggttcagag actcagggcc      960
ccagcactaa agcagtggac accaggagtc cctggtaata agtactgtgt acagaattct     1020
gctacctcac tggggtcctg gggcctcgga gcctcatccg aggcagggtc aggagagggg     1080
cagaacagcc gctcctgtct gccagccagc agccagctct cagccaacga gtaatttatt     1140 gttttttcctt gtatttaaat attaaatatg ttagcaaaga gttaatatat agaagggtac     1200
cttgaacact gggggagggg acattgaaca agttgtttca ttgactatca aactgaagcc     1260
agaaataaag ttggtgacag at                                              1282
```

<210> SEQ ID NO 21
<211> LENGTH: 427
<212> TYPE: PRT
<213> ORGANISM: Homo sapiens
<220> FEATURE:
<221> NAME/KEY: SIGNAL
<222> LOCATION: (1)..(21)
<220> FEATURE:
<221> NAME/KEY: mat_peptide
<222> LOCATION: (22)..(427)

<400> SEQUENCE: 21

```
Met Glu Trp Pro Ala Arg Leu Cys Gly Leu Trp Ala Leu Leu Leu Cys
    -20                 -15                 -10

Ala Gly Gly Gly Gly Gly Gly Gly Ala Ala Pro Thr Glu Thr Gln
 -5              -1   1               5                  10

Pro Pro Val Thr Asn Leu Ser Val Ser Val Glu Asn Leu Cys Thr Val
                15                  20                  25

Ile Trp Thr Trp Asn Pro Pro Glu Gly Ala Ser Ser Asn Cys Ser Leu
                30                  35                  40

Trp Tyr Phe Ser His Phe Gly Asp Lys Gln Asp Lys Lys Ile Ala Pro
                45                  50                  55

Glu Thr Arg Arg Ser Ile Glu Val Pro Leu Asn Glu Arg Ile Cys Leu
 60                  65                  70                  75

Gln Val Gly Ser Gln Cys Ser Thr Asn Glu Ser Glu Lys Pro Ser Ile
                80                  85                  90

Leu Val Glu Lys Cys Ile Ser Pro Pro Glu Gly Asp Pro Glu Ser Ala
                95                 100                 105

Val Thr Glu Leu Gln Cys Ile Trp His Asn Leu Ser Tyr Met Lys Cys
                110                 115                 120

Ser Trp Leu Pro Gly Arg Asn Thr Ser Pro Asp Thr Asn Tyr Thr Leu
                125                 130                 135
```

Tyr Tyr Trp His Arg Ser Leu Glu Lys Ile His Gln Cys Glu Asn Ile
140                 145                 150                 155

Phe Arg Glu Gly Gln Tyr Phe Gly Cys Ser Phe Asp Leu Thr Lys Val
            160                 165                 170

Lys Asp Ser Ser Phe Glu Gln His Ser Val Gln Ile Met Val Lys Asp
        175                 180                 185

Asn Ala Gly Lys Ile Lys Pro Ser Phe Asn Ile Val Pro Leu Thr Ser
    190                 195                 200

Arg Val Lys Pro Asp Pro His Ile Lys Asn Leu Ser Phe His Asn
205                 210                 215

Asp Asp Leu Tyr Val Gln Trp Glu Asn Pro Gln Asn Phe Ile Ser Arg
220                 225                 230                 235

Cys Leu Phe Tyr Glu Val Glu Val Asn Asn Ser Gln Thr Glu Thr His
                240                 245                 250

Asn Val Phe Tyr Val Gln Glu Ala Lys Cys Glu Asn Pro Glu Phe Glu
            255                 260                 265

Arg Asn Val Glu Asn Thr Ser Cys Phe Met Val Pro Gly Val Leu Pro
        270                 275                 280

Asp Thr Leu Asn Thr Val Arg Ile Arg Val Lys Thr Asn Lys Leu Cys
    285                 290                 295

Tyr Glu Asp Asp Lys Leu Trp Ser Asn Trp Ser Gln Glu Met Ser Ile
300                 305                 310                 315

Gly Lys Lys Arg Asn Ser Thr Leu Tyr Ile Thr Met Leu Leu Ile Val
                320                 325                 330

Pro Val Ile Val Ala Gly Ala Ile Ile Val Leu Leu Leu Tyr Leu Lys
            335                 340                 345

Arg Leu Lys Ile Ile Ile Phe Pro Pro Ile Pro Asp Pro Gly Lys Ile
        350                 355                 360

Phe Lys Glu Met Phe Gly Asp Gln Asn Asp Asp Thr Leu His Trp Lys
    365                 370                 375

Lys Tyr Asp Ile Tyr Glu Lys Gln Thr Lys Glu Glu Thr Asp Ser Val
380                 385                 390                 395

Val Leu Ile Glu Asn Leu Lys Lys Ala Ser Gln
                400                 405

<210> SEQ ID NO 22
<211> LENGTH: 4006
<212> TYPE: DNA
<213> ORGANISM: Homo sapiens

<400> SEQUENCE: 22
tgccaaggct ccagcccggc cgggctccga ggcgagaggc tgcatggagt ggccggcgcg     60
gctctgcggg ctgtgggcgc tgctgctctg cgccggcggc gggggcgggg gcggggcgc    120 cgcgcctacg gaaactcagc cacctgtgac aaatttgagt gtctctgttg aaaacctctg    180
cacagtaata tggacatgga atccacccga gggagccagc tcaaattgta gtctatggta    240 tttagtcat tttggcgaca aacaagataa gaaatagct ccggaaactc gtcgttcaat    300
agaagtaccc ctgaatgaga ggatttgtct gcaagtgggg tcccagtgta gcaccaatga    360
gagtgagaag cctagcattt tggttgaaaa atgcatctca ccccagaag gtgatcctga    420 gtctgctgtg actgagcttc aatgcatttg gcacaacctg agctacatga agtgttcttg    480
gctccctgga aggaatacca gtcccgacac taactatact ctctactatt ggcacagaag    540
cctggaaaaa attcatcaat gtgaaaacat ctttagagaa ggccaatact ttggttgttc    600

```
ctttgatctg accaaagtga aggattccag ttttgaacaa cacagtgtcc aaataatggt    660
caaggataat gcaggaaaaa ttaaaccatc cttcaatata gtgcctttaa cttcccgtgt    720
gaaacctgat cctccacata ttaaaaacct ctccttccac aatgatgacc tatatgtgca    780
atgggagaat ccacagaatt ttattagcag atgcctattt tatgaagtag aagtcaataa    840
cagccaaact gagacacata atgttttcta cgtccaagag gctaaatgtg agaatccaga    900
atttgagaga aatgtggaga atacatcttg tttcatggtc cctggtgttc ttcctgatac    960
tttgaacaca gtcagaataa gagtcaaaac aaataagtta tgctatgagg atgacaaact   1020
ctggagtaat tggagccaag aaatgagtat aggtaagaag cgcaattcca cactctacat   1080
aaccatgtta ctcattgttc cagtcatcgt cgcaggtgca atcatagtac tcctgcttta   1140
cctaaaaagg ctcaagatta ttatattccc tccaattcct gatcctggca agattttaa    1200 agaaatgttt ggagaccaga atgatgatac tctgcactgg aagaagtacg acatctatga   1260
gaagcaaacc aaggaggaaa ccgactctgt agtgctgata gaaaacctga gaaaagcctc   1320
tcagtgatgg agataattta ttttttacctt cactgtgacc ttgagaagat tcttcccatt   1380 ctccattttgt tatctgggaa cttattaaat ggaaactgaa actactgcac catttaaaaa   1440
caggcagctc ataagagcca caggtcttta tgttgagtcg cgcaccgaaa aactaaaaat   1500
aatgggcgct ttggagaaga gtgtggagtc attctcattg aattataaaa gccagcaggc   1560
ttcaaactag gggacaaagc aaaaagtgat gatagtggtg gagttaatct tatcaagagt   1620
tgtgacaact tcctgaggga tctatacttg cttttgtgttc tttgtgtcaa catgaacaaa   1680
ttttatttgt aggggaactc atttggggtg caaatgctaa tgtcaaactt gagtcacaaa   1740
gaacatgtag aaaacaaaat ggataaaatc tgatatgtat tgtttgggat cctattgaac   1800
catgtttgtg gctattaaaa ctcttttaac agtctgggct gggtccggtg gctcacgcct   1860
gtaatcccag caattgggga gtccgaggcg ggcggatcac tcgaggtcag gagttccaga   1920
ccagcctgac caaaatggtg aaacctcctc tctactaaaa ctacaaaaat taactgggtg   1980
tggtggcgcg tgcctgtaat cccagctact cgggaagctg aggcaggtga attgtttgaa   2040
cctgggaggt ggaggttgca gtgagcagag atcacaccac tgcactctag cctgggtgac   2100
agagcaagac tctgtctaaa aaacaaaaca aacaaaaca aaacaaaaaa acctcttaat    2160
attctggagt catcattccc ttcgacagca ttttcctctg ctttgaaagc cccagaaatc   2220
agtgttggcc atgatgacaa ctacagaaaa accagaggca gcttctttgc caagaccttt   2280
caaagccatt ttaggctgtt aggggcagtg gaggtagaat gactccttgg gtattagagt   2340
ttcaaccatg aagtctctaa caatgtattt tcttcacctc tgctactcaa gtagcattta   2400 ctgtgtctttt ggtttgtgct aggccccgg gtgtgaagca cagacccctt ccaggggttt   2460
acagtctatt tgagactcct cagttcttgc cactttttt tttaatctcc accagtcatt   2520
tttcagacct tttaactcct caattccaac actgatttcc ccttttgcat tctccctcct   2580
tcccttcctt gtagccttt gactttcatt ggaaattagg atgtaaatct gctcaggaga   2640
cctggaggag cagaggataa ttagcatctc aggttaagtg tgagtaatct gagaaacaat   2700
gactaattct tgcatatttt gtaacttcca tgtgagggtt ttcagcattg atatttgtgc   2760
attttctaaa cagagatgag gtggtatctt cacgtagaac attggtattc gcttgagaaa   2820
aaaagaatag ttgaacctat ttctctttct ttacaagatg ggtccaggat tcctctttc    2880 tctgccataa atgattaatt aaatagcttt tgtgtcttac attggtagcc agccagccaa   2940
```

-continued

```
ggctctgttt atgcttttgg ggggcatata ttgggttcca ttctcaccta tccacacaac    3000
atatccgtat atatcccctc tactcttact tcccccaaat ttaaagaagt atgggaaatg    3060
agaggcattt cccccacccc atttctctcc tcacacacag actcatatta ctggtaggaa    3120
cttgagaact ttatttccaa gttgttcaaa catttaccaa tcatattaat acaatgatgc    3180
tatttgcaat tcctgctcct aggggagggg agataagaaa ccctcactct ctacaggttt    3240
gggtacaagt ggcaacctgc ttccatggcc gtgtagaagc atggtgccct ggcttctctg    3300
aggaagctgg ggttcatgac aatggcagat gtaaagttat tcttgaagtc agattgaggc    3360
tgggagacag ccgtagtaga tgttctactt tgttctgctg ttctctagaa agaatatttg    3420
gttttcctgt ataggaatga gattaattcc tttccaggta ttttataatt ctgggaagca    3480
aaacccatgc ctccccctag ccattttttac tgttatccta tttagatggc catgaagagg    3540
atgctgtgaa attcccaaca acattgatg ctgacagtca tgcagtctgg gagtggggaa    3600
gtgatctttt gttcccatcc tcttctttta gcagtaaaat agctgaggga aaagggaggg    3660
aaaaggaagt tatgggaata cctgtggtgg ttgtgatccc taggtcttgg gagctcttgg    3720
aggtgtctgt atcagtggat ttcccatccc ctgtgggaaa ttagtaggct catttactgt    3780
tttaggtcta gcctatgtgg attttttcct aacataccta agcaaaccca gtgtcaggat    3840
ggtaattctt attctttcgt tcagttaagt ttttcccttc atctgggcac tgaagggata    3900
tgtgaaacaa tgttaacatt tttggtagtc ttcaaccagg gattgtttct gtttaacttc    3960
ttataggaaa gcttgagtaa aataaatatt gtcttttttgt atgtca               4006
```

<210> SEQ ID NO 23
<211> LENGTH: 380
<212> TYPE: PRT
<213> ORGANISM: Homo sapiens
<220> FEATURE:
<221> NAME/KEY: SIGNAL
<222> LOCATION: (1)..(26)
<220> FEATURE:
<221> NAME/KEY: mat_peptide
<222> LOCATION: (27)..(380)

<400> SEQUENCE: 23

```
Met Ala Phe Val Cys Leu Ala Ile Gly Cys Leu Tyr Thr Phe Leu Ile
    -25                 -20                 -15

Ser Thr Thr Phe Gly Cys Thr Ser Ser Ser Asp Thr Glu Ile Lys Val
-10                  -5                  -1   1               5

Asn Pro Pro Gln Asp Phe Glu Ile Val Asp Pro Gly Tyr Leu Gly Tyr
                 10                  15                  20

Leu Tyr Leu Gln Trp Gln Pro Pro Leu Ser Leu Asp His Phe Lys Glu
         25                  30                  35

Cys Thr Val Glu Tyr Glu Leu Lys Tyr Arg Asn Ile Gly Ser Glu Thr
     40                  45                  50

Trp Lys Thr Ile Ile Thr Lys Asn Leu His Tyr Lys Asp Gly Phe Asp
 55                  60                  65                  70

Leu Asn Lys Gly Ile Glu Ala Lys Ile His Thr Leu Leu Pro Trp Gln
                 75                  80                  85

Cys Thr Asn Gly Ser Glu Val Gln Ser Ser Trp Ala Glu Thr Thr Tyr
         90                  95                  100

Trp Ile Ser Pro Gln Gly Ile Pro Glu Thr Lys Val Gln Asp Met Asp
     105                 110                 115

Cys Val Tyr Tyr Asn Trp Gln Tyr Leu Leu Cys Ser Trp Lys Pro Gly
 120                 125                 130
```

Ile Gly Val Leu Leu Asp Thr Asn Tyr Asn Leu Phe Tyr Trp Tyr Glu
135                 140                 145                 150

Gly Leu Asp His Ala Leu Gln Cys Val Asp Tyr Ile Lys Ala Asp Gly
            155                 160                 165

Gln Asn Ile Gly Cys Arg Phe Pro Tyr Leu Glu Ala Ser Asp Tyr Lys
            170                 175                 180

Asp Phe Tyr Ile Cys Val Asn Gly Ser Ser Glu Asn Lys Pro Ile Arg
            185                 190                 195

Ser Ser Tyr Phe Thr Phe Gln Leu Gln Asn Ile Val Lys Pro Leu Pro
200                 205                 210

Pro Val Tyr Leu Thr Phe Thr Arg Glu Ser Ser Cys Glu Ile Lys Leu
215                 220                 225                 230

Lys Trp Ser Ile Pro Leu Gly Pro Ile Pro Ala Arg Cys Phe Asp Tyr
                235                 240                 245

Glu Ile Glu Ile Arg Glu Asp Asp Thr Thr Leu Val Thr Ala Thr Val
                250                 255                 260

Glu Asn Glu Thr Tyr Thr Leu Lys Thr Thr Asn Glu Thr Arg Gln Leu
            265                 270                 275

Cys Phe Val Val Arg Ser Lys Val Asn Ile Tyr Cys Ser Asp Asp Gly
280                 285                 290

Ile Trp Ser Glu Trp Ser Asp Lys Gln Cys Trp Glu Gly Glu Asp Leu
295                 300                 305                 310

Ser Lys Lys Thr Leu Leu Arg Phe Trp Leu Pro Gly Phe Ile Leu
            315                 320                 325

Ile Leu Val Ile Phe Val Thr Gly Leu Leu Leu Arg Lys Pro Asn Thr
            330                 335                 340

Tyr Pro Lys Met Ile Pro Glu Phe Phe Cys Asp Thr
            345                 350

<210> SEQ ID NO 24
<211> LENGTH: 1376
<212> TYPE: DNA
<213> ORGANISM: Homo sapiens

<400> SEQUENCE: 24
gtaagaacac tctcgtgagt ctaacggtct tccggatgaa ggctatttga agtcgccata      60
acctggtcag aagtgtgcct gtcggcgggg agagaggcaa tatcaaggtt ttaaatctcg     120
gagaaatggc tttcgtttgc ttggctatcg gatgcttata tacctttctg ataagcacaa     180
catttggctg tacttcatct tcagacaccg agataaaagt taaccctcct caggattttg     240
agatagtgga tcccggatac ttaggttatc tctatttgca atggcaaccc ccactgtctc     300
tggatcattt taaggaatgc acagtggaat atgaactaaa ataccgaaac attggtagtg     360
aaacatggaa gaccatcatt actaagaatc tacattacaa agatgggttt gatcttaaca     420
agggcattga agcgaagata cacacgcttt taccatggca atgcacaaat ggatcagaag     480
ttcaaagttc ctgggcagaa actacttatt ggatatcacc acaaggaatt ccagaaacta     540
aagttcagga tatggattgc gtatattaca attggcaata tttactctgt tcttggaaac     600
ctggcatagg tgtacttctt gataccaatt acaacttgtt ttactggtat gagggcttgg     660
atcatgcatt acagtgtgtt gattacatca aggctgatgg acaaaatata ggatgcagat     720
ttccctattt ggaggcatca gactataaag atttctatat ttgtgttaat ggatcatcag     780
agaacaagcc tatcagatcc agttatttca cttttcagct tcaaaatata gttaaacctt     840

-continued

```
tgccgccagt ctatcttact tttactcggg agagttcatg tgaaattaag ctgaaatgga    900
gcatacctttt gggacctatt ccagcaaggt gttttgatta tgaaattgag atcagagaag    960
atgatactac cttggtgact gctacagttg aaaatgaaac atacaccttg aaaacaacaa   1020
atgaaacccg acaattatgc tttgtagtaa gaagcaaagt gaatatttat tgctcagatg   1080
acggaatttg gagtgagtgg agtgataaac aatgctggga aggtgaagac ctatcgaaga   1140
aaactttgct acgtttctgg ctaccatttg gtttcatctt aatattagtt atatttgtaa   1200
ccggtctgct tttgcgtaag ccaaacacct acccaaaaat gattccagaa tttttctgtg   1260
atacatgaag actttccata tcaagagaca tggtattgac tcaacagttt ccagtcatgg   1320
ccaaatgttc aatatgagtc tcaataaact gaatttttct tgcgaatgtt gaaaaa       1376
```

<210> SEQ ID NO 25
<211> LENGTH: 479
<212> TYPE: PRT
<213> ORGANISM: Artificial Sequence
<220> FEATURE:
<223> OTHER INFORMATION: Synthetic Polypeptide

<400> SEQUENCE: 25

```
Met Glu Thr Asp Thr Leu Leu Leu Trp Val Leu Leu Leu Trp Val Pro
  1               5                  10                  15

Gly Ser Thr Gly Asp Ala Ala Gln Pro Ala Gln Val Gln Leu Gln Gln
             20                  25                  30

Pro Gly Ala Glu Leu Val Arg Pro Gly Ala Ser Val Lys Leu Ser Cys
         35                  40                  45

Lys Ala Ser Gly Tyr Thr Phe Ser Asn Tyr Leu Met Asn Trp Val Lys
     50                  55                  60

Gln Arg Pro Glu Gln Asp Leu Asp Trp Ile Gly Arg Ile Asp Pro Tyr
 65                  70                  75                  80

Asp Gly Asp Ile Asp Tyr Asn Gln Asn Phe Lys Asp Lys Ala Ile Leu
                 85                  90                  95

Thr Val Asp Lys Ser Ser Ser Thr Ala Tyr Met Gln Leu Ser Ser Leu
            100                 105                 110

Thr Ser Glu Asp Ser Ala Val Tyr Tyr Cys Ala Arg Gly Tyr Gly Thr
        115                 120                 125

Ala Tyr Gly Val Asp Tyr Trp Gly Gln Gly Thr Ser Val Thr Val Ser
    130                 135                 140

Ser Ala Lys Thr Thr Pro Pro Lys Leu Glu Glu Gly Glu Phe Ser Glu
145                 150                 155                 160

Ala Arg Val Asp Ile Val Leu Thr Gln Ser Pro Ala Ser Leu Ala Val
                165                 170                 175

Ser Leu Gly Gln Arg Ala Thr Ile Ser Cys Arg Ala Ser Glu Ser Val
            180                 185                 190

Asp Asn Tyr Gly Ile Ser Phe Met Asn Trp Phe Gln Gln Lys Pro Gly
        195                 200                 205

Gln Pro Pro Lys Leu Leu Ile Tyr Ala Ala Ser Arg Gln Gly Ser Gly
    210                 215                 220

Val Pro Ala Arg Phe Ser Gly Ser Gly Ser Gly Thr Asp Phe Ser Leu
225                 230                 235                 240

Asn Ile His Pro Met Glu Glu Asp Asp Thr Ala Met Tyr Phe Cys Gln
                245                 250                 255

Gln Ser Lys Glu Val Pro Trp Thr Phe Gly Gly Gly Thr Lys Leu Glu
            260                 265                 270
```

Ile Lys Ala Ala Ala Gly Gly Gly Ser Gly Gly Gly Ser Gly
            275                 280                 285

Gly Gly Gly Ser Thr Ser Glu Glu Thr Ile Ser Thr Val Gln Glu Lys
    290                 295                 300

Gln Gln Asn Ile Ser Pro Leu Val Arg Glu Arg Gly Pro Gln Arg Val
305                 310                 315                 320

Ala Ala His Ile Thr Gly Thr Arg Gly Arg Ser Asn Thr Leu Ser Ser
                325                 330                 335

Pro Asn Ser Lys Asn Glu Lys Ala Leu Gly Arg Lys Ile Asn Ser Trp
            340                 345                 350

Glu Ser Ser Arg Ser Gly His Ser Phe Leu Ser Asn Leu His Leu Arg
        355                 360                 365

Asn Gly Glu Leu Val Ile His Glu Lys Gly Phe Tyr Tyr Ile Tyr Ser
    370                 375                 380

Gln Thr Tyr Phe Arg Phe Gln Glu Glu Ile Lys Glu Asn Thr Lys Asn
385                 390                 395                 400

Asp Lys Gln Met Val Gln Tyr Ile Tyr Lys Tyr Thr Ser Tyr Pro Asp
                405                 410                 415

Pro Ile Leu Leu Met Lys Ser Ala Arg Asn Ser Cys Trp Ser Lys Asp
            420                 425                 430

Ala Glu Tyr Gly Leu Tyr Ser Ile Tyr Gln Gly Gly Ile Phe Glu Leu
        435                 440                 445

Lys Glu Asn Asp Arg Ile Phe Val Ser Val Thr Asn Glu His Leu Ile
    450                 455                 460

Asp Met Asp His Glu Ala Ser Phe Phe Gly Ala Phe Leu Val Gly
465                 470                 475

<210> SEQ ID NO 26
<211> LENGTH: 1440
<212> TYPE: DNA
<213> ORGANISM: Artificial Sequence
<220> FEATURE:
<223> OTHER INFORMATION: Synthetic Polynucleotide

<400> SEQUENCE: 26
atggagacag acacactcct gctatgggta ctgctgctct gggttccagg ttccactggt      60
gacgcggccc agccggccca ggtccaactg cagcagcctg ggctgagct ggtgaggcct      120 gggcttcag tgaagctgtc ctgcaaggct tctggctaca cgttctccaa ctacttgatg      180
aactgggtta agcagaggcc tgagcaagac cttgactgga ttggaaggat tgatccttac      240
gatggtgaca ttgactacaa tcaaaacttc aaggacaagg ccatattgac tgtagacaaa      300
tcctccagca cagcctacat gcaactcagc agcctgacat ctgaggactc tgcggtctat      360
tactgtgcaa gaggttatgg cacggcctat ggtgtggact actggggtca aggaaccctca     420 gtcaccgtct cctcagccaa aacgacaccc ccaaagcttg aagaaggtga attttcagaa      480
gcacgcgtag atattgtgct aactcagtct ccagcttctt ggctgtgtc tctaggacag      540 agggccacca tctcctgcag agccagcgaa agtgttgata ttatggcat agtttttatg      600 aactggttcc aacagaaacc aggacagcca cccaaactcc tcatctatgc tgcatccagg      660
caaggatccg gggtccctgc caggtttagt ggcagtggg ctgggacaga cttcagcctc      720
aacatccatc ctatggagga ggatgatact gcaatgtatt tctgtcagca aagtaaggag      780
gttccgtgga cgttcggtgg aggcaccaag ctggaaatca aagcggccgc tggcggaggc      840
ggttcgggcg gaggtggctc tggcggtggc ggatcaacct ctgaggaaac catttctaca      900

```
gttcaagaaa agcaacaaaa tatttctccc ctagtgagag aaagaggtcc tcagagagta   960
gcagctcaca taactgggac cagaggaaga agcaacacat tgtcttctcc aaactccaag  1020
aatgaaaagg ctctgggccg caaaataaac tcctgggaat catcaaggag tgggcattca  1080
ttcctgagca acttgcactt gaggaatggt gaactggtca tccatgaaaa agggttttac  1140
tacatctatt cccaaacata ctttcgattt caggaggaaa taaagaaaaa cacaaagaac  1200
gacaaacaaa tggtccaata tatttacaaa tacacaagtt atcctgaccc tatattgttg  1260
atgaaaagtg ctagaaatag ttgttggtct aaagatgcag aatatggact ctattccatc  1320
tatcaagggg gaatatttga gcttaaggaa aatgacagaa ttttttgtttc tgtaacaaat  1380 gagcacttga tagacatgga ccatgaagcc agttttttcg gggcctttt agttggctaa  1440
```

<210> SEQ ID NO 27
<211> LENGTH: 187
<212> TYPE: PRT
<213> ORGANISM: Artificial Sequence
<220> FEATURE:
<223> OTHER INFORMATION: Synthetic Polypeptide

<400> SEQUENCE: 27

Thr Ser Glu Glu Thr Ile Ser Thr Val Gln Glu Lys Gln Gln Asn Ile
1               5                   10                  15

Ser Pro Leu Val Arg Glu Arg Gly Pro Gln Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
    50                  55                  60

Ser Gly His Ser Phe Leu Ser Asn Leu His Leu Arg Asn Gly Glu Leu
65                  70                  75                  80

Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
        115                 120                 125

Met Lys Ser Ala Arg Asn Ser Cys Trp Ser Lys Asp Ala Glu Tyr Gly
    130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly
            180                 185

<210> SEQ ID NO 28
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 28

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
                35                  40                  45

Gln Asn Gly Val Leu Asn Ser Trp Thr Asp Gln Asp Ser Lys Asp Ser
         50                  55                  60

Thr Tyr Ser Met Ser Ser Thr Leu Thr Leu Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
                100                 105

<210> SEQ ID NO 29
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 29
cgggctgatg ctgcaccaac tgtatccatc ttcccaccat ccagtgagca gttaacatct     60
ggaggtgcct cagtcgtgtg cttcttgaac aacttctacc ccaaagacat caatgtcaag    120
tggaagattg atggcagtga acgacaaaat ggcgtcctga acagttggac tgatcaggac    180
agcaaagaca gcacctacag catgagcagc accctcacgt tgaccaagga cgagtatgaa    240
cgacataaca gctatacctg tgaggccact cacaagacat caacttcacc cattgtcaag    300
agcttcaaca ggaatgagtg ttag                                           324

<210> SEQ ID NO 30
<211> LENGTH: 324
<212> TYPE: PRT
<213> ORGANISM: Artificial Sequence
<220> FEATURE:
<223> OTHER INFORMATION: Synthetic Polypeptide

<400> SEQUENCE: 30

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
                35                  40                  45

Gly Val His Thr Phe Pro Ala Val Leu Gln Ser Asp Leu Tyr Thr Leu
         50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
                115                 120                 125

Thr Ile Thr Leu Thr Pro Lys Val Thr Cys Val Val Val Asp Ile Ser
         130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr

```
                165                 170                 175
Phe Arg Ser Val Ser Glu Leu Pro Ile Met His Gln Asp Trp Leu Asn
            180                 185                 190
Gly Lys Glu Phe Lys Cys Arg Val Asn Ser Ala Ala Phe Pro Ala Pro
        195                 200                 205
Ile Glu Lys Thr Ile Ser Lys Thr Lys Gly Arg Pro Lys Ala Pro Gln
    210                 215                 220
Val Tyr Thr Ile Pro Pro Pro Lys Glu Gln Met Ala Lys Asp Lys Val
225                 230                 235                 240
Ser Leu Thr Cys Met Ile Thr Asp Phe Phe Pro Glu Asp Ile Thr Val
                245                 250                 255
Glu Trp Gln Trp Asn Gly Gln Pro Ala Glu Asn Tyr Lys Asn Thr Gln
            260                 265                 270
Pro Ile Met Asp Thr Asp Gly Ser Tyr Phe Val Tyr Ser Lys Leu Asn
        275                 280                 285
Val Gln Lys Ser Asn Trp Glu Ala Gly Asn Thr Phe Thr Cys Ser Val
    290                 295                 300
Leu His Glu Gly Leu His Asn His His Thr Glu Lys Ser Leu Ser His
305                 310                 315                 320
Ser Pro Gly Lys
```

<210> SEQ ID NO 31
<211> LENGTH: 975
<212> TYPE: DNA
<213> ORGANISM: Artificial Sequence
<220> FEATURE:
<223> OTHER INFORMATION: Synthetic Polynucleotide

<400> SEQUENCE: 31

```
gccaaaacga caccccatc tgtctatcca ctggcccctg gatctgctgc ccaaactaac     60
tccatggtga ccctgggatg cctggtcaag ggctatttcc ctgagccagt gacagtgacc    120
tggaactctg gatccctgtc cagcggtgtg cacaccttcc cagctgtcct gcagtctgac    180
ctctacactc tgagcagctc agtgactgtc ccctccagca cctggcccag cgagaccgtc    240
acctgcaacg ttgcccaccc ggccagcagc accaaggtgg acaagaaaat tgtgcccagg    300
gattgtggtt gtaagccttg catatgtaca gtcccagaag tatcatctgt cttcatcttc    360
cccccaaagc ccaaggatgt gctcaccatt actctgactc taaggtcac gtgtgttgtg    420
gtagacatca gcaaggatga tcccgaggtc cagttcagct ggtttgtaga tgatgtggag    480
gtgcacacag ctcagacgca accccgggag gagcagttca acagcacttt ccgctcagtc    540
agtgaacttc ccatcatgca ccaggactgg ctcaatggca aggagttcaa atgcagggtc    600
aacagtgcag ctttccctgc ccccatcgag aaaaccatct ccaaaaccaa aggcagaccg    660
aaggctccac aggtgtacac cattccacct cccaaggagc agatgccaa ggataaagtc     720
agtctgacct gcatgataac agacttcttc cctgaagaca ttactgtgga gtggcagtgg    780
aatgggcagc cagcggagaa ctacaagaac actcagccca tcatggacac agatggctct    840
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aatga                                                    975
```

<210> SEQ ID NO 32
<211> LENGTH: 19
<212> TYPE: PRT

<213> ORGANISM: Artificial Sequence
<220> FEATURE:
<223> OTHER INFORMATION: Synthetic Polypeptide

<400> SEQUENCE: 32

Met Asp Trp Ile Trp Arg Ile Leu Phe Leu Val Gly Ala Ala Thr Gly
1               5                   10                  15

Ala His Ser

<210> SEQ ID NO 33
<211> LENGTH: 267
<212> TYPE: PRT
<213> ORGANISM: Artificial Sequence
<220> FEATURE:
<223> OTHER INFORMATION: Synthetic Polypeptide

<400> SEQUENCE: 33

Met Asp Trp Ile Trp Arg Ile Leu Phe Leu Val Gly Ala Ala Thr Gly
1               5                   10                  15

Ala His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Ser Asn Tyr Leu Met Asn Trp Val Lys Gln Arg Pro Glu Gln Asp Leu
    50                  55                  60

Asp Trp Ile Gly Arg Ile Asp Pro Tyr Asp Gly Asp Ile Asp Tyr Asn
65                  70                  75                  80

Gln Asn Phe Lys Asp Lys Ala Ile Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Ser Val Thr Val Ser Ser Ala Lys Thr Thr Pro Pro
130                 135                 140

Lys Leu Glu Glu Gly Glu Phe Ser Glu Ala Arg Val Asp Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Glu Ser Val Asp Asn Tyr Gly Ile Ser Phe
            180                 185                 190

Met Asn Trp Phe Gln Gln Lys Pro Gly Gln Pro Pro Lys Leu Leu Ile
        195                 200                 205

Tyr Ala Ala Ser Arg Gln Gly Ser Gly Val Pro Ala Arg Phe Ser Gly
    210                 215                 220

Ser Gly Ser Gly Thr Asp Phe Ser Leu Asn Ile His Pro Met Glu Glu
225                 230                 235                 240

Asp Asp Thr Ala Met Tyr Phe Cys Gln Gln Ser Lys Glu Val Pro Trp
                245                 250                 255

Thr Phe Gly Gly Gly Thr Lys Leu Glu Ile Lys
            260                 265

<210> SEQ ID NO 34
<211> LENGTH: 801
<212> TYPE: DNA
<213> ORGANISM: Artificial Sequence
<220> FEATURE:
<223> OTHER INFORMATION: Synthetic Polynucleotide

<400> SEQUENCE: 34

```
atggactgga tctggcgcat cctgtttctc gtgggagccg ccacaggcgc ccattctcag    60
gtgcagctgc agcagcctgg cgctgaactc gtgcggccag gcgcttctgt gaagctgagc   120
tgtaaagcca gcggctacac cttcagcaac tacctgatga ctgggtcaa gcagcggccc    180
gagcaggacc tggattggat cggcagaatc gaccccacg acggcgacat cgactacaac    240
cagaacttca aggacaaggc catcctgacc gtggacaaga gcagcagcac cgcctacatg    300
cagctgtcca gcctgaccag cgaggacagc gccgtgtact actgcgccag aggctacggc    360
acagcctacg gcgtggacta ttggggccag ggcacaagcg tgaccgtgtc cagcgccaag    420
accaccccc ctaagctgga gagggcgag ttctccgagg cccggggtgga cattgtgctg    480
acacagtctc cagccagcct ggccgtgtcc ctgggacaga gagccaccat cagctgtagg    540
gccagcgaga gcgtggacaa ctacggcatc agcttcatga attggttcca gcagaagccc    600
ggccagcccc ccaagctgct gatctatgcc gccagcagac agggcagcgg agtgcctgcc    660
agattttctg gcagcggctc cggcaccgac ttcagcctga acatccaccc tatggaagag    720
gacgacaccg ccatgtactt ttgccagcag agcaagagg tgccctggac ctttggcgga    780
ggcaccaagc tggaaatcaa g                                              801
```

<210> SEQ ID NO 35
<211> LENGTH: 236
<212> TYPE: PRT
<213> ORGANISM: Artificial Sequence
<220> FEATURE:
<223> OTHER INFORMATION: Synthetic Polypeptide

<400> SEQUENCE: 35

```
Asp Pro Ala Glu Pro Lys Ser Pro Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205
```

Asn Val Phe Ser Cys Ser Val Met His Glu Ala Leu His Asn His Tyr
    210                 215                 220

Thr Gln Lys Ser Leu Ser Leu Ser Pro Gly Lys Lys
225                 230                 235

<210> SEQ ID NO 36
<211> LENGTH: 708
<212> TYPE: DNA
<213> ORGANISM: Artificial Sequence
<220> FEATURE:
<223> OTHER INFORMATION: Synthetic Polynucleotide

<400> SEQUENCE: 36
gatcccgccg agcccaaatc tcctgacaaa actcacacat gcccaccgtg cccagcacct      60
gaactcctgg gggaccgtc agtcttcctc ttccccccaa acccaagga caccctcatg      120 atctcccgga cccctgaggt cacatgcgtg gtggtggacg tgagccacga agaccctgag      180
gtcaagttca actggtacgt ggacggcgtg gaggtgcata atgccaagac aaagccgcgg      240
gaggagcagt acaacagcac gtaccgtgtg gtcagcgtcc tcaccgtcct gcaccaggac      300
tggctgaatg gcaaggagta caagtgcaag gtctccaaca aagccctccc agcccccatc      360
gagaaaacca tctccaaagc caaagggcag ccccgagaac cacaggtgta caccctgccc      420
ccatcccggg atgagctgac caagaaccag gtcagcctga cctgcctggt caaaggcttc      480
tatcccagcg acatcgccgt ggagtgggag agcaatgggc aaccggagaa caactacaag      540
accacgcctc ccgtgctgga ctccgacggc tccttcttcc tctacagcaa gctcaccgtg      600
gacaagagca ggtggcagca ggggaacgtc ttctcatgct ccgtgatgca tgaggctctg      660
cacaaccact acacgcagaa gagcctctcc ctgtctccgg gtaaaaaa                  708

<210> SEQ ID NO 37
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 37

Asp Leu Glu Pro Lys Ser Cys Asp Lys Thr His Thr Cys Pro Pro Cys
1               5                   10                  15

Pro

<210> SEQ ID NO 38
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 38
gatctcgagc ccaaatcttg tgacaaaact cacacatgcc caccgtgccc g              51

<210> SEQ ID NO 39
<211> LENGTH: 68
<212> TYPE: PRT
<213> ORGANISM: Artificial Sequenc
<220> FEATURE:
<223> OTHER INFORMATION: Synthetic Polypeptide

<400> SEQUENCE: 39

Phe Trp Val Leu Val Val Val Gly Gly Val Leu Ala Cys Tyr Ser Leu

```
                1               5                  10                 15
Leu Val Thr Val Ala Phe Ile Ile Phe Trp Val Arg Ser Lys Arg Ser
                20                 25                 30

Arg Leu Leu His Ser Asp Tyr Met Asn Met Thr Pro Arg Arg Pro Gly
        35                 40                 45

Pro Thr Arg Lys His Tyr Gln Pro Tyr Ala Pro Arg Asp Phe Ala
    50                 55                 60

Ala Tyr Arg Ser
65

<210> SEQ ID NO 40
<211> LENGTH: 204
<212> TYPE: DNA
<213> ORGANISM: Artificial Sequence
<220> FEATURE:
<223> OTHER INFORMATION: Synthetic Polynucleotide

<400> SEQUENCE: 40
ttttgggtgc tggtggtggt tggtggagtc ctggcttgct atagcttgct agtaacagtg      60
gcctttatta ttttctgggt gaggagtaag aggagcaggc tcctgcacag tgactacatg     120
aacatgactc cccgccgccc cgggcccacc cgcaagcatt accagcccta tgccccacca     180
cgcgacttcg cagcctatcg ctcc                                            204

<210> SEQ ID NO 41
<211> LENGTH: 112
<212> TYPE: PRT
<213> ORGANISM: Artificial Sequenc
<220> FEATURE:
<223> OTHER INFORMATION: Synthetic Polypeptide

<400> SEQUENCE: 41

Arg Val Lys Phe Ser Arg Ser Ala Asp Ala Pro Ala Tyr Gln Gln Gly
1               5                  10                 15

Gln Asn Gln Leu Tyr Asn Glu Leu Asn Leu Gly Arg Arg Glu Glu Tyr
            20                 25                 30

Asp Val Leu Asp Lys Arg Arg Gly Arg Asp Pro Glu Met Gly Gly Lys
        35                 40                 45

Pro Arg Arg Lys Asn Pro Gln Glu Gly Leu Tyr Asn Glu Leu Gln Lys
    50                 55                 60

Asp Lys Met Ala Glu Ala Tyr Ser Glu Ile Gly Met Lys Gly Glu Arg
65                  70                 75                 80

Arg Arg Gly Lys Gly His Asp Gly Leu Tyr Gln Gly Leu Ser Thr Ala
                85                 90                 95

Thr Lys Asp Thr Tyr Asp Ala Leu His Met Gln Ala Leu Pro Pro Arg
            100                105                110

<210> SEQ ID NO 42
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 42
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
```

```
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgc                              336
```

```
<210> SEQ ID NO 43
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 43

Phe Trp Val Leu Val Val Val Gly Gly Val Leu Ala Cys Tyr Ser Leu
1               5                   10                  15

Leu
```

```
<210> SEQ ID NO 44
<211> LENGTH: 105
<212> TYPE: DNA
<213> ORGANISM: Artificial Sequence
<220> FEATURE:
<223> OTHER INFORMATION: Synthetic Polynucleotide

<400> SEQUENCE: 44
ttttgggtgc tggtggtggt tgtggagtc ctggcttgct atagcttgct agtaacagtg    60
gcctttatta ttttctgggt gaggagtaag aggagcaggc cctg                    105
```

```
<210> SEQ ID NO 45
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 45

Phe Trp Val Leu Val Val Val Gly Gly Val Leu Ala Cys Tyr Ser Leu
1               5                   10                  15

Leu Val Thr Val Ala Phe Ile Ile
            20
```

```
<210> SEQ ID NO 46
<211> LENGTH: 105
<212> TYPE: DNA
<213> ORGANISM: Artificial Sequence
<220> FEATURE:
<223> OTHER INFORMATION: Synthetic Polynucleotide

<400> SEQUENCE: 46
ttttgggtgc tggtggtggt tgtggagtc ctggcttgct atagcttgct agtaacagtg    60
gcctttatta ttttctgggt gaggagtaag aggagcaggc cctg                    105
```

```
<210> SEQ ID NO 47
<211> LENGTH: 180
<212> TYPE: PRT
<213> ORGANISM: Artificial Sequence
<220> FEATURE:
<223> OTHER INFORMATION: Synthetic Polypeptide

<400> SEQUENCE: 47

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
```

```
                    20                  25                  30
Arg Leu Leu His Ser Asp Tyr Met Asn Met Thr Pro Arg Arg Pro Gly
                35                  40                  45

Pro Thr Arg Lys His Tyr Gln Pro Tyr Ala Pro Pro Arg Asp Phe Ala
             50                  55                  60

Ala Tyr Arg Ser Arg Val Lys Phe Ser Arg Ser Ala Asp Ala Pro Ala
 65                  70                  75                  80

Tyr Gln Gln Gly Gln Asn Gln Leu Tyr Asn Glu Leu Asn Leu Gly Arg
                 85                  90                  95

Arg Glu Glu Tyr Asp Val Leu Asp Lys Arg Arg Gly Arg Asp Pro Glu
            100                 105                 110

Met Gly Gly Lys Pro Arg Arg Lys Asn Pro Gln Glu Gly Leu Tyr Asn
            115                 120                 125

Glu Leu Gln Lys Asp Lys Met Ala Glu Ala Tyr Ser Glu Ile Gly Met
        130                 135                 140

Lys Gly Glu Arg Arg Arg Gly Lys Gly His Asp Gly Leu Tyr Gln Gly
145                 150                 155                 160

Leu Ser Thr Ala Thr Lys Asp Thr Tyr Asp Ala Leu His Met Gln Ala
                165                 170                 175

Leu Pro Pro Arg
            180

<210> SEQ ID NO 48
<211> LENGTH: 540
<212> TYPE: DNA
<213> ORGANISM: Artificial Sequence
<220> FEATURE:
<223> OTHER INFORMATION: Synthetic Polynucleotide

<400> SEQUENCE: 48
ttttgggtgc tggtggtggt tggtggagtc ctggcttgct atagcttgct agtaacagtg      60
gcctttatta ttttctgggt gaggagtaag aggagcaggc tcctgcacag tgactacatg     120
aacatgactc cccgccgccc cgggcccacc cgcaagcatt accagcccta tgccccacca     180
cgcgacttcg cagcctatcg ctccagagtg aagttcagca ggagcgcaga cgcccccgcg     240
taccagcagg gccagaacca gctctataac gagctcaatc taggacgaag agaggagtac     300
gatgttttgg acaagagacg tggccgggac cctgagatgg ggggaaagcc gagaaggaag     360
aaccctcagg aaggcctgta caatgaactg cagaaagata agatggcgga ggcctacagt     420
gagattggga tgaaaggcga gcgccggagg ggcaagggc acgatggcct ttaccagggt     480
ctcagtacag ccaccaagga cacctacgac gcccttcaca tgcaggccct gccccctcgc     540

<210> SEQ ID NO 49
<211> LENGTH: 419
<212> TYPE: PRT
<213> ORGANISM: Artificial Sequence
<220> FEATURE:
<223> OTHER INFORMATION: Synthetic Polypeptide

<400> SEQUENCE: 49

Asp Pro Ala Glu Pro Lys Ser Pro Asp Lys Thr His Thr Cys Pro Pro
 1               5                  10                  15

Cys Pro Ala Pro Glu Leu Leu Gly Gly Pro Ser Val Phe Leu Phe Pro
                20                  25                  30

Pro Lys Pro Lys Asp Thr Leu Met Ile Ser Arg Thr Pro Glu Val Thr
            35                  40                  45
```

```
Cys Val Val Asp Val Ser His Glu Asp Pro Glu Val Lys Phe Asn
     50              55                  60

Trp Tyr Val Asp Gly Val Glu Val His Asn Ala Lys Thr Lys Pro Arg
65               70                  75                  80

Glu Glu Gln Tyr Asn Ser Thr Tyr Arg Val Val Ser Val Leu Thr Val
                 85                  90                  95

Leu His Gln Asp Trp Leu Asn Gly Lys Glu Tyr Lys Cys Lys Val Ser
             100                 105                 110

Asn Lys Ala Leu Pro Ala Pro Ile Glu Lys Thr Ile Ser Lys Ala Lys
             115                 120                 125

Gly Gln Pro Arg Glu Pro Gln Val Tyr Thr Leu Pro Pro Ser Arg Asp
130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                 165                 170                 175

Asn Asn Tyr Lys Thr Thr Pro Pro Val Leu Asp Ser Asp Gly Ser Phe
             180                 185                 190

Phe Leu Tyr Ser Lys Leu Thr Val Asp Lys Ser Arg Trp Gln Gln Gly
             195                 200                 205

Asn Val Phe Ser Cys Ser Val Met His Glu Ala Leu His Asn His Tyr
210                 215                 220

Thr Gln Lys Ser Leu Ser Leu Ser Pro Gly Lys Lys Asp Pro Lys Phe
225                 230                 235                 240

Trp Val Leu Val Val Val Gly Gly Val Leu Ala Cys Tyr Ser Leu Leu
                 245                 250                 255

Val Thr Val Ala Phe Ile Ile Phe Trp Val Arg Ser Lys Arg Ser Arg
             260                 265                 270

Leu Leu His Ser Asp Tyr Met Asn Met Thr Pro Arg Arg Pro Gly Pro
             275                 280                 285

Thr Arg Lys His Tyr Gln Pro Tyr Ala Pro Pro Arg Asp Phe Ala Ala
             290                 295                 300

Tyr Arg Ser Arg Val Lys Phe Ser Arg Ser Ala Asp Ala Pro Ala Tyr
305                 310                 315                 320

Gln Gln Gly Gln Asn Gln Leu Tyr Asn Glu Leu Asn Leu Gly Arg Arg
                 325                 330                 335

Glu Glu Tyr Asp Val Leu Asp Lys Arg Arg Gly Arg Asp Pro Glu Met
             340                 345                 350

Gly Gly Lys Pro Arg Arg Lys Asn Pro Gln Glu Gly Leu Tyr Asn Glu
             355                 360                 365

Leu Gln Lys Asp Lys Met Ala Glu Ala Tyr Ser Glu Ile Gly Met Lys
370                 375                 380

Gly Glu Arg Arg Arg Gly Lys Gly His Asp Gly Leu Tyr Gln Gly Leu
385                 390                 395                 400

Ser Thr Ala Thr Lys Asp Thr Tyr Asp Ala Leu His Met Gln Ala Leu
             405                 410                 415

Pro Pro Arg
```

<210> SEQ ID NO 50
<211> LENGTH: 1257
<212> TYPE: DNA
<213> ORGANISM: Artificial Sequence
<220> FEATURE:
<223> OTHER INFORMATION: Synthetic Polynucleotide

<400> SEQUENCE: 50

```
gatcccgccg agcccaaatc tcctgacaaa actcacacat gcccaccgtg cccagcacct    60
gaactcctgg ggggaccgtc agtcttcctc ttccccccaa acccaagga caccctcatg   120
atctcccgga cccctgaggt cacatgcgtg gtggtggacg tgagccacga agaccctgag   180
gtcaagttca actggtacgt ggacggcgtg gaggtgcata atgccaagac aaagccgcgg   240
gaggagcagt acaacagcac gtaccgtgtg gtcagcgtcc tcaccgtcct gcaccaggac   300
tggctgaatg gcaaggagta caagtgcaag gtctccaaca aagcccctcc cagccccatc   360
gagaaaacca tctccaaagc caaagggcag ccccgagaac cacaggtgta caccctgccc   420
ccatcccggg atgagctgac caagaaccag gtcagcctga cctgcctggt caaaggcttc   480
tatcccagcg acatcgccgt ggagtgggag agcaatgggc aaccggagaa caactacaag   540
accacgcctc ccgtgctgga ctccgacggc tccttcttcc tctacagcaa gctcaccgtg   600
gacaagagca ggtggcagca ggggaacgtc ttctcatgct ccgtgatgca tgaggctctg   660
cacaaccact acacgcagaa gagcctctcc ctgtctccgg gtaaaaaaga tcccaaattt   720
tgggtgctgg tggtggttgg tggagtcctg gcttgctata gcttgctagt aacagtggcc   780
tttattattt tctgggtgag gagtaagagg agcaggctcc tgcacagtga ctacatgaac   840
atgactcccc gccgcccgg gcccacccgc aagcattacc agccctatgc cccaccacgc   900
gacttcgcag cctatcgctc cagagtgaag ttcagcagga gcgcagacgc ccccgcgtac   960
cagcagggcc agaaccagct ctataacgag ctcaatctag gacgaagaga ggagtacgat  1020
gttttggaca agagacgtgg ccgggaccct gagatgggg gaaagccgag aaggaagaac  1080
cctcaggaag gcctgtacaa tgaactgcag aaagataaga tggcggaggc ctacagtgag  1140
attgggatga aggcgagcg ccggaggggc aaggggcacg atggccttta ccagggtctc  1200
agtacagcca ccaaggacac ctacgacgcc cttcacatgc aggccctgcc ccctcgc    1257
```

<210> SEQ ID NO 51
<211> LENGTH: 200
<212> TYPE: PRT
<213> ORGANISM: Artificial Sequence
<220> FEATURE:
<223> OTHER INFORMATION: Synthetic Polypeptide

<400> SEQUENCE: 51

```
Asp Leu Glu Pro Lys Ser Cys Asp Lys Thr His Thr Cys Pro Pro Cys
 1               5                  10                  15

Pro Asp Pro Lys Phe Trp Val Leu Val Val Gly Gly Val Leu Ala
            20                  25                  30

Cys Tyr Ser Leu Leu Val Thr Val Ala Phe Ile Ile Phe Trp Val Arg
        35                  40                  45

Ser Lys Arg Ser Arg Leu Leu His Ser Asp Tyr Met Asn Met Thr Pro
    50                  55                  60

Arg Arg Pro Gly Pro Thr Arg Lys His Tyr Gln Pro Tyr Ala Pro Pro
65                  70                  75                  80

Arg Asp Phe Ala Ala Tyr Arg Ser Arg Val Lys Phe Ser Arg Ser Ala
                85                  90                  95

Asp Ala Pro Ala Tyr Gln Gln Gly Gln Asn Gln Leu Tyr Asn Glu Leu
            100                 105                 110

Asn Leu Gly Arg Arg Glu Glu Tyr Asp Val Leu Asp Lys Arg Arg Gly
        115                 120                 125

Arg Asp Pro Glu Met Gly Gly Lys Pro Arg Arg Lys Asn Pro Gln Glu
```

```
                 130                 135                 140
Gly Leu Tyr Asn Glu Leu Gln Lys Asp Lys Met Ala Glu Ala Tyr Ser
145                 150                 155                 160

Glu Ile Gly Met Lys Gly Glu Arg Arg Gly Lys Gly His Asp Gly
                165                 170                 175

Leu Tyr Gln Gly Leu Ser Thr Ala Thr Lys Asp Thr Tyr Asp Ala Leu
                180                 185                 190

His Met Gln Ala Leu Pro Pro Arg
                195                 200

<210> SEQ ID NO 52
<211> LENGTH: 600
<212> TYPE: PRT
<213> ORGANISM: Artificial Sequence
<220> FEATURE:
<223> OTHER INFORMATION: Synthetic Polypeptide

<400> SEQUENCE: 52

Gly Ala Thr Cys Thr Cys Gly Ala Gly Cys Cys Cys Ala Ala Ala Thr
1               5                   10                  15

Cys Thr Thr Gly Thr Gly Ala Cys Ala Ala Ala Cys Thr Cys Ala
                20                  25                  30

Cys Ala Cys Ala Thr Gly Cys Cys Ala Cys Cys Gly Thr Gly Cys
            35                  40                  45

Cys Cys Gly Gly Ala Thr Cys Cys Cys Ala Ala Ala Thr Thr Thr Thr
50                  55                  60

Gly Gly Gly Thr Gly Cys Thr Gly Gly Thr Gly Gly Thr Gly Gly Thr
65                  70                  75                  80

Thr Gly Gly Thr Gly Gly Ala Gly Thr Cys Cys Thr Gly Gly Cys Thr
                85                  90                  95

Thr Gly Cys Thr Ala Thr Ala Gly Cys Thr Thr Gly Cys Thr Ala Gly
                100                 105                 110

Thr Ala Ala Cys Ala Gly Thr Gly Gly Cys Cys Thr Thr Thr Ala Thr
            115                 120                 125

Thr Ala Thr Thr Thr Thr Cys Thr Gly Gly Thr Gly Ala Gly Gly
                130                 135                 140

Ala Gly Thr Ala Ala Gly Ala Gly Gly Ala Gly Cys Ala Gly Gly Cys
145                 150                 155                 160

Thr Cys Cys Thr Gly Cys Ala Cys Ala Gly Thr Gly Ala Cys Thr Ala
                165                 170                 175

Cys Ala Thr Gly Ala Ala Cys Ala Thr Gly Ala Cys Thr Cys Cys Cys
            180                 185                 190

Cys Gly Cys Cys Gly Cys Cys Cys Gly Gly Gly Cys Cys Cys Ala
                195                 200                 205

Cys Cys Cys Gly Cys Ala Ala Gly Cys Ala Thr Thr Ala Cys Cys Ala
            210                 215                 220

Gly Cys Cys Cys Thr Ala Thr Gly Cys Cys Cys Ala Cys Cys Ala
225                 230                 235                 240

Cys Gly Cys Gly Ala Cys Thr Thr Cys Gly Cys Ala Gly Cys Cys Thr
                245                 250                 255

Ala Thr Cys Gly Cys Thr Cys Cys Ala Gly Ala Gly Thr Gly Ala Ala
                260                 265                 270

Gly Thr Thr Cys Ala Gly Cys Ala Gly Ala Gly Cys Gly Cys Ala
                275                 280                 285

Gly Ala Cys Gly Cys Cys Cys Cys Cys Gly Cys Gly Thr Ala Cys Cys
```

```
            290                 295                 300
Ala Gly Cys Ala Gly Gly Cys Cys Ala Gly Ala Ala Cys Cys Ala
305                 310                 315                 320

Gly Cys Thr Cys Thr Ala Thr Ala Ala Cys Gly Ala Gly Cys Thr Cys
                325                 330                 335

Ala Ala Thr Cys Thr Ala Gly Gly Ala Cys Gly Ala Ala Gly Ala Gly
                340                 345                 350

Ala Gly Gly Ala Gly Thr Ala Cys Gly Ala Thr Gly Thr Thr Thr
                355                 360                 365

Gly Gly Ala Cys Ala Ala Gly Ala Gly Ala Cys Gly Thr Gly Gly Cys
                370                 375                 380

Cys Gly Gly Gly Ala Cys Cys Thr Gly Ala Gly Ala Thr Gly Gly
385                 390                 395                 400

Gly Gly Gly Gly Ala Ala Ala Gly Cys Cys Gly Ala Gly Ala Ala Gly
                405                 410                 415

Gly Ala Ala Gly Ala Ala Cys Cys Cys Thr Cys Ala Gly Gly Ala Ala
                420                 425                 430

Gly Gly Cys Cys Thr Gly Thr Ala Cys Ala Ala Thr Gly Ala Ala Cys
                435                 440                 445

Thr Gly Cys Ala Gly Ala Ala Ala Gly Ala Thr Ala Ala Gly Ala Thr
450                 455                 460

Gly Gly Cys Gly Gly Ala Gly Gly Cys Cys Thr Ala Cys Ala Gly Thr
465                 470                 475                 480

Gly Ala Gly Ala Thr Thr Gly Gly Gly Ala Thr Gly Ala Ala Ala Gly
                485                 490                 495

Gly Cys Gly Ala Gly Cys Gly Cys Cys Gly Gly Ala Gly Gly Gly Gly
                500                 505                 510

Cys Ala Ala Gly Gly Gly Gly Cys Ala Cys Gly Ala Thr Gly Gly Cys
                515                 520                 525

Cys Thr Thr Thr Ala Cys Cys Ala Gly Gly Thr Cys Thr Cys Ala
530                 535                 540

Gly Thr Ala Cys Ala Gly Cys Cys Ala Cys Cys Ala Ala Gly Gly Ala
545                 550                 555                 560

Cys Ala Cys Cys Thr Ala Cys Gly Ala Cys Gly Cys Cys Thr Thr
                565                 570                 575

Cys Ala Cys Ala Thr Gly Cys Ala Gly Gly Cys Cys Thr Gly Cys
                580                 585                 590

Cys Cys Cys Cys Thr Cys Gly Cys
            595                 600

<210> SEQ ID NO 53
<211> LENGTH: 688
<212> TYPE: PRT
<213> ORGANISM: Artificial Sequence
<220> FEATURE:
<223> OTHER INFORMATION: Synthetic Polypeptide

<400> SEQUENCE: 53

Met Asp Trp Ile Trp Arg Ile Leu Phe Leu Val Gly Ala Ala Thr Gly
1               5                   10                  15

Ala His Ser Gln Val Gln Leu Gln Gln Pro Gly Ala Glu Leu Val Arg
                20                  25                  30

Pro Gly Ala Ser Val Lys Leu Ser Cys Lys Ala Ser Gly Tyr Thr Phe
            35                  40                  45

Ser Asn Tyr Leu Met Asn Trp Val Lys Gln Arg Pro Glu Gln Asp Leu
```

```
            50                  55                  60
Asp Trp Ile Gly Arg Ile Asp Pro Tyr Asp Gly Ile Asp Tyr Asn
 65                  70                  75                  80

Gln Asn Phe Lys Asp Lys Ala Ile Leu Thr Val Asp Lys Ser Ser Ser
                 85                  90                  95

Thr Ala Tyr Met Gln Leu Ser Ser Leu Thr Ser Glu Asp Ser Ala Val
                100                 105                 110

Tyr Tyr Cys Ala Arg Gly Tyr Gly Thr Ala Tyr Gly Val Asp Tyr Trp
                115                 120                 125

Gly Gln Gly Thr Ser Val Thr Val Ser Ser Ala Lys Thr Thr Pro Pro
        130                 135                 140

Lys Leu Glu Glu Gly Glu Phe Ser Glu Ala Arg Val Asp Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Glu Ser Val Asp Asn Tyr Gly Ile Ser Phe
                180                 185                 190

Met Asn Trp Phe Gln Gln Lys Pro Gly Gln Pro Pro Lys Leu Leu Ile
        195                 200                 205

Tyr Ala Ala Ser Arg Gln Gly Ser Gly Val Pro Ala Arg Phe Ser Gly
210                 215                 220

Ser Gly Ser Gly Thr Asp Phe Ser Leu Asn Ile His Pro Met Glu Glu
225                 230                 235                 240

Asp Asp Thr Ala Met Tyr Phe Cys Gln Gln Ser Lys Glu Val Pro Trp
                245                 250                 255

Thr Phe Gly Gly Gly Thr Lys Leu Glu Ile Lys Ala Glu Asp Pro Ala
                260                 265                 270

Glu Pro Lys Ser Pro Asp Lys Thr His Thr Cys Pro Pro Cys Pro Ala
                275                 280                 285

Pro Glu Leu Leu Gly Gly Pro Ser Val Phe Leu Phe Pro Pro Lys Pro
        290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
                340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
        370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Asp Glu Leu Thr
                405                 410                 415

Lys Asn Gln Val Ser Leu Thr Cys Leu Val Lys Gly Phe Tyr Pro Ser
                420                 425                 430

Asp Ile Ala Val Glu Trp Glu Ser Asn Gly Gln Pro Glu Asn Asn Tyr
                435                 440                 445

Lys Thr Thr Pro Pro Val Leu Asp Ser Asp Gly Ser Phe Phe Leu Tyr
        450                 455                 460

Ser Lys Leu Thr Val Asp Lys Ser Arg Trp Gln Gln Gly Asn Val Phe
465                 470                 475                 480
```

Ser Cys Ser Val Met His Glu Ala Leu His Asn His Tyr Thr Gln Lys
            485                 490                 495

Ser Leu Ser Leu Ser Pro Gly Lys Lys Asp Pro Lys Phe Trp Val Leu
            500                 505                 510

Val Val Val Gly Gly Val Leu Ala Cys Tyr Ser Leu Leu Val Thr Val
            515                 520                 525

Ala Phe Ile Ile Phe Trp Val Arg Ser Lys Arg Ser Arg Leu Leu His
            530                 535                 540

Ser Asp Tyr Met Asn Met Thr Pro Arg Arg Pro Gly Pro Thr Arg Lys
545                 550                 555                 560

His Tyr Gln Pro Tyr Ala Pro Pro Arg Asp Phe Ala Ala Tyr Arg Ser
                565                 570                 575

Arg Val Lys Phe Ser Arg Ser Ala Asp Ala Pro Ala Tyr Gln Gln Gly
                580                 585                 590

Gln Asn Gln Leu Tyr Asn Glu Leu Asn Leu Gly Arg Arg Glu Glu Tyr
                595                 600                 605

Asp Val Leu Asp Lys Arg Arg Gly Arg Asp Pro Glu Met Gly Gly Lys
            610                 615                 620

Pro Arg Arg Lys Asn Pro Gln Glu Gly Leu Tyr Asn Glu Leu Gln Lys
625                 630                 635                 640

Asp Lys Met Ala Glu Ala Tyr Ser Glu Ile Gly Met Lys Gly Glu Arg
                645                 650                 655

Arg Arg Gly Lys Gly His Asp Gly Leu Tyr Gln Gly Leu Ser Thr Ala
                660                 665                 670

Thr Lys Asp Thr Tyr Asp Ala Leu His Met Gln Ala Leu Pro Pro Arg
            675                 680                 685

<210> SEQ ID NO 54
<211> LENGTH: 2064
<212> TYPE: PRT
<213> ORGANISM: Artificial Sequence
<220> FEATURE:
<223> OTHER INFORMATION: Synthetic Polynucleotide

<400> SEQUENCE: 54

Ala Thr Gly Gly Ala Cys Thr Gly Gly Ala Thr Cys Thr Gly Gly Cys
1               5                   10                  15

Gly Cys Ala Thr Cys Cys Thr Gly Thr Thr Thr Cys Thr Cys Gly Thr
            20                  25                  30

Gly Gly Gly Ala Gly Cys Cys Gly Cys Cys Ala Cys Ala Gly Gly Cys
        35                  40                  45

Gly Cys Cys Cys Ala Thr Thr Cys Thr Cys Ala Gly Gly Thr Gly Cys
    50                  55                  60

Ala Gly Cys Thr Gly Cys Ala Gly Cys Ala Gly Cys Cys Thr Gly Gly
65                  70                  75                  80

Cys Gly Cys Thr Gly Ala Ala Cys Thr Gly Thr Gly Cys Gly Gly Gly
                85                  90                  95

Cys Cys Ala Gly Gly Cys Gly Cys Thr Thr Cys Thr Gly Thr Gly Ala
            100                 105                 110

Ala Gly Cys Thr Gly Ala Gly Cys Thr Gly Thr Ala Ala Ala Gly Cys
            115                 120                 125

Cys Ala Gly Cys Gly Gly Cys Thr Ala Cys Ala Cys Cys Thr Thr Cys
        130                 135                 140

Ala Gly Cys Ala Ala Cys Thr Ala Cys Thr Gly Gly Ala Thr Gly Ala
145                 150                 155                 160

-continued

```
Ala Cys Thr Gly Gly Gly Thr Cys Ala Ala Gly Cys Ala Gly Cys Gly
                165                 170                 175
Gly Cys Cys Cys Gly Ala Gly Cys Ala Gly Gly Ala Cys Cys Thr Gly
            180                 185                 190

Gly Ala Thr Thr Gly Gly Ala Thr Cys Gly Gly Cys Ala Gly Ala Ala
        195                 200                 205

Thr Cys Gly Ala Cys Cys Cys Cys Thr Ala Cys Gly Ala Cys Gly Gly
    210                 215                 220
Cys Gly Ala Cys Ala Thr Cys Gly Ala Cys Thr Ala Cys Ala Ala Cys
225                 230                 235                 240
Cys Ala Gly Ala Ala Cys Thr Thr Cys Ala Ala Gly Gly Ala Cys Ala
                245                 250                 255
Ala Gly Gly Cys Cys Ala Thr Cys Cys Thr Gly Ala Cys Cys Gly Thr
            260                 265                 270

Gly Gly Ala Cys Ala Ala Gly Ala Gly Cys Ala Gly Cys Ala Gly Cys
        275                 280                 285

Ala Cys Cys Gly Cys Cys Thr Ala Cys Ala Thr Gly Cys Ala Gly Cys
    290                 295                 300

Thr Gly Thr Cys Cys Ala Gly Cys Cys Thr Gly Ala Cys Cys Ala Gly
305                 310                 315                 320

Cys Gly Ala Gly Gly Ala Cys Ala Gly Cys Gly Cys Cys Gly Thr Gly
                325                 330                 335

Thr Ala Cys Thr Ala Cys Thr Gly Cys Gly Cys Cys Ala Gly Ala Gly
            340                 345                 350

Gly Cys Thr Ala Cys Gly Gly Cys Ala Cys Ala Gly Cys Cys Thr Ala
        355                 360                 365

Cys Gly Gly Cys Gly Thr Gly Gly Ala Cys Thr Ala Thr Thr Gly Gly
    370                 375                 380

Gly Gly Cys Cys Ala Gly Gly Gly Cys Ala Cys Ala Ala Gly Cys Gly
385                 390                 395                 400

Thr Gly Ala Cys Cys Gly Thr Gly Thr Cys Cys Ala Gly Cys Gly Cys
                405                 410                 415

Cys Ala Ala Gly Ala Cys Cys Ala Cys Cys Cys Cys Cys Cys Cys Thr
            420                 425                 430

Ala Ala Gly Cys Thr Gly Gly Ala Ala Gly Ala Gly Gly Gly Cys Gly
        435                 440                 445

Ala Gly Thr Thr Cys Thr Cys Cys Gly Ala Gly Gly Cys Cys Cys Gly
    450                 455                 460

Gly Gly Thr Gly Gly Ala Cys Ala Thr Thr Gly Thr Gly Cys Thr Gly
465                 470                 475                 480

Ala Cys Ala Cys Ala Gly Thr Cys Thr Cys Cys Ala Gly Cys Cys Ala
                485                 490                 495

Gly Cys Cys Thr Gly Gly Cys Cys Gly Thr Gly Thr Cys Cys Cys Thr
            500                 505                 510

Gly Gly Gly Ala Cys Ala Gly Ala Gly Ala Gly Cys Cys Ala Cys Cys
        515                 520                 525

Ala Thr Cys Ala Gly Cys Thr Gly Thr Ala Gly Gly Gly Cys Cys Ala
    530                 535                 540

Gly Cys Gly Ala Gly Ala Gly Cys Gly Thr Gly Gly Ala Cys Ala Ala
545                 550                 555                 560

Cys Thr Ala Cys Gly Gly Cys Ala Thr Cys Ala Gly Cys Thr Thr Cys
                565                 570                 575
```

-continued

```
Ala Thr Gly Ala Ala Thr Thr Gly Thr Thr Cys Cys Ala Gly Cys
            580              585              590

Ala Gly Ala Ala Gly Cys Cys Cys Gly Cys Cys Ala Gly Cys Cys
            595              600              605

Cys Cys Cys Cys Ala Ala Gly Cys Thr Gly Cys Thr Gly Ala Thr Cys
    610              615              620

Thr Ala Thr Gly Cys Cys Gly Cys Cys Ala Gly Cys Ala Gly Ala Cys
625              630              635              640

Ala Gly Gly Gly Cys Ala Gly Cys Gly Gly Ala Gly Thr Gly Cys Cys
            645              650              655

Thr Gly Cys Cys Ala Gly Ala Thr Thr Thr Cys Thr Gly Gly Cys
            660              665              670

Ala Gly Cys Gly Gly Cys Thr Cys Cys Gly Gly Cys Ala Cys Cys Gly
            675              680              685

Ala Cys Thr Thr Cys Ala Gly Cys Cys Thr Gly Ala Ala Cys Ala Thr
            690              695              700

Cys Cys Ala Cys Cys Thr Ala Thr Gly Gly Ala Ala Gly Ala Gly
705              710              715              720

Gly Ala Cys Gly Ala Cys Ala Cys Cys Gly Cys Cys Ala Thr Gly Thr
            725              730              735

Ala Cys Thr Thr Thr Thr Gly Cys Cys Ala Gly Cys Ala Gly Ala Gly
            740              745              750

Cys Ala Ala Ala Gly Ala Gly Gly Thr Gly Cys Cys Cys Thr Gly Gly
            755              760              765

Ala Cys Cys Thr Thr Gly Gly Cys Gly Gly Ala Gly Gly Cys Ala
            770              775              780

Cys Cys Ala Ala Gly Cys Thr Gly Gly Ala Ala Ala Thr Cys Ala Ala
785              790              795              800

Gly Gly Cys Cys Gly Ala Gly Gly Ala Thr Cys Cys Gly Cys Cys
            805              810              815

Gly Ala Gly Cys Cys Cys Ala Ala Ala Thr Cys Thr Thr Gly Thr Gly
            820              825              830

Ala Cys Ala Ala Ala Ala Cys Thr Cys Ala Cys Ala Cys Ala Thr Gly
            835              840              845

Cys Cys Cys Ala Cys Cys Gly Thr Gly Cys Cys Ala Gly Cys Ala
            850              855              860

Cys Cys Thr Gly Ala Ala Cys Thr Cys Cys Thr Gly Gly Gly Gly Gly
865              870              875              880

Gly Ala Cys Cys Gly Thr Cys Ala Gly Thr Cys Thr Thr Cys Cys Thr
            885              890              895

Cys Thr Thr Cys Cys Cys Cys Cys Cys Ala Ala Ala Ala Cys Cys Cys
            900              905              910

Ala Ala Gly Gly Ala Cys Ala Cys Cys Cys Thr Cys Ala Thr Gly Ala
            915              920              925

Thr Cys Thr Cys Cys Cys Gly Gly Ala Cys Cys Cys Cys Thr Gly Ala
            930              935              940

Gly Gly Thr Cys Ala Cys Ala Thr Gly Cys Gly Thr Gly Gly Thr Gly
945              950              955              960

Gly Thr Gly Gly Ala Cys Gly Thr Gly Ala Gly Cys Cys Ala Cys Gly
                965              970              975

Ala Ala Gly Ala Cys Cys Cys Thr Gly Ala Gly Gly Thr Cys Ala Ala
            980              985              990

Gly Thr Thr Cys Ala Ala Cys Thr  Gly Gly Thr Ala Cys  Gly Thr Gly
```

```
           995                 1000                1005
Gly Ala  Cys Gly Gly Cys Gly  Thr Gly Gly Ala Gly  Gly Thr Gly
    1010                 1015                 1020

Cys Ala  Thr Ala Ala Thr Gly  Cys Cys Ala Ala Gly  Ala Cys Ala
    1025                 1030                 1035

Ala Ala  Gly Cys Cys Gly Cys  Gly Gly Gly Ala Gly  Gly Ala Gly
    1040                 1045                 1050

Cys Ala  Gly Thr Ala Cys Ala  Ala Cys Ala Gly Cys  Ala Cys Gly
    1055                 1060                 1065

Thr Ala  Cys Cys Gly Thr Gly  Thr Gly Gly Thr Cys  Ala Gly Cys
    1070                 1075                 1080

Gly Thr  Cys Cys Thr Cys Ala  Cys Cys Gly Thr Cys  Cys Thr Gly
    1085                 1090                 1095

Cys Ala  Cys Cys Ala Gly Gly  Ala Cys Thr Gly Gly  Cys Thr Gly
    1100                 1105                 1110

Ala Ala  Thr Gly Gly Cys Ala  Ala Gly Gly Ala Gly  Thr Ala Cys
    1115                 1120                 1125

Ala Ala  Gly Thr Gly Cys Ala  Ala Gly Gly Thr Cys  Thr Cys Cys
    1130                 1135                 1140

Ala Ala  Cys Ala Ala Ala Gly  Cys Cys Cys Thr Cys  Cys Cys Ala
    1145                 1150                 1155

Gly Cys  Cys Cys Cys Cys Ala  Thr Cys Gly Ala Gly  Ala Ala Ala
    1160                 1165                 1170

Ala Cys  Cys Ala Thr Cys Thr  Cys Cys Ala Ala Ala  Gly Cys Cys
    1175                 1180                 1185

Ala Ala  Ala Gly Gly Gly Cys  Ala Gly Cys Cys Cys  Cys Gly Ala
    1190                 1195                 1200

Gly Ala  Ala Cys Cys Ala Cys  Ala Gly Gly Thr Gly  Thr Ala Cys
    1205                 1210                 1215

Ala Cys  Cys Cys Thr Gly Cys  Cys Cys Cys Cys Ala  Thr Cys Cys
    1220                 1225                 1230

Cys Gly  Gly Gly Ala Thr Gly  Ala Gly Cys Thr Gly  Ala Cys Cys
    1235                 1240                 1245

Ala Ala  Gly Ala Ala Cys Cys  Ala Gly Gly Thr Cys  Ala Gly Cys
    1250                 1255                 1260

Cys Thr  Gly Ala Cys Cys Thr  Gly Cys Cys Thr Gly  Gly Thr Cys
    1265                 1270                 1275

Ala Ala  Ala Gly Gly Cys Thr  Thr Cys Thr Ala Thr  Cys Cys Cys
    1280                 1285                 1290

Ala Gly  Cys Gly Ala Cys Ala  Thr Cys Gly Cys Cys  Gly Thr Gly
    1295                 1300                 1305

Gly Ala  Gly Thr Gly Gly Gly  Ala Gly Ala Gly Cys  Ala Ala Thr
    1310                 1315                 1320

Gly Gly  Gly Cys Ala Ala Cys  Cys Gly Gly Ala Gly  Ala Ala Cys
    1325                 1330                 1335

Ala Ala  Cys Thr Ala Cys Ala  Ala Gly Ala Cys Cys  Ala Cys Gly
    1340                 1345                 1350

Cys Cys  Thr Cys Cys Cys Gly  Thr Gly Cys Thr Gly  Gly Ala Cys
    1355                 1360                 1365

Thr Cys  Cys Gly Ala Cys Gly  Gly Cys Thr Cys Cys  Thr Thr Cys
    1370                 1375                 1380

Thr Thr  Cys Cys Thr Cys Thr  Ala Cys Ala Gly Cys  Ala Ala Gly
    1385                 1390                 1395
```

```
Cys Thr Cys Ala Cys Cys Gly Thr Gly Ala Cys Ala Ala Gly
    1400            1405            1410

Ala Gly Cys Ala Gly Gly Thr Gly Gly Cys Ala Gly Cys Ala Gly
        1415            1420            1425

Gly Gly Gly Ala Ala Cys Gly Thr Cys Thr Thr Cys Thr Cys Ala
    1430            1435            1440

Thr Gly Cys Thr Cys Cys Gly Thr Gly Ala Thr Gly Cys Ala Thr
    1445            1450            1455

Gly Ala Gly Gly Cys Thr Cys Thr Gly Cys Ala Cys Ala Ala Cys
    1460            1465            1470

Cys Ala Cys Thr Ala Cys Ala Cys Gly Cys Ala Gly Ala Ala Gly
    1475            1480            1485

Ala Gly Cys Cys Thr Cys Thr Cys Cys Cys Thr Gly Thr Cys Thr
    1490            1495            1500

Cys Cys Gly Gly Gly Thr Ala Ala Ala Ala Ala Gly Ala Thr
    1505            1510            1515

Cys Cys Cys Ala Ala Ala Thr Thr Thr Gly Gly Gly Thr Gly
    1520            1525            1530

Cys Thr Gly Gly Thr Gly Gly Thr Gly Gly Thr Thr Gly Gly Thr
    1535            1540            1545

Gly Gly Ala Gly Thr Cys Cys Thr Gly Gly Cys Thr Thr Gly Cys
    1550            1555            1560

Thr Ala Thr Ala Gly Cys Thr Thr Gly Cys Thr Ala Gly Thr Ala
    1565            1570            1575

Ala Cys Ala Gly Thr Gly Gly Cys Cys Thr Thr Thr Ala Thr Thr
    1580            1585            1590

Ala Thr Thr Thr Thr Cys Thr Gly Gly Gly Thr Gly Ala Gly Gly
    1595            1600            1605

Ala Gly Thr Ala Ala Gly Ala Gly Gly Ala Gly Cys Ala Gly Gly
    1610            1615            1620

Cys Thr Cys Cys Thr Gly Cys Ala Cys Ala Gly Thr Gly Ala Cys
    1625            1630            1635

Thr Ala Cys Ala Thr Gly Ala Ala Cys Ala Thr Gly Ala Cys Thr
    1640            1645            1650

Cys Cys Cys Cys Gly Cys Cys Gly Cys Cys Cys Gly Gly Gly
    1655            1660            1665

Cys Cys Cys Ala Cys Cys Cys Gly Cys Ala Ala Gly Cys Ala Thr
    1670            1675            1680

Thr Ala Cys Cys Ala Gly Cys Cys Cys Thr Ala Thr Gly Cys Cys
    1685            1690            1695

Cys Cys Ala Cys Cys Ala Cys Gly Cys Gly Ala Cys Thr Thr Cys
    1700            1705            1710

Gly Cys Ala Gly Cys Cys Thr Ala Thr Cys Gly Cys Thr Cys Cys
    1715            1720            1725

Ala Gly Ala Gly Thr Gly Ala Ala Gly Thr Thr Cys Ala Gly Cys
    1730            1735            1740

Ala Gly Gly Ala Gly Cys Gly Cys Ala Gly Ala Cys Gly Cys Cys
    1745            1750            1755

Cys Cys Cys Gly Cys Gly Thr Ala Cys Ala Gly Cys Ala Gly
    1760            1765            1770

Gly Gly Cys Cys Ala Gly Ala Ala Cys Cys Ala Gly Cys Thr Cys
    1775            1780            1785
```

-continued

```
Thr Ala Thr Ala Ala Cys Gly Ala Gly Cys Thr Cys Ala Ala Thr
    1790            1795                1800
Cys Thr Ala Gly Gly Ala Cys Gly Ala Ala Gly Ala Gly Ala Gly
    1805            1810                1815
Gly Ala Gly Thr Ala Cys Gly Ala Thr Gly Thr Thr Thr Thr Gly
    1820            1825                1830
Gly Ala Cys Ala Ala Gly Ala Gly Ala Cys Gly Thr Gly Gly Cys
    1835            1840                1845
Cys Gly Gly Gly Ala Cys Cys Cys Thr Gly Ala Gly Ala Thr Gly
    1850            1855                1860
Gly Gly Gly Gly Gly Ala Ala Ala Gly Cys Cys Gly Ala Gly Ala
    1865            1870                1875
Ala Gly Gly Ala Ala Gly Ala Ala Cys Cys Cys Thr Cys Ala Gly
    1880            1885                1890
Gly Ala Ala Gly Gly Cys Cys Thr Gly Thr Ala Cys Ala Ala Thr
    1895            1900                1905
Gly Ala Ala Cys Thr Gly Cys Ala Gly Ala Ala Ala Gly Ala Thr
    1910            1915                1920
Ala Ala Gly Ala Thr Gly Gly Cys Gly Gly Ala Gly Gly Cys Cys
    1925            1930                1935
Thr Ala Cys Ala Gly Thr Gly Ala Gly Ala Thr Thr Gly Gly Gly
    1940            1945                1950
Ala Thr Gly Ala Ala Ala Gly Gly Cys Gly Ala Gly Cys Gly Cys
    1955            1960                1965
Cys Gly Gly Ala Gly Gly Gly Cys Ala Ala Gly Gly Gly Gly Gly
    1970            1975                1980
Cys Ala Cys Gly Ala Thr Gly Gly Cys Cys Thr Thr Ala Cys Cys
    1985            1990                1995
Cys Ala Gly Gly Gly Thr Cys Thr Cys Ala Gly Thr Ala Cys Ala
    2000            2005                2010
Gly Cys Cys Ala Cys Cys Ala Ala Gly Gly Ala Cys Ala Cys Cys
    2015            2020                2025
Thr Ala Cys Gly Ala Cys Gly Cys Cys Thr Thr Cys Ala Cys Cys
    2030            2035                2040
Ala Thr Gly Cys Ala Gly Gly Cys Cys Thr Gly Cys Cys Cys
    2045            2050                2055
Cys Cys Thr Cys Gly Cys
    2060
```

<210> SEQ ID NO 55
<211> LENGTH: 467
<212> TYPE: PRT
<213> ORGANISM: Artificial Sequence
<220> FEATURE:
<223> OTHER INFORMATION: Synthetic Polypeptide

<400> SEQUENCE: 55

```
Met Asp Trp Ile Trp Arg Ile Leu Phe Leu Val Gly Ala Ala Thr Gly
1               5                   10                  15

Ala His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Ser Asn Tyr Leu Met Asn Trp Val Lys Gln Arg Pro Glu Gln Asp Leu
    50                  55                  60
```

```
Asp Trp Ile Gly Arg Ile Asp Pro Tyr Asp Gly Asp Ile Asp Tyr Asn
 65                  70                  75                  80

Gln Asn Phe Lys Asp Lys Ala Ile Leu Thr Val Asp Lys Ser Ser Ser
                 85                  90                  95

Thr Ala Tyr Met Gln Leu Ser Ser Leu Thr Ser Glu Asp Ser Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Ser Val Thr Val Ser Ser Ala Lys Thr Thr Pro Pro
    130                 135                 140

Lys Leu Glu Glu Gly Glu Phe Ser Glu Ala Arg Val Asp Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Glu Ser Val Asp Asn Tyr Gly Ile Ser Phe
            180                 185                 190

Met Asn Trp Phe Gln Gln Lys Pro Gly Gln Pro Pro Lys Leu Leu Ile
        195                 200                 205

Tyr Ala Ala Ser Arg Gln Gly Ser Gly Val Pro Ala Arg Phe Ser Gly
    210                 215                 220

Ser Gly Ser Gly Thr Asp Phe Ser Leu Asn Ile His Pro Met Glu Glu
225                 230                 235                 240

Asp Asp Thr Ala Met Tyr Phe Cys Gln Gln Ser Lys Glu Val Pro Trp
                245                 250                 255

Thr Phe Gly Gly Gly Thr Lys Leu Glu Ile Lys Asp Leu Glu Pro Lys
            260                 265                 270

Ser Cys Asp Lys Thr His Thr Cys Pro Pro Cys Pro Asp Pro Lys Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
        435                 440                 445

Ser Thr Ala Thr Lys Asp Thr Tyr Asp Ala Leu His Met Gln Ala Leu
    450                 455                 460

Pro Pro Arg
465
```

<210> SEQ ID NO 56
<211> LENGTH: 1401
<212> TYPE: DNA
<213> ORGANISM: Artificial Sequence
<220> FEATURE:
<223> OTHER INFORMATION: Synthetic Polynucleotide

<400> SEQUENCE: 56

| | |
|---|---|
| atggactgga tctggcgcat cctgtttctc gtgggagccg ccacaggcgc ccattctcag | 60 |
| gtgcagctgc agcagcctgg cgctgaactc gtgcggccag gcgcttctgt gaagctgagc | 120 |
| tgtaaagcca gcggctacac cttcagcaac tacctgatga actgggtcaa gcagcggccc | 180 |
| gagcaggacc tggattggat cggcagaatc gaccccctacg acggcgacat cgactacaac | 240 |
| cagaacttca aggacaaggc catcctgacc gtggacaaga gcagcagcac cgcctacatg | 300 |
| cagctgtcca gcctgaccag cgaggacagc gccgtgtact actgcgccag aggctacggc | 360 |
| acagcctacg gcgtggacta ttggggccag ggcacaagcg tgaccgtgtc cagcgccaag | 420 |
| accaccccc ctaagctgga agagggcgag ttctccgagg cccgggtgga cattgtgctg | 480 |
| acacagtctc cagccagcct ggccgtgtcc ctgggacaga gagccaccat cagctgtagg | 540 |
| gccagcgaga gcgtggacaa ctacggcatc agcttcatga attggttcca gcagaagccc | 600 |
| ggccagcccc ccaagctgct gatctatgcc gccagcagac agggcagcgg agtgcctgcc | 660 |
| agattttctg gcgcggctc cggcaccgac ttcagcctga catccaccc tatggaagag | 720 |
| gacgacaccg ccatgtactt tgccagcag agcaaagagg tgccctggac ctttggcgga | 780 |
| ggcaccaagc tggaaatcaa ggatctcgag cccaaatctt gtgacaaaac tcacacatgc | 840 |
| ccaccgtgcc cggatcccaa attttgggtg ctggtggtgg ttggtggagt cctggcttgc | 900 |
| tatagcttgc tagtaacagt ggcctttatt attttctggg tgaggagtaa gaggagcagg | 960 |
| ctcctgcaca gtgactacat gaacatgact ccccgccgcc ccgggcccac ccgcaagcat | 1020 |
| taccagcccct atgccccacc acgcgacttc gcagcctatc gctccagagt gaagttcagc | 1080 |
| aggagcgcag acgcccccgc gtaccagcag gccagaacc agctctataa cgagctcaat | 1140 |
| ctaggacgaa gagaggagta cgatgttttg acaagagac gtggccggga ccctgagatg | 1200 |
| gggggaaagc cgagaaggaa gaaccctcag gaaggcctgt acaatgaact gcagaaagat | 1260 |
| aagatggcgg aggcctacag tgagattggg atgaaaggcg agcgccggag gggcaagggg | 1320 |
| cacgatggcc tttaccaggg tctcagtaca gccaccaagg acacctacga cgcccttcac | 1380 |
| atgcaggccc tgccccctcg c | 1401 |

<210> SEQ ID NO 57
<211> LENGTH: 257
<212> TYPE: PRT
<213> ORGANISM: Artificial Sequence
<220> FEATURE:
<223> OTHER INFORMATION: Synthetic Polypeptide

<400> SEQUENCE: 57

Asp Pro Ala Glu Pro Lys Ser Pro Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

| | | | | | | | | | | | | | | | |
|---|---|---|---|---|---|---|---|---|---|---|---|---|---|---|---|
|Trp|Tyr|Val|Asp|Gly|Val|Glu|Val|His|Asn|Ala|Lys|Thr|Lys|Pro|Arg|
|65| | | |70| | | |75| | | |80| | | |

Glu Glu Gln Tyr Asn Ser Thr Tyr Arg Val Val Ser Val Leu Thr Val
            85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
            115                 120                 125

Gly Gln Pro Arg Glu Pro Gln Val Tyr Thr Leu Pro Pro Ser Arg Asp
        130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
210                 215                 220

Thr Gln Lys Ser Leu Ser Leu Ser Pro Gly Lys Lys Asp Pro Lys Phe
225                 230                 235                 240

Trp Val Leu Val Val Val Gly Gly Val Leu Ala Cys Tyr Ser Leu Leu
                245                 250                 255

His

<210> SEQ ID NO 58
<211> LENGTH: 822
<212> TYPE: DNA
<213> ORGANISM: Artificial Sequence
<220> FEATURE:
<223> OTHER INFORMATION: Synthetic Polynucleotide

<400> SEQUENCE: 58

```
gatcccgccg agcccaaatc tcctgacaaa actcacacat gcccaccgtg cccagcacct      60
gaactcctgg ggggaccgtc agtcttcctc ttccccccaa acccaaggac accctcatg     120
atctcccgga cccctgaggt cacatgcgtg gtggtggacg tgagccacga agaccctgag     180
gtcaagttca actggtacgt ggacggcgtg gaggtgcata atgccaagac aaagccgcgg     240
gaggagcagt acaacagcac gtaccgtgtg gtcagcgtcc tcaccgtcct gcaccaggac     300
tggctgaatg gcaaggagta caagtgcaag gtctccaaca aagccctccc agcccccatc     360
gagaaaacca tctccaaagc caagggcag ccccgagaac acaggtgta ccctctgccc      420
ccatcccggg atgagctgac caagaaccag gtcagcctga cctgcctggt caaaggcttc     480
tatcccagcg acatcgccgt ggagtgggag agcaatgggc aaccggagaa caactacaag     540
accacgcctc ccgtgctgga ctccgacggc tccttcttcc tctacagcaa gctcaccgtg     600
gacaagagca ggtggcagca ggggaacgtc ttctcatgct ccgtgatgca tgaggctctg     660
cacaaccact acacgcagaa gagcctctcc ctgtctccgg gtaaaaagga tcccaaattt     720
tgggtgctgg tggtggttgg tggagtcctg gcttgctata gcttgctagt aacagtggcc     780
tttattattt tctgggtgag gagtaagagg agcaggctcc tg                       822
```

<210> SEQ ID NO 59
<211> LENGTH: 44

```
<212> TYPE: PRT
<213> ORGANISM: Artificial Sequence
<220> FEATURE:
<223> OTHER INFORMATION: Synthetic Polypeptide

<400> SEQUENCE: 59

Asp Leu Glu Pro Lys Ser Cys Asp Lys Thr His Thr Cys Pro Pro Cys
1               5                   10                  15

Pro Asp Pro Lys Phe Trp Val Leu Val Val Val Gly Gly Val Leu Ala
            20                  25                  30

Cys Tyr Ser Leu Leu Val Thr Val Ala Phe Ile Ile
        35                  40

<210> SEQ ID NO 60
<211> LENGTH: 165
<212> TYPE: DNA
<213> ORGANISM: Artificial Sequence
<220> FEATURE:
<223> OTHER INFORMATION: Synthetic Polynucleotide

<400> SEQUENCE: 60
gatctcgagc ccaaatcttg tgacaaaact cacacatgcc caccgtgccc ggatcccaaa    60
ttttgggtgc tggtggtggt tggtggagtc ctggcttgct atagcttgct agtaacagtg   120
gcctttatta ttttctgggt gaggagtaag aggagcaggc cctg                    165

<210> SEQ ID NO 61
<211> LENGTH: 526
<212> TYPE: PRT
<213> ORGANISM: Artificial Sequence
<220> FEATURE:
<223> OTHER INFORMATION: Synthetic Polypeptide

<400> SEQUENCE: 61

Met Asp Trp Ile Trp Arg Ile Leu Phe Leu Val Gly Ala Ala Thr Gly
1               5                   10                  15

Ala His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Ser Asn Tyr Leu Met Asn Trp Val Lys Gln Arg Pro Glu Gln Asp Leu
    50                  55                  60

Asp Trp Ile Gly Arg Ile Asp Pro Tyr Asp Gly Asp Ile Asp Tyr Asn
65                  70                  75                  80

Gln Asn Phe Lys Asp Lys Ala Ile Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Ser Val Thr Val Ser Ser Ala Lys Thr Thr Pro Pro
    130                 135                 140

Lys Leu Glu Glu Gly Glu Phe Ser Glu Ala Arg Val Asp Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Glu Ser Val Asp Asn Tyr Gly Ile Ser Phe
            180                 185                 190

Met Asn Trp Phe Gln Gln Lys Pro Gly Gln Pro Pro Lys Leu Leu Ile
```

```
            195                 200                 205
Tyr Ala Ser Arg Gln Gly Ser Gly Val Pro Ala Arg Phe Ser Gly
    210                 215                 220

Ser Gly Ser Gly Thr Asp Phe Ser Leu Asn Ile His Pro Met Glu Glu
225                 230                 235                 240

Asp Asp Thr Ala Met Tyr Phe Cys Gln Gln Ser Lys Glu Val Pro Trp
                245                 250                 255

Thr Phe Gly Gly Gly Thr Lys Leu Glu Ile Lys Ala Glu Asp Pro Ala
            260                 265                 270

Glu Pro Lys Ser Pro Asp Lys Thr His Thr Cys Pro Pro Cys Pro Ala
                275                 280                 285

Pro Glu Leu Leu Gly Gly Pro Ser Val Phe Leu Phe Pro Pro Lys Pro
            290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
                355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Asp Glu Leu Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
            435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys Lys Asp Pro Lys Phe Trp Val Leu
            500                 505                 510

Val Val Val Gly Gly Val Leu Ala Cys Tyr Ser Leu Leu His
            515                 520                 525

<210> SEQ ID NO 62
<211> LENGTH: 1632
<212> TYPE: DNA
<213> ORGANISM: Artificial Sequence
<220> FEATURE:
<223> OTHER INFORMATION: Synthetic Polynucleotide

<400> SEQUENCE: 62
atggactgga tctggcgcat cctgtttctc gtgggagccg ccacaggcgc ccattctcag      60
gtgcagctgc agcagcctgg cgctgaactc gtgcggccag cgcttctgt gaagctgagc     120 tgtaaagcca gcggctacac cttcagcaac tacctgatga actgggtcaa gcagcggccc     180
gagcaggacc tggattggat cggcagaatc gaccctacg acggcgacat cgactacaac     240
```

```
cagaacttca aggacaaggc catcctgacc gtggacaaga gcagcagcac cgcctacatg    300
cagctgtcca gcctgaccag cgaggacagc gccgtgtact actgcgccag aggctacggc    360
acagcctacg cgtggactat ttggggccag ggcacaagcg tgaccgtgtc cagcgccaag    420
accacccccc ctaagctgga agagggcgag ttctccgagg cccgggtgga cattgtgctg    480
acacagtctc cagccagcct ggccgtgtcc ctgggacaga gagccaccat cagctgtagg    540
gccagcgaga gcgtggacaa ctacggcatc agcttcatga attggttcca gcagaagccc    600
ggccagcccc ccaagctgct gatctatgcc gccagcagac agggcagcgg agtgcctgcc    660
agattttctg gcagcggctc cggcaccgac ttcagcctga acatccaccc tatggaagag    720
gacgacaccg ccatgtactt ttgccagcag agcaaagagg tgccctggac ctttggcgga    780
ggcaccaagc tggaaatcaa ggccgaggat cccgccgagc ccaaatctcc tgacaaaact    840
cacacatgcc caccgtgccc agcacctgaa ctcctggggg gaccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag    1020
gtgcataatg ccaagacaaa gccgcgggag gagcagtaca acagcacgta ccgtgtggtc    1080
agcgtcctca ccgtcctgca ccaggactgg ctgaatggca aggagtacaa gtgcaaggtc    1140
tccaacaaag ccctcccagc cccatcgag aaaaccatct ccaaagccaa agggcagccc    1200
cgagaaccac aggtgtacac cctgccccca tcccgggatg agctgaccaa gaaccaggtc    1260
agcctgacct gcctggtcaa aggcttctat cccagcgaca tcgccgtgga gtgggagagc    1320
aatgggcaac cggagaacaa ctacaagacc acgcctcccg tgctggactc cgacggctcc    1380
ttcttcctct acagcaagct caccgtggac aagagcaggt ggcagcaggg gaacgtcttc    1440
tcatgctccg tgatgcatga ggctctgcac aaccactaca cgcagaagag cctctccctg    1500
tctccgggta aaaagatccc caaattttgg gtgctggtgg tggttggtgg agtcctggct    1560
tgctatagct tgctagtaac agtggccttt attattttct gggtgaggag taagaggagc    1620
aggctcctga ct                                                        1632
```

<210> SEQ ID NO 63
<211> LENGTH: 312
<212> TYPE: PRT
<213> ORGANISM: Artificial Sequence
<220> FEATURE:
<223> OTHER INFORMATION: Synthetic Polypeptide

<400> SEQUENCE: 63

```
Met Asp Trp Ile Trp Arg Ile Leu Phe Leu Val Gly Ala Ala Thr Gly
1               5                   10                  15

Ala His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Ser Asn Tyr Leu Met Asn Trp Val Lys Gln Arg Pro Glu Gln Asp Leu
    50                  55                  60

Asp Trp Ile Gly Arg Ile Asp Pro Tyr Asp Gly Asp Ile Asp Tyr Asn
65                  70                  75                  80

Gln Asn Phe Lys Asp Lys Ala Ile Leu Thr Val Asp Lys Ser Ser Ser
                85                  90                  95

Thr Ala Tyr Met Gln Leu Ser Ser Leu Thr Ser Glu Asp Ser Ala Val
            100                 105                 110
```

Tyr Tyr Cys Ala Arg Gly Tyr Gly Thr Ala Tyr Gly Val Asp Tyr Trp
            115                 120                 125

Gly Gln Gly Thr Ser Val Thr Val Ser Ser Ala Lys Thr Thr Pro Pro
130                 135                 140

Lys Leu Glu Glu Gly Glu Phe Ser Glu Ala Arg Val Asp Ile Val Leu
145                 150                 155                 160

Thr Gln Ser Pro Ala Ser Leu Ala Val Ser Leu Gly Gln Arg Ala Thr
            165                 170                 175

Ile Ser Cys Arg Ala Ser Glu Ser Val Asp Asn Tyr Gly Ile Ser Phe
            180                 185                 190

Met Asn Trp Phe Gln Gln Lys Pro Gly Gln Pro Pro Lys Leu Leu Ile
            195                 200                 205

Tyr Ala Ala Ser Arg Gln Gly Ser Gly Val Pro Ala Arg Phe Ser Gly
            210                 215                 220

Ser Gly Ser Gly Thr Asp Phe Ser Leu Asn Ile His Pro Met Glu Glu
225                 230                 235                 240

Asp Asp Thr Ala Met Tyr Phe Cys Gln Gln Ser Lys Glu Val Pro Trp
            245                 250                 255

Thr Phe Gly Gly Gly Thr Lys Leu Glu Ile Lys Asp Leu Glu Pro Lys
            260                 265                 270

Ser Cys Asp Lys Thr His Thr Cys Pro Pro Cys Pro Asp Pro Lys Phe
            275                 280                 285

Trp Val Leu Val Val Val Gly Val Leu Ala Cys Tyr Ser Leu Leu
            290                 295                 300

Val Thr Val Ala Phe Ile Ile His
305                 310

<210> SEQ ID NO 64
<211> LENGTH: 969
<212> TYPE: DNA
<213> ORGANISM: Artificial Sequence
<220> FEATURE:
<223> OTHER INFORMATION: Synthetic Polynucleotide

<400> SEQUENCE: 64
atggactgga tctggcgcat cctgtttctc gtgggagccg ccacaggcgc ccattctcag     60
gtgcagctgc agcagcctgg cgctgaactc gtgcggccag cgcttctgt gaagctgagc    120 tgtaaagcca gcggctacac cttcagcaac tacctgatga actgggtcaa gcagcggccc    180
gagcaggacc tggattggat cggcagaatc gaccccctacg acggcgacat cgactacaac    240
cagaacttca aggacaaggc catcctgacc gtggacaaga gcagcagcac cgcctacatg    300
cagctgtcca gcctgaccag cgaggacagc gccgtgtact actgcgccag aggctacggc    360
acagcctacg gcgtggacta ttggggccag ggcacaagcg tgaccgtgtc cagcgccaag    420
accacccccc ctaagctgga agagggcgag ttctccgagg cccgggtgga cattgtgctg    480
acacagtctc cagccagcct ggccgtgtcc ctggacagag agccaccat cagctgtagg    540 gccagcgaga gcgtggacaa ctacggcatc agcttcatga attggttcca gcagaagccc    600
ggccagcccc caagctgct gatctatgcc gccagcagac agggcagcgg agtgcctgcc    660 agatttctg gcagcggctc cggcaccgac ttcagcctga acatccaccc tatggaagag    720
gacgacaccg ccatgtactt tgccagcag agcaaagagg tgccctggac ctttggcgga    780
ggcaccaagc tggaaatcaa ggatctcgag cccaaatctt gtgacaaaac tcacacatgc    840
ccaccgtgcc cggatcccaa atttggggtg ctggtggtgg ttggtggagt cctggcttgc    900

```
tatagcttgc tagtaacagt ggcctttatt attttctggg tgaggagtaa gaggagcagg    960
ctcctgact                                                            969

<210> SEQ ID NO 65
<211> LENGTH: 747
<212> TYPE: DNA
<213> ORGANISM: Artificial Sequence
<220> FEATURE:
<223> OTHER INFORMATION: Synthetic Polynucleotide

<400> SEQUENCE: 65
tctcaggtgc agctgcagca gcctggcgct gaactcgtgc ggccaggcgc ttctgtgaag     60
ctgagctgta aagccagcgg ctacaccttc agcaactacc tgatgaactg ggtcaagcag    120
cggcccgagc aggacctgga ttggatcggc agaatcgacc cctacgacgg cgacatcgac    180
tacaaccaga acttcaagga caaggccatc ctgaccgtgg acaagagcag cagcaccgcc    240
tacatgcagc tgtccagcct gaccagcgag gacagcgccg tgtactactg cgccagaggc    300
tacggcacag cctacggcgt ggactattgg ggccagggca agcgtgac cgtgtccagc    360 gccaagacca ccccccctaa gctggaagag gcgagttct ccgaggcccg ggtggacatt    420
gtgctgacac agtctccagc cagcctggcc gtgtccctgg acagagagc caccatcagc    480 tgtagggcca gcgagagcgt ggacaactac ggcatcagct tcatgaattg gttccagcag    540
aagcccggcc agcccccaa gctgctgatc tatgccgcca gcagacaggg cagcggagtg    600
cctgccagat tttctggcag cggctccggc accgacttca gcctgaacat ccaccctatg    660
gaagaggacg acaccgccat gtactttgc cagcagagca aagaggtgcc ctggacctt    720 ggcggaggca ccaagctgga aatcaag                                        747

<210> SEQ ID NO 66
<211> LENGTH: 690
<212> TYPE: DNA
<213> ORGANISM: Artificial Sequence
<220> FEATURE:
<223> OTHER INFORMATION: Synthetic Polynucleotide

<400> SEQUENCE: 66
caggtccaac tgcagcagcc tggggctgag ctggtgaggc ctggggcttc agtgaagctg     60
tcctgcaagg cttctggcta cacgttctcc aactacttga tgaactgggt taagcagagg    120
cctgagcaag accttgactg gattggaagg attgatcctt acgatggtga cattgactac    180
aatcaaaact tcaaggacaa ggccatattg actgtagaca atcctccag cacagcctac    240 atgcaactca gcagcctgac atctgaggac tctgcggtct attactgtgc aagaggttat    300
ggcacggcct atggtgtgga ctactgggt caaggaacct cagtcaccgt ctcctcagat    360
attgtgctaa ctcagtctcc agcttctttg gctgtgtctc taggacagag ggccaccatc    420
tcctgcagag ccagcgaaag tgttgataat tatggcatta gttttatgaa ctggttccaa    480
cagaaaccag gacagccacc caaactcctc atctatgctg catccaggca aggatccggg    540
gtccctgcca ggtttagtgg cagtgggtct gggacagact tcagcctcaa catccatcct    600
atggaggagg atgatactgc aatgtatttc tgtcagcaaa gtaaggaggt tccgtggacg    660
ttcggtggag gcaccaagct ggaaatcaaa                                     690

<210> SEQ ID NO 67
<211> LENGTH: 1488
<212> TYPE: PRT
```

<213> ORGANISM: Artificial Sequence
<220> FEATURE:
<223> OTHER INFORMATION: Synthetic Polynucleotide

<400> SEQUENCE: 67

```
Cys Ala Gly Gly Thr Gly Cys Ala Gly Cys Thr Gly Cys Ala Gly Cys
1               5                   10                  15

Ala Gly Cys Cys Thr Gly Gly Cys Gly Cys Thr Gly Ala Ala Cys Thr
            20                  25                  30

Cys Gly Thr Gly Cys Gly Gly Cys Cys Ala Gly Gly Cys Gly Cys Thr
        35                  40                  45

Thr Cys Thr Gly Thr Gly Ala Ala Gly Cys Thr Gly Ala Gly Cys Thr
    50                  55                  60

Gly Thr Ala Ala Ala Gly Cys Cys Ala Gly Cys Gly Gly Cys Thr Ala
65                  70                  75                  80

Cys Ala Cys Cys Thr Thr Cys Ala Gly Cys Ala Ala Cys Thr Ala Cys
                85                  90                  95

Cys Thr Gly Ala Thr Gly Ala Ala Cys Thr Gly Gly Gly Thr Cys Ala
            100                 105                 110

Ala Gly Cys Ala Gly Cys Gly Gly Cys Cys Cys Gly Ala Gly Cys Ala
        115                 120                 125

Gly Gly Ala Cys Cys Thr Gly Gly Ala Thr Thr Gly Gly Ala Thr Cys
    130                 135                 140

Gly Gly Cys Ala Gly Ala Ala Thr Cys Gly Ala Cys Cys Cys Cys Thr
145                 150                 155                 160

Ala Cys Gly Ala Cys Gly Gly Cys Gly Ala Cys Ala Thr Cys Gly Ala
                165                 170                 175

Cys Thr Ala Cys Ala Ala Cys Cys Ala Gly Ala Ala Cys Thr Thr Cys
            180                 185                 190

Ala Ala Gly Gly Ala Cys Ala Ala Gly Gly Cys Cys Ala Thr Cys Cys
        195                 200                 205

Thr Gly Ala Cys Cys Gly Thr Gly Gly Ala Cys Ala Ala Gly Ala Gly
    210                 215                 220

Cys Ala Gly Cys Ala Gly Cys Ala Cys Cys Gly Cys Cys Thr Ala Cys
225                 230                 235                 240

Ala Thr Gly Cys Ala Gly Cys Thr Gly Thr Cys Cys Ala Gly Cys Cys
                245                 250                 255

Thr Gly Ala Cys Cys Ala Gly Cys Gly Ala Gly Gly Ala Cys Ala Gly
            260                 265                 270

Cys Gly Cys Cys Gly Thr Gly Thr Ala Cys Thr Ala Cys Thr Gly Cys
        275                 280                 285

Gly Cys Cys Ala Gly Ala Gly Gly Cys Thr Ala Cys Gly Gly Cys Ala
    290                 295                 300

Cys Ala Gly Cys Cys Thr Ala Cys Gly Gly Cys Gly Thr Gly Gly Ala
305                 310                 315                 320

Cys Thr Ala Thr Thr Gly Gly Gly Gly Cys Cys Ala Gly Gly Gly Cys
                325                 330                 335

Ala Cys Ala Ala Gly Cys Gly Thr Gly Ala Cys Cys Gly Thr Gly Thr
            340                 345                 350

Cys Cys Ala Gly Cys Gly Cys Cys Ala Ala Gly Ala Cys Cys Ala Cys
        355                 360                 365

Cys Cys Cys Cys Cys Cys Thr Ala Ala Gly Cys Thr Gly Gly Ala Ala
    370                 375                 380

Gly Ala Gly Gly Gly Cys Gly Ala Gly Thr Thr Cys Thr Cys Cys Gly
```

-continued

```
            385                 390                 395                 400
Ala Gly Gly Cys Cys Cys Gly Gly Thr Gly Gly Ala Cys Ala Thr
                    405                 410                 415
Thr Gly Thr Gly Cys Thr Gly Ala Cys Ala Cys Ala Gly Thr Cys Thr
                    420                 425                 430
Cys Cys Ala Gly Cys Cys Ala Gly Cys Cys Thr Gly Gly Cys Cys Gly
                    435                 440                 445
Thr Gly Thr Cys Cys Cys Thr Gly Gly Ala Cys Ala Gly Ala Gly
        450                 455                 460
Ala Gly Cys Cys Ala Cys Cys Ala Thr Cys Ala Gly Cys Thr Gly Thr
465                 470                 475                 480
Ala Gly Gly Gly Cys Cys Ala Gly Cys Gly Ala Gly Ala Gly Cys Gly
                    485                 490                 495
Thr Gly Gly Ala Cys Ala Ala Cys Thr Ala Cys Gly Gly Cys Ala Thr
            500                 505                 510
Cys Ala Gly Cys Thr Thr Cys Ala Thr Gly Ala Ala Thr Thr Gly Gly
                515                 520                 525
Thr Thr Cys Cys Ala Gly Cys Ala Gly Ala Ala Gly Cys Cys Cys Gly
    530                 535                 540
Gly Cys Cys Ala Gly Cys Cys Cys Cys Cys Ala Ala Gly Cys Thr
545                 550                 555                 560
Gly Cys Thr Gly Ala Thr Cys Thr Ala Thr Gly Cys Cys Gly Cys Cys
                565                 570                 575
Ala Gly Cys Ala Gly Cys Ala Gly Gly Cys Ala Gly Cys Gly
                580                 585                 590
Gly Ala Gly Thr Gly Cys Cys Thr Gly Cys Cys Ala Gly Ala Thr Thr
        595                 600                 605
Thr Thr Cys Thr Gly Gly Cys Ala Gly Cys Gly Gly Cys Thr Cys Cys
    610                 615                 620
Gly Gly Cys Ala Cys Cys Gly Ala Cys Thr Thr Cys Ala Gly Cys Cys
625                 630                 635                 640
Thr Gly Ala Ala Cys Ala Thr Cys Cys Ala Cys Cys Cys Thr Ala Thr
                645                 650                 655
Gly Gly Ala Ala Gly Ala Gly Ala Cys Gly Ala Cys Ala Cys Cys
                660                 665                 670
Gly Cys Cys Ala Thr Gly Thr Ala Cys Thr Thr Thr Thr Gly Cys Cys
            675                 680                 685
Ala Gly Cys Ala Gly Ala Gly Cys Ala Ala Gly Ala Gly Gly Thr
        690                 695                 700
Gly Cys Cys Cys Thr Gly Gly Ala Cys Thr Thr Thr Gly Gly Cys
705                 710                 715                 720
Gly Gly Ala Gly Gly Cys Ala Cys Cys Ala Gly Cys Thr Gly Gly
                725                 730                 735
Ala Ala Ala Thr Cys Ala Ala Gly Cys Ala Gly Gly Thr Gly Cys Ala
            740                 745                 750
Gly Cys Thr Gly Cys Ala Gly Cys Ala Gly Cys Cys Thr Gly Gly Cys
        755                 760                 765
Gly Cys Thr Gly Ala Ala Cys Thr Cys Gly Thr Gly Cys Gly Gly Cys
        770                 775                 780
Cys Ala Gly Gly Cys Gly Cys Thr Thr Cys Thr Gly Thr Gly Ala Ala
785                 790                 795                 800
Gly Cys Thr Gly Ala Gly Cys Thr Gly Thr Ala Ala Ala Gly Cys Cys
                805                 810                 815
```

```
Ala Gly Cys Gly Gly Cys Thr Ala Cys Ala Cys Thr Cys Ala
            820                 825                 830

Gly Cys Ala Ala Cys Thr Ala Cys Thr Gly Ala Thr Gly Ala Ala
            835                 840                 845

Cys Thr Gly Gly Gly Thr Cys Ala Ala Gly Cys Ala Gly Cys Gly Gly
            850                 855                 860

Cys Cys Cys Gly Ala Gly Cys Ala Gly Gly Ala Cys Cys Thr Gly Gly
865             870                 875                 880

Ala Thr Thr Gly Gly Ala Thr Cys Gly Gly Cys Ala Gly Ala Ala Thr
                885                 890                 895

Cys Gly Ala Cys Cys Cys Thr Ala Cys Gly Ala Cys Gly Gly Cys
            900                 905                 910

Gly Ala Cys Ala Thr Cys Gly Ala Cys Thr Ala Cys Ala Ala Cys Cys
            915                 920                 925

Ala Gly Ala Ala Cys Thr Thr Cys Ala Ala Gly Gly Ala Cys Ala Ala
            930                 935                 940

Gly Gly Cys Cys Ala Thr Cys Cys Thr Gly Ala Cys Cys Gly Thr Gly
945             950                 955                 960

Gly Ala Cys Ala Ala Gly Ala Gly Cys Ala Gly Cys Ala Gly Cys Ala
            965                 970                 975

Cys Cys Gly Cys Cys Thr Ala Cys Ala Thr Gly Cys Ala Gly Cys Thr
            980                 985                 990

Gly Thr Cys Cys Ala Gly Cys Cys  Thr Gly Ala Cys Cys  Ala Gly Cys
            995                 1000                1005

Gly Ala  Gly Gly Ala Cys Ala  Gly Cys Gly Cys Cys  Gly Thr Gly
            1010                1015                1020

Thr Ala  Cys Thr Ala Cys Thr  Gly Cys Gly Cys Cys  Ala Gly Ala
            1025                1030                1035

Gly Gly  Cys Thr Ala Cys Gly  Gly Cys Ala Cys Ala  Gly Cys Cys
            1040                1045                1050

Thr Ala  Cys Gly Gly Cys Gly  Thr Gly Gly Ala Cys  Thr Ala Thr
            1055                1060                1065

Thr Gly  Gly Gly Gly Cys Cys  Ala Gly Gly Gly Cys  Ala Cys Ala
            1070                1075                1080

Ala Gly  Cys Gly Thr Gly Ala  Cys Cys Gly Thr Gly  Thr Cys Cys
            1085                1090                1095

Ala Gly  Cys Gly Cys Cys Ala  Ala Gly Ala Cys Cys  Ala Cys Cys
            1100                1105                1110

Cys Cys  Cys Cys Cys Thr Ala  Ala Gly Cys Thr Gly  Gly Ala Ala
            1115                1120                1125

Gly Ala  Gly Gly Gly Cys Gly  Ala Gly Thr Thr Cys  Thr Cys Cys
            1130                1135                1140

Gly Ala  Gly Gly Cys Cys Gly  Gly Gly Thr Gly  Gly Ala Cys
            1145                1150                1155

Ala Thr  Thr Gly Thr Gly Cys  Thr Gly Ala Cys Ala  Cys Ala Gly
            1160                1165                1170

Thr Cys  Thr Cys Cys Ala Gly  Cys Cys Ala Gly Cys  Cys Thr Gly
            1175                1180                1185

Gly Cys  Cys Gly Thr Gly Thr  Cys Cys Thr Gly  Gly Gly Ala
            1190                1195                1200

Cys Ala  Gly Ala Gly Ala Gly  Cys Cys Ala Cys  Ala Thr Cys
            1205                1210                1215
```

```
Ala Gly Cys Thr Gly Thr Ala Gly Gly Cys Cys Ala Gly Cys
    1220            1225             1230

Gly Ala Gly Ala Gly Cys Gly Thr Gly Ala Cys Ala Ala Cys
    1235            1240             1245

Thr Ala Cys Gly Gly Cys Ala Thr Cys Ala Gly Cys Thr Thr Cys
    1250            1255             1260

Ala Thr Gly Ala Ala Thr Thr Gly Gly Thr Thr Cys Cys Ala Gly
    1265            1270             1275

Cys Ala Gly Ala Ala Gly Cys Cys Cys Gly Gly Cys Cys Ala Gly
    1280            1285             1290

Cys Cys Cys Cys Cys Cys Ala Ala Gly Cys Thr Gly Cys Thr Gly
    1295            1300             1305

Ala Thr Cys Thr Ala Thr Gly Cys Cys Gly Cys Ala Gly Cys
    1310            1315             1320

Ala Gly Ala Cys Ala Gly Gly Cys Ala Gly Cys Gly Gly Ala
    1325            1330             1335

Gly Thr Gly Cys Cys Thr Gly Cys Cys Ala Gly Ala Thr Thr Thr
    1340            1345             1350

Thr Cys Thr Gly Gly Cys Ala Gly Cys Gly Gly Cys Thr Cys Cys
    1355            1360             1365

Gly Gly Cys Ala Cys Cys Gly Ala Cys Thr Thr Cys Ala Gly Cys
    1370            1375             1380

Cys Thr Gly Ala Ala Cys Ala Thr Cys Cys Ala Cys Cys Cys Thr
    1385            1390             1395

Ala Thr Gly Gly Ala Ala Gly Ala Gly Ala Cys Gly Ala Cys
    1400            1405             1410

Ala Cys Cys Gly Cys Cys Ala Thr Gly Thr Ala Cys Thr Thr Thr
    1415            1420             1425

Thr Gly Cys Cys Ala Gly Cys Ala Gly Ala Gly Cys Ala Ala Ala
    1430            1435             1440

Gly Ala Gly Gly Thr Gly Cys Cys Cys Thr Gly Gly Ala Cys Cys
    1445            1450             1455

Thr Thr Thr Gly Gly Cys Gly Ala Gly Gly Cys Ala Cys Cys
    1460            1465             1470

Ala Ala Gly Cys Thr Gly Gly Ala Ala Ala Thr Cys Ala Ala Gly
    1475            1480             1485

<210> SEQ ID NO 68
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 68

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 69
<211> LENGTH: 144
<212> TYPE: DNA
<213> ORGANISM: Artificial Sequence
<220> FEATURE:
```

-continued

<223> OTHER INFORMATION: Synthetic Polynucleotide

<400> SEQUENCE: 69

```
caacgaagga aatatagatc aaacaaagga gaaagtcctg tggagcctgc agagccttgt    60
cgttacagct gccccaggga ggaggagggc agcaccatcc ccatccagga ggattaccga   120
aaaccggagc ctgcctgctc cccc                                         144
```

<210> SEQ ID NO 70
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 70

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 71
<211> LENGTH: 186
<212> TYPE: DNA
<213> ORGANISM: Artificial Sequence
<220> FEATURE:
<223> OTHER INFORMATION: Synthetic Polynucleotide

<400> SEQUENCE: 71

```
aagaaggtgg ccaagaagcc caccaacaag gcccccacc ctaagcagga accccaggaa    60
atcaacttcc ccgacgacct gcccggcagc aatactgctg ctcccgtgca ggaaaccctg   120
cacggctgtc agcctgtgac ccaggaagat ggcaaagaaa gccggatcag cgtgcaggaa   180
cggcag                                                             186
```

<210> SEQ ID NO 72
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 72

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile
        35

<210> SEQ ID NO 73
<211> LENGTH: 108
<212> TYPE: DNA
<213> ORGANISM: Artificial Sequence
<220> FEATURE:
<223> OTHER INFORMATION: Synthetic Polynucleotide

<400> SEQUENCE: 73

```
agggaccaga ggctgccccc cgatgcccac aagcccctg ggggaggcag tttccggacc      60
cccatccaag aggagcaggc cgacgcccac tccaccctgg ccaagatc                  108
```

```
<210> SEQ ID NO 74
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 74
```

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

```
<210> SEQ ID NO 75
<211> LENGTH: 126
<212> TYPE: DNA
<213> ORGANISM: Artificial Sequence
<220> FEATURE:
<223> OTHER INFORMATION: Synthetic Polynucleotide

<400> SEQUENCE: 75
```

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

```
<210> SEQ ID NO 76
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 76
```

```
Cys Trp Leu Thr Lys Lys Lys Tyr Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35
```

```
<210> SEQ ID NO 77
<211> LENGTH: 114
<212> TYPE: DNA
<213> ORGANISM: Artificial Sequence
<220> FEATURE:
<223> OTHER INFORMATION: Synthetic Polynucleotide

<400> SEQUENCE: 77
```

```
tgctggctga ccaaaaaaaa atatagcagc agcgtgcatg atccgaacgg cgaatatatg    60
tttatgcgcg cggtgaacac cgcgaaaaaa agccgcctga ccgatgtgac cctg         114
```

```
<210> SEQ ID NO 78
<211> LENGTH: 172
<212> TYPE: PRT
<213> ORGANISM: Artificial Sequence
<220> FEATURE:
<223> OTHER INFORMATION: Synthetic Polypeptide
```

<400> SEQUENCE: 78

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Ala Glu Lys Pro
        115                 120                 125

Leu Gln Val Ala Ala Val Asp Ser Ser Val Pro Arg Thr Ala Glu Leu
130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 79
<211> LENGTH: 516
<212> TYPE: DNA
<213> ORGANISM: Artificial Sequence
<220> FEATURE:
<223> OTHER INFORMATION: Synthetic Polynucleotide

<400> SEQUENCE: 79
atggctgctg gcggacctgg cgccggatct gctgctcctg tgtctagcac aagcagcctg      60
cctctggccg ccctgaacat gagagtgcgg agaaggctga gcctgttcct gaacgtgcgg     120
acacaggtgg ccgccgattg gacagccctg gccgaggaaa tggacttcga gtacctggaa     180
atccggcagc tggaaaccca ggccgaccct acaggcagac tgctggatgc ttggcagggc     240
agaccaggcg cttctgtggg aaggctgctg gaactgctga ccaagctggg cagggacgac     300
gtgctgctgg aactgggccc tagcatcgaa gaggactgcc agaagtacat cctgaagcag     360
cagcaggaag aggccgagaa gcctctgcag gtggcagccg tggatagcag cgtgccaaga     420
acagccgagc tggccggcat caccaccctg gatgatcctc tgggccacat gcccgagaga     480
ttcgacgcct tcatctgcta ctgccccagc gacatc                               516

<210> SEQ ID NO 80
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 80

Ala Lys Thr Thr Pro Pro Lys Leu Glu Glu Gly Glu Phe Ser Glu Ala
1               5                   10                  15

Arg Val

<210> SEQ ID NO 81
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 81

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 82
<211> LENGTH: 126
<212> TYPE: DNA
<213> ORGANISM: Artificial Sequence
<220> FEATURE:
<223> OTHER INFORMATION: Synthetic Polynucleotide

<400> SEQUENCE: 82
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                               126

<210> SEQ ID NO 83
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 83

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile
        35

<210> SEQ ID NO 84
<211> LENGTH: 108
<212> TYPE: DNA
<213> ORGANISM: Artificial Sequence
<220> FEATURE:
<223> OTHER INFORMATION: Synthetic Polynucleotide

<400> SEQUENCE: 84
agggaccaga ggctgccccc cgatgcccac aagccccctg ggggaggcag tttccggacc      60
cccatccaag aggagcaggc cgacgcccac tccaccctgg ccaagatc                 108

<210> SEQ ID NO 85
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 85

Cys Asp Ile Tyr Ile Trp Ala Pro Leu Ala Gly Thr Cys Gly Val Leu

<210> SEQ ID NO 86
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 86

```
tgtgatatct acatctgggc gcccttggcc gggacttgtg gggtccttct cctgtcactg      60
gttatcaccc tttactgcaa ccacaggaac                                      90
```

<210> SEQ ID NO 87
<211> LENGTH: 154
<212> TYPE: PRT
<213> ORGANISM: Artificial Sequence
<220> FEATURE:
<223> OTHER INFORMATION: Synthetic Polypeptide

<400> SEQUENCE: 87

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Gln Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140

Ala Leu His Met Gln Ala Leu Pro Pro Arg
145                 150

<210> SEQ ID NO 88
<211> LENGTH: 462
<212> TYPE: DNA
<213> ORGANISM: Artificial Sequence
<220> FEATURE:
<223> OTHER INFORMATION: Synthetic Polynucleotide

<400> SEQUENCE: 88

```
aaacggggca gaaagaaact cctgtatata ttcaaacaac catttatgag accagtacaa      60
actactcaag aggaagatgg ctgtagctgc cgatttccag aagaagaaga aggaggatgt     120
gaactgagag tgaagttcag caggagcgca gacgcccccg cgtaccagca gggccagaac     180
cagctctata acgagctcaa tctaggacga agagaggagt acgatgtttt ggacaagaga     240
cgtggccggg accctgagat ggggggaaag ccgagaagga agaaccctca ggaaggcctg     300
```

1               5                   10                  15
Leu Leu Ser Leu Val Ile Thr Leu Tyr Cys Asn His Arg Asn
            20                  25                  30

```
tacaatgaac tgcagaaaga taagatggcg gaggcctaca gtgagattgg gatgaaaggc    360
gagcgccgga ggggcaaggg gcacgatggc ctttaccagg gtctcagtac agccaccaag    420
gacacctacg acgcccttca catgcaggcc ctgccccctc gc                      462
```

<210> SEQ ID NO 89
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 89

```
Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile Arg Val Lys Phe Ser Arg Ser Ala Asp Ala Pro Ala
        35                  40                  45

Tyr Gln Gln Gly Gln Asn Gln Leu Tyr Asn Glu Leu Asn Leu Gly Arg
    50                  55                  60

Arg Glu Glu Tyr Asp Val Leu Asp Lys Arg Arg Gly Arg Asp Pro Glu
65                  70                  75                  80

Met Gly Gly Lys Pro Arg Arg Lys Asn Pro Gln Glu Gly Leu Tyr Asn
                85                  90                  95

Glu Leu Gln Lys Asp Lys Met Ala Glu Ala Tyr Ser Glu Ile Gly Met
            100                 105                 110

Lys Gly Glu Arg Arg Arg Gly Lys Gly His Asp Gly Leu Tyr Gln Gly
        115                 120                 125

Leu Ser Thr Ala Thr Lys Asp Thr Tyr Asp Ala Leu His Met Gln Ala
    130                 135                 140

Leu Pro Pro Arg
145
```

<210> SEQ ID NO 90
<211> LENGTH: 444
<212> TYPE: DNA
<213> ORGANISM: Artificial Sequence
<220> FEATURE:
<223> OTHER INFORMATION: Synthetic Polynucleotide

<400> SEQUENCE: 90

```
agggaccaga ggctgccccc cgatgcccac aagccccctg ggggaggcag tttccggacc     60
cccatccaag aggagcaggc cgacgcccac tccaccctgg ccaagatcag agtgaagttc    120
agcaggagcg cagacgcccc cgcgtaccag cagggccaga accagctcta taacgagctc    180
aatctaggac gaagagagga gtacgatgtt ttggacaaga gacgtggccg ggaccctgag    240
atggggggaa agccgagaag gaagaaccct caggaaggcc tgtacaatga actgcagaaa    300
gataagatgg cggaggccta cagtgagatt ggatgaaagg cgagcgccg gaggggcaag    360 gggcacgatg gcctttacca gggtctcagt acagccacca aggacaccta cgacgccctt    420
cacatgcagg ccctgccccc tcgc                                           444
```

<210> SEQ ID NO 91
<211> LENGTH: 222
<212> TYPE: PRT
<213> ORGANISM: Artificial Sequence
<220> FEATURE:
<223> OTHER INFORMATION: Synthetic Polypeptide

<400> SEQUENCE: 91

| Phe | Trp | Val | Leu | Val | Val | Gly | Gly | Val | Leu | Ala | Cys | Tyr | Ser | Leu |
|---|---|---|---|---|---|---|---|---|---|---|---|---|---|---|
| 1 | | | | 5 | | | | | 10 | | | | | 15 |

| Leu | Val | Thr | Val | Ala | Phe | Ile | Ile | Phe | Trp | Val | Arg | Ser | Lys | Arg | Ser |
|---|---|---|---|---|---|---|---|---|---|---|---|---|---|---|---|
| | | | 20 | | | | | 25 | | | | | 30 | | |

| Arg | Leu | Leu | His | Ser | Asp | Tyr | Met | Asn | Met | Thr | Pro | Arg | Arg | Pro | Gly |
|---|---|---|---|---|---|---|---|---|---|---|---|---|---|---|---|
| | | | 35 | | | | 40 | | | | | 45 | | | |

| Pro | Thr | Arg | Lys | His | Tyr | Gln | Pro | Tyr | Ala | Pro | Pro | Arg | Asp | Phe | Ala |
|---|---|---|---|---|---|---|---|---|---|---|---|---|---|---|---|
| | 50 | | | | | 55 | | | | | 60 | | | | |

| Ala | Tyr | Arg | Ser | Lys | Arg | Gly | Arg | Lys | Lys | Leu | Leu | Tyr | Ile | Phe | Lys |
|---|---|---|---|---|---|---|---|---|---|---|---|---|---|---|---|
| 65 | | | | | 70 | | | | | 75 | | | | | 80 |

| Gln | Pro | Phe | Met | Arg | Pro | Val | Gln | Thr | Thr | Gln | Glu | Glu | Asp | Gly | Cys |
|---|---|---|---|---|---|---|---|---|---|---|---|---|---|---|---|
| | | | | 85 | | | | | 90 | | | | | 95 | |

| Ser | Cys | Arg | Phe | Pro | Glu | Glu | Glu | Gly | Gly | Cys | Glu | Leu | Arg | Val |
|---|---|---|---|---|---|---|---|---|---|---|---|---|---|---|
| | | | | 100 | | | | | 105 | | | | 110 | |

| Lys | Phe | Ser | Arg | Ser | Ala | Asp | Ala | Pro | Ala | Tyr | Gln | Gln | Gly | Gln | Asn |
|---|---|---|---|---|---|---|---|---|---|---|---|---|---|---|---|
| | | | 115 | | | | 120 | | | | | 125 | | | |

| Gln | Leu | Tyr | Asn | Glu | Leu | Asn | Leu | Gly | Arg | Arg | Glu | Glu | Tyr | Asp | Val |
|---|---|---|---|---|---|---|---|---|---|---|---|---|---|---|---|
| | 130 | | | | | 135 | | | | | 140 | | | | |

| Leu | Asp | Lys | Arg | Arg | Gly | Arg | Asp | Pro | Glu | Met | Gly | Gly | Lys | Pro | Arg |
|---|---|---|---|---|---|---|---|---|---|---|---|---|---|---|---|
| 145 | | | | | 150 | | | | | 155 | | | | | 160 |

| Arg | Lys | Asn | Pro | Gln | Glu | Gly | Leu | Tyr | Asn | Glu | Leu | Gln | Lys | Asp | Lys |
|---|---|---|---|---|---|---|---|---|---|---|---|---|---|---|---|
| | | | | 165 | | | | | 170 | | | | | 175 | |

| Met | Ala | Glu | Ala | Tyr | Ser | Glu | Ile | Gly | Met | Lys | Gly | Glu | Arg | Arg |
|---|---|---|---|---|---|---|---|---|---|---|---|---|---|---|
| | | 180 | | | | | 185 | | | | | 190 | | |

| Gly | Lys | Gly | His | Asp | Gly | Leu | Tyr | Gln | Gly | Leu | Ser | Thr | Ala | Thr | Lys |
|---|---|---|---|---|---|---|---|---|---|---|---|---|---|---|---|
| | | | 195 | | | | 200 | | | | | 205 | | | |

| Asp | Thr | Tyr | Asp | Ala | Leu | His | Met | Gln | Ala | Leu | Pro | Pro | Arg |
|---|---|---|---|---|---|---|---|---|---|---|---|---|---|
| | 210 | | | | | 215 | | | | | 220 | | |

<210> SEQ ID NO 92
<211> LENGTH: 666
<212> TYPE: DNA
<213> ORGANISM: Artificial Sequence
<220> FEATURE:
<223> OTHER INFORMATION: Synthetic Polynucleotide

<400> SEQUENCE: 92

```
ttttgggtgc tggtggtggt tggtggagtc ctggcttgct atagcttgct agtaacagtg     60
gcctttatta ttttctgggt gaggagtaag aggagcaggc tcctgcacag tgactacatg    120
aacatgactc cccgccgccc cgggcccacc cgcaagcatt accagcccta tgccccacca    180
cgcgacttcg cagcctatcg ctccaaacgg ggcagaaaga aactcctgta tatattcaaa    240
caaccattta tgagaccagt acaaactact caagaggaag atggctgtag ctgccgattt    300
ccagaagaag aagaaggagg atgtgaactg agagtgaagt tcagcaggag cgcagacgcc    360
cccgcgtacc agcagggcca gaaccagctc tataacgagc tcaatctagg acgaagagag    420
gagtacgatg ttttggacaa gagacgtggc cgggaccctg agatgggggg aaagccgaga    480
aggaagaacc ctcaggaagg cctgtacaat gaactgcaga agataagat ggcggaggcc    540
tacagtgaga ttgggatgaa aggcgagcgc ggaggggca aggggcacga tggcctttac    600
cagggtctca gtacagccac caaggacacc tacgacgccc ttcacatgca ggccctgccc    660
cctcgc                                                              666
```

<210> SEQ ID NO 93
<211> LENGTH: 184
<212> TYPE: PRT
<213> ORGANISM: Artificial Sequence
<220> FEATURE:
<223> OTHER INFORMATION: Synthetic Polypeptide

<400> SEQUENCE: 93

```
Cys Asp Ile Tyr Ile Trp Ala Pro Leu Ala Gly Thr Cys Gly Val Leu
1               5                   10                  15

Leu Leu Ser Leu Val Ile Thr Leu Tyr Cys Asn His Arg Asn Lys Arg
            20                  25                  30

Gly Arg Lys Lys Leu Leu Tyr Ile Phe Lys Gln Pro Phe Met Arg Pro
        35                  40                  45

Val Gln Thr Thr Gln Glu Glu Asp Gly Cys Ser Cys Arg Phe Pro Glu
    50                  55                  60

Glu Glu Glu Gly Gly Cys Glu Leu Arg Val Lys Phe Ser Arg Ser Ala
65                  70                  75                  80

Asp Ala Pro Ala Tyr Gln Gln Gly Gln Asn Gln Leu Tyr Asn Glu Leu
                85                  90                  95

Asn Leu Gly Arg Arg Glu Glu Tyr Asp Val Leu Asp Lys Arg Arg Gly
            100                 105                 110

Arg Asp Pro Glu Met Gly Gly Lys Pro Arg Arg Lys Asn Pro Gln Glu
        115                 120                 125

Gly Leu Tyr Asn Glu Leu Gln Lys Asp Lys Met Ala Glu Ala Tyr Ser
    130                 135                 140

Glu Ile Gly Met Lys Gly Glu Arg Arg Arg Gly Lys Gly His Asp Gly
145                 150                 155                 160

Leu Tyr Gln Gly Leu Ser Thr Ala Thr Lys Asp Thr Tyr Asp Ala Leu
                165                 170                 175

His Met Gln Ala Leu Pro Pro Arg
            180
```

<210> SEQ ID NO 94
<211> LENGTH: 552
<212> TYPE: DNA
<213> ORGANISM: Artificial Sequence
<220> FEATURE:
<223> OTHER INFORMATION: Synthetic Polynucleotide

<400> SEQUENCE: 94

```
tgtgatatct acatctgggc gcccttggcc gggacttgtg gggtccttct cctgtcactg      60
gttatcaccc tttactgcaa ccacaggaac aaacggggca gaaagaaact cctgtatata     120
ttcaaacaac catttatgag accagtacaa actactcaag aggaagatgg ctgtagctgc     180
cgatttccag aagaagaaga aggaggatgt gaactgagag tgaagttcag caggagcgca     240
gacgccccg cgtaccagca gggccagaac cagctctata acgagctcaa tctaggacga     300
agagaggagt acgatgtttt ggacaagaga cgtggccggg accctgagat gggggggaaag     360
ccgagaagga agaaccctca ggaaggcctg tacaatgaac tgcagaaaga taagatggcg     420
gaggcctaca gtgagattgg gatgaaaggc gagcgccgga ggggcaaggg gcacgatggc     480
ctttaccagg gtctcagtac agccaccaag gacacctacg acgcccttca catgcaggcc     540
ctgccccctc gc                                                          552
```

<210> SEQ ID NO 95
<211> LENGTH: 216

```
<212> TYPE: PRT
<213> ORGANISM: Artificial Sequence
<220> FEATURE:
<223> OTHER INFORMATION: Synthetic Polypeptide

<400> SEQUENCE: 95

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Arg Asp Phe Ala
    50                  55                  60

Ala Tyr Arg Ser Arg Asp Gln Arg Leu Pro Pro Asp Ala His Lys Pro
65                  70                  75                  80

Pro Gly Gly Gly Ser Phe Arg Thr Pro Ile Gln Glu Glu Gln Ala Asp
                85                  90                  95

Ala His Ser Thr Leu Ala Lys Ile Arg Val Lys Phe Ser Arg Ser Ala
            100                 105                 110

Asp Ala Pro Ala Tyr Gln Gln Gly Gln Asn Gln Leu Tyr Asn Glu Leu
        115                 120                 125

Asn Leu Gly Arg Arg Glu Glu Tyr Asp Val Leu Asp Lys Arg Arg Gly
130                 135                 140

Arg Asp Pro Glu Met Gly Gly Lys Pro Arg Arg Lys Asn Pro Gln Glu
145                 150                 155                 160

Gly Leu Tyr Asn Glu Leu Gln Lys Asp Lys Met Ala Glu Ala Tyr Ser
                165                 170                 175

Glu Ile Gly Met Lys Gly Glu Arg Arg Arg Gly Lys Gly His Asp Gly
            180                 185                 190

Leu Tyr Gln Gly Leu Ser Thr Ala Thr Lys Asp Thr Tyr Asp Ala Leu
        195                 200                 205

His Met Gln Ala Leu Pro Pro Arg
    210                 215

<210> SEQ ID NO 96
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 96
ttttgggtgc tggtggtggt tggtggagtc ctggcttgct atagcttgct agtaacagtg      60
gcctttatta ttttctgggt gaggagtaag aggagcaggc tcctgcacag tgactacatg     120
aacatgactc cccgccgccc cgggcccacc cgcaagcatt accagcccta tgccccacca     180
cgcgacttcg cagcctatcg ctccagggac cagaggctgc cccccgatgc cacaagccc      240 cctgggggag gcagtttccg gacccccatc aagaggagc aggccgacgc ccactccacc      300
ctggccaaga tcagagtgaa gttcagcagg agcgcagacg cccccgcgta ccagcagggc     360
cagaaccagc tctataacga gctcaatcta ggacgaagag aggagtacga tgttttggac     420
aagagacgtg gccgggaccc tgagatgggg ggaaagccga aaggaagaa ccctcaggaa      480 ggcctgtaca atgaactgca gaaagataag atggcgaggc ctacagtga gattgggatg      540 aaaggcgagc gccggagggg caaggggcac gatggccttt accagggtct cagtacagcc     600
```
accaaggaca cctacgacgc ccttcacatg caggccctgc cccctcgc            648

<210> SEQ ID NO 97
<211> LENGTH: 509
<212> TYPE: PRT
<213> ORGANISM: Artificial Sequence
<220> FEATURE:
<223> OTHER INFORMATION: Synthetic Polypeptide

<400> SEQUENCE: 97

```
Met Asp Trp Ile Trp Arg Ile Leu Phe Leu Val Gly Ala Ala Thr Gly
1               5                   10                  15

Ala His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Ser Asn Tyr Leu Met Asn Trp Val Lys Gln Arg Pro Glu Gln Asp Leu
    50                  55                  60

Asp Trp Ile Gly Arg Ile Asp Pro Tyr Asp Gly Asp Ile Asp Tyr Asn
65                  70                  75                  80

Gln Asn Phe Lys Asp Lys Ala Ile Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Ser Val Thr Val Ser Ser Ala Lys Thr Thr Pro Pro
    130                 135                 140

Lys Leu Glu Glu Gly Glu Phe Ser Glu Ala Arg Val Asp Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Glu Ser Val Asp Asn Tyr Gly Ile Ser Phe
            180                 185                 190

Met Asn Trp Phe Gln Gln Lys Pro Gly Gln Pro Pro Lys Leu Leu Ile
        195                 200                 205

Tyr Ala Ala Ser Arg Gln Gly Ser Gly Val Pro Ala Arg Phe Ser Gly
    210                 215                 220

Ser Gly Ser Gly Thr Asp Phe Ser Leu Asn Ile His Pro Met Glu Glu
225                 230                 235                 240

Asp Asp Thr Ala Met Tyr Phe Cys Gln Gln Ser Lys Glu Val Pro Trp
                245                 250                 255

Thr Phe Gly Gly Gly Thr Lys Leu Glu Ile Lys Asp Leu Glu Pro Lys
            260                 265                 270

Ser Cys Asp Lys Thr His Thr Cys Pro Pro Cys Pro Asp Pro Lys Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Lys Arg Gly Arg Lys Lys Leu Leu Tyr Ile Phe Lys Gln
```

|     |     |     |     | 355 |     |     |     |     | 360 |     |     |     |     | 365 |     |
| --- | --- | --- | --- | --- | --- | --- | --- | --- | --- | --- | --- | --- | --- | --- | --- |

Pro Phe Met Arg Pro Val Gln Thr Thr Gln Glu Glu Asp Gly Cys Ser
370                     375                     380

Cys Arg Phe Pro Glu Glu Glu Gly Gly Cys Glu Leu Arg Val Lys
385                     390                     395                     400

Phe Ser Arg Ser Ala Asp Ala Pro Ala Tyr Gln Gln Gly Gln Asn Gln
                405                     410                     415

Leu Tyr Asn Glu Leu Asn Leu Gly Arg Arg Glu Glu Tyr Asp Val Leu
            420                     425                     430

Asp Lys Arg Arg Gly Arg Asp Pro Glu Met Gly Gly Lys Pro Arg Arg
        435                     440                     445

Lys Asn Pro Gln Glu Gly Leu Tyr Asn Glu Leu Gln Lys Asp Lys Met
    450                     455                     460

Ala Glu Ala Tyr Ser Glu Ile Gly Met Lys Gly Glu Arg Arg Arg Gly
465                     470                     475                     480

Lys Gly His Asp Gly Leu Tyr Gln Gly Leu Ser Thr Ala Thr Lys Asp
                485                     490                     495

Thr Tyr Asp Ala Leu His Met Gln Ala Leu Pro Pro Arg
            500                     505

<210> SEQ ID NO 98
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 98

```
atggactgga tctggcgcat cctgtttctc gtgggagccg ccacaggcgc ccattctcag      60
gtgcagctgc agcagcctgg cgctgaactc gtgcggccag gcgcttctgt gaagctgagc     120
tgtaaagcca gcggctacac cttcagcaac tacctgatga actgggtcaa gcagcggccc     180
gagcaggacc tggattggat cggcagaatc gaccccctac gacggcgacat cgactacaac     240
cagaacttca aggacaaggc catcctgacc gtggacaaga gcagcagcac cgcctacatg     300
cagctgtcca gcctgaccag cgaggacagc gccgtgtact actgcgccag aggctacggc     360
acagcctacg gcgtggacta ttggggccag ggcacaagcg tgaccgtgtc cagcgccaag     420
accaccccc ctaagctgga agagggcgag ttctccgagg cccgggtgga cattgtgctg     480
acacagtctc cagccagcct ggccgtgtcc ctgggacaga gagccaccat cagctgtagg     540
gccagcgaga gcgtggacaa ctacggcatc agcttcatga attggttcca gcagaagccc     600
ggccagcccc ccaagctgct gatctatgcc gccagcagac agggcagcgg agtgcctgcc     660
agatttctg gcagcggctc cggcaccgac ttcagcctga catccacccc tatggaagag     720
gacgacaccg ccatgtactt ttgccagcag agcaaagagg tgccctggac ctttggcgga     780
ggcaccaagc tggaaatcaa ggatctcgag cccaaatctt gtgacaaaac tcacacatgc     840
ccaccgtgcc cggatcccaa attttgggtg ctggtggtgg ttggtggagt cctggcttgc     900
tatagcttgc tagtaacagt ggcctttatt attttctggg tgaggagtaa gaggagcagg     960
ctcctgcaca gtgactacat gaacatgact ccccgccgcc ccgggcccac ccgcaagcat    1020
taccagccct atgccccacc acgcgacttc gcagcctatc gctccaaacg ggcagaaag    1080
aaactcctgt atatattcaa caaccatttt atgagaccag tacaaactac tcaagaggaa    1140
gatggctgta gctgccgatt ccagaagaa gaagaaggag gatgtgaact gagagtgaag    1200
```

```
ttcagcagga gcgcagacgc ccccgcgtac cagcagggcc agaaccagct ctataacgag    1260
ctcaatctag gacgaagaga ggagtacgat gttttggaca agagacgtgg ccgggaccct    1320
gagatggggg gaaagccgag aaggaagaac cctcaggaag gcctgtacaa tgaactgcag    1380
aaagataaga tggcggaggc ctacagtgag attgggatga aggcgagcg ccggaggggc    1440 aaggggcacg atggccttta ccagggtctc agtacagcca ccaaggacac ctacgacgcc    1500
cttcacatgc aggccctgcc ccctcgc                                       1527
```

<210> SEQ ID NO 99
<211> LENGTH: 503
<212> TYPE: PRT
<213> ORGANISM: Artificial Sequence
<220> FEATURE:
<223> OTHER INFORMATION: Synthetic Polypeptide

<400> SEQUENCE: 99

```
Met Asp Trp Ile Trp Arg Ile Leu Phe Leu Val Gly Ala Ala Thr Gly
1               5                   10                  15

Ala His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Ser Asn Tyr Leu Met Asn Trp Val Lys Gln Arg Pro Glu Gln Asp Leu
    50                  55                  60

Asp Trp Ile Gly Arg Ile Asp Pro Tyr Asp Gly Asp Ile Asp Tyr Asn
65                  70                  75                  80

Gln Asn Phe Lys Asp Lys Ala Ile Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Ser Val Thr Val Ser Ser Ala Lys Thr Thr Pro Pro
    130                 135                 140

Lys Leu Glu Glu Gly Glu Phe Ser Glu Ala Arg Val Asp Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Glu Ser Val Asp Asn Tyr Gly Ile Ser Phe
            180                 185                 190

Met Asn Trp Phe Gln Gln Lys Pro Gly Gln Pro Pro Lys Leu Leu Ile
        195                 200                 205

Tyr Ala Ala Ser Arg Gln Gly Ser Gly Val Pro Ala Arg Phe Ser Gly
    210                 215                 220

Ser Gly Ser Gly Thr Asp Phe Ser Leu Asn Ile His Pro Met Glu Glu
225                 230                 235                 240

Asp Asp Thr Ala Met Tyr Phe Cys Gln Gln Ser Lys Glu Val Pro Trp
                245                 250                 255

Thr Phe Gly Gly Gly Thr Lys Leu Glu Ile Lys Asp Leu Glu Pro Lys
            260                 265                 270

Ser Cys Asp Lys Thr His Thr Cys Pro Pro Cys Pro Asp Pro Lys Phe
        275                 280                 285

Trp Val Leu Val Val Val Gly Gly Val Leu Ala Cys Tyr Ser Leu Leu
    290                 295                 300
```

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Arg Asp Gln Arg Leu Pro Pro Asp Ala His Lys Pro Pro
        355                 360                 365

Gly Gly Gly Ser Phe Arg Thr Pro Ile Gln Glu Glu Gln Ala Asp Ala
    370                 375                 380

His Ser Thr Leu Ala Lys Ile Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
                500

<210> SEQ ID NO 100
<211> LENGTH: 1509
<212> TYPE: DNA
<213> ORGANISM: Artificial Sequence
<220> FEATURE:
<223> OTHER INFORMATION: Synthetic Polynucleotide

<400> SEQUENCE: 100
atggactgga tctggcgcat cctgtttctc gtgggagccg ccacaggcgc ccattctcag    60
gtgcagctgc agcagcctgg cgctgaactc gtgcggccag cgcttctgt gaagctgagc    120 tgtaaagcca gcggctacac cttcagcaac tacctgatga ctgggtcaa gcagcggccc    180 gagcaggacc tggattggat cggcagaatc gacccctacg acggcgacat cgactacaac    240
cagaacttca aggacaaggc catcctgacc gtggacaaga gcagcagcac cgcctacatg    300
cagctgtcca gcctgaccag cgaggacagc gccgtgtact actgcgccag aggctacggc    360
acagcctacg gcgtggacta ttggggccag ggcacaagcg tgaccgtgtc cagcgccaag    420 accaccccc ctaagctgga gagggcgag ttctccgagg cccggtgga cattgtgctg    480 acacagtctc cagccagcct ggccgtgtcc ctgggacaga gagccaccat cagctgtagg    540
gccagcgaga gcgtggacaa ctacggcatc agcttcatga attggttcca gcagaagccc    600
ggccagcccc ccaagctgct gatctatgcc gccagcagac agggcagcgg agtgcctgcc    660
agattttctg gcagcggctc cggcaccgac ttcagcctga acatccaccc tatggaagag    720
gacgacaccg ccatgtactt ttgccagcag agcaaagagg tgccctggac ctttggcgga    780
ggcaccaagc tggaaatcaa ggatctcgag cccaaatctt gtgacaaaac tcacacatgc    840
ccaccgtgcc cggatcccaa attttgggtg ctggtggtgg ttggtggagt cctggcttgc    900

```
tatagcttgc tagtaacagt ggcctttatt attttctggg tgaggagtaa gaggagcagg    960
ctcctgcaca gtgactacat gaacatgact ccccgccgcc ccgggcccac ccgcaagcat   1020
taccagccct atgccccacc acgcgacttc gcagcctatc gctccaggga ccagaggctg   1080
cccccgatg cccacaagcc ccctggggga ggcagtttcc ggaccccat ccaagaggag    1140
caggccgacg cccactccac cctggccaag atcagagtga agttcagcag gagcgcagac   1200
gccccgcgt accagcaggg ccagaaccag ctctataacg agctcaatct aggacgaaga    1260
gaggagtacg atgttttgga caagagacgt ggccgggacc ctgagatggg gggaaagccg   1320
agaaggaaga accctcagga aggcctgtac aatgaactgc agaaagataa gatggcggag   1380
gcctacagtg agattgggat gaaaggcgag cgccggaggg caaggggca cgatggcctt    1440
taccagggtc tcagtacagc caccaaggac acctacgacg cccttcacat gcaggccctg   1500
ccccctcgc                                                           1509
```

<210> SEQ ID NO 101
<211> LENGTH: 471
<212> TYPE: PRT
<213> ORGANISM: Artificial Sequence
<220> FEATURE:
<223> OTHER INFORMATION: Synthetic Polypeptide

<400> SEQUENCE: 101

```
Met Asp Trp Ile Trp Arg Ile Leu Phe Leu Val Gly Ala Ala Thr Gly
1               5                   10                  15
Ala His Ser Gln Val Gln Leu Gln Gln Pro Gly Ala Glu Leu Val Arg
            20                  25                  30
Pro Gly Ala Ser Val Lys Leu Ser Cys Lys Ala Ser Gly Tyr Thr Phe
        35                  40                  45
Ser Asn Tyr Leu Met Asn Trp Val Lys Gln Arg Pro Glu Gln Asp Leu
    50                  55                  60
Asp Trp Ile Gly Arg Ile Asp Pro Tyr Asp Gly Asp Ile Asp Tyr Asn
65                  70                  75                  80
Gln Asn Phe Lys Asp Lys Ala Ile Leu Thr Val Asp Lys Ser Ser Ser
                85                  90                  95
Thr Ala Tyr Met Gln Leu Ser Ser Leu Thr Ser Glu Asp Ser Ala Val
            100                 105                 110
Tyr Tyr Cys Ala Arg Gly Tyr Gly Thr Ala Tyr Gly Val Asp Tyr Trp
        115                 120                 125
Gly Gln Gly Thr Ser Val Thr Val Ser Ser Ala Lys Thr Thr Pro Pro
    130                 135                 140
Lys Leu Glu Glu Gly Glu Phe Ser Glu Ala Arg Val Asp Ile Val Leu
145                 150                 155                 160
Thr Gln Ser Pro Ala Ser Leu Ala Val Ser Leu Gly Gln Arg Ala Thr
                165                 170                 175
Ile Ser Cys Arg Ala Ser Glu Ser Val Asp Asn Tyr Gly Ile Ser Phe
            180                 185                 190
Met Asn Trp Phe Gln Gln Lys Pro Gly Gln Pro Pro Lys Leu Leu Ile
        195                 200                 205
Tyr Ala Ala Ser Arg Gln Gly Ser Gly Val Pro Ala Arg Phe Ser Gly
    210                 215                 220
Ser Gly Ser Gly Thr Asp Phe Ser Leu Asn Ile His Pro Met Glu Glu
225                 230                 235                 240
Asp Asp Thr Ala Met Tyr Phe Cys Gln Gln Ser Lys Glu Val Pro Trp
                245                 250                 255
```

Thr Phe Gly Gly Gly Thr Lys Leu Glu Ile Lys Asp Leu Glu Pro Lys
          260                 265                 270

Ser Cys Asp Lys Thr His Thr Cys Pro Pro Cys Pro Ala Pro Lys Cys
      275                 280                 285

Asp Ile Tyr Ile Trp Ala Pro Leu Ala Gly Thr Cys Gly Val Leu Leu
      290                 295                 300

Leu Ser Leu Val Ile Thr Leu Tyr Cys Asn His Arg Asn Lys Arg Gly
305                 310                 315                 320

Arg Lys Lys Leu Leu Tyr Ile Phe Lys Gln Pro Phe Met Arg Pro Val
                  325                 330                 335

Gln Thr Thr Gln Glu Glu Asp Gly Cys Ser Cys Arg Phe Pro Glu Glu
          340                 345                 350

Glu Glu Gly Gly Cys Glu Leu Arg Val Lys Phe Ser Arg Ser Ala Asp
      355                 360                 365

Ala Pro Ala Tyr Gln Gln Gly Gln Asn Gln Leu Tyr Asn Glu Leu Asn
      370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                  405                 410                 415

Leu Tyr Asn Glu Leu Gln Lys Asp Lys Met Ala Glu Ala Tyr Ser Glu
          420                 425                 430

Ile Gly Met Lys Gly Glu Arg Arg Arg Gly Lys Gly His Asp Gly Leu
      435                 440                 445

Tyr Gln Gly Leu Ser Thr Ala Thr Lys Asp Thr Tyr Asp Ala Leu His
      450                 455                 460

Met Gln Ala Leu Pro Pro Arg
465                 470

<210> SEQ ID NO 102
<211> LENGTH: 1413
<212> TYPE: DNA
<213> ORGANISM: Artificial Sequence
<220> FEATURE:
<223> OTHER INFORMATION: Synthetic Polynucleotide

<400> SEQUENCE: 102
atggactgga tctggcgcat cctgtttctc gtgggagccg ccacaggcgc ccattctcag      60
gtgcagctgc agcagcctgg cgctgaactc gtgcggccag cgcttctgt gaagctgagc      120 tgtaaagcca gcggctacac cttcagcaac tacctgatga actgggtcaa gcagcggccc      180
gagcaggacc tggattggat cggcagaatc gaccoctacg acggcgacat cgactacaac      240
cagaacttca ggacaaggc catcctgacc gtggacaaga gcagcagcac cgcctacatg      300
cagctgtcca gcctgaccag cgaggacagc gccgtgtact actgcgccag aggctacggc      360
acagcctacg cgtggactta ttggggccag ggcacaagcg tgaccgtgtc cagcgccaag      420 accaccccc ctaagctgga gagggcgag ttctccgagg cccgggtgga cattgtgctg      480
acacagtctc cagccagcct ggccgtgtcc ctgggacaga gagccaccat cagctgtagg      540
gccagcgaga gcgtggacaa ctacggcatc agcttcatga attggttcca gcagaagccc      600
ggccagcccc ccaagctgct gatctatgcc gccagcagac agggcagcgg agtgcctgcc      660
agattttctg gcagcggctc cggcaccgac ttcagcctga acatccaccc tatggaagag      720
gacgacaccg ccatgtactt tgccagcag agcaaagagg tgccctggac ctttggcgga      780

```
ggcaccaagc tggaaatcaa ggatctcgag cccaaatctt gtgacaaaac tcacacatgc      840
ccaccgtgcc cggatcccaa atgtgatatc tacatctggg cgcccttggc cgggacttgt      900
ggggtccttc tcctgtcact ggttatcacc ctttactgca accacaggaa caaacggggc      960
agaaagaaac tcctgtatat attcaaacaa ccatttatga ccagtacaa actactcaa       1020 gaggaagatg gctgtagctg ccgatttcca gaagaagaag aaggaggatg tgaactgaga     1080
gtgaagttca gcaggagcgc agacgccccc gcgtaccagc agggccagaa ccagctctat     1140
aacgagctca atctaggacg aagagaggag tacgatgttt tggacaagag acgtggccgg     1200
gaccctgaga tggggggaaa gccgagaagg aagaaccctc aggaaggcct gtacaatgaa     1260
ctgcagaaag ataagatggc ggaggcctac agtgagattg ggatgaaagg cgagcgccgg     1320
aggggcaagg ggcacgatgg cctttaccag ggtctcagta cagccaccaa ggacacctac     1380 gacgccttc acatgcaggc cctgccccct cgc                                   1413
```

<210> SEQ ID NO 103
<211> LENGTH: 18
<212> TYPE: PRT
<213> ORGANISM: Homo sapiens
<220> FEATURE:
<221> NAME/KEY: MISC_FEATURE
<223> OTHER INFORMATION: Hinge region of hIgG1

<400> SEQUENCE: 103

Pro Lys Ser Cys Asp Lys Thr His Thr Cys Pro Pro Cys Pro Ala Pro
1               5                   10                  15

Glu Leu

<210> SEQ ID NO 104
<211> LENGTH: 291
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Clone 47 heavy chain constant region 1

<400> SEQUENCE: 104

```
gccaaaacga cacccccatc tgtctatcca ctggcccctg gatctgctgc ccaaactaac       60
tccatggtga cccctgggatg cctggtcaag ggctatttcc ctgagccagt gacagtgacc     120
tggaactctg gatccctgtc cagcggtgtg cacaccttcc cagctgtcct gcagtctgac     180
ctctacactc tgagcagctc agtgactgtc ccctccagca cctggcccag cgagaccgtc     240
acctgcaacg ttgcccaccc ggccagcagc accaaggtgg acaagaaaat t              291
```

<210> SEQ ID NO 105
<211> LENGTH: 321
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Clone 47 heavy chain constant region 2

<400> SEQUENCE: 105

```
gtcccagaag tatcatctgt cttcatcttc ccccaaagc ccaaggatgt gctcaccatt        60
actctgactc ctaaggtcac gtgtgttgtg gtagacatca gcaaggatga tcccgaggtc      120
cagttcagct ggtttgtaga tgatgtggag gtgcacacag ctcagacgca acccgggag       180
```

```
gagcagttca acagcacttt ccgctcagtc agtgaacttc ccatcatgca ccaggactgg     240
ctcaatggca aggagttcaa atgcagggtc aacagtgcag cttccctgc ccccatcgag      300
```
(Note: second line per image reads: ctcaatggca aggagttcaa atgcagggtc aacagtgcag cttccctgc ccccatcgag 300)

```
ctcaatggca aggagttcaa atgcagggtc aacagtgcag ctttccctgc ccccatcgag     300
aaaaccatct ccaaaaccaa a                                               321
```

<210> SEQ ID NO 106
<211> LENGTH: 287
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Clone 47 heavy chain constant region 3

<400> SEQUENCE: 106

```
ggcagaccga aggctccaca ggtgtacacc attccacctc ccaaggagca gatggccaag      60
gataaagtca gtctgacctg catgataaca gacttcttcc ctgaagacat tactgtggag     120
tggcagtgga tgggcagcc agcggagaac tacaagaaca ctcagcccat catggacaca     180
gatggctctt acttcgtcta cagcaagctc aatgtgcaga gagcaactg ggaggcagga     240 aatactttca cctgctctgt gttacatgag ggcctgcaca accacca                  287
```

<210> SEQ ID NO 107
<211> LENGTH: 324
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Clone 47 light chain constant region

<400> SEQUENCE: 107

```
cgggctgatg ctgcaccaac tgtatccatc ttcccaccat ccagtgagca gttaacatct      60
ggaggtgcct cagtcgtgtg cttcttgaac aacttctacc ccaaagacat caatgtcaag     120
tggaagattg atggcagtga acgacaaaat ggcgtcctga cagttggac tgatcaggac     180 agcaaagaca gcacctacag catgagcagc accctcacgt tgaccaagga cgagtatgaa     240
cgacataaca gctatacctg tgaggccact cacaagacat caacttcacc cattgtcaag     300
agcttcaaca ggaatgagtg ttag                                            324
```

<210> SEQ ID NO 108
<211> LENGTH: 39
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Clone 47 hinge region

<400> SEQUENCE: 108

```
gtgcccaggg attgtggttg taagccttgc atatgtaca                             39
```